(12) United States Patent
Ziesche

(10) Patent No.: US 10,604,806 B2
(45) Date of Patent: *Mar. 31, 2020

(54) METHODS OF DIAGNOSING CHRONIC OBSTRUCTIVE PULMONARY DISEASE (COPD) USING NOVEL MOLECULAR BIOMARKERS

(71) Applicant: Transgenion—International Institute for Regenerative Translational Medicine GmbH, Vienna (AT)

(72) Inventor: Rolf Ziesche, Neusiedl am See (AT)

(73) Assignee: Transgenion—International Institute for Regenerative Translational Medicine GmbH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 15/316,258

(22) PCT Filed: Jun. 3, 2015

(86) PCT No.: PCT/EP2015/062440
§ 371 (c)(1),
(2) Date: Dec. 5, 2016

(87) PCT Pub. No.: WO2015/185658
PCT Pub. Date: Dec. 10, 2015

(65) Prior Publication Data
US 2017/0335393 A1    Nov. 23, 2017

(30) Foreign Application Priority Data
Jun. 5, 2014  (EP) .................................... 14171385

(51) Int. Cl.
*C12Q 1/6883* (2018.01)
*A61K 31/44* (2006.01)

(52) U.S. Cl.
CPC ............ *C12Q 1/6883* (2013.01); *A61K 31/44* (2013.01); *C12Q 2600/106* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 2005/0208496 A1* | 9/2005 | Ohtani | C12Q 1/6809 435/6.18 |
| 2013/0095110 A1 | 4/2013 | Yoshida et al. | |
| 2013/0165343 A1 | 6/2013 | Robinson et al. | |
| 2013/0324428 A1* | 12/2013 | Ryu | C12Q 1/6876 506/9 |
| 2017/0107574 A1 | 4/2017 | Ziesche | |
| 2017/0349947 A1 | 12/2017 | Ziesche | |

FOREIGN PATENT DOCUMENTS

| | | |
|---|---|---|
| JP | 2012-010699 | 1/2012 |
| JP | 2013-35871 | 2/2013 |
| WO | WO 2008/003701 | 1/2008 |

(Continued)

OTHER PUBLICATIONS

Bhattacharya et al. American J Respir Cell and Molec Biology. 2009. 40: 359-367.*
Liu et al Clinical Immunology. 2004. 112: 225-230.*
Coleman, R. Drug Discovery Today. 2003. 8: 233-235.*
Palmer et al. BMC Genomics. 2006. 7:115.*
Min et al BMC Genomics. 2010. 11:96.*
Haynes et al Electrophoresis. 1998. 19: 1862-1871.*
Chen et al. Molecular & Cellular Proteomics. 2002. 1: 304-313.*
Vogel et al Nature Review Genet. Mar. 2012. 13(4): 227-232.*
Affymetrix NetAffx. Expression Probeset Details for Human Genome U95 Sets for the KIA1199, TMSB15A, and DMBT1 genes, available via URL: <affynnetrix.com/analysis/netaffx/xmlquery.affx?netaffx=netaffx4_annot>, printed on Jan. 8, 2019, 14 pages.*
Affymetrix Inc. Human Genome U95 Set. GeneChip® Human Genome U95 Set, available via URL: < tools.thermofisher.com/content/sfs/brochures/hgu95_datasheet.pdf>, 2001-2003, printed on Jan. 8, 2019, pp. 1-2.*

(Continued)

*Primary Examiner* — Carla J Myers
(74) *Attorney, Agent, or Firm* — Parker Highlander PLLC

(57) ABSTRACT

The present invention relates to in vitro methods for the diagnosis of chronic obstructive pulmonary disease (COPD), wherein the expression of the marker gene KIAA1199 is determined. In particular, the invention relates to an in vitro diagnostic method of assessing the susceptibility of a subject to develop progressive COPD involving the appearance of irreversible lung damage, wherein the expression of the marker gene KIAA1199 and optionally one or more further marker genes selected from DMBT1, TMSB15A, DPP6, SLC51B, NUDT11, ELF5, AZGP1, PRRX1, AQP3, SFN, GPR110, GDF15, RASGRF2, RND1, PLA1A, FGG, CEACAMS, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. The invention also relates to an in vitro method of diagnosing stable COPD or assessing the susceptibility of a subject to develop stable COPD, wherein the expression of KIAA1199 and optionally one or more further marker genes selected from DMBT1, TMSB15A, DPP6, SLC51B, NUDT11, ELF5, AZGP1, PRRX1, AQP3, SFN, GPR110, GDF15, RASGRF2, RND1, PLA1A, FGG, CEACAMS, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. Furthermore, the invention relates to the use of primers for transcripts of the aforementioned marker genes, the use of nucleic acid probes to transcripts of these marker genes, the use of microarrays comprising nucleic acid probes to transcripts of these marker genes, and the use of antibodies against the proteins expressed from these marker genes in corresponding in vitro methods. In vitro methods of monitoring the progression of COPD are also provided, in which the expression of marker genes according to the invention is determined.

20 Claims, 30 Drawing Sheets

Figure 1:
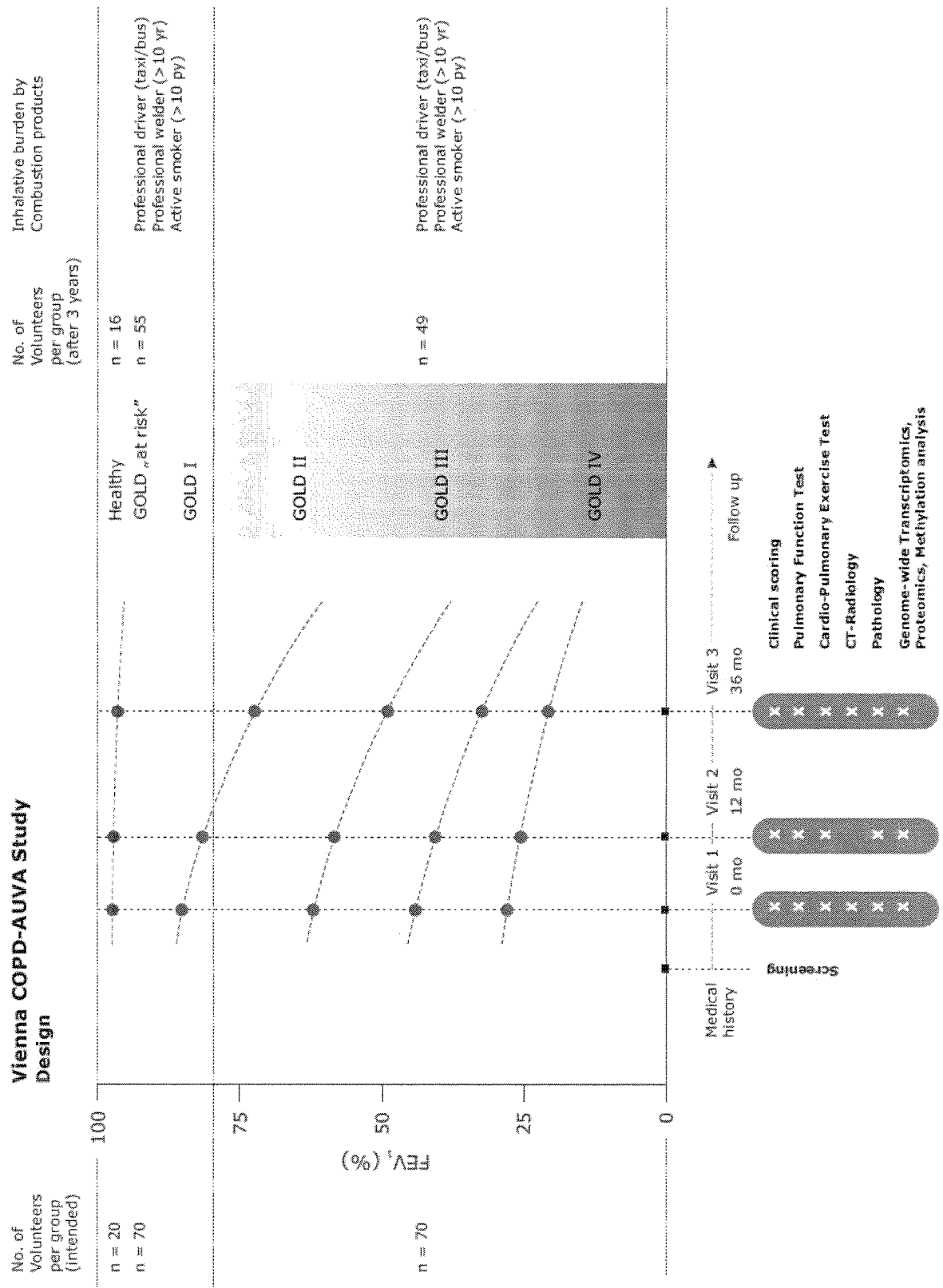

Specification includes a Sequence Listing.

(56) References Cited

FOREIGN PATENT DOCUMENTS

| WO | WO 2010/064702 | 6/2010 |
| WO | WO 2013/104990 | 7/2013 |
| WO | WO 2013/177060 | 11/2013 |
| WO | WO 2013/190092 | 12/2013 |
| WO | WO 2015/185653 | 12/2015 |
| WO | WO 2015/185656 | 12/2015 |

OTHER PUBLICATIONS

Bhattacharya et al., "Molecular biomarkers for quantitative and discrete COPD phenotypes," *American Journal of Respiratory and Cell and Molecular Biology*, 40(3):359-367, 2009.

Gosselink et al., "Differential expression of tissue repair genes in the pathogenesis of chronic obstructive pulmonary disease," *American Journal of Respiratory and Critical Care Medicine*, 181(12):1329-1335, 2010.

PCT International Preliminary Report on Patentability issued in International Application No. PCT/EP2015/062440, dated Dec. 15, 2016.

PCT International Search Report and Written Opinion issued in International Application No. PCT/EP2015/062440, dated Dec. 18, 2015.

Savarimuthu Francis et al., "Genes and gene ontologies common to airflow obstruction and emphysema in the lungs of patients with COPD," *PLOS ONE*, 6(3):e17442, 2011.

Steiling et al., "A dynamic bronchial airway gene expression signature of chronic.obstructive pulmonary disease and lung function impairment," *American Journal of Respiratory and Critical Care Medicine*, 187(9):933-942, 2013.

Bahr et al., "Peripheral blood mononuclear cell gene expression in chronic obstructive pulmonary disease", *Am. J. Respir. Cell Mol. Biol.*, 49:316-323, 2013.

Banyard et al., "Differential regulation of human thymosin beta 15 isoforms by transforming growth factor beta 1", *Genes Chromosomes Cancer*, 48(6):502-509, 2009.

Baye et al., "Roflumilast (Daliresp) A Novel Phosphodiesterase-4 Inhibitor for the Treatment of Severe Chronic Obstructive Pulmonary Disease", *Pharm. Ther.*, 37(3):149-150, 157-161, 2012.

Calverley et al., "Effect of 1-year treatment with roflumilast in severe chronic obstructive pulmonary disease", *Am. J. Respir. Crit. Care Med.*, 176:154-161, 2007.

Calverley et al., "Roflumilast in symptomatic chronic obstructive pulmonary disease: two randomised clinical trials", *Lancet*, 374:685-694, 2009.

Chan et al., "Integrating transcriptomics and proteomics", *G&P Magazine*, 6(3):20-26, 2006.

Hoshikawa et al., "Hypoxia induces different genes in the lungs of rats when compared with mice", *Phys. Genomics*, 12:209-219, 2003.

Kendrick et al., "A gene's mRNA level does not usually predict its protein level", Kendrick Labs, Inc., Sep. 25, 2014.

Llinas et al., "Similar gene expression profiles in smokers and patients with moderate COPD", *Pulm. Pharmacol. Ther.*, 24:32-41, 2011.

Maier et al., "Correlation of mRNA and protein in complex biological samples", *FEBS Lett.*, 583:3966-3973, 2009.

Pascal et al., "Correlation of mRNA and protein levels: cell type-specific gene expression of cluster designation antigens in the prostate", *BMC Genomics*, 9:246, 2008.

Rabe et al., "Roflumilast—an oral anti-inflammatory treatment for chronic obstructive pulmonary disease: a randomised controlled trial", *Lancet*, 366:563-571, 2005.

Renner et al., "DMBT1 confers mucosal protection in vivo and a deletion variant is associated with Crohn's disease", *Gastroenterol.*, 133:1499-1509, 2007.

Richens et al., "Systems biology coupled with label-free high-throughput detection as a novel approach for diagnosis of chronic obstructive pulmonary disease," *Respiratory Research*, 10(1):29, 2009.

Saito-Hisaminato et al., "Genome-wide profiling of gene expression in 29 normal human tissues with a cDNA microarray", *DNA Res.*, 9:35-45, 2002.

Spira et al., "Gene expression profiling of human lung tissue from smokers with severe emphysema", *Am. J. Respir. Care Mol. Biol.*, 31:601-610, 2004.

Steiling et al., "Personalized Management of Chronic Obstructive Pulmonary Disease via Transcriptomic Profiling of the Airway and Lung", *Ann. Am. Thorac.*, 10(Suppl.):S190-S196, 2013.

Van den Berge et al., "Airway gene expression in COPD is dynamic with inhaled corticosteroid treatment and reflects biological pathways associated with disease activity", *Thorax*, 69:14-23, 2014.

Whitehead et al., "Variation in tissue-specific gene expression among natural populations", *Genome Biol.*, 6:R13, 2005.

Office Action issued in Japanese Application No. 2017-516196, dated Jun. 4, 2019.

Office Action issued in Japanese Application No. 2017-516198, dated Jun. 4, 2019.

Office Communication issued in corresponding Japanese Patent Application No. 2017-516198, dated Jan. 7, 2020.

\* cited by examiner

FIG. 3A

Healthy participants

| Initials | Gender | ID | Clinical strata | Age | GOLD | | | Bronchitis & Phlegm | | | Pack Years | Smoking habits | | |
|---|---|---|---|---|---|---|---|---|---|---|---|---|---|---|
| | | | | | V1 | V2 | V3 | V1 | V2 | V3 | Total | V1 | V2 | V3 |
| AC | F | 145 | Healthy | 40.2 | 0 | 0 | 0 | n.a. | n.a. | n.a. | n.a. | -1 | -1 | -1 |
| BR | M | 24 | Healthy | 48.3 | 0 | 0 | 0 | n.a. | n.a. | n.a. | n.a. | -1 | -1 | -1 |
| GI | F | 159 | Healthy | 24.2 | 0 | 0 | 0 | n.a. | n.a. | n.a. | n.a. | -1 | -1 | -1 |
| HD | F | 44 | Healthy | 33.0 | 0 | 0 | 0 | n.a. | n.a. | n.a. | n.a. | -1 | -1 | -1 |
| KH | M | 35 | Healthy | 62.7 | 0 | 0 | 0 | n.a. | n.a. | n.a. | n.a. | -1 | -1 | -1 |
| LH | F | 161 | Healthy | 33.3 | 0 | 0 | 0 | n.a. | n.a. | n.a. | n.a. | -1 | -1 | -1 |
| MA | F | 158 | Healthy | 24.2 | 0 | 0 | 0 | n.a. | n.a. | n.a. | n.a. | -1 | -1 | -1 |
| MO | F | 31 | Healthy | 41.5 | 0 | 0 | 0 | n.a. | n.a. | n.a. | n.a. | -1 | -1 | -1 |
| SE | M | 57 | Healthy | 35.6 | 0 | 0 | 0 | n.a. | n.a. | n.a. | n.a. | -1 | -1 | -1 |
| SH | M | 23 | Healthy | 45.2 | 0 | 0 | 0 | n.a. | n.a. | n.a. | n.a. | -1 | -1 | -1 |
| SS | M | 34 | Healthy | 27.2 | 0 | 0 | 0 | n.a. | n.a. | n.a. | n.a. | -1 | -1 | -1 |
| TK | F | 163 | Healthy | 24.6 | 0 | 0 | 0 | n.a. | n.a. | n.a. | n.a. | -1 | -1 | -1 |
| TT | M | 50 | Healthy | 58.9 | 0 | 0 | 0 | n.a. | n.a. | n.a. | n.a. | -1 | -1 | -1 |
| WH | M | 123 | Healthy | 27.0 | 0 | 0 | 0 | n.a. | n.a. | n.a. | n.a. | -1 | -1 | -1 |
| WW | M | 155 | Healthy | 28.2 | 0 | 0 | 0 | n.a. | n.a. | n.a. | n.a. | -1 | -1 | -1 |
| ZB | M | 128 | Healthy | 28.0 | 0 | 0 | 0 | n.a. | n.a. | n.a. | n.a. | -1 | -1 | -1 |
| | | n 16 | Age (yrs, mean) | 36.4 | | | | | | | | | | |

FIG. 3B

COPD "at risk" at Visit 1 (Gold 0)

| Initials | Gender | ID | Clinical strata | Age | GOLD V1 | GOLD V2 | GOLD V3 | Intensity of Bronchitis V1 | Intensity of Bronchitis V2 | Intensity of Bronchitis V3 | Pack Years Total | Smoking habits V1 | Smoking habits V2 | Smoking habits V3 |
|---|---|---|---|---|---|---|---|---|---|---|---|---|---|---|
| AA | M | 1 | Car/Bus driver COPD °0 | 42.0 | 0 | 0 | 0 | 2 | 2 | 2 | 30 | 4 | 4 | 4 |
| BH | M | 140 | Welder COPD °0 | 31.2 | 0 | 0 | 0 | 1 | 2 | 3 | 16 | 5 | 5 | 5 |
| BM | M | 106 | Welder COPD °0 | 40.2 | 0 | 0 | 0 | 3 | 0 | 0 | 10 | 3 | 0 | 0 |
| BR | M | 166 | Welder COPD °0 | 37.7 | 0 | 0 | 0 | 3 | 1 | 1 | 15 | 3 | 3 | 2 |
| DA | M | 84 | Welder COPD °0 | 46.4 | 0 | 2 | 0 | 0 | 0 | 0 | 13 | 2 | 2 | 1 |
| DM | F | 88 | Car/Bus driver COPD °0 | 50.2 | 0 | 1 | 1 | 0 | 0 | 1 | 70 | 3 | 2 | 2 |
| DE | M | 103 | Welder COPD °0 | 33.0 | 0 | 0 | n.d. | 3 | 1 | n.d. | 6 | 1 | 2 | n.d. |
| ER | M | 165 | Welder COPD °0 | 40.7 | 0 | 0 | n.d. | 0 | -1 | n.d. | 30 | 2 | 2 | n.d. |
| EF | M | 25 | Car/Bus driver COPD °0 | 53.0 | 0 | 0 | 0 | 1 | 1 | 0 | 25 | 0 | 0 | 0 |
| ES | M | 39 | Car/Bus driver COPD °0 | 67.7 | 0 | 0 | 0 | 0 | 2 | 2 | 150 | 6 | 5 | 5 |
| FE | F | 131 | Car/Bus driver COPD °0 | 64.7 | 0 | 0 | 0 | 1 | 1 | 0 | 8 | 0 | 0 | 0 |
| GT | M | 134 | Car/Bus driver COPD °0 | 47.5 | 0 | 2 | 1 | 2 | 2 | 0 | 45 | 5 | 4 | 4 |
| HJ | M | 20 | Car/Bus driver COPD °0 | 50.4 | 0 | 0 | 0 | 3 | 3 | 3 | 15 | 2 | 2 | 2 |
| HA | F | 72 | Car/Bus driver COPD °0 | 49.2 | 0 | 0 | 0 | 0 | 0 | 0 | 14 | 2 | 2 | 2 |
| HK | M | 97 | Car/Bus driver COPD °0 | 52.1 | 0 | 0 | 0 | 3 | 3 | 2 | 40 | 2 | n.d. | n.d. |
| JW | M | 40 | Car/Bus driver COPD °0 | 68.8 | 0 | 0 | 0 | 1 | 1 | 1 | 20 | 5 | 5 | 5 |
| JS | F | 32 | Car/Bus driver COPD °0 | 46.5 | 0 | 0 | 0 | 0 | 0 | 1 | 10 | 1 | 1 | 1 |
| KR | M | 86 | Car/Bus driver COPD °0 | 49.5 | 0 | 0 | 0 | 0 | 0 | 0 | 30 | 3 | 3 | 3 |
| KE | M | 176 | Welder COPD °0 | 50.7 | 0 | 2 | n.d. | 2 | 2 | n.d. | 55 | 5 | 3 | n.d. |
| KJ | M | 168 | Welder COPD °0 | 32.1 | 0 | 0 | 0 | 2 | 2 | 1 | 10 | 3 | 0 | 1 |
| KG | M | 16 | Car/Bus driver COPD °0 | 43.8 | 0 | 0 | 0 | 0 | 0 | 0 | 20 | 3 | 3 | 3 |
| KEM | F | 101 | Car/Bus driver COPD °0 | 65.2 | 0 | 0 | 0 | 2 | 2 | 3 | 40 | 3 | 4 | 4 |
| KJ | M | 13 | Car/Bus driver COPD °0 | 54.2 | 0 | 0 | 0 | 0 | 0 | -1 | 35 | 5 | 0 | 0 |
| KH | M | 47 | Car/Bus driver COPD °0 | 65.5 | 0 | 0 | 0 | 0 | -1 | -1 | 50 | 3 | 5 | 3 |
| LJ | M | 4 | Car/Bus driver COPD °0 | 56.3 | 0 | 1 | n.d. | 0 | 0 | n.d. | 40 | 0 | 0 | n.d. |
| MT | M | 154 | Welder COPD °0 | 37.6 | 0 | 0 | 2 | 2 | 3 | 1 | 20 | 3 | 2 | 1 |
| MW | M | 58 | Car/Bus driver COPD °0 | 58.4 | 0 | 0 | 0 | 1 | 1 | 1 | 30 | 0 | 0 | 0 |
| MP | M | 79 | Welder COPD °0 | 53.2 | 0 | 0 | 0 | 0 | 0 | 1 | 32 | 3 | 4 | 3 |

FIG. 3B Cont.

| Initials | Gender | Clinical strata | ID | Age | GOLD | | | Intensity of Bronchitis | | | Pack Years Total | Smoking habits | | |
|---|---|---|---|---|---|---|---|---|---|---|---|---|---|---|
| | | | | | V1 | V2 | V3 | V1 | V2 | V3 | | V1 | V2 | V3 |
| | | COPD "at risk" | | | | | | | | | | | | |
| MS | M | Car/Bus driver COPD °0 | 10 | 36.3 | 0 | 0 | 0 | 1 | 1 | 0 | 18 | 3 | 3 | 3 |
| OI | M | Welder COPD °0 | 167 | 52.7 | 0 | 0 | n.d. | 1 | 0 | n.d. | 10 | 0 | 0 | n.d. |
| PC | M | Car/Bus driver COPD °0 | 139 | 61.8 | 0 | 2 | n.d. | 1 | 1 | n.d. | 30 | 0 | 0 | n.d. |
| PEM | M | Welder COPD °0 | 90 | 46.1 | 0 | 0 | 0 | 2 | 2 | 3 | 17 | 1 | 1 | 0 |
| PEM | M | Welder COPD °0 | 74 | 47.0 | 0 | 0 | 0 | -1 | -1 | 1 | 0 | -1 | -1 | -1 |
| PRM | M | Car/Bus driver COPD °0 | 5 | 57.2 | 0 | 2 | 2 | 1 | 1 | 1 | 60 | 6 | 6 | 5 |
| RM | M | Welder COPD °0 | 115 | 45.8 | 0 | 0 | 0 | 2 | 2 | 1 | 35 | 0 | 3 | 1 |
| RR | M | Car/Bus driver COPD °0 | 36 | 55.2 | 0 | 0 | 0 | 1 | 1 | 1 | 38 | 0 | 0 | 0 |
| RH | M | Welder COPD °0 | 91 | 61.1 | 0 | 0 | 0 | 1 | 1 | 0 | 85 | 5 | 3 | 3 |
| SB | F | Car/Bus driver COPD °0 | 67 | 49.3 | 0 | 0 | 0 | 0 | 0 | 0 | 15 | 2 | 2 | 2 |
| SW | M | Car/Bus driver COPD °0 | 117 | 52.2 | 0 | 0 | 0 | 0 | 0 | 1 | 40 | 0 | 2 | 2 |
| SIW | M | Welder COPD °0 | 118 | 49.7 | 0 | 0 | 0 | 0 | 0 | 2 | 27 | 3 | 3 | 2 |
| SR | M | Car/Bus driver COPD °0 | 152 | 38.6 | 0 | 0 | 0 | 0 | 0 | -1 | 10 | 0 | 0 | 0 |
| STJ | M | Car/Bus driver COPD °0 | 21 | 60.8 | 0 | 0 | 0 | 1 | 1 | 0 | 50 | 4 | 3 | 0 |
| STB | F | Car/Bus driver COPD °0 | 56 | 61.3 | 0 | 0 | n.d. | 0 | 0 | 0 | 25 | 0 | 0 | 0 |
| STS | M | Welder COPD °0 | 83 | 48.2 | 0 | 0 | 0 | 2 | 2 | 3 | 60 | 5 | 5 | 5 |
| STP | M | Welder COPD °0 | 156 | 47.0 | 0 | 0 | 0 | 0 | 0 | 0 | 15 | 0 | 0 | 0 |
| STA | M | Car/Bus driver COPD °0 | 17 | 45.4 | 0 | 0 | 0 | 0 | 0 | 2 | 20 | 4 | 4 | 4 |
| TJ | M | Car/Bus driver COPD °0 | 19 | 53.9 | 0 | 0 | 0 | 1 | 1 | 1 | 40 | 4 | 4 | 2 |
| TA | F | Car/Bus driver COPD °0 | 46 | 58.1 | 0 | 2 | 2 | 0 | 1 | -1 | 100 | 5 | 4 | 6 |
| WC | M | Welder COPD °0 | 172 | 42.9 | 0 | 0 | 0 | 0 | 2 | 0 | 36 | 4 | 4 | 3 |
| WW | M | Welder COPD °0 | 124 | 44.0 | 0 | 2 | 2 | 1 | 1 | 2 | 30 | 0 | 0 | 0 |
| WS | M | Welder COPD °0 | 65 | 30.5 | 0 | 0 | 1 | 0 | -1 | -1 | 10 | 0 | 0 | 0 |
| WR | M | Welder COPD °0 | 160 | 56.9 | 0 | 2 | 0 | 1 | 1 | 1 | 30 | 0 | 0 | 0 |
| WIR | M | Welder COPD °0 | 125 | 63.4 | 0 | 0 | 0 | 1 | 1 | 2 | 45 | 2 | 3 | 2 |
| ZAE | M | Welder COPD °0 | 93 | 51.7 | 0 | 0 | 0 | 2 | 2 | 2 | 10 | 1 | 1 | 0 |
| ZE | M | Car/Bus driver COPD °0 | 6 | 45.7 | 0 | 0 | 0 | 1 | 1 | 1 | 35 | 4 | 4 | 4 |
| n 55 | | | | Age (yrs, mean) 50.0 | | | | | | | PY (mean) 32.2 | | | |

FIG. 3C

Manifest COPD at Visit 1

| Initials | Gender | ID | Clinical strata COPD (manifest) | Age | GOLD V1 | GOLD V2 | GOLD V3 | Intensity of Bronchitis V1 | Intensity of Bronchitis V2 | Intensity of Bronchitis V3 | Pack Years Total | Smoking habits V1 | Smoking habits V2 | Smoking habits V3 |
|---|---|---|---|---|---|---|---|---|---|---|---|---|---|---|
| CW | M | 45 | Driver COPD °I-III | 59.0 | 1 | 0 | 0 | 1 | 0 | 1 | 10 | 0 | 0 | 0 |
| DJ | M | 85 | Driver COPD °I-III | 41.6 | 1 | 0 | 0 | 1 | 1 | 1 | 8 | 1 | 2 | 2 |
| GW | M | 102 | Driver COPD °I-III | 55.9 | 1 | 0 | 0 | -1 | -1 | -1 | 30 | 0 | 0 | 0 |
| HP | M | 98 | Driver COPD °I-III | 70.2 | 1 | 1 | 2 | 1 | 1 | 1 | 20 | 0 | 0 | 0 |
| KA | M | 107 | Welder COPD °I-III | 48.8 | 1 | 0 | 1 | 2 | 2 | 1 | 30 | 3 | 3 | 3 |
| KW | M | 55 | Driver COPD °I-III | 54.1 | 1 | 0 | 0 | 1 | 1 | 1 | 50 | 2 | 2 | 2 |
| MM | F | 114 | Driver COPD °I-III | 57.3 | 1 | 0 | 0 | 1 | 1 | 4 | 35 | 5 | 5 | 5 |
| RH | M | 116 | Driver COPD °I-III | 71.6 | 1 | 1 | n.d. | 2 | 2 | n.d. | 45 | 0 | 0 | 0 |
| WH | M | 92 | Welder COPD °I-III | 44.2 | 1 | 2 | 1 | 0 | 2 | 1 | 35 | 4 | 3 | 3 |
| DK | M | 87 | Welder COPD °I-III | 50.8 | 2 | 2 | 2 | -1 | -1 | -1 | 5 | 1 | 1 | 1 |
| GG | M | 133 | Driver COPD °I-III | 52.5 | 2 | 2 | n.d. | 0 | 0 | n.d. | 30 | 0 | 0 | 0 |
| AG | M | 71 | Welder COPD °I-III | 56.5 | 2 | 2 | 2 | 1 | 1 | 3 | 20 | 0 | 0 | 0 |
| BD | M | 148 | Driver COPD °I-III | 43.2 | 2 | 3 | 4 | 2 | 3 | -1 | 25 | 5 | 2 | 5 |
| CA | M | 37 | Driver COPD °I-III | 65.8 | 2 | 0 | 1 | 1 | 1 | 2 | 40 | 3 | 3 | 3 |
| GG | M | 136 | Welder COPD °I-III | 51.8 | 2 | 2 | 2 | 1 | 0 | 0 | 30 | 3 | 3 | 4 |
| HAH | M | 96 | Driver COPD °I-III | 46.2 | 2 | 3 | 2 | 1 | 0 | 2 | 40 | 4 | 4 | 0 |
| HE | M | 99 | Driver COPD °I-III | 48.9 | 2 | 2 | 2 | 1 | 1 | 1 | 25 | 0 | 0 | 3 |
| HF | M | 147 | Driver COPD °I-III | 63.3 | 2 | 2 | 2 | 1 | 3 | 2 | 30 | 3 | 3 | 3 |
| HH | M | 151 | Driver COPD °I-III | 56.2 | 2 | 2 | 2 | 3 | 1 | 1 | 30 | 3 | 3 | 1 |
| KT | M | 94 | Driver COPD °I-III | 50.8 | 2 | 2 | 2 | 1 | 1 | 2 | 30 | 5 | 0 | 3 |
| LG | M | 109 | Driver COPD °I-III | 60.0 | 2 | 2 | 2 | 1 | 1 | 1 | 40 | 4 | 3 | 3 |
| MB | F | 113 | Driver COPD °I-III | 69.7 | 2 | 2 | 2 | 0 | 0 | 2 | 35 | 3 | 3 | 5 |
| MJ | M | 112 | Welder COPD °I-III | 68.2 | 2 | 2 | 2 | 1 | 2 | 3 | 80 | 5 | 5 | 0 |
| MJ | M | 68 | Welder COPD °I-III | 47.5 | 2 | 2 | 2 | 1 | 2 | 2 | 50 | 0 | 0 | 3 |
| MT | M | 171 | Welder COPD °I-III | 48.8 | 2 | 1 | 2 | 1 | 1 | 1 | 35 | 2 | 3 | 3 |
| RJ | M | 75 | Driver COPD °I-III | 49.8 | 2 | 2 | 2 | 1 | 1 | 1 | 40 | 3 | 3 | 1 |
| SCHR | M | 76 | Driver COPD °I-III | 51.1 | 2 | 2 | 2 | 1 | 1 | 1 | 30 | 3 | 3 | 1 |

FIG. 3C Cont.

| Initials | Gender | ID | Clinical strata COPD "at risk" | Age | GOLD V1 | GOLD V2 | GOLD V3 | Intensity of Bronchitis V1 | Intensity of Bronchitis V2 | Intensity of Bronchitis V3 | Pack Years Total | Smoking habits V1 | Smoking habits V2 | Smoking habits V3 |
|---|---|---|---|---|---|---|---|---|---|---|---|---|---|---|
| SCHS | F | 130 | Driver COPD °I-III | 53.0 | 2 | 2 | 3 | 1 | 2 | 2 | 30 | 4 | 4 | 3 |
| SE | F | 119 | Driver COPD °I-III | 52.5 | 2 | 2 | 2 | 1 | 1 | 0 | 40 | 0 | 0 | 0 |
| SS | M | 104 | Welder COPD °I-III | 39.9 | 2 | 0 | 0 | 2 | 2 | 2 | 15 | 2 | 2 | 2 |
| VA | M | 121 | Welder COPD °I-III | 49.8 | 2 | 2 | 3 | 1 | 1 | 1 | 30 | 4 | 3 | 3 |
| WM | M | 9 | Driver COPD °I-III | 48.2 | 2 | 2 | 2 | -1 | 0 | -1 | 25 | 3 | 3 | 3 |
| WT | M | 69 | Welder COPD °I-III | 47.5 | 2 | 2 | 0 | 1 | 1 | 1 | 60 | 2 | 2 | 1 |
| ZJ | M | 78 | Welder COPD °I-III | 60.2 | 2 | 2 | 2 | 1 | 1 | 2 | 35 | 0 | 0 | 2 |
| ZS | M | 127 | Driver COPD °I-III | 27.4 | 2 | 2 | 0 | 2 | 4 | 4 | 9 | 3 | 5 | 4 |
| BH | M | 2 | Driver COPD °I-III | 46.4 | 3 | 2 | 2 | 0 | 0 | -1 | 25 | 3 | 0 | 0 |
| CP | M | 100 | Welder COPD °I-III | 70.8 | 3 | 3 | 3 | 0 | 1 | 0 | 70 | 0 | 0 | 0 |
| FW | M | 132 | Driver COPD °I-III | 65.3 | 3 | 3 | 3 | 0 | 0 | 1 | 40 | 3 | 3 | 3 |
| BW | M | 38 | Driver COPD °I-III | 68.5 | 3 | 3 | 3 | 1 | 1 | 1 | 60 | 4 | 4 | 3 |
| KE | M | 108 | Welder COPD °I-III | 51.5 | 3 | 4 | 4 | 1 | 2 | 1 | 45 | 4 | 5 | 4 |
| KK | M | 73 | Welder COPD °I-III | 55.5 | 3 | 3 | 3 | 1 | 1 | 3 | 25 | 1 | 1 | 1 |
| LH | M | 80 | Welder COPD °I-III | 69.8 | 3 | 3 | n.d. | 1 | 1 | n.d. | 70 | 3 | 3 | 3 |
| MC | F | 111 | Driver COPD °I-III | 62.2 | 3 | 3 | 4 | 0 | 0 | 0 | 40 | 0 | 0 | 0 |
| NP | M | 70 | Driver COPD °I-III | 64.2 | 3 | 3 | 4 | 1 | 1 | 2 | 100 | 0 | 0 | 0 |
| SCHB | M | 146 | Driver COPD °I-III | 57.8 | 3 | 3 | 3 | 2 | 2 | 2 | 60 | 3 | 4 | 3 |
| TG | M | 129 | Driver COPD °I-III | 62.5 | 3 | 2 | 2 | 1 | 1 | 2 | 60 | 2 | 2 | 2 |
| WJ | M | 63 | Driver COPD °I-III | 55.8 | 3 | 3 | 3 | 1 | 1 | 1 | 40 | 0 | 0 | 0 |
| HOH | M | 48 | Driver COPD °I-III | 70.8 | 4 | 3 | 3 | -1 | 0 | 2 | 100 | 0 | 0 | 0 |
| JR | M | 110 | Driver COPD °I-III | 55.3 | 4 | 3 | n.d. | 1 | 1 | n.d. | 40 | 4 | 1 | n.d. | n 49     Age (yrs, mean) 55.5     PY (mean) 38.7

Fig. 3 (cont.)

D)

| No. of participants | | Healthy<br>16 | | GOLD at risk<br>55 | | GOLD I<br>9 | | | GOLD II<br>26 | | | GOLD III<br>12 | | | GOLD IV<br>2 | | | Total<br>120 | |
|---|---|---|---|---|---|---|---|---|---|---|---|---|---|---|---|---|---|---|---|
| Age | | 36 ± 12.2 | | 50 ± 9.5 | | 56 ± 10.4 | | p=0.083 | 52 ± 9.0 | | p=0.304 | 61 ± 7.6 | | p=0.0004 | 63 ± 11.0 | | p=0.054 | | |
| Packyears | | 0 | | 32 ± 26 | | 29 ± 15 | | p=0.729 | 33 ± 15 | | p=0.815 | 53 ± 21 | | p=0.004 | 70 ± 42 | | p=0.022 | | |
| Gender | F | 7 | (44%) | 8 | (15%) | 1 | (11%) | | 3 | (12%) | | 1 | (8%) | | 0 | | | 20 | (17%) |
| | M | 9 | (56%) | 47 | (85%) | 8 | (89%) | | 23 | (88%) | | 11 | (92%) | | 2 | (100%) | p=0.931 | 100 | (83%) |
| Occupation | Control (healthy) | 16 | | 0 | | 0 | | | 0 | | | 0 | | | 0 | | | 16 | (13%) |
| | Taxi/Bus driver | 0 | | 31 | (56%) | 7 | (78%) | | 16 | (62%) | | 8 | (67%) | | 2 | (100%) | p=0.594 | 64 | (53%) |
| | Welder | 0 | | 24 | (44%) | 2 | (22%) | | 10 | (38%) | | 4 | (33%) | | 0 | | | 40 | (33%) |
| Symptoms of chronic bronchitis (Cough & Phlegm) | No symptoms | 16 | (100%) | 0 | | 0 | | | 0 | | | 0 | | | 0 | | | 16 | (13%) |
| | frequently dry | 0 | | 24 | (44%) | 2 | (22%) | | 4 | (15%) | | 4 | (33%) | | 1 | (50%) | p=0.054 | 35 | (29%) |
| | productive | 0 | | 16 | (29%) | 5 | (56%) | | 18 | (69%) | | 7 | (58%) | | 1 | (50%) | | 47 | (39%) |
| | discolored | 0 | | 15 | (27%) | 2 | (22%) | | 4 | (15%) | | 1 | (8%) | | 0 | | | 22 | (18%) |
| Changes between baseline and visit 3 | | | | | | | | | | | | | | | | | | | |
| GOLD stage | deterioration | 0 | | 7 | (13%) | 1 | (11%) | | 3 | (12%) | | 3 | (25%) | | 0 | | | 14 | (12%) |
| | stable | 16 | (100%) | 48 | (87%) | 3 | (33%) | | 18 | (69%) | | 7 | (58%) | | 1 | (50%) | p=0.001 | 93 | (78%) |
| | improvement | 0 | | 0 | | 5 | (56%) | | 5 | (19%) | | 2 | (17%) | | 1 | (50%) | | 13 | (11%) |
| Cough & Phlegm | deterioration | 0 | | 11 | (20%) | 2 | (22%) | | 9 | (35%) | | 4 | (33%) | | 1 | (50%) | | 27 | (23%) |
| | stable | 16 | (100%) | 26 | (47%) | 5 | (56%) | | 12 | (46%) | | 7 | (58%) | | 0 | | p=0.058 | 66 | (55%) |
| | improvement | 0 | | 18 | (33%) | 2 | (22%) | | 5 | (19%) | | 1 | (8%) | | 1 | (50%) | | 27 | (23%) |
| Exacerbations (month 1-12) | yes | 0 | | 12 | (22%) | 3 | (33%) | | 4 | (15%) | | 5 | (42%) | | 1 | (50%) | | 25 | (21%) |
| | no | 16 | (100%) | 43 | (78%) | 6 | (67%) | | 22 | (85%) | | 7 | (58%) | | 1 | (50%) | p=0.308 | 95 | (79%) |
| Exacerbations (month 12-36) | yes | 0 | | 10 | (18%) | 3 | (33%) | | 14 | (54%) | | 5 | (42%) | | 0 | | | 32 | (27%) |
| | no | 16 | (100%) | 45 | (82%) | 6 | (67%) | | 12 | (46%) | | 7 | (58%) | | 2 | (100%) | p=0.008 | 88 | (73%) |

A)

B)

C)

D)

A)

B)

C)

D)

E)

F)

G)

Figure 5:
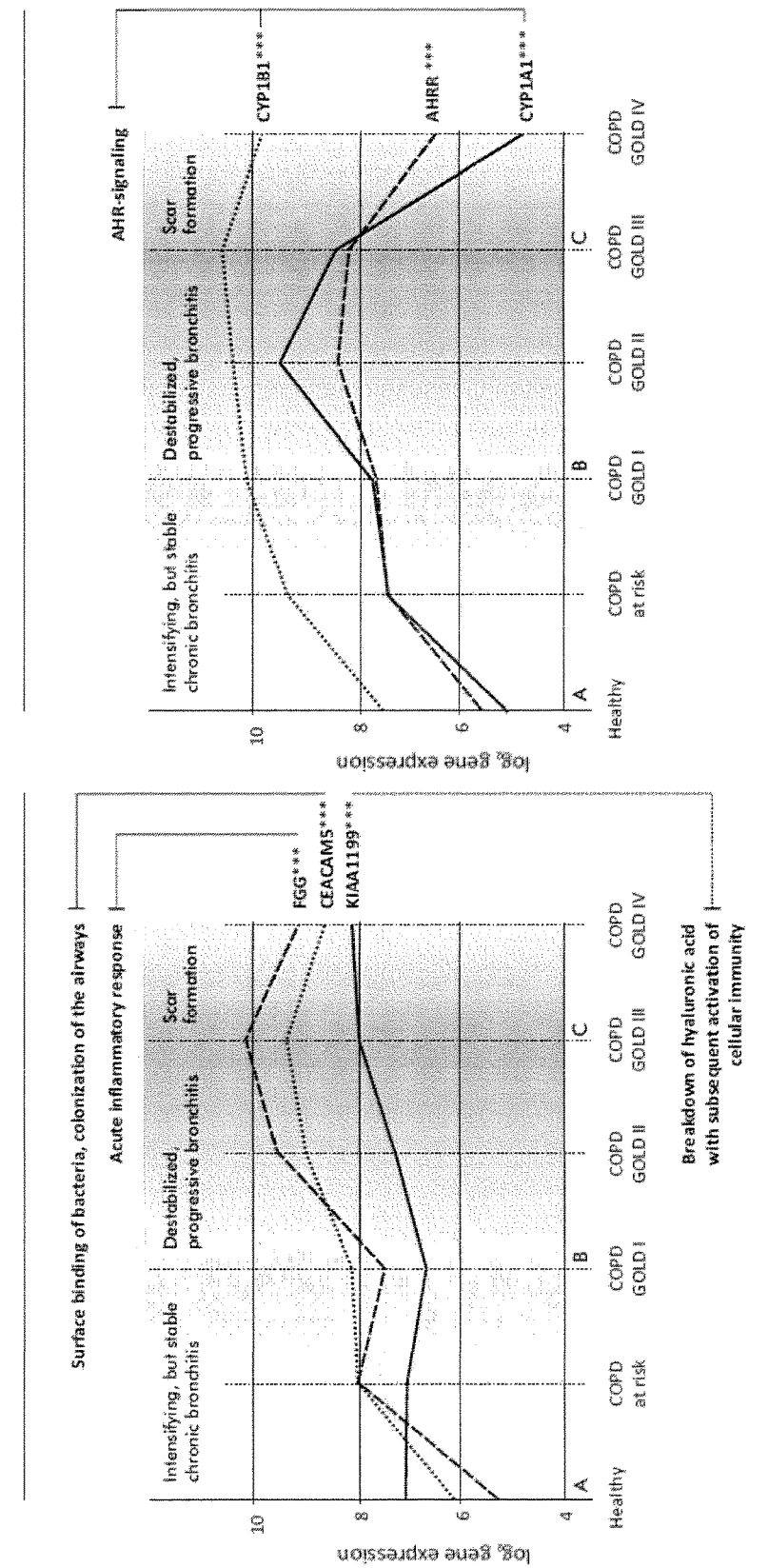
Figure 5:
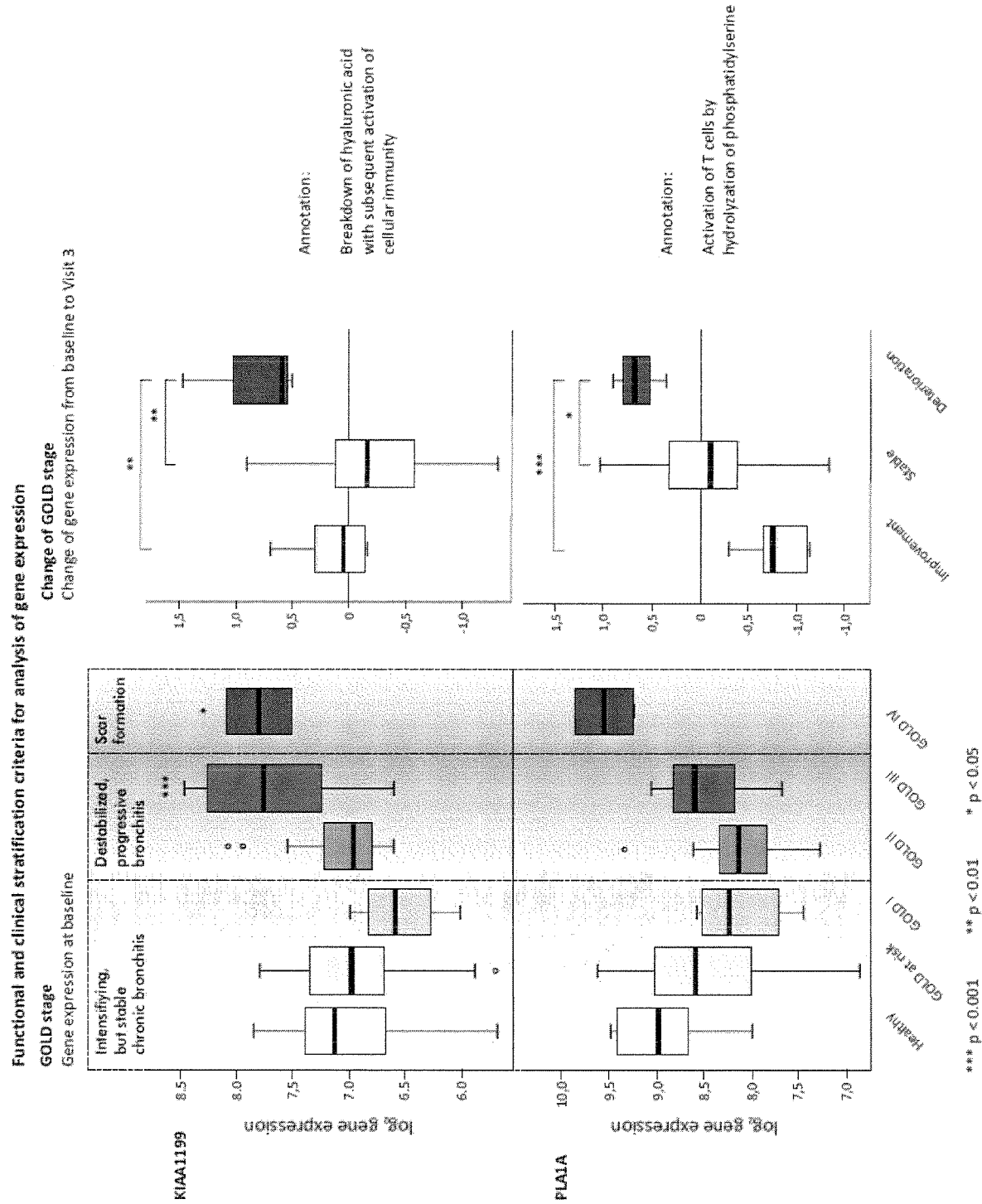
Figure 5:
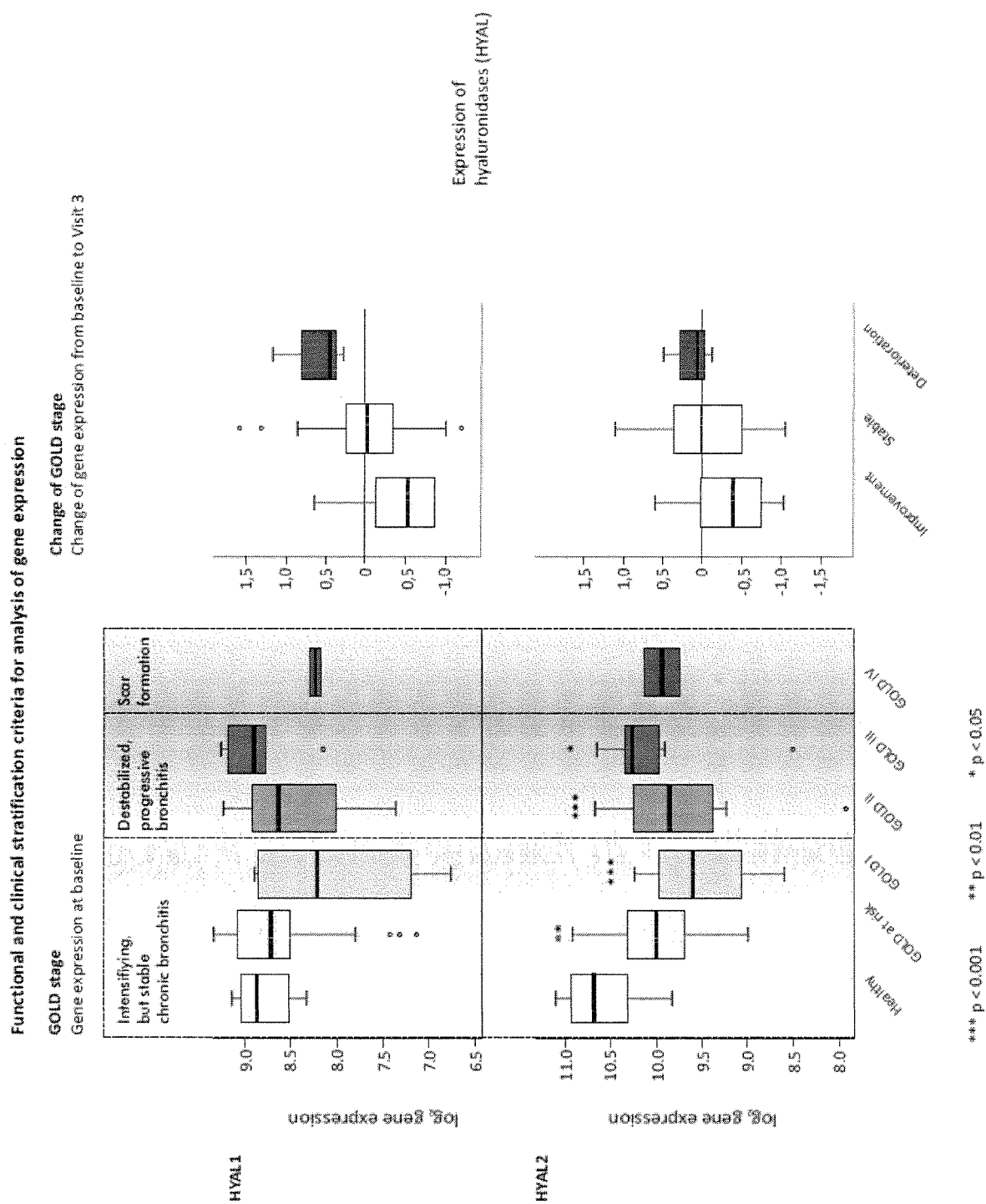
Figure 5:
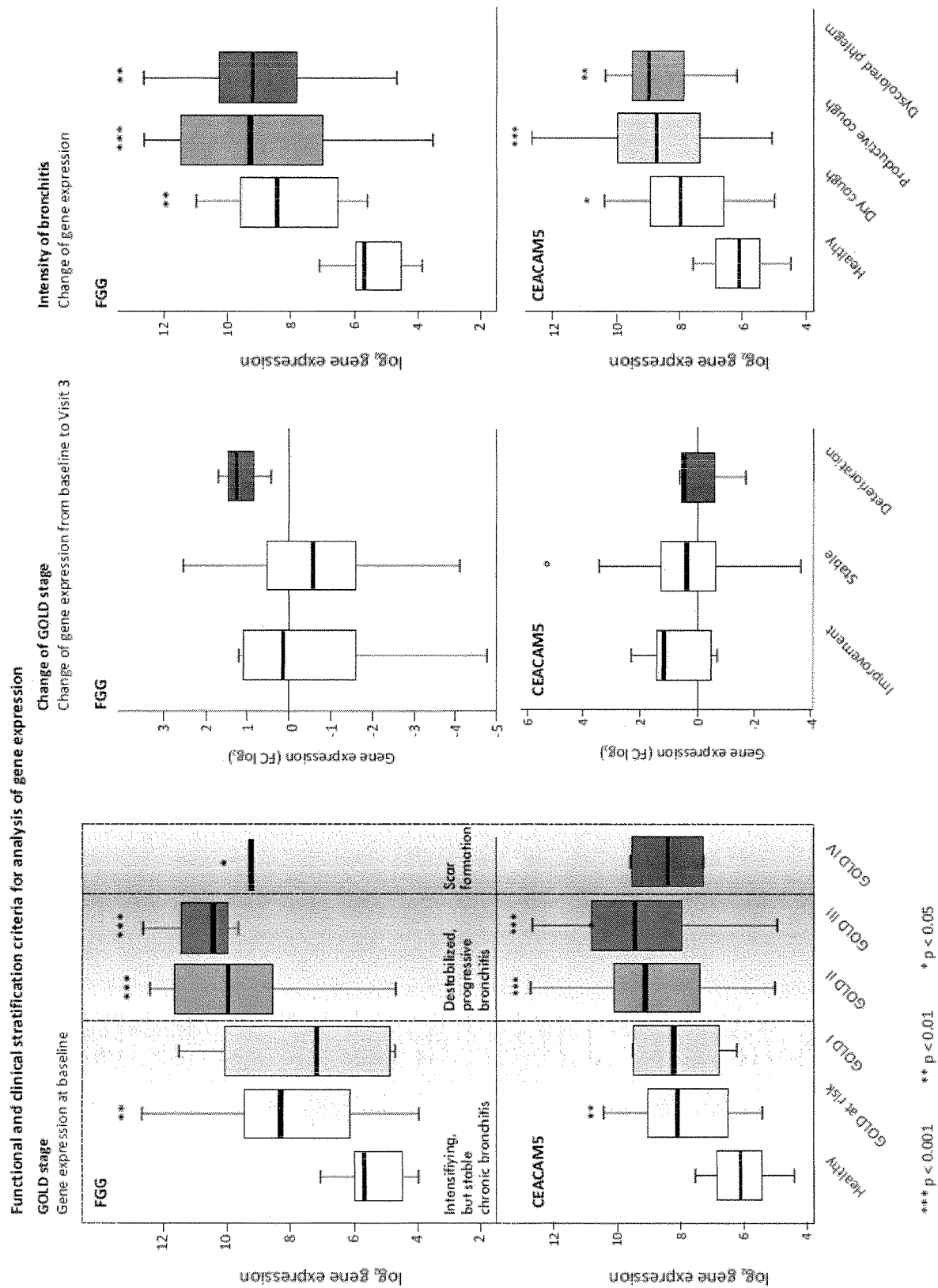
Figure 5:
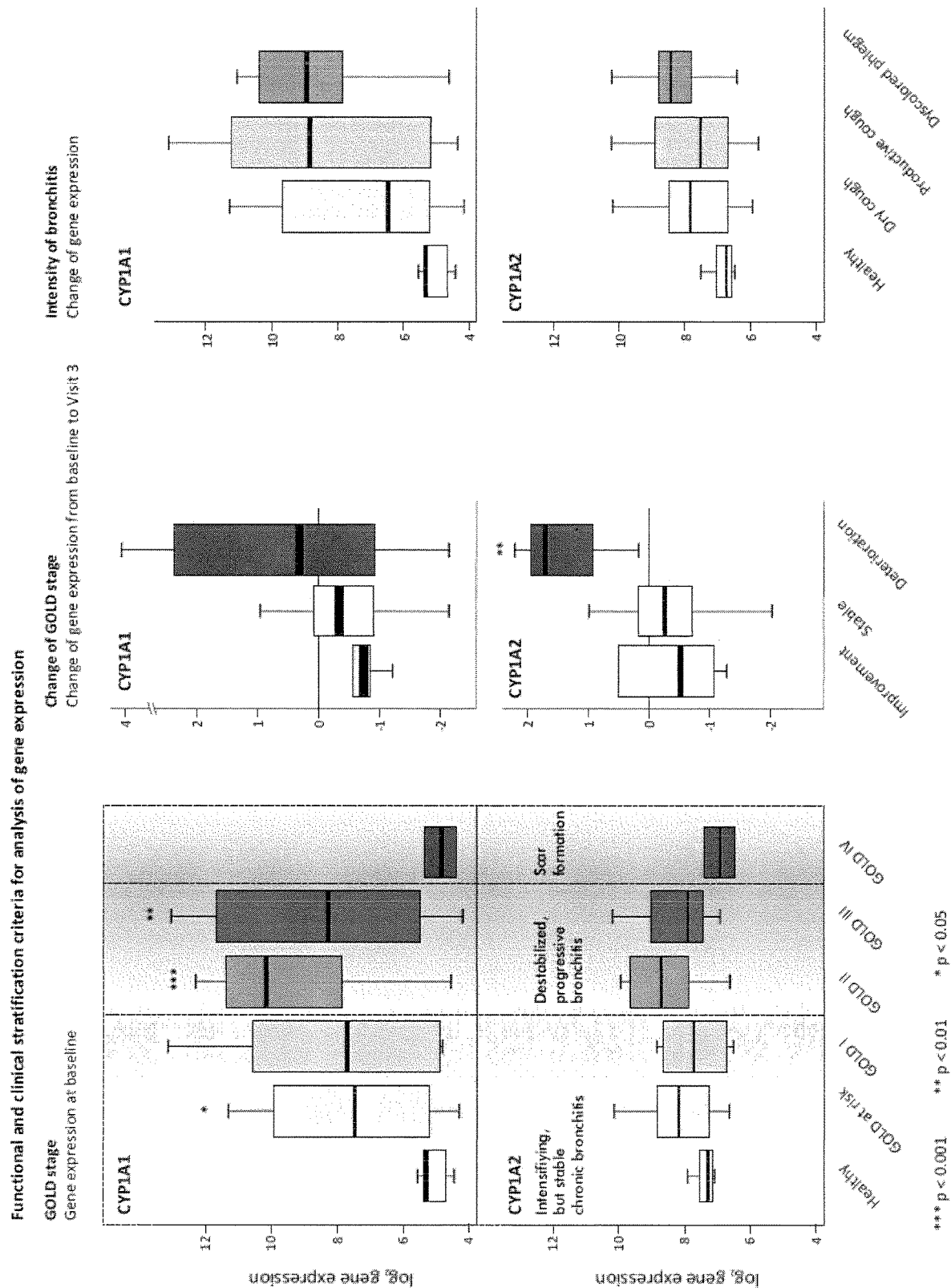
Figure 5:
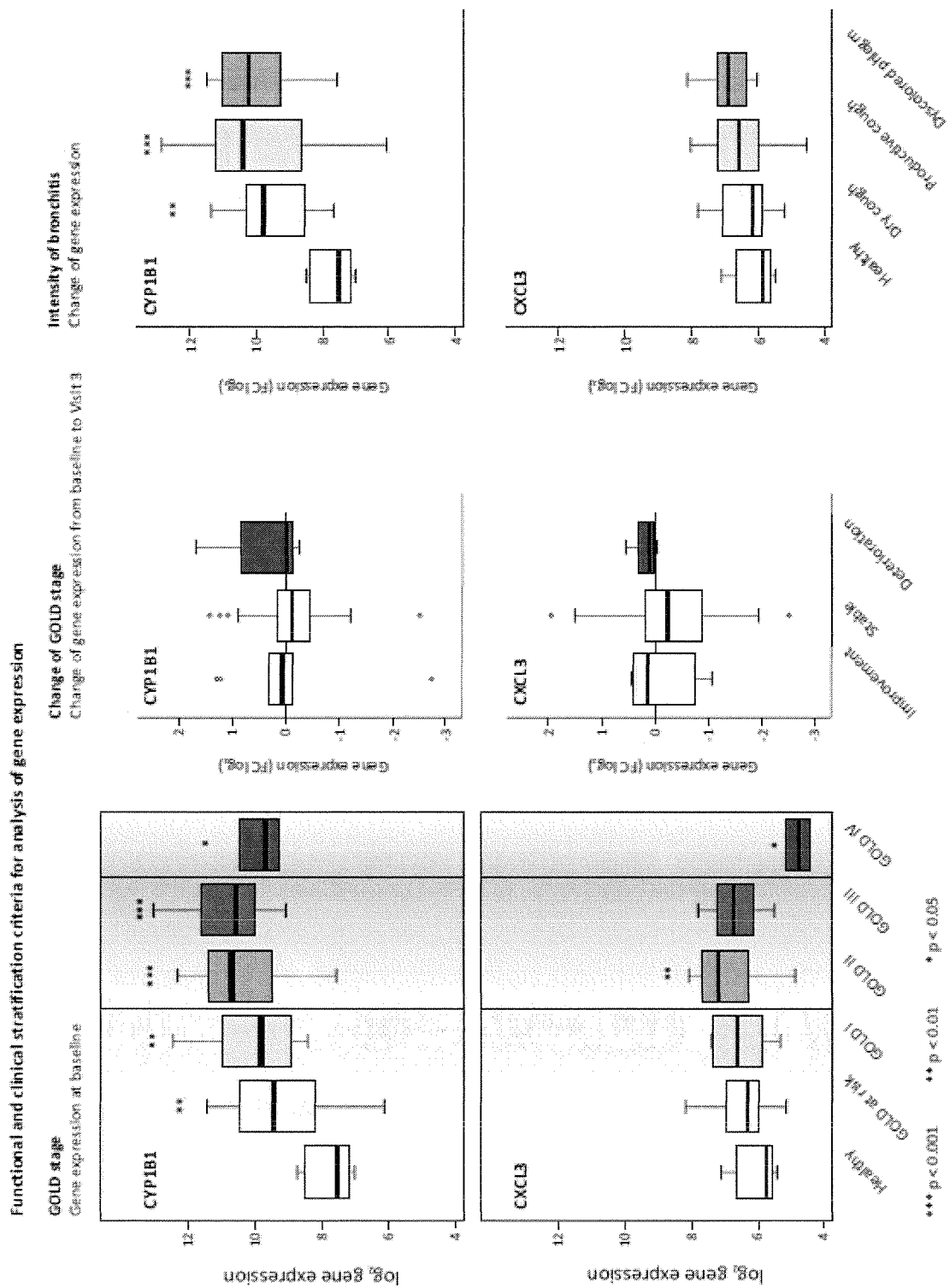
Figure 5:
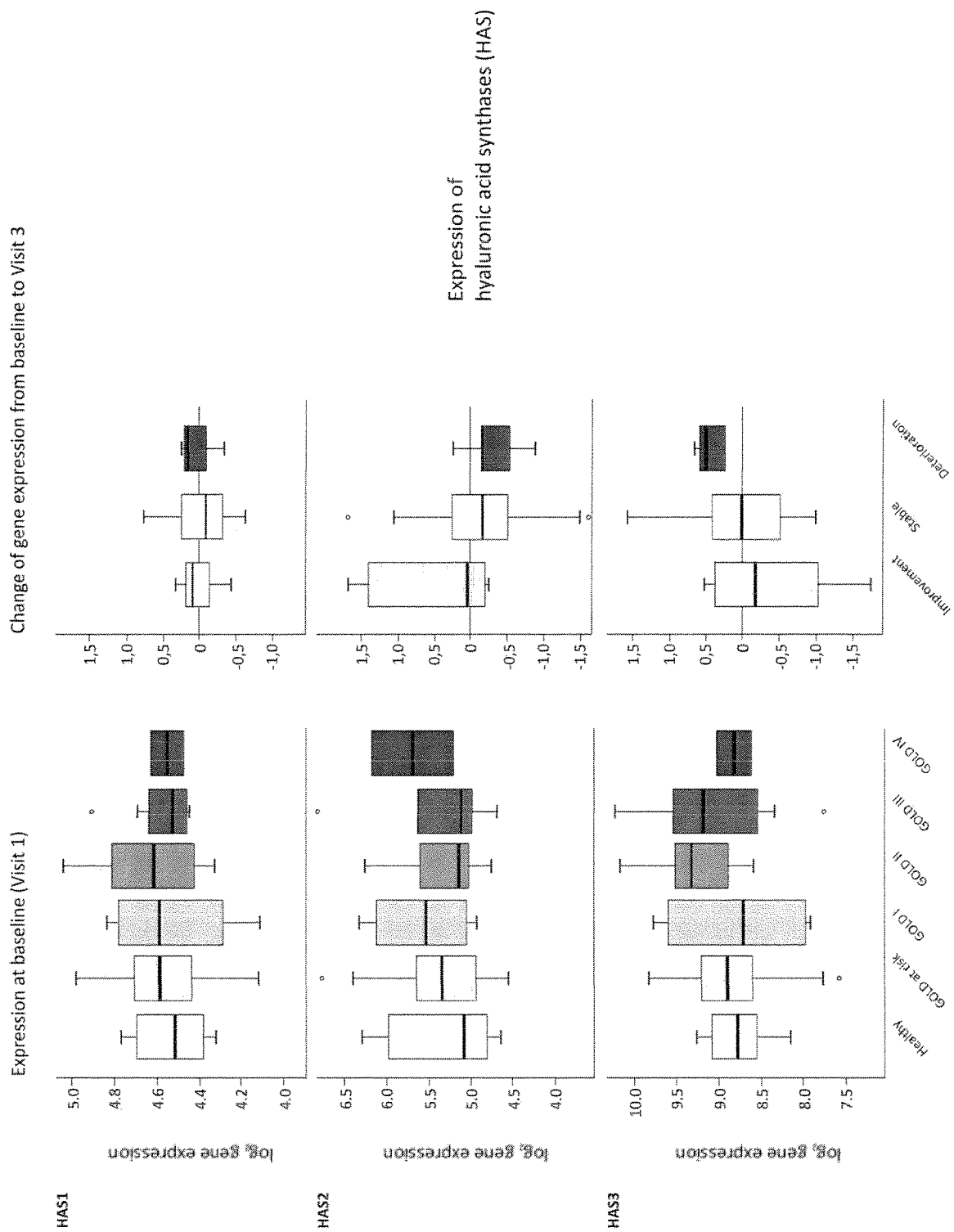

Fig. 5 (cont.)
H)
Gene expression during progression of COPD (GOLD criteria)
Activation of mucosal immunity
Immune mechanisms
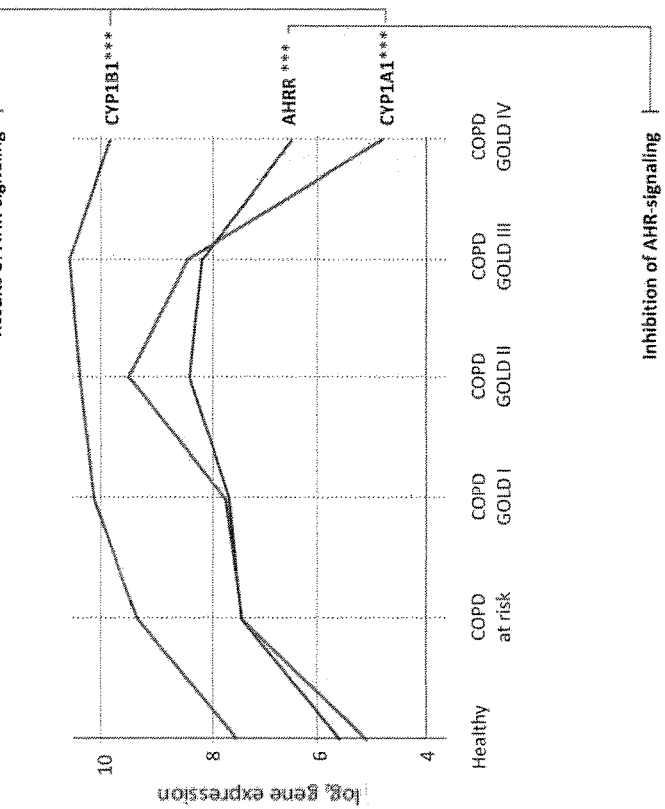
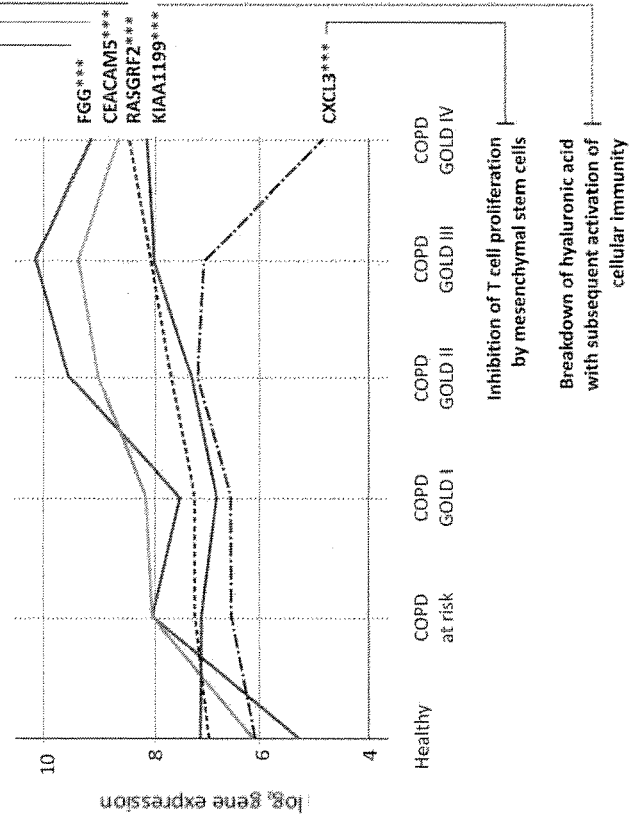
*** $p < 0.005$

Figure 6:
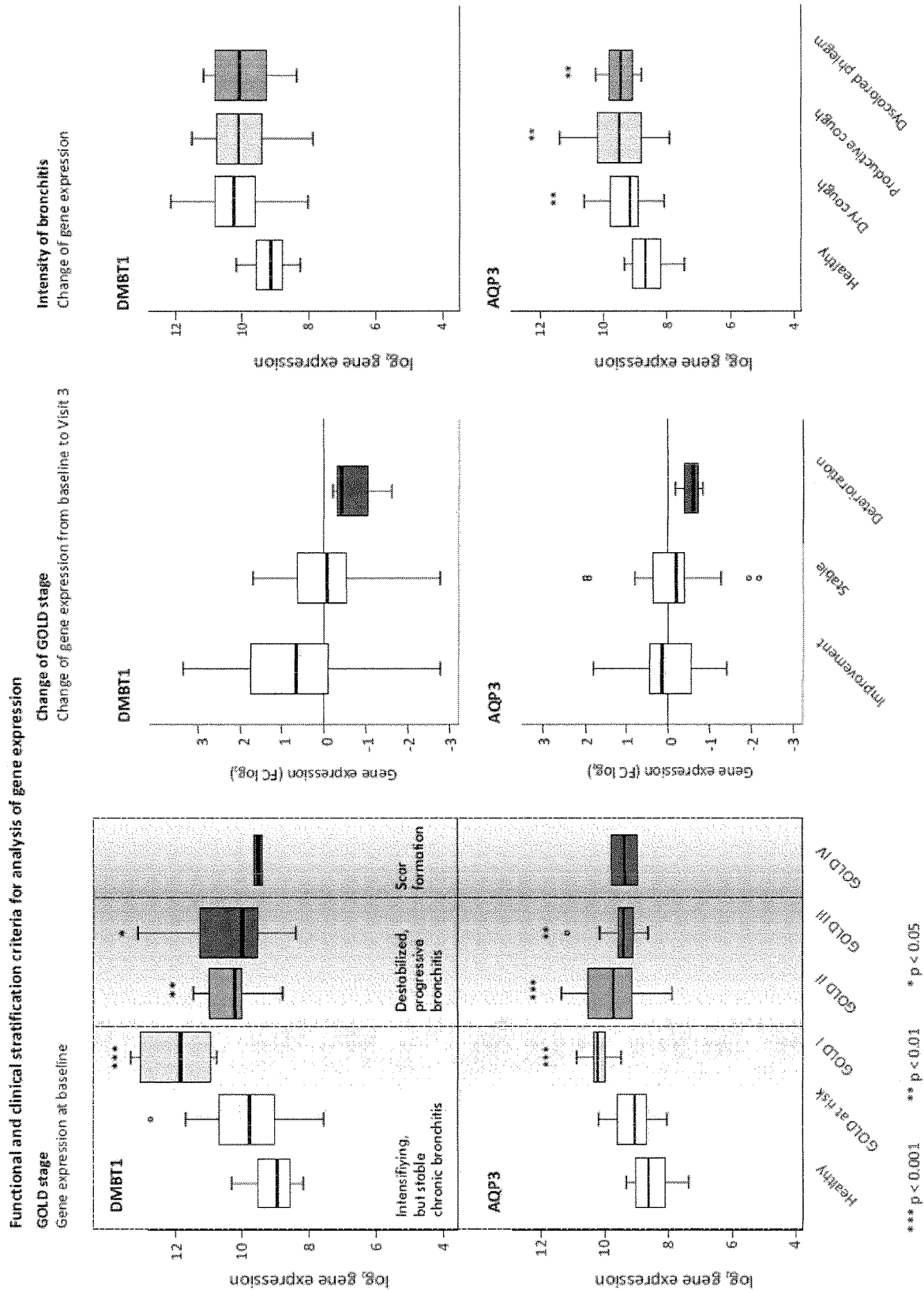
Figure 6:
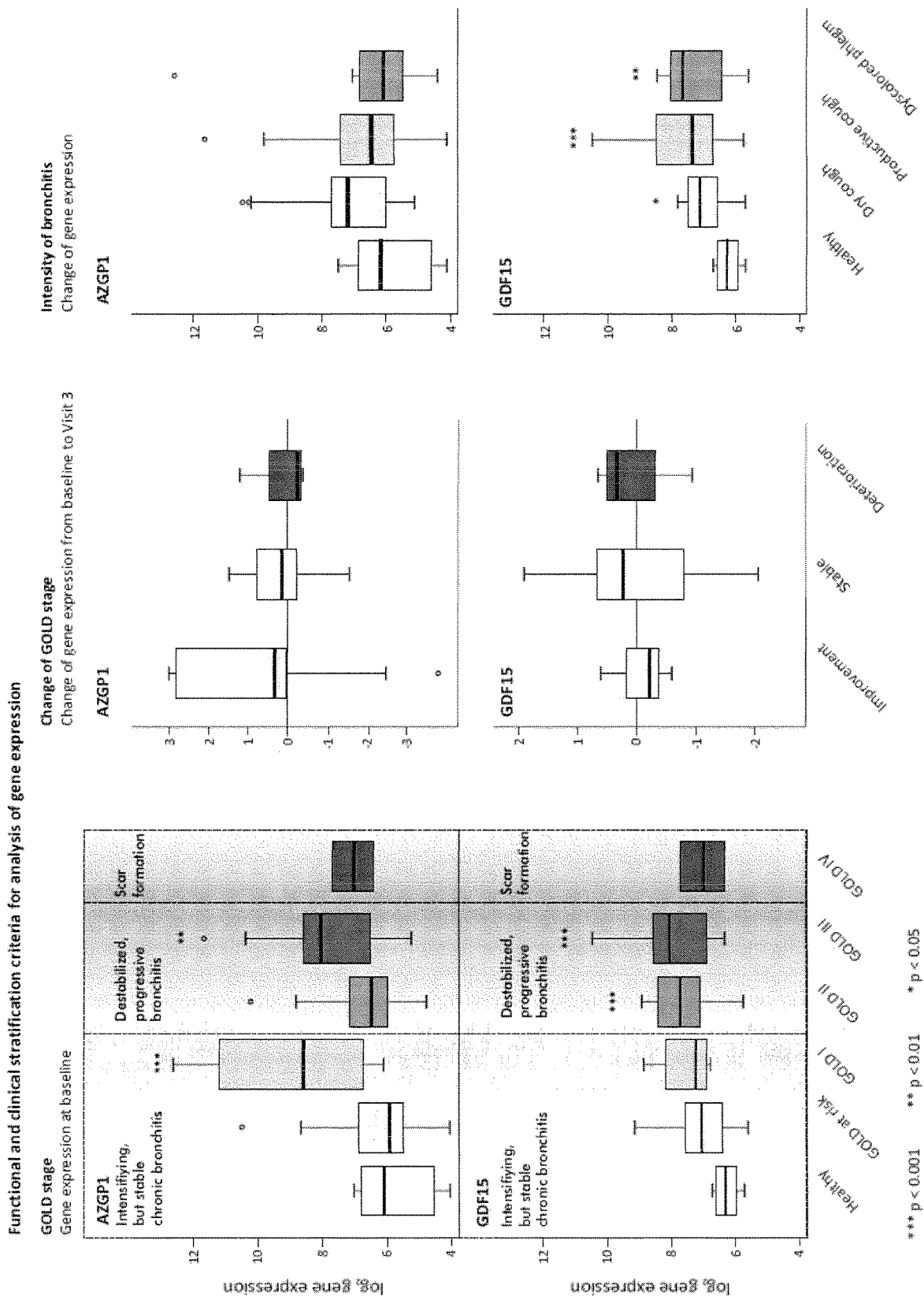
Figure 6:
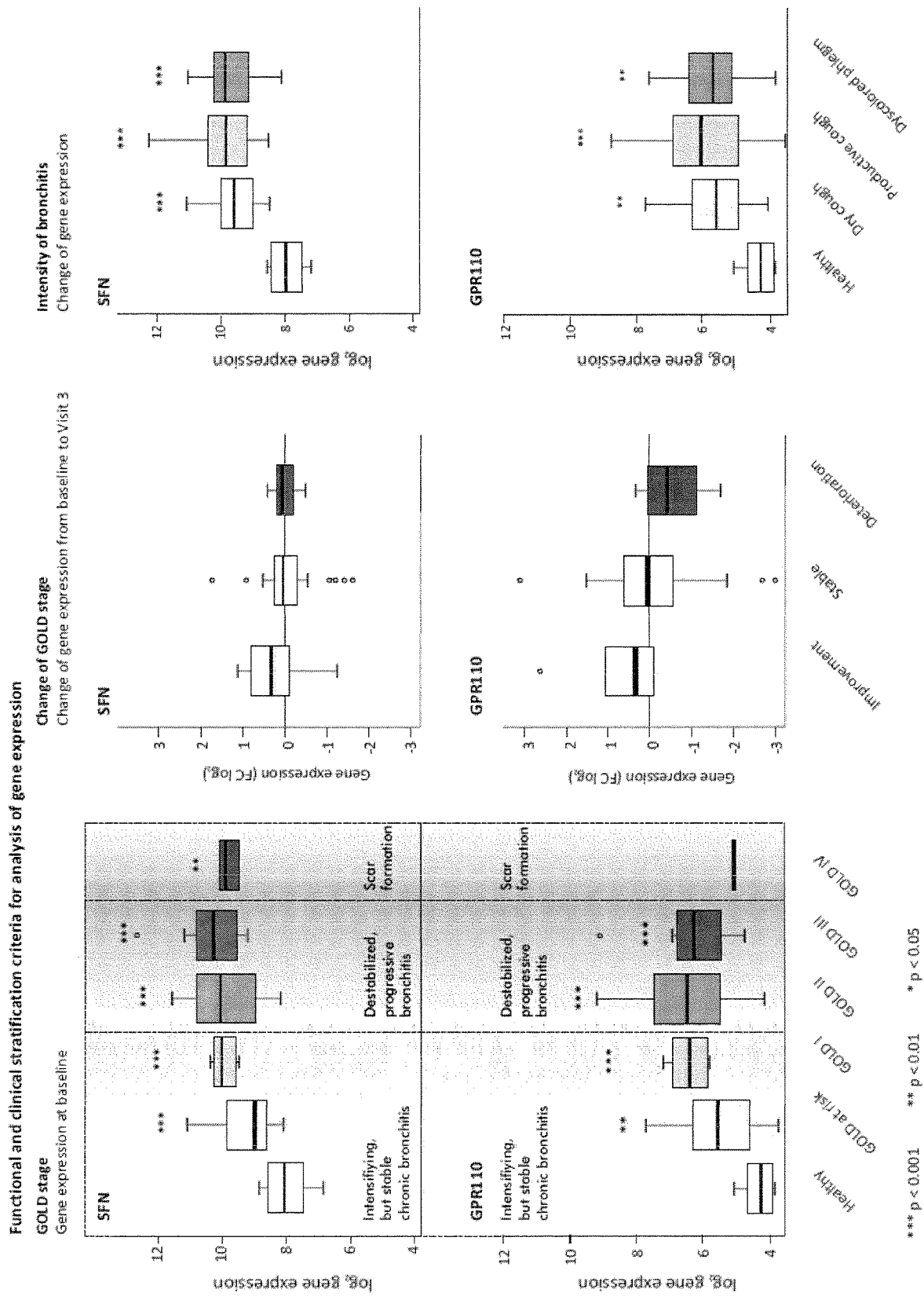
Figure 6:
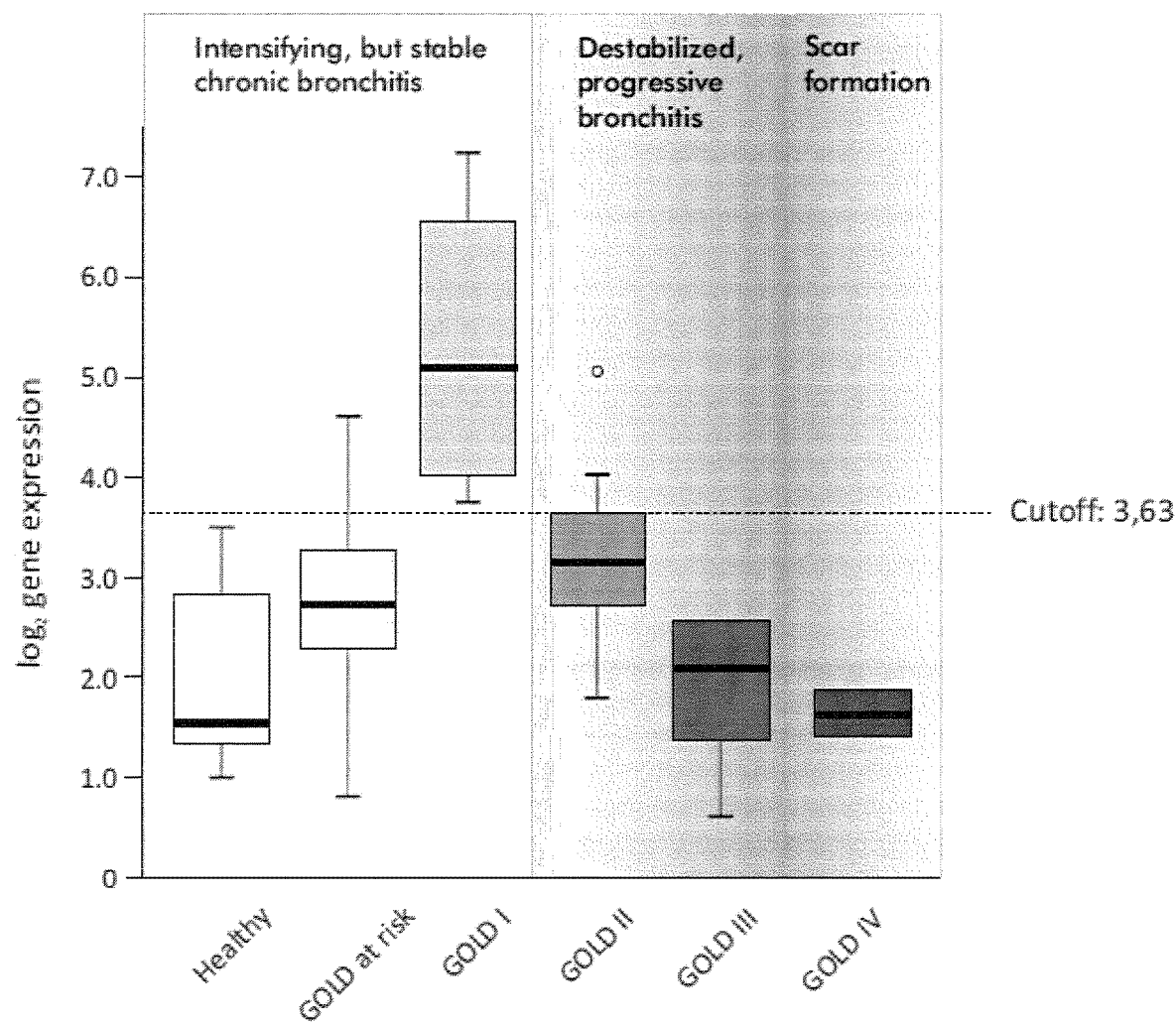

Fig. 6
A)
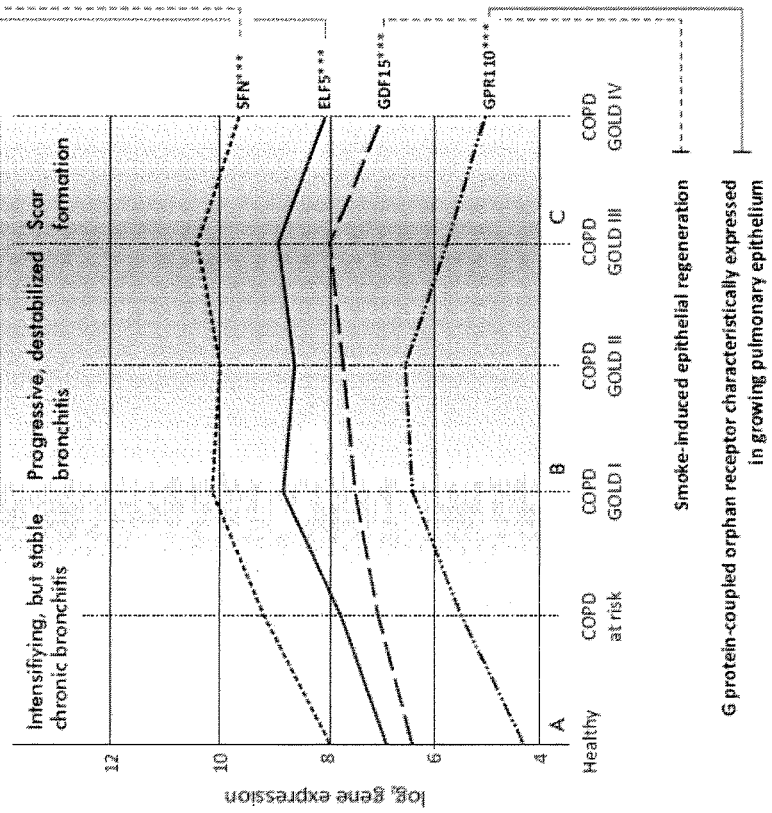
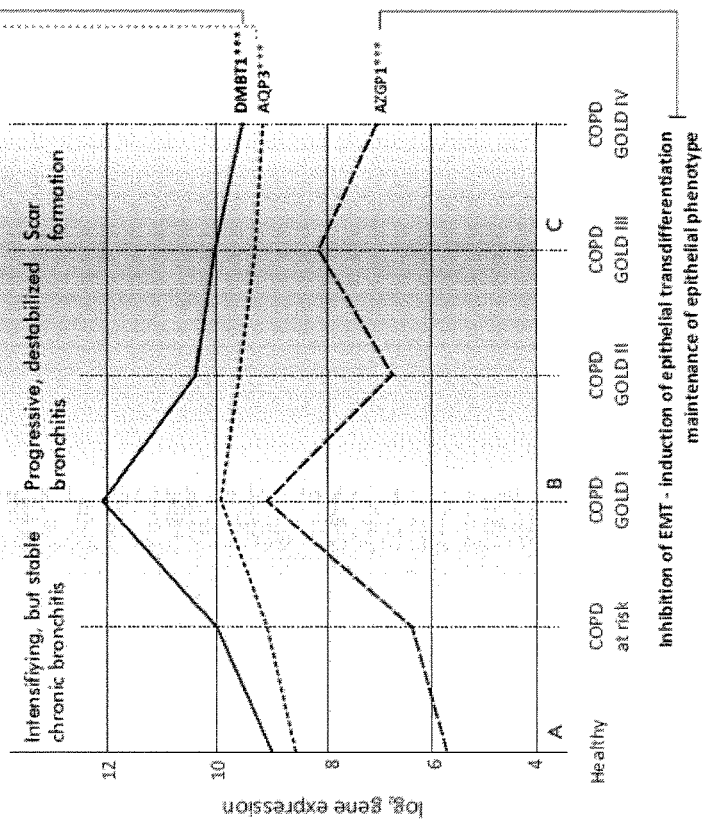

B)

C)

D)

E)

A)

B)

c)

D)

SEQUENCE LISTING

```
<160> NUMBER OF SEQ ID NOS: 59

<210> SEQ ID NO 1
<211> LENGTH: 2471
<212> TYPE: DNA
<213> ORGANISM: Homo sapiens

<400> SEQUENCE: 1
agaaagcgag cagccaccca gctcccgcc accgccatgg tccccgacac cgcctgcgtt      60
cttctgctca ccctggctgc cctcggcgcg tccggacagg gccagagccc gttgggctca     120
gacctgggcc cgcagatgct tcgggaactg caggaaacca acgcggcgct gcaggacgtg     180
cgggagctgc tgcggcagca ggtcaggggag atcacgttcc tgaaaaacac ggtgatggag    240
tgtgacgcgt gcgggatgca gcagtcagta cgcaccggcc tacccagcgt gcggcccctg    300
ctccactgcg cgcccggctt ctgcttcccc ggcgtggcct gcatccagac ggagagcggc    360
gcgcgctgcg gcccctgccc cgcgggcttc acgggcaacg gctcgcactg caccgacgtc    420
aacgagtgca cgcccaccc ctgcttcccc cgagtccgct gtatcaacac cagcccgggg    480
ttccgctgcg aggcttgccc gccggggtac agcggcccca cccaccaggg cgtggggctg    540
gctttcgcca aggccaacaa gcaggtttgc acggacatca acgagtgtga accgggcaa    600 cataactgcg tccccaactc cgtgtgcatc aacacccggg gctccttcca gtgcggcccg    660
tgccagcccg gcttcgtggg cgaccaggcg tccggctgcc agcggcgcgc acagcgcttc    720
tgccccgacg gctcgcccag cgagtgccac gagcatgcag actgcgtcct agagcgcgat    780
ggctcgcggt cgtgcgtgtg tgccgttggc tgggccggca acgggatcct ctgtggtcgc    840
gacactgacc tagacggctt cccggacgag aagctgcgct gcccggagcg ccagtgccgt    900
aaggacaact gcgtgactgt gcccaactca gggcaggagg atgtggaccg cgatggcatc    960
ggagacgcct gcgatccgga tgccgacggg gacggggtcc ccaatgaaaa ggacaactgc   1020
ccgctggtgc ggaacccaga ccagcgcaac acggacgagg acaagtgggg cgatgcgtgc   1080
gacaactgcc ggtcccagaa gaacgacgac caaaaggaca cagaccagga cggccgggc   1140
```

```
gatgcgtgcg acgacgacat cgacggcgac cggatccgca accaggccga caactgccct    1200
agggtaccca actcagacca gaaggacagt gatggcgatg gtatagggga tgcctgtgac    1260
aactgtcccc agaagagcaa cccggatcag gcggatgtgg accacgactt tgtgggagat    1320
gcttgtgaca gcgatcaaga ccaggatgga gacggacatc aggactctcg ggacaactgt    1380
cccacggtgc ctaacagtgc ccaggaggac tcagaccacg atggccaggg tgatgcctgc    1440
gacgacgacg acgacaatga cggagtccct gacagtcggg acaactgccg cctggtgcct    1500
aaccccggcc aggaggacgc ggacagggac ggcgtgggcg acgtgtgcca ggacgacttt    1560
gatgcagaca aggtggtaga caagatcgac gtgtgtccgg agaacgctga agtcacgctc    1620
accgacttca gggccttcca gacagtcgtg ctggacccgg agggtgacgc gcagattgac    1680
cccaactggg tggtgctcaa ccagggaagg gagatcgtgc agacaatgaa cagcgaccca    1740
ggcctggctg tgggttacac tgccttcaat ggcgtggact tcgagggcac gttccatgtg    1800
aacacggtca cggatgacga ctatgcgggc ttcatctttg gctaccagga cagctccagc    1860
ttctacgtgg tcatgtggaa gcagatggag caaacgtatt ggcaggcgaa ccccttccgt    1920
gctgtggccg agcctggcat ccaactcaag gctgtgaagt cttccacagg ccccggggaa    1980
cagctgcgga acgctctgtg gcatacagga gacacagagt cccaggtgcg gctgctgtgg    2040
aaggacccgc gaaacgtggg ttggaaggac aagaagtcct atcgttggtt cctgcagcac    2100 cggcccaag tgggctacat cagggtgcga ttctatgagg gccctgagct ggtggccgac    2160
agcaacgtgg tcttggacac aaccatgcgg ggtggccgcc tggggtctt ctgcttctcc    2220 caggagaaca tcatctgggc caacctgcgt taccgctgca atgacaccat cccagaggac    2280
tatgagaccc atcagctgcg gcaagcctag ggaccagggt gaggaccgc cggatgacag    2340 ccaccctcac cgcggctgga tgggggctct gcacccagcc caaggggtg gccgtcctga    2400 gggggaagtg agaagggctc agagaggaca aaataaagtg tgtgtgcagg gaaaaaaaaa    2460 aaaaaaaaa a                                                          2471

<210> SEQ ID NO 2
<211> LENGTH: 5160
<212> TYPE: DNA
<213> ORGANISM: Homo sapiens

<400> SEQUENCE: 2
aaaacccgga ggagcgggat ggcgcgcttt gactctggag tgggagtggg agcgagcgct      60
tctgcgactc cagttgtgag agccgcaagg gcatgggaat tgacgccact caccgacccc     120
cagtctcaat ctcaacgctg tgaggaaacc tcgactttgc caggtcccca agggcagcgg     180
ggctcggcga gcgaggcacc cttctccgtc cccatcccaa tccaagcgct cctggcactg     240
acgacgccaa gagactcgag tgggagttaa agcttccagt gagggcagca ggtgtccagg     300
ccgggcctgc gggttcctgt tgacgtcttg ccctaggcaa aggtcccagt tccttctcgg     360
agccggctgt cccgcgccac tggaaaccgc acctccccgc agcatgggca ccagcctcag     420
cccgaacgac ccttggccgc taaacccgct gtccatccag cagaccacgc tcctgctact     480
cctgtcggtg ctggccactg tgcatgtggg ccagcggctg ctgaggcaac ggaggcggca     540
gctccggtcc gcgccccgg gcccgtttgc gtggccactg atcggaaacg gcggcggcgt     600
gggccaggcg gctcacctct cgttcgctcg cctggcgcgg cgctacgcg acgtttttcca     660 gatccgcctg ggcagctgcc ccatagtggt gctgaatggc gagcgcgcca tccaccaggc     720
```

```
cctggtgcag cagggctcgg ccttcgccga ccggccggcc ttcgcctcct tccgtgtggt    780
gtccggcggc cgcagcatgg cttcggcca ctactcggag cactggaagg tgcagcggcg     840
cgcagcccac agcatgatgc gcaacttctt cacgcgccag ccgcgcagcc gccaagtcct    900
cgagggccac gtgctgagcg aggcgcgcga gctggtggcg ctgctggtgc gcggcagcgc    960
ggacggcgcc ttcctcgacc cgaggccgct gaccgtcgtg gccgtggcca acgtcatgag   1020
tgccgtgtgt ttcggctgcc gctacagcca cgacgacccc gagttccgtg agctgctcag   1080
ccacaacgaa gagttcgggc gcacggtggg cgcgggcagc ctggtggacg tgatgccctg   1140
gctgcagtac ttccccaacc cggtgcgcac cgttttccgc gaattcgagc agctcaaccg   1200
caacttcagc aacttcatcc tggacaagtt cttgaggcac tgcgaaagcc ttcggcccgg   1260
ggccgccccc cgcgacatga tggacgcctt tatcctctct gcggaaaaga aggcggccgg   1320
ggactcgcac ggtggtggcg cgcggctgga tttggagaac gtaccggcca ctatcactga   1380
catcttcggc gccagccagg acaccctgtc caccgcgctg cagtggctgc tcctcctctt   1440
caccaggtat cctgatgtgc agactcgagt gcaggcagaa ttggatcagg tcgtggggag   1500
ggaccgtctg ccttgtatgg gtgaccagcc caacctgccc tatgtcctgg ccttccttta   1560
tgaagccatg cgcttctcca gctttgtgcc tgtcactatt cctcatgcca ccactgccaa   1620
cacctctgtc ttgggctacc acattcccaa ggacactgtg gttttgtca accagtggtc    1680
tgtgaatcat gacccactga gtggcctaa cccggagaac tttgatccag ctcgattctt    1740
ggacaaggat ggcctcatca caaggaccct gaccagcaga gtgatgattt tttcagtggg   1800
caaaaggcgg tgcattggcg aagaactttc taagatgcag ctttttctct tcatctccat   1860
cctggctcac cagtgcgatt tcagggccaa cccaaatgag cctgcgaaaa tgaatttcag   1920
ttatggtcta accattaaac ccaagtcatt taaagtcaat gtcactctca gagagtccat   1980
ggagctcctt gatagtgctg tccaaaattt acaagccaag gaaacttgcc aataagaagc   2040
aagaggcaag ctgaaatttt agaaatattc acatcttcgg agatgaggag taaaattcag   2100
tttttttcca gttcctcttt tgtgctgctt ctcaattagc gtttaaggtg agcataaatc   2160
aactgtccat caggtgaggt gtgctccata cccagcggtt cttcatgagt agtgggctat   2220
gcaggagctt ctgggagatt ttttgagtc aaagacttaa agggcccaat gaattattat    2280
atacatactg catcttggtt atttctgaag gtagcattct ttggagttaa aatgcacata   2340
tagacacata cacccaaaca cttacaccaa actactgaat gaagcagtat tttggtaacc   2400
aggccatttt tggtgggaat ccaagattgg tctcccatat gcagaaatag acaaaagta    2460
tattaaacaa agtttcagag tatattgttg aagagacaga gacaagtaat ttcagtgtaa   2520
agtgtgtgat tgaaggtgat aagggaaaag ataaagacca gaaattccct tttcaccttt   2580
tcaggaaaat aacttagact ctagtattta tgggtggatt tatccttttg ccttctggta   2640
tacttcctta ctttaagga taaatcataa agtcagttgc tcaaaagaa atcaatagtt     2700
gaattagtga gtatagtggg gttccatgag ttatcatgaa tttaaagta tgcattatta    2760
aattgtaaaa ctccaaggtg atgttgtacc tcttttgctt gccaaagtac agaatttgaa   2820
ttatcagcaa agaaaaaaaa aaagccagc caagctttaa attatgtgac cataatgtac    2880
tgatttcagt aagtctcata ggttaaaaaa aaaagtcacc aaatagtgtg aaatatatta   2940
cttaactgtc cgtaagcagt atattagtat tatcttgttc aggaaaaggt tgaataatat   3000
atgccttgta taatattgaa aattgaaaag tacaactaac gcaaccaagt gtgctaaaaa   3060
tgagcttgat taaatcaacc acctattttt gacatggaaa tgaagcaggg tttcttttct   3120
```

```
tcactcaaat tttggcgaat ctcaaaatta gatcctaaga tgtgttctta tttttataac   3180
atctttattg aaattctatt tataatacag aatcttgttt tgaaaataac ctaattaata   3240
tattaaaatt ccaaattcat ggcatgctta aattttaact aaattttaaa gccattctga   3300
ttattgagtt ccagttgaag ttagtggaaa tctgaacatt ctcctgtgga aggcagagaa   3360
atctaagctg tgtctgccca atgaataatg gaaaatgcca tgaattacct ggatgttctt   3420
tttacgaggt gacaagagtt ggggacagaa ctcccattac aactgaccaa gtttctcttc   3480
tagatgattt tttgaaagtt aacattaatg cctgcttttt ggaaagtcag aatcagaaga   3540
tagtcttgga agctgtttgg aaaagacagt ggagatgagg tcagttgtgt tttttaagat   3600
ggcaattact ttggtagctg ggaaagcata aagctcaaat gaaatgtatg cattcacatt   3660
tagaaaagtg aattgaagtt tcaagtttta aagttcattg caattaaact tccaaagaaa   3720
gttctacagt gtcctaagtg ctaagtgctt attacatttt attaagcttt ttggaatctt   3780
tgtaccaaaa ttttaaaaaa gggagttttt gatagttgtg tgtatgtgtg tgtggggtgg   3840
ggggatggta agagaaaaga gagaaacact gaaaagaagg aaagatggtt aaacattttc   3900
ccactcattc tgaattaatt aatttggagc acaaaattca aagcatggac atttagaaga   3960
aagatgtttg gcgtagcaga gttaaatctc aaataggcta ttaaaaaagt ctacaacata   4020
gcagatctgt tttgtggttt ggaatattaa aaaacttcat gtaattttat tttaaaattt   4080
catagctgta cttcttgaat ataaaaaatc atgccagtat ttttaaaggc attagagtca   4140
actacacaaa gcaggcttgc ccagtacatt taaatttttt ggcacttgcc attccaaaat   4200
attatgcccc accaaggctg agacagtgaa tttgggctgc tgtagcctat ttttttagat   4260
tgagaaatgt gtagctgcaa aaataatcat gaaccaatct ggatgcctca ttatgtcaac   4320
caggtccaga tgtgctataa tctgttttta cgtatgtagg cccagtcgtc atcagatgct   4380
tgcggcaaaa ggaaagctgt gtttatatgg aagaaagtaa ggtgcttgga gtttacctgg   4440
cttatttaat atgcttataa cctagttaaa gaaaggaaaa gaaaacaaaa aacgaatgaa   4500 ataactgaa tttggaggct ggagtaatca gattactgct ttaatcagaa accctcattg   4560
tgtttctacc ggagagagaa tgtatttgct gacaaccatt aaagtcagaa gttttactcc   4620
aggttattgc aataaagtat aatgtttatt aaatgcttca tttgtatgtc aaagctttga   4680
ctctataagc aaattgcttt tttccaaaac aaaaagatgt ctcaggtttg ttttgtgaat   4740
tttctaaaag ctttcatgtc ccagaactta gcctttacct gtgaagtgtt actacagcct   4800
taatattttc ctagtagatc tatattagat caaatagttg catagcagta tatgttaatt   4860
tgtgtgtttt tagctgtgac acaactgtgt gattaaaagg tatactttag tagacattta   4920
taactcaagg ataccttctt atttaatctt ttcttatttt tgtactttat catgaatgct   4980
tttagtgtgt gcataatagc tacagtgcat agttgtagac aaagtacatt ctggggaaac   5040
aacatttata tgtagccttt actgtttgat ataccaaatt aaaaaaaaat tgtatctcat   5100
tacttatact gggacaccat taccaaaata ataaaaatca ctttcataat cttgaaaaaa   5160
```

<210> SEQ ID NO 3
<211> LENGTH: 2608
<212> TYPE: DNA
<213> ORGANISM: Homo sapiens

<400> SEQUENCE: 3

```
ctcaccctga aggtgacagt tccttggaac cttccctgat ccttgtgatc ccaggctcca     60
```

```
agagtccacc cttcccagct cagctcagta cctcagccac ctccaagatc cctacactga    120
tcatgctttt cccaatctcc atgtcggcca cggagtttct tctggcctct gtcatcttct    180
gtctggtatt ctgggtaatc agggcctcaa gacctcaggt ccccaaaggc ctgaagaatc    240
caccagggcc atgggctgg cctctgattg gcacatgct gaccctggga agaacccgc       300 acctggcact gtcaaggatg agccagcagt atgggacgt gctgcagatc cgaattggct     360
ccacacccgt ggtggtgctg agcggcctgg acaccatccg gcaggccctg gtgcggcagg    420
gcgatgattt caagggccgg cccgacctct acaccttcac cctcatcagt aatggtcaga    480
gcatgtcctt cagcccagac tctgaccag tgtgggctgc ccgccggcgc ctggcccaga     540
atggcctgaa aagtttctcc attgcctctg acccagcctc ctcaacctcc tgctacctgg    600
aagagcatgt gagcaaggag gctgaggtcc tgataagcac gttgcaggag ctgatggcag    660
ggcctgggca ctttaacccc tacaggtatg tggtggtatc agtgaccaat gtcatctgtg    720
ccatttgctt tggccggcgc tatgaccaca accaccaaga actgcttagc ctagtcaacc    780
tgaataataa tttcggggag gtggttggct ctggaaaccc agctgacttc atccctattc    840
ttcgctacct acccaaccct tccctgaatg ccttcaagga cctgaatgag aagttctaca    900
gcttcatgca gaagatggtc aaggagcact acaaaacctt tgagaagggc cacatccggg    960
acatcacaga cagcctgatt gagcactgtc aggagaagca gctggatgag aacgccaatg   1020
tccagctgtc agatgagaag atcattaaca tcgtcttgga cctctttgga gctgggtttg   1080
acacagtcac aactgctatc tcctggagcc tcatgtattt ggtgatgaac cccagggtac   1140
agagaaagat ccaagaggag ctagacacag tgattggcag gtcacggcgg ccccggctct   1200
ctgacagatc ccatctgccc tatatggagg ccttcatcct ggagaccttc cgacactctt   1260
ccttcgtccc cttcaccatc ccccacagca acaagagaga caagtttga aaaggctttt    1320 acatccccaa ggggcgttgt gtctttgtaa accagtggca gatcaaccat gaccagaagc   1380
tatgggtcaa cccatctgag ttcctacctg aacggtttct caccccctgat ggtgctatcg   1440 acaaggtgtt aagtgagaag gtgattatct ttggcatggg caagcggaag tgtatcggtg   1500
agaccattgc ccgctgggag gtcttttctct tcctggctat cctgctgcaa cgggtggaat   1560
tcagcgtgcc actgggcgtg aaggtggaca tgaccccccat ctatgggcta accatgaagc   1620
atgcctgctg tgagcacttc caaatgcagc tgcgctctta ggtgcttgag agccctgagg    1680
cctagactct gtctacctgg tctggttggg cagccagacc agcaggctgg cctatgtggt    1740
ctaaggttca gcctgaaact catagacact gatctggctg cagttttgct atctgggctg    1800
tgggcaagcc taagggatcc tgcctgcccc taccctggac ttgcctctgc acaccctcca    1860
gagacaacag gtaaaacagg gccacataga tgctgatgga gccttcccaa gttgtgcttg    1920
agccaggagg cctgctaggg ttaggaggtc cttaggcctc tgagaagctc tgaagaactc    1980
tctggaagcc cctgggccca gtacctagct ggctctgtga gggtgctgac tggcttcagc    2040
aagttagaac tagccaaacc aggaccctgt ccaatctttg acaattggga gctgccaaga    2100
gtgaagggaa gagacagccc aggatactgg cacagaggta gtctcactgc ttgaactagg    2160
ctgagcaatc tgaccctatg ggtctaggac acagttcctg gaacatcac attcctctgc     2220 ccttcctgca ggcaggaaca aacagggctg ccttctggcc ttgtaagacc cttattgctg    2280
tcctggaggg gctggggact tgtgtctgcg gggatcagag cgcacaggga gtgcacatat   2340
ccaggcacca ggactagggc tggagtgagg gggggtatt tcaattacct tctattggtc    2400
tcccttctct acactcttgt aataaaatgt ctattttaa tgtttgtaca caacaatcct     2460
```

```
tctattctag cctgcattga gcttgcatgc ttgcataaga gcttaagaac cattgattta    2520
atgtaatagg gaaaattcta acccaggtat ccaaaaatgt gtaagaacaa ctacctgagc    2580
taaataaaga tattgttcag aaatccta                                      2608
```

<210> SEQ ID NO 4
<211> LENGTH: 1665
<212> TYPE: DNA
<213> ORGANISM: Homo sapiens

<400> SEQUENCE: 4

```
cttctggtaa ggaggccccg tgatcagctc cagccatttg cagtcctggc tatcccagga     60
gcttacataa agggacaatt ggagcctgag aggtgacagt gctgacacta caaggctcgg    120
agctccgggc actcagacat catgagttgg tccttgcacc cccggaattt aattctctac    180
ttctatgctc tttatttct ctcttcaaca tgtgtagcat atgttgctac cagagacaac    240
tgctgcatct tagatgaaag attcggtagt tattgtccaa ctacctgtgg cattgcagat    300
ttcctgtcta cttatcaaac caaagtagac aaggatctac agtctttgga agacatctta    360
catcaagttg aaaacaaaac atcagaagtc aaacagctga taaaagcaat ccaactcact    420
tataatcctg atgaatcatc aaaaccaaat atgatagacg ctgctacttt gaagtccagg    480
aaaatgttag aagaaattat gaaatatgaa gcatcgattt taacacatga ctcaagtatt    540
cgatatttgc aggaaatata taattcaaat aatcaaaaga ttgttaacct gaaagagaag    600
gtagcccagc ttgaagcaca gtgccaggaa ccttgcaaag acacggtgca aatccatgat    660
atcactggga aagattgtca agacattgcc aataagggag ctaaacagag cgggctttac    720
tttattaaac ctctgaaagc taaccagcaa ttcttagtct actgtgaaat cgatgggtct    780
ggaaatggat ggactgtgtt tcagaagaga cttgatggca gtgtagattt caagaaaaac    840
tggattcaat ataagaagg atttggacat ctgtctccta ctggcacaac agaattttgg    900
ctgggaaatg agaagattca tttgataagc acacagtctg ccatcccata tgcattaaga    960
gtggaactgg aagactggaa tgcagaacc agtactgcag actatgccat gttcaaggtg   1020
ggacctgaag ctgacaagta ccgcctaaca tatgcctact tcgctggtgg ggatgctgga   1080
gatgcctttg atggctttga ttttggcgat gatcctagtg acaagttttt cacatcccat   1140
aatggcatgc agttcagtac ctgggacaat gacaatgata gtttgaagg caactgtgct   1200 gaacaggatg gatctggttg gtggatgaac aagtgtcacg ctggccatct caatggagtt   1260
tattaccaag gtggcactta ctcaaaagca tctactccta atggttatga taatggcatt   1320
atttgggcca cttggaaaac ccggtggtat tccatgaaga aaccactat gaagataatc   1380 ccattcaaca gactcacaat tggagaagga cagcaacacc acctgggggg agccaaacag   1440
gctggagacg tttaaaagac cgtttcaaaa gagatttact tttttaaagg actttatctg   1500
aacagagaga tataatattt ttcctattgg acaatggact tgcaaagctt cacttcattt   1560
taagagcaaa agaccccatg ttgaaaactc cataacagtt ttatgctgat gataattat   1620 ctacatgcat ttcaataaac ctttttgtttc ctaagactag aaaaa                 1665
```

<210> SEQ ID NO 5
<211> LENGTH: 840
<212> TYPE: DNA
<213> ORGANISM: Homo sapiens

<400> SEQUENCE: 5

| | |
|---|---:|
| agacccagag ccaatgcgtg gattagtccc tcctcctagt tgcagtctgg tagttgtcgc | 60 |
| tggccgtgtg acggctcgct gttgccctga aggcaggcga gccagctgcc caggaaaggt | 120 |
| ggaaagtggt agaagctgac ccctgagccc tggcaggtct ttaagtgcgt tgtgcagcc | 180 |
| gatttcaagg ctaagagaga aagactgcct ctgatccctg aaggaagaaa aaaaaaaaa | 240 |
| aaacaggaaa aaaactcaac atggaaaatg tccccaagga aacaaagtt gtggagaagg | 300 |
| ccccagtgca gaatgaagcc cccgctttag gaggtggtga ataccaggag cctgaggaa | 360 |
| atgttaaagg ggtttgggct ccacctgccc cgggttttgg agaggatgtg cccaataggc | 420 |
| ttgtcgataa cattgatatg atagatggag atggagatga tatggaacgg ttcatggagg | 480 |
| agatgagaga gctaaggagg aaaattaggg aacttcagtt gaggtacagt ctgcgcattc | 540 |
| ttataggggga ccctcctcac catgatcatc atgatgagtt ttgccttatg ccttgaatct | 600 |
| tgaggttaat aatcataaaa tccctgcttt ctaaattcgc attttttcctg gtgtacctt | 660 |
| aatgtgaacc ttttggcatt cttctgcaat tttctgattg gagattgcat tttgacctag | 720 |
| tctgtaagtt tttctgtcag aagaggactt tcatcaactt tcatggaaag atgtttattg | 780 |
| catactgtaa agttaataaa gcaatttaaa agcagtctaa aaaaaaaaaa aaaaaaaaa | 840 |

<210> SEQ ID NO 6
<211> LENGTH: 8340
<212> TYPE: DNA
<213> ORGANISM: Homo sapiens

<400> SEQUENCE: 6

| | |
|---|---:|
| actaattttc tggagtttct gcccctgctc tgcgtcagcc ctcacgtcac ttcgccagca | 60 |
| gtagcagagg cggcggcggc ggctcccgga attgggttgg agcaggagcc tcgctggctg | 120 |
| cttcgctcgc gctctacgcg ctcagtcccc ggcggtagca ggagcctgga cccaggcgcc | 180 |
| gccggcgggc gtgaggcgcc ggagcccggc ctcgaggtgc ataccggacc cccattcgca | 240 |
| tctaacaagg aatctgcgcc ccagagagtc ccggagcgc cgccggtcgg tgcccggcgc | 300 |
| gccgggccat gcagcgacgg ccgccgcgga gctccgagca gcggtagcgc ccccctgtaa | 360 |
| agcggttcgc tatgccgggg ccactgtgaa ccctgccgcc tgccggaaca ctcttcgctc | 420 |
| cggaccagct cagcctctga taagctggac tcggcacgcc cgcaacaagc accgaggagt | 480 |
| taagagagcc gcaagcgcag ggaaggcctc cccgcacggg tgggggaaag cggccggtgc | 540 |
| agcgcgggga caggcactcg ggctggcact ggctgctagg gatgtcgtcc tggataaggt | 600 |
| ggcatggacc cgccatggcg cggctctggg gcttctgctg gctggttgtg ggcttctgga | 660 |
| gggccgcttt cgcctgtccc acgtcctgca aatgcagtgc ctctcggatc tggtgcagcg | 720 |
| acccttctcc tggcatcgtg gcatttccga gattggagcc taacagtgta gatcctgaga | 780 |
| acatcaccga atttttcatc gcaaaccaga aaggttaga aatcatcaac gaagatgatg | 840 |
| ttgaagctta tgtgggactg agaaatctga caattgtgga ttctggatta aaatttgtgg | 900 |
| ctcataaagc atttctgaaa aacagcaacc tgcagcacat caattttacc cgaaacaaac | 960 |
| tgacgagttt gtctaggaaa catttccgtc accttgactt gtctgaactg atcctggtgg | 1020 |
| gcaatccatt tacatgctcc tgtgacatta tgtggatcaa gactctccaa gaggctaaat | 1080 |
| ccagtccaga cactcaggat ttgtactgcc tgaatgaaag cagcaagaat attcccctgg | 1140 |
| caaacctgca gatacccaat tgtggttttgc catctgcaaa tctggccgca cctaacctca | 1200 |
| ctgtggagga aggaaagtct atcacattat cctgtagtgt ggcaggtgat ccggttccta | 1260 |
| atatgtattg ggatgttggt aacctggttt ccaaacatat gaatgaaaca agccacacac | 1320 |

-continued

```
agggctcctt aaggataact aacatttcat ccgatgacag tgggaagcag atctcttgtg      1380
tggcggaaaa tcttgtagga gaagatcaag attctgtcaa cctcactgtg cattttgcac      1440
caactatcac atttctcgaa tctccaacct cagaccacca ctggtgcatt ccattcactg      1500
tgaaaggcaa ccccaaacca gcgcttcagt ggttctataa cggggcaata ttgaatgagt      1560
ccaaatacat ctgtactaaa atacatgtta ccaatcacac ggagtaccac ggctgcctcc      1620
agctggataa tcccactcac atgaacaatg gggactacac tctaatagcc aagaatgagt      1680
atgggaagga tgagaaacag atttctgctc acttcatggg ctggcctgga attgacgatg      1740
gtgcaaaccc aaattatcct gatgtaattt atgaagatta tggaactgca gcgaatgaca      1800
tcggggacac cacgaacaga agtaatgaaa tcccttccac agacgtcact gataaaaccg      1860
gtcgggaaca tctctcggtc tatgctgtgg tggtgattgc gtctgtggtg ggattttgcc      1920
ttttggtaat gctgtttctg cttaagttgg caagacactc caagtttggc atgaaagatt      1980
tctcatggtt tggatttggg aaagtaaaat caagacaagg tgttggccca gcctccgtta      2040
tcagcaatga tgatgactct gccagcccac tccatcacat ctccaatggg agtaacactc      2100
catcttcttc ggaaggtggc ccagatgctg tcattattgg aatgaccaag atccctgtca      2160
ttgaaaatcc ccagtacttt ggcatcacca acagtcagct caagccagac acatggccca      2220
gaggttcccc caagaccgcc tgataataat ttggtatttg gaggctcctg tgtcactgca      2280
ggaactaaag gaggctaaat ccatgcctga tggaggagaa gagttctatg gttatctgca      2340
aattctggcc agacaacatc ttgacgtcac tccttagctt ccataaccta gccaagcaag      2400
aagttgcctt tccaagacaa agcagtgtgc tctaatgact aacccctcaa agtactatgc      2460
cactttaact atagacccat ctcctcgatc aatcaggatg gcaagatgga gctgaggagc      2520
tcagcaacat caagtctgga gttggtcttt aactcaacta gctcgtttag acgtgtctga      2580
acaccacatc acctgacagc acggggtggt ttcccagtaa aatttacaaa ctcagctcaa      2640
gggcagctgt gttgctttcc tttccttgac tgctgagaaa cttttttgaca gggaacaatg      2700 gaaacacacc ttctgagctg aaacaaacaa acagaaacaa aacatactaa ccagcaaaat      2760
ccccaaatca tcaatcttgg gttctcttga agggcaggag tgtgtttttat cttctcccgt      2820 cggagcaaac actatagatg tcctccctaa aattctgtct tccctagagc agccttgtaa      2880
attagctagg gtcctagggt tgaggcctaa atcaacttaa aattgtctct aaatatgtac      2940
ctggatgtgt ttgtacttgc agagcatgcc ctcttcatgt gcctagggct agtaactccc      3000
tgtggcagag gcatgtaaag tattctgact ttttttttt caacttaatt ccatttccaa      3060
tgaaatggat ttttaaaaat tttctccaga gtgtgccata cttctccagc tattatagtt      3120
aatgtgtgtg tatccttgtg tatatgtgtg tttgtgtgtg catatgtgtt ttcctagtgg      3180
ttacatgctt actaggcaat tatgtaaata agcacagatt cataggccag ctaggcctga      3240
ggaaagaaga cattataaag ggagggagta ttttaacatt agctaaagct atcacacaag      3300
gcacccattc tgctcccctc aacagccaca gcccacttcg tccttgtctt accaataagg      3360
ggaaaggctg gaggtgatat ttttcacaga accgcagagg ttttgaacat atttgcaaca      3420
ttactttgag tacacatgag caaaaattct gaattacatc caggacccca gaagctcatt      3480
agatcaaaga gtgcggggcc cctcagagtt accagagatt atctgcagac ttcagtgcaa      3540
tcgaatgacc atggtccatt ttgatggtca gaggtaggac tgaaaacgg gtagaaacaa      3600 ttgctttagc gcttccttct gtactttgcc tattaatgtt ttgtctttca aaatatatt       3660
```

```
ttctcctaat tgtttaattg gccaaataat ggctgctttg ggagttgttt gtatgccttg    3720
gaaggccatg gcctgcactt taaaaataag ctaagtccat tctgcccagc acgagcatta    3780
ggacagagaa tgcacttatt ttaggatcct taaaaattgc ttcttttatg gcacactggg    3840
ttgacgactc atctcgtggg agccttcatg gcacattgct gctgttctgc aggtcccaat    3900
acaattcctt cccctctca gtgccacggc cccccattg ctagctacaa caatttgata    3960
tcatattccc ttttcaactc caaggagat gataagaagc tatcaaataa tgctttaaaa    4020
aagcaacttg agtttcttaa aagaaaggaa atgaatacat gctgcataat tacatttaaa    4080
atgtaagcca tgttattata agccgcactg agatgaagat tgttagcaa accagtttca    4140 agcacactca cagtgaagta aaatcatgtt tttagcatct gaccattggg taatattatt    4200
ctttgttatc aaaagagaaa tatcacccaa gtatagtata cttagacctc ctagaggaaa    4260
cactccagtc ctaagcttgg tgtctgaaaa gaaaaacaaa aataaagatt atggatttag    4320
gtcagggaga cagagtgata ttctgaagac tgtgtttact ccctcatcat cggccaacca    4380
agatggagtt ctgcatcctg cacatatcag acatttcagt ccaatttcac caaagcatca    4440
gtgatgttct agaagcatcc cagcagatgg aggatcctaa tgtatttgtt ctgggtattt    4500
cccaaggccc agcctgactg gagtgtgtgt accaacagga tgaatccaat caagctacgc    4560
ccccattttg gtttcggatt ggccactctt gcatgtgcta gtagattgtg gaccaggacc    4620
agctgagcaa acacagttgc agagtagcct cctatgttgc taagaagctc ctgctaccca    4680
ggtgctttga acaattgagt gctccctctg gttaagtaga gatggcacca ccggagtttt    4740
tcttggatgt gaggctcaat cctttacggc agctattata acaaagtgaa ggttttctcc    4800
ctgggaaatg cagcttttct ctgtctttac taattctgcc agcctgtgag agtaaccacc    4860
gtagctgggc ttcttctcag attaattgtc atgccaggtc tccttcctgg ggagctgtga    4920
tgctgctctg aggttgattg ctgaggttgt agtgggtttt tgtttgtttt tgtttagttt    4980
ttcttgattg ttcttcttc tcttgaatgg caagagaaga aacactttct ctaacccacg    5040
gccaggaagg aaatggggag agagctactt cttagttcaa cctggttgcc acataaagga    5100
atctctctcc ttggactcag cccctaactg gaagcaagag ccactgccct ctgagactga    5160
gagagcagcc cgaggaggag atgaatccat tctgcccttt gtttgggttt gcttcctgtc    5220
agtgagagaa tgctgaggca gttcctgtta tgtgaaactt tcatttttaa aaccaggaca    5280
gtcctaaaca gactggaatg agttggtcaa tcccagttgg tataggccca atgattttg    5340 ctagtaagat aggattgtct tcctcaccca aaatgcctc aagtgcccta aaatgggtat    5400
tttaaaataa gaataaataa tgtagattta gtagaaaacc tggaaaacat aagaaacaaa    5460
gatgaaacga aaagtcccat gtaattccac cagttagagt taaccactga tatcgtttgg    5520
atatatggct ttctagtctt gtggatatcc ttttaatctc ttgtaatata aagtctgacc    5580
atatgtgtcc ttgcatttgt ttgtactgga ctctgttaat atttctatag taatggctca    5640
ctttggggag attgtgctgc acagtgtgta ggaagcacat tgggtgtatt attcccagtt    5700
ttgtattttg tatttccttg gagatgtgca ggggttaaga gcggggtct ggccatagct    5760 ggccacgtca gactctcata tggtaagtat cacagagcac atgaggcctg tgttatgcgc    5820
tggaaagact caggaaatga gaggctctct tgttctgaca aggcaggctg agagctctca    5880
tttagggtca tcactccaga taactccaaa tgcagtttat tgctcaactg aagcagatga    5940
tcactttttg cctccaagtt cttcacccta gctagctcct ttcaaagagc cgagtatgct    6000
ggatcttaaa gggccaaact agttacatct catacatttc ctgatgttta gggatgcctt    6060
```

```
cacttccatc aaggatacct tggctgtgca aggacctctg atagctggag tctccttttg    6120
gtcactccca gctttgctta aacttgatgg agtttgctgt ccagtgatcc ccggatcttt    6180
catcatgaaa gccttccttc ctctcctgat gtctcaggcc tctagaccta gactggggtt    6240
ctggcaagga ggcctctatc aatagtatga catccaataa tatgttagtg ttgatatttt    6300
gcacagtaat attaagttta agagattata aaatgagtt caaatgaata agttcctgtg    6360
atgtaagaga ttagatatgt gtgatttcag aaccaaaggc agggggaat cccagaaaga    6420 aaacaataat ataatcctag tttctatata ttattttat tcattactgt atatgggtag    6480
agatcaatat tctttcttat gctgttacta ttaattaaca catttttaa ccatgccatt    6540 gaacttttgg gtgcattaaa gtggaaccca agctcctcat tagataataa tggcatttgg    6600
actgagtgcc atattcctaa atttccaata aagtggttga tatagagagg acaggataaa    6660
gccctatagt gtgcagttat atcaaaacag ctagtctcca ctttagggaa tgcctttact    6720
agagattaca tgaaatgtct gcttataaaa taagcagaga tggcaccact aagcagccac    6780
ctgaattgtt ttcctacagg aatgattact tttcagatcc atttatgttt tcatgctcaa    6840
tacttactcc ccttccctgc aacacccaaa gagtttactt ttgcaagtca tttggtcttc    6900
agtctactac tgaggaatag agaggcacta actgctttac ccaggatcag aactcatgtt    6960
cttaccttct attaatagag tacttgagcc agatggacta actggtctca cattttctct    7020
atcttggttt tacttccata aacatcaata tctttaccca catgattttt ccatcctccc    7080
atttttttcc atatgtatta gggttcagga actatgatgc taatgatcac atttcttcct    7140
agttcctaat ttcattagtg ccatttcctg atatctacag aaacaattat caatacatgt    7200
agctgcttga gccttattta gaaggctagc ctttcttttc caagtgctgt cagaatgtat    7260
acatttagtc tgtcttttc ccttttagga gtctttgttc tgggttgatg gcaaaattcc    7320 tcttttaca tgtgagattt ttgatttcac tgaattctac ctagattttt atggacattg    7380
gattttaaag aggaaaacac tcattttctt agtaagatat tggtgataca tagctatgcc    7440
attgatttcc atactcctga gctttgggga gggagacagt ggccaagtag caggcagaat    7500
aagatcatca ctcatgtcct gaatcaatca cactttcctt ctcggattgt gtatatgctc    7560
tgccacttcc tacatattac atcctgagtt tttaagtaaa gtggatctta gccagatttg    7620
agtctaatgg ctgattcatc ggcatagttc ttggcgttaa catctcagtg tcctcttttag   7680 ttctctttga ggattcatgt cattgagggc ctttgtgcct ccacttgtct cagtatgagg    7740
aagaactttg gtgtgagggc ggagctatgt gaagggttgc tgggttgggg gattagttca    7800
tatggtcccc atgccatcta tttacttttg gagagagggg actttgagtg ggtgggtatg    7860
gatagatgtt cctcaaggaa accctgctgg ctaatgggca ctacatctgt gtattactgt    7920
gattctctct gtaagctccc catgtggcca aggaccccc tcctaccagg gcacttcctg    7980
ccacctcatt gcactggtct caaccattca gcctgctgct gctgcaccat gttgggctgc    8040
ggtaggatag ggaaggggtt ctgttgattg ctaaatgttg cctaactta tttccctctc    8100 ccacatttca tgcaagggag cggacctaac acatgacttg cattctcttc ctatgttcag    8160
aaactccagg gcttgcccac gtgtatgtat gagtgaccaa tggagcttgg aattctttat    8220
ctatatgatc tgtccgaaaa tgagatcttt tgtactggaa tttgtgatgt agttgatcat    8280
tcagagccaa acgcatatac caataaagac aagactgtca tataaaaaaa aaaaaaaaa    8340
```

<210> SEQ ID NO 7

<211> LENGTH: 8292
<212> TYPE: DNA
<213> ORGANISM: Homo sapiens

<400> SEQUENCE: 7

```
actaattttc tggagtttct gccctgctc tgcgtcagcc ctcacgtcac ttcgccagca    60
gtagcagagg cggcggcggc ggctcccgga attgggttgg agcaggagcc tcgctggctg   120
cttcgctcgc gctctacgcg ctcagtcccc ggcggtagca ggagcctgga cccaggcgcc   180
gccggcgggc gtgaggcgcc ggagcccggc ctcgaggtgc ataccggacc cccattcgca   240
tctaacaagg aatctgcgcc ccagagagtc ccgggagcgc cgccggtcgg tgcccggcgc   300
gccgggccat gcagcgacgg ccgccgcgga gctccgagca gcggtagcgc cccctgtaa   360
agcggttcgc tatgccgggg ccactgtgaa ccctgccgcc tgccggaaca ctcttcgctc   420
cggaccagct cagcctctga taagctggac tcggcacgcc cgcaacaagc accgaggagt   480
taagagagcc gcaagcgcag ggaaggcctc cccgcacggg tggggaaag cggccggtgc    540
agcgcgggga caggcactcg ggctggcact ggctgctagg gatgtcgtcc tggataaggt   600
ggcatggacc cgccatggcg cggctctggg gcttctgctg ctggttgtg ggcttctgga    660
gggccgcttt cgcctgtccc acgtcctgca aatgcagtgc ctctcggatc tggtgcagcg   720
acccttctcc tggcatcgtg gcatttccga gattggagcc taacagtgta gatcctgaga   780
acatcaccga aattttcatc gcaaaccaga aaaggttaga aatcatcaac gaagatgatg   840
ttgaagctta tgtgggactg agaaatctga caattgtgga ttctggatta aaatttgtgg   900
ctcataaagc atttctgaaa aacagcaacc tgcagcacat caattttacc cgaaacaaac   960
tgacgagttt gtctaggaaa catttccgtc accttgactt gtctgaactg atcctggtgg  1020
gcaatccatt tacatgctcc tgtgacatta tgtggatcaa gactctccaa gaggctaaat  1080
ccagtccaga cactcaggat ttgtactgcc tgaatgaaag cagcaagaat attcccctgg  1140
caaacctgca gatacccaat tgtggttttgc catctgcaaa tctggccgca cctaacctca  1200
ctgtggagga aggaaagtct atcacattat cctgtagtgt ggcaggtgat ccggttccta  1260
atatgtattg gatgttggt aacctggttt ccaaacatat gaatgaaaca agccacacac  1320
agggctcctt aaggataact aacatttcat ccgatgacag tgggaagcag atctcttgtg  1380
tggcggaaaa tcttgtagga gaagatcaag attctgtcaa cctcactgtg cattttgcac  1440
caactatcac atttctcgaa tctccaacct cagaccacca ctggtgcatt ccattcactg  1500
tgaaaggcaa ccccaaacca gcgcttcagt ggttctataa cggggcaata ttgaatgagt  1560
ccaaatacat ctgtactaaa atacatgtta ccaatcacac ggagtaccac ggctgcctcc  1620
agctggataa tcccactcac atgaacaatg gggactacac tctaatagcc aagaatgagt  1680
atgggaagga tgagaaacag atttctgctc acttcatggg ctggcctgga attgacgatg  1740
gtgcaaaccc aaattatcct gatgtaattt atgaagatta tggaactgca gcgaatgaca  1800
tcggggacac cacgaacaga agtaatgaaa tcccttccac agacgtcact gataaaaccg  1860
gtcgggaaca tctctcggtc tatgctgtgg tggtgattgc gtctgtggtg ggattttgcc  1920
ttttggtaat gctgtttctg cttaagttgg caagacactc caagtttggc atgaaaggcc  1980
cagcctccgt tatcagcaat gatgatgact ctgccagccc actccatcac atctccaatg  2040
ggagtaacac tccatcttct tcggaaggtg gcccagatgc tgtcattatt ggaatgacca  2100
agatccctgt cattgaaaat ccccagtact ttggcatcac caacagtcag ctcaagccag  2160
acacatggcc cagaggttcc cccaagaccg cctgataata atttggtatt tggaggctcc  2220
```

```
tgtgtcactg caggaactaa aggaggctaa atccatgcct gatggaggag aagagttcta   2280
tggttatctg caaattctgg ccagacaaca tcttgacgtc actccttagc ttccataacc   2340
tagccaagca agaagttgcc tttccaagac aaagcagtgt gctctaatga ctaaccctc    2400 aaagtactat gccactttaa ctatagaccc atctcctcga tcaatcagga tggcaagatg   2460
gagctgagga gctcagcaac atcaagtctg gagttggtct ttaactcaac tagctcgttt   2520
agacgtgtct gaacaccaca tcacctgaca gcacggggtg gtttcccagt aaaatttaca   2580
aactcagctc aagggcagct gtgttgcttt cctttccttg actgctgaga aacttttga    2640 cagggaacaa tggaaacaca ccttctgagc tgaaacaaac aaacagaaac aaaacatact   2700
aaccagcaaa atccccaaat catcaatctt gggttctctt gaagggcagg agtgtgtttt   2760
atcttctccc gtcggagcaa acactataga tgtcctccct aaaattctgt cttccctaga   2820
gcagccttgt aaattagcta gggtcctagg gttgaggcct aaatcaactt aaaattgtct   2880
ctaaatatgt acctggatgt gtttgtactt gcagagcatg ccctcttcat gtgcctaggg   2940
ctagtaactc cctgtggcag aggcatgtaa agtattctga cttttttttt ttcaacttaa   3000
ttccatttcc aatgaaatgg attttttaaaa attttctcca gagtgtgcca tacttctcca   3060
gctattatag ttaatgtgtg tgtatccttg tgtatatgtg tgtttgtgtg tgcatatgtg   3120
ttttcctagt ggttacatgc ttactaggca attatgtaaa taagcacaga ttcataggcc   3180
agctaggcct gaggaaagaa gacattataa agggagggag tattttaaca ttagctaaag   3240
ctatcacaca aggcacccat tctgctcccc tcaacagcca cagccacttc cgtccttgtc   3300
ttaccaataa ggggaaaggc tggaggtgat attttttcaca gaaccgcaga ggttttgaac   3360
atatttgcaa cattactttg agtacacatg agcaaaaatt ctgaattaca tccaggaccc   3420
cagaagctca ttagatcaaa gagtgcgggg cccctcagag ttaccagaga ttatctgcag   3480
acttcagtgc aatcgaatga ccatggtcca ttttgatggt cagaggtagg actgaaaaac   3540
gggtagaaac aattgcttta gcgcttcctt ctgtactttg cctattaatg ttttgtcttt   3600
caaaaatata ttttctccta attgtttaat tggccaaata atggctgctt tgggagttgt   3660
ttgtatgcct tggaaggcca tggcctgcac tttaaaaata agctaagtcc attctgccca   3720
gcacgagcat taggacagag aatgcactta ttttaggatc cttaaaaatt gcttctttta   3780
tggcacactg ggttgacgac tcatctcgtg ggagccttca tggcacattg ctgctgttct   3840
gcaggtccca atacaattcc ttccccctct cagtgccacg gccccccat tgctagctac     3900 aacaatttga tatcatattc ccttttcaac tccaaggag atgataagaa gctatcaaat     3960
aatgctttaa aaaagcaact tgagtttctt aaaagaaagg aaatgaatac atgctgcata   4020
attacattta aaatgtaagc catgttatta taagccgcac tgagatgaag atttgttagc   4080
aaaccagttt caagcacact cacagtgaag taaaatcatg ttttagcat ctgaccattg    4140 ggtaatatta ttctttgtta tcaaaagaga aatatcaccc aagtatagta tacttagacc   4200
tcctagagga aacactccag tcctaagctt ggtgtctgaa aagaaaaaca aaaataaaga   4260
ttatggattt aggtcaggga gacagagtga tattctgaag actgtgttta ctccctcatc   4320
atcggccaac caagatggag ttctgcatcc tgcacatatc agacatttca gtccaatttc   4380
accaaagcat cagtgatgtt ctagaagcat cccagcagat ggaggatcct aatgtatttg   4440
ttctgggtat ttcccaaggc ccagcctgac tggagtgtgt gtaccaacag gatgaatcca   4500
atcaagctac gccccccattt tggtttcgga ttggccactc ttgcatgtgc tagtagattg   4560
```

```
tggaccagga ccagctgagc aaacacagtt gcagagtagc ctcctatgtt gctaagaagc    4620
tcctgctacc caggtgcttt gaacaattga gtgctccctc tggttaagta gagatggcac    4680
caccggagtt tttcttggat gtgaggctca atcctttacg gcagctatta taacaaagtg    4740
aaggttttct ccctgggaaa tgcagctttt ctctgtcttt actaattctg ccagcctgtg    4800
agagtaacca ccgtagctgg gcttcttctc agattaattg tcatgccagg tctccttcct    4860
ggggagctgt gatgctgctc tgaggttgat tgctgaggtt gtagtgggtt tttgtttgtt    4920
tttgtttagt ttttcttgat tgttcttctt tctcttgaat ggcaagagaa gaaacacttt    4980
ctctaaccca cggccaggaa ggaaatgggg agagagctac ttcttagttc aacctggttg    5040
ccacataaag gaatctctct ccttggactc agcccctaac tggaagcaag agccactgcc    5100
ctctgagact gagagagcag cccgaggagg agatgaatcc attctgccct tgtttgggt    5160 ttgcttcctg tcagtgagag aatgctgagg cagttcctgt tatgtgaaac tttcattttt    5220
aaaaccagga cagtcctaaa cagactggaa tgagttggtc aatcccagtt ggtataggcc    5280
caatgatttt tgctagtaag ataggattgt cttcctcacc caaaatgcct tcaagtgccc    5340
taaaatgggt attttaaaat aagaataaat aatgtagatt tagtagaaaa cctggaaaac    5400
ataagaaaca aagatgaaac gaaaagtccc atgtaattcc accagttaga gttaaccact    5460
gatatcgttt ggatatatgg cttttctagtc ttgtggatat ccttttaatc tcttgtaata    5520
taaagtctga ccatatgtgt ccttgcattt gtttgtactg gactctgtta atatttctat    5580
agtaatggct cactttgggg agattgtgct gcacagtgtg taggaagcac attgggtgta    5640
ttattcccag ttttgtattt tgtatttcct tggagatgtg caggggttaa gagcgggggt    5700
ctggccatag ctggccacgt cagactctca tatggtaagt atcacagagc acatgaggcc    5760
tgtgttatgc gctggaaaga ctcaggaaat gagaggctct cttgttctga caaggcaggc    5820
tgagagctct catttagggt catcactcca gataactcca aatgcagttt attgctcaac    5880
tgaagcagat gatcacttt tgcctccaag ttcttcaccc tagctagctc cttcaagga    5940 gccgagtatg ctggatctta aagggccaaa ctagttacat ctcatacatt tcctgatgtt    6000
tagggatgcc ttcacttcca tcaaggatac cttggctgtg caaggacctc tgatagctgg    6060
agtctccttt tggtcactcc cagctttgct taaacttgat ggagtttgct gtccagtgat    6120
ccccggatct ttcatcatga aagccttcct tcctctcctg atgtctcagg cctctagacc    6180
tagactgggg ttctggcaag gaggcctcta tcaatagtat gacatccaat aatatgttag    6240
tgttgatatt ttgcacagta atattaagtt taagagatta taaaaatgag ttcaaatgaa    6300
taagttcctg tgatgtaaga gattagatat gtgtgatttc agaaccaaag gcaggggga    6360 atcccagaaa gaaacaata atataatcct agtttctata tattattttt attcattact    6420
gtatatgggt agagatcaat attctttctt atgctgttac tattaattaa cacatttttt    6480
aaccatgcca ttgaactttt gggtgcatta aagtggaacc caagctcctc attagataat    6540
aatggcattt ggactgagtg ccatattcct aaatttccaa taaagtggtt gatatagaga    6600
ggacaggata aagccctata gtgtgcagtt atatcaaaac agctagtctc cactttaggg    6660
aatgccttta ctagagatta catgaaatgt ctgcttataa aataagcaga gatggcacca    6720
ctaagcagcc acctgaattg ttttcctaca ggaatgatta cttttcagat ccatttatgt    6780
tttcatgctc aatacttact cccctcccct gcaacaccca aagagtttac ttttgcaagt    6840
catttggtct tcagtctact actgaggaat agagaggcac taactgcttt acccaggatc    6900
agaactcatg ttcttaccctt ctattaatag agtacttgag ccagatggac taactggtct    6960
```

```
cacatttttct ctatcttggt tttacttcca taaacatcaa tatctttacc cacatgattt    7020
ttccatcctc ccattttttt ccatatgtat tagggttcag gaactatgat gctaatgatc    7080
acatttcttc ctagttccta atttcattag tgccatttcc tgatatctac agaaacaatt    7140
atcaatacat gtagctgctt gagccttatt tagaaggcta gcctttcttt tccaagtgct    7200
gtcagaatgt atacatttag tctgtctttt tcccttttag gagtctttgt tctgggttga    7260
tggcaaaatt cctcttttta catgtgagat ttttgatttc actgaattct acctagattt    7320
ttatggacat tggattttaa agaggaaaac actcattttc ttagtaagat attggtgata    7380
catagctatg ccattgattt ccatactcct gagctttggg gagggagaca gtggccaagt    7440
agcaggcaga ataagatcat cactcatgtc ctgaatcaat cacactttcc ttctcggatt    7500
gtgtatatgc tctgccactt cctacatatt acatcctgag tttttaagta aagtggatct    7560
tagccagatt tgagtctaat ggctgattca tcggcatagt tcttggcgtt aacatctcag    7620
tgtcctcttt agttctcttt gaggattcat gtcattgagg gcctttgtgc ctccacttgt    7680
ctcagtatga ggaagaactt tggtgtgagg gcggagctat gtgaagggtt gctgggttgg    7740
gggattagtt catatggtcc ccatgccatc tatttacttt tggagagagg ggactttgag    7800
tgggtgggta tggatagatg ttcctcaagg aaaccctgct ggctaatggg cactacatct    7860
gtgtattact gtgattctct ctgtaagctc cccatgtggc caaggacccc cctcctacca    7920
gggcacttcc tgccacctca ttgcactggt ctcaaccatt cagcctgctg ctgctgcacc    7980 atgtgggct cgcgtaggat agggaagggg ttctgttgat tgctaaatgt tgcctaactt    8040
tatttccctc tcccacattt catgcaaggg agcggaccta acacatgact tgcattctct    8100
tcctatgttc agaaactcca gggcttgccc acgtgtatgt atgagtgacc aatggagctt    8160
ggaattcttt atctatatga tctgtccgaa aatgagatct tttgtactgg aatttgtgat    8220
gtagttgatc attcagagcc aaacgcatat accaataaag acaagactgt catataaaaa    8280
aaaaaaaaaa aa                                                         8292

<210> SEQ ID NO 8
<211> LENGTH: 549
<212> TYPE: DNA
<213> ORGANISM: Homo sapiens

<400> SEQUENCE: 8
acctccgcca ggaactgcag gcccacctgt ctgcaaccca gctgaggcca tgccctcccc      60
agggaccgtc tgcagcctcc tgctcctcgg catgctctgg ctggacttgg ccatggcagg     120
ctccagcttc ctgagccctg aacaccagag agtccagaga aggagtcga agaagccacc      180 agccaagctg cagccccgag ctctagcagg ctggctccgc ccggaagatg gaggtcaagc     240
agaaggggca gaggatgaac tggaagtccg gttcaacgcc ccctttgatg ttggaatcaa     300
gctgtcaggg gttcagtacc agcagcacag ccaggccctg ggaagtttc ttcaggacat      360 cctctgggaa gaggccaaag aggccccagc cgacaagtga tcgcccacaa gccttactca     420
cctctctcta agtttagaag cgctcatctg gcttttcgct tgcttctgca gcaactccca     480
cgactgttgt acaagctcag gaggcgaata aatgttcaaa ctgtaaaaaa aaaaaaaaa      540 aaaaaaaaa                                                             549

<210> SEQ ID NO 9
<211> LENGTH: 501
<212> TYPE: DNA
```

<213> ORGANISM: Homo sapiens

<400> SEQUENCE: 9

| | | | | | |
|---|---|---|---|---|---|
| agttccccaa | agataacaca | gctttgcaca | gtggatgttt | acttgctggt | ggtcttatct | 60 |
| aagatcaaca | ttggcagctg | tgcccggaga | ggcctccagg | gtccagcaga | gaaaggagtc | 120 |
| gaagaagcca | ccagccaagc | tgcagccccg | agctctagca | ggctggctcc | gcccggaaga | 180 |
| tggaggtcaa | gcagaagggg | cagaggatga | actggaagtc | cggttcaacg | ccccctttga | 240 |
| tgttggaatc | aagctgtcag | gggttcagta | ccagcagcac | agccaggccc | tggggaagtt | 300 |
| tcttcaggac | atcctctggg | aagaggccaa | agaggcccca | gccgacaagt | gatcgcccac | 360 |
| aagccttact | cacctctctc | taagtttaga | gcgctcatc | tggcttttcg | cttgcttctg | 420 |
| cagcaactcc | cacgactgtt | gtacaagctc | aggaggcgaa | taaatgttca | aactgtaaaa | 480 |
| aaaaaaaaaa | aaaaaaaaa | a | | | | 501 |

<210> SEQ ID NO 10
<211> LENGTH: 498
<212> TYPE: DNA
<213> ORGANISM: Homo sapiens

<400> SEQUENCE: 10

| | | | | | |
|---|---|---|---|---|---|
| agttccccaa | agataacaca | gctttgcaca | gtggatgttt | acttgctggt | ggtcttatct | 60 |
| aagatcaaca | ttggcagctg | tgcccggaga | ggcctccagg | gtccagagaa | aggagtcgaa | 120 |
| gaagccacca | gccaagctgc | agccccgagc | tctagcaggc | tggctccgcc | cggaagatgg | 180 |
| aggtcaagca | gaaggggcag | aggatgaact | ggaagtccgg | ttcaacgccc | ctttgatgt | 240 |
| tggaatcaag | ctgtcagggg | ttcagtacca | gcagcacagc | caggccctgg | gaagtttct | 300 |
| tcaggacatc | ctctgggaag | aggccaaaga | ggccccagcc | gacaagtgat | cgcccacaag | 360 |
| ccttactcac | ctctctctaa | gtttagaagc | gctcatctgg | cttttcgctt | gcttctgcag | 420 |
| caactcccac | gactgttgta | caagctcagg | aggcgaataa | atgttcaaac | tgtaaaaaaa | 480 |
| aaaaaaaaaa | aaaaaaaa | | | | | 498 |

<210> SEQ ID NO 11
<211> LENGTH: 384
<212> TYPE: DNA
<213> ORGANISM: Homo sapiens

<400> SEQUENCE: 11

| | | | | | |
|---|---|---|---|---|---|
| agttccccaa | agataacaca | gctttgcaca | gtggatgttt | acttgctggt | ggtcttatct | 60 |
| aagatcaaca | ttggcagctg | tgcccggaga | ggcctccagg | gtccagttca | acgccccctt | 120 |
| tgatgttgga | atcaagctgt | caggggttca | gtaccagcag | cacagccagg | ccctggggaa | 180 |
| gtttcttcag | gacatcctct | gggaagaggc | caaagaggcc | ccagccgaca | agtgatcgcc | 240 |
| cacaagcctt | actcacctct | ctctaagttt | agaagcgctc | atctggcttt | tcgcttgctt | 300 |
| ctgcagcaac | tcccacgact | gttgtacaag | ctcaggaggc | gaataaatgt | tcaaactgta | 360 |
| aaaaaaaaaa | aaaaaaaaaa | aaaa | | | | 384 |

<210> SEQ ID NO 12
<211> LENGTH: 1939
<212> TYPE: DNA
<213> ORGANISM: Homo sapiens

<400> SEQUENCE: 12

| | | | | | |
|---|---|---|---|---|---|
| agtttggacg | gctgcttccc | accagcaaag | accacgactg | gagagccgag | ccggaggcag | 60 |

```
ctgggaaaca tgaagagcgt cttgctgctg accacgctcc tcgtgcctgc acacctggtg      120
gccgcctgga gcaataatta tgcggtggac tgccctcaac actgtgacag cagtgagtgc      180
aaaagcagcc cgcgctgcaa gaggacagtg ctcgacgact gtggctgctg ccgagtgtgc      240
gctgcagggc ggggagaaac ttgctaccgc acagtctcag gcatggatgg catgaagtgt      300
ggcccggggc tgaggtgtca gccttctaat ggggaggatc cttttggtga gagtttggt       360 atctgcaaag agcatgacat ggcatctgga gatggcaata ttgtgagaga agaagttgtg      420
aaagagaatg ctgccgggtc tcccgtaatg aggaaatggt taaatccacg ctgatcccgg      480
ctgtgatttc tgagagaagg ctctattttc gtgattgttc aacacacagc caacattta      540 ggaactttct agattatagc ataaggacat gtaattttg aagaccaaat gtgatgcatg       600
gtggatccag aaaacaaaaa gtaggatact tacaatccat aacatccata tgactgaaca      660
cttgtatgtg tttgttaaat attcgaatgc atgtagattt gttaaatgtg tgtgtatagt      720
aacactgaag aactaaaaat gcaatttagg taatcttacg tggagacagg tcaaccaaag      780
agggagctag gcaaagctga agaccgcagt gagtcaaatt agttctttga ctttgatgta      840
cattaatgtt gggatatgga atgaagactt aagagcagga gaagatgggg aggggtggg       900 agtgggaaat aaaatatttta gcccttcctt ggtaggtagc ttctctagaa tttaattgtg      960 ctttttttt ttttttggc tttgggaaaa gtcaaaataa acaaccaga aaaccccctga       1020 aggaagtaag atgtttgaag cttatggaaa tttgagtaac aaacagcttt gaactgagag      1080 caattt caaa aggctgctga tgtagttccc gggttacctg tatctgaagg acggttctgg      1140
ggcataggaa acacatacac ttccataaat agctttaacg tatgccacct cagagataaa      1200
tctaagaagt attttacccca ctggtggttt gtgtgtgtat gaaggtaaat atttatatat      1260
ttttataaat aaatgtgtta gtgcaagtca tcttccctac ccatatttat catcctcttg      1320
aggaaagaaa tctagtatta tttgttaaaa atggttagaa taaaactatg actctataag      1380
gttttcaaac atctgaggca tgataaattt attatccata attatagtaa taataacctt      1440
aataagcata agaaaaacag agtcactctg gatttcaaaa atgtcaaaaa atgagcaaca      1500
gagggtcctt atttaaacat aagtgctgtg acttaggtga attttcaatt taaggtagaa      1560
aataagtttt taggaggttt gtaaaagaag aatcaatttt cagcagaaaa catgtcaact      1620
ttaaaatata gtttatttc atatttttt cttttaaact tggttgataa gtggaattag        1680 gagtatatt gaaagaatct tagcacaaac aggactgttg tactagatgt tcttaggaaa       1740
tatctcagaa gtatttttatt tgaagtgaag aacttattta agaattattt cagtatttac      1800 ctgtattta ttcttgaagt tggccaacag agttgtgaat gtgtgtggga aggcctttga       1860
atgtaaagct gcataagctg ttaggttttg ttttaaaagg acatgtttat tattgttcaa      1920 taaaaagaa caagataca                                                    1939
```

<210> SEQ ID NO 13
<211> LENGTH: 882
<212> TYPE: DNA
<213> ORGANISM: Homo sapiens

<400> SEQUENCE: 13

```
caccctttcc agatacacac ccgtttagtg cgagaaatgg agcggttggg gagaggatct       60
cccgaggggg ctggattgag aatgggtacc atttgagatc tcctaggagg ccggccatcg      120
ggcaatgtct gatggagtcc agccggtgga ggagactgaa aggaaacagc ctgcttcctg      180
```

```
caggtccgcg ggagggaggt ctttaagtgc gtttgtgcag ccgatttcaa ggctaagaga      240
gaaagactgc ctctgatccc tgaaggaaga aaaaaaaaaa aaaaacagga aaaaaactca      300
acatggaaaa tgtccccaag gaaaacaaag ttgtggagaa ggccccagtg cagaatgaag      360
cccccgcttt aggaggtggt gaataccagg agcctggagg aaatgttaaa ggggtttggg      420
ctccacctgc cccgggtttt ggagaggatg tgcccaatag gcttgtcgat aacattgata      480
tgatagatgg agatggagat gatatggaac ggttcatgga ggagatgaga gagctaagga      540
ggaaaattag ggaacttcag ttgaggtaca gtctgcgcat tcttataggg gaccctcctc      600
accatgatca tcatgatgag ttttgcctta tgccttgaat cttgaggtta ataatcataa      660
aatccctgct ttctaaattc gcattttttcc tggtgtacct ttaatgtgaa ccttttggca      720
ttcttctgca attttctgat ggagattgc attttgacct agtctgtaag ttttttctgtc      780 agaagaggac tttcatcaac tttcatggaa agatgtttat tgcatactgt aaagttaata      840
aagcaattta aaagcagtct aaaaaaaaaa aaaaaaaaa aa                          882
```

```
<210> SEQ ID NO 14
<211> LENGTH: 1278
<212> TYPE: DNA
<213> ORGANISM: Homo sapiens

<400> SEQUENCE: 14
```

```
ccattggcct gtagattcac ctcccctggg cagggcccca ggacccagga taatatctgt       60
gcctcctgcc cagaaccctc caagcagaca caatggtaag aatggtgcct gtcctgctgt      120
ctctgctgct gcttctgggt cctgctgtcc cccaggagaa ccaagatggt cgttactctc      180
tgacctatat ctacactggg ctgtccaagc atgttgaaga cgtccccgcg tttcaggccc      240
ttggctcact caatgacctc cagttcttta gatacaacag taaagacagg aagtctcagc      300
ccatgggact ctggagacag gtggaaggaa tggaggattg gaagcaggac agccaacttc      360
agaaggccag ggaggacatc tttatggaga ccctgaaaga catcgtggag tattacaacg      420
acagtaacgg gtctcacgta ttgcagggaa ggtttggttg tgagatcgag aataacagaa      480
gcagcggagc attctggaaa tattactatg atggaaagga ctacattgaa ttcaacaaag      540
aaatcccagc ctgggtcccc ttcgacccag cagcccagat aaccaagcag aagtgggagg      600
cagaaccagt ctacgtgcag cgggccaagg cttacctgga ggaggagtgc ctgcgactc      660 tgcggaaata cctgaaatac agcaaaaata tcctggaccg gcaagatcct ccctctgtgg      720
tggtcaccag ccaccaggcc caggagaaa agaagaaact gaagtgcctg gcctacgact      780
tctacccagg gaaaattgat gtgcactgga ctcgggccgg cgaggtgcag gagcctgagt      840
tacggggaga tgttcttcac aatggaaatg gcacttacca gtcctgggtg gtggtggcag      900
tgcccccgca ggacacagcc ccctactcct gccacgtgca gcacagcagc ctggcccagc      960
ccctcgtggt gccctgggag gccagctagg aagcaagggt tggaggcaat gtgggatctc     1020
agacccagta gctgcccttc ctgcctgatg tgggagctga accacagaaa tcacagtcaa     1080
tggatccaca aggcctgagg agcagtgtgg ggggacagac aggaggtgga tttggagacc     1140
gaagactggg atgcctgtct tgagtagact tggacccaaa aaatcatctc accttgagcc     1200
cacccccacc ccattgtcta atctgtagaa gctaataaat aatcatccct ccttgcctag     1260
cataaaaaaa aaaaaaaa                                                   1278
```

```
<210> SEQ ID NO 15
<211> LENGTH: 1801
```

<212> TYPE: DNA
<213> ORGANISM: Homo sapiens

<400> SEQUENCE: 15

```
gggttatatg atctctttgg ctttagggaa ttactccata ccagctctga gatttccagc      60
tcagcgatgc ccccaggtcc ctgggagagc tgcttctggg tgggggggcct cattttgtgg    120
ctcagcgttg aagttcagg ggatgcacct cctaccccac agccaaagtg cgctgacttc     180
cagagcgcca acctttttga aggcaccgat ctcaaagtcc agtttctcct ctttgtccct    240
tcgaatccta gctgtgggca gctagtagaa ggaagcagtg acctccaaaa ctctgggttc    300
aatgccactc tgggaaccaa actaattatc catggattca gggttttagg aacaaagcct    360
tcctggattg acacatttat tagaacccctt ctgcgtgcaa cgaatgctaa tgtgattgcc    420
gtggactgga tttatgggtc tacaggagtc tacttctcag ctgtgaaaaa tgtgctgggt    480
gtgtcggaat cctcaatcca catcattggt gttagcctgg gggcccacgt tggggggcatg    540
gtgggacagc tcttcggagg ccagctggga cagatcacag gcctgacccc cgctggacct    600
gagtacacca gggccagtgt ggaagagcgc ttggatgctg agatgccct cttcgtggaa     660
gccatccaca cagacaccga caatttgggt attcggattc ccgttggaca tgtgactac    720
ttcgtcaacg gaggccaaga ccaacctggc tgccccacct tcttttacgc aggttatagt    780
tatctgatct gtgatcacat gagggctgtg cacctctaca tcagcgccct ggagaattcc    840
tgtccactga tggccttttcc ctgtgccagc tacaaggcct tccttgctgg acgctgtctg    900
gattgcttta acccttttct gctttcctgc ccaaggatag gactggtgga acaaggtggt    960
gtcaagatag agccgctccc caaggaagtg aaagtctacc tcctgactac ttccagtgct   1020
ccgtactgca tgcatcacag cctcgtggag tttcacttga aggaactgag aaacaaggac   1080
accaacatcg aggttacctt ccttagcagt aacatcacct cttcatctaa gatcaccata   1140
cctaagcagc aacgctatgg gaaaggaatc atagcccatg ccaccccaca atgccagata   1200
aaccaagtga aattcaagtt tcagtcttcc aaccgagttt ggaaaaaaga ccggactacc   1260
attattggga agttctgcac tgccccttttg cctgtcaatg acagagaaaa gatggtctgc   1320
ttacctgaac cagtgaactt acaagcaagt gtgactgttt cctgtgacct gaagatagcc   1380
tgtgtgtagt ttaacctggg caggacacat ctccctgcat tttttttttt ttttttgagag   1440
agaggtgtga tgagggatgt gtgtgtgcag cttattgtag accattacta ctaaggagaa   1500
aagcaaagct ctttcttatt ttcctcataa tcagctaccc tggaggggag ggagaactca   1560
ttttacagaa cttggtttcc tttgccgatc ttatgtacat acccatttta gctttcccat   1620
gcatacttaa ctgcacttgc tttatctcct tgggcattcg tacttaggat tcaatagaaa   1680
catgtacagg gtaaacaatt ttttaaaaat aaaacttcat ggagtatctg aaaaaaaaaa   1740
aaaaaaaaaa aaaaaaaaaa aaaaaaaaaa aaaaaaaaaa aaaaaaaaaa aaaaaaaaaa   1800
a                                                                    1801
```

<210> SEQ ID NO 16
<211> LENGTH: 1647
<212> TYPE: DNA
<213> ORGANISM: Homo sapiens

<400> SEQUENCE: 16

```
gggttatatg atctctttgg ctttagggaa ttactccata ccagctctga gatttccagc      60
tcagcgatgc ccccaggtcc ctgggagagc tgcttctggg tgggggggcct cattttgtgg    120
```

-continued

| | |
|---|---|
| ctcagcgttg aagttcagg gttttaggaa caaagccttc ctggattgac acatttatta | 180 |
| gaacccttct gcgtgcaacg aatgctaatg tgattgccgt ggactggatt tatgggtcta | 240 |
| caggagtcta cttctcagct gtgaaaaatg tgattaagtt gagcctcgag atctcccttt | 300 |
| tcctcaataa actcctggtg ctgggtgtgt cggaatcctc aatccacatc attggtgtta | 360 |
| gcctggggc ccacgttggg ggcatggtgg acagctctt cggaggccag ctgggacaga | 420 |
| tcacaggcct ggaccccgct ggacctgagt acaccagggc cagtgtggaa gagcgcttgg | 480 |
| atgctggaga tgccctcttc gtggaagcca tccacacaga caccgacaat tgggtattc | 540 |
| ggattcccgt tggacatgtg gactacttcg tcaacggagg ccaagaccaa cctggctgcc | 600 |
| ccaccttctt ttacgcaggt tatagttatc tgatctgtga tcacatgagg gctgtgcacc | 660 |
| tctacatcag cgccctggag aattcctgtc cactgatggc ctttccctgt gccagctaca | 720 |
| aggccttcct tgctggacgc tgtctggatt gctttaaccc ttttctgctt tcctgcccaa | 780 |
| ggataggact ggtggaacaa ggtggtgtca agatagagcc gctccccaag gaagtgaaag | 840 |
| tctacctcct gactacttcc agtgctccgt actgcatgca tcacagcctc gtggagtttc | 900 |
| acttgaagga actgagaaac aaggacacca catcgaggt taccttcctt agcagtaaca | 960 |
| tcacctcttc atctaagatc accataccta agcagcaacg ctatgggaaa ggaatcatag | 1020 |
| cccatgccac cccacaatgc cagataaacc aagtgaaatt caagtttcag tcttccaacc | 1080 |
| gagtttggaa aaaagaccgg actaccatta ttgggaagtt ctgcactgcc cttttgcctg | 1140 |
| tcaatgacag agaaaagatg gtctgcttac ctgaaccagt gaacttacaa gcaagtgtga | 1200 |
| ctgtttcctg tgacctgaag atagcctgtg tgtagtttaa cctgggcagg acacatctcc | 1260 |
| ctgcattttt ttttttttt tgagagagag gtgtgatgag ggatgtgtgt gtgcagctta | 1320 |
| ttgtagacca ttactactaa ggagaaaagc aaagctcttt cttatttcc tcataatcag | 1380 |
| ctaccctgga ggggagggag aactcatttt acagaacttg gtttcctttg ccgatcttat | 1440 |
| gtacataccc attttagctt tcccatgcat acttaactgc acttgcttta tctccttggg | 1500 |
| cattcgtact taggattcaa tagaaacatg tacagggtaa acaatttttt aaaaataaaa | 1560 |
| cttcatggag tatctgaaaa aaaaaaaaaa aaaaaaaaaa aaaaaaaaaa aaaaaaaaaa | 1620 |
| aaaaaaaaaa aaaaaaaaaa aaaaaaa | 1647 |

<210> SEQ ID NO 17
<211> LENGTH: 5622
<212> TYPE: DNA
<213> ORGANISM: Homo sapiens

<400> SEQUENCE: 17

| | |
|---|---|
| ggcacgtgga ctcccttta tccagtgact gtcaggtcga tcatatgccg aggacgatga | 60 |
| tcccgccggg ggagtgcacg tacgcgggcc ggaagcggag gaggcccctg cagaaacaga | 120 |
| ggcccgccgt gggggcagag aagtccaacc cctccaagcg acaccgggac cgcctcaacg | 180 |
| ccgagttgga ccacctggcc agcctgctgc cgttcccgcc tgacatcatc tccaagctgg | 240 |
| acaagctttc tgtcctgcgc ctcagtgtca gttacctccg ggtgaagagc ttcttccaag | 300 |
| tcgtgcagga gcagagctca cggcagcctg cggccgcgc cccctcgccc ggagacagct | 360 |
| gtcctcttgc agggtctgcc gtgctggagg gaaggctgct gttggagtct cttaatggct | 420 |
| ttgctctggt cgtgagtgca gaagggacga tattttatgc atcagcaacg atcgtggact | 480 |
| atctgggctt ccatcagacg gatgtaatgc accagaacat ttatgactac atccacgtgg | 540 |
| acgaccgcca ggacttctgc cggcagctcc actgggccat ggaccctccc caggtggtgt | 600 |

```
ttgggcagcc cccgcccttg gagacaggag atgatgctat cctggggagg ctgctcaggg    660
cccaggagtg gggcacaggc acgcccaccg agtactcggc cttcctgacc cgctgcttca    720
tctgccgtgt gcgctgcctg ctggacagca cctcgggctt cctgacgatg cagtttcaag    780
gaaaactaaa attcctgttt ggacagaaga agaaggcgcc gtcaggagcc atgctcccgc    840
cgcggctgtc gctgttctgc attgcggcac ccgttctcct ccctccgca gcggagatga     900 aaatgaggag cgcgctcctg agggcaaaac ccagagcaga caccgcagcc accgcggatg    960
caaaagtaaa agccaccacc agtctgtgcg aatcggaact gcatggaaaa cccaattact   1020
cagcaggaag gagcagcaga gagagcggcg ttttggtgct cagggaacag actgacgctg   1080
gccgatgggc acaggttccc gccagggccc catgcctgtg cctccggggt ggccctgacc   1140
ttgtccttga ccccaagggg ggctcagggg acagggagga ggagcagcac aggatgctga   1200
gcagggcctc tggagtgaca gggcggaggg agactccagg acccacaaag cccctgccct   1260
ggacagcggg aaagcacagt gaggatggtg ccaggccgag gctgcagccc agcaagaatg   1320
acccgccctc cctgcgcccc atgccccgcg gctcctgcct gccctgcccg tgtgtccagg   1380
gcactttcag gaactcgccc atctctcacc cgccgagccc gtcccccagt gcctactcca   1440
gccggaccag cagacccatg cgggatgtcg gtgaggacca ggtgcaccct cccctctgcc   1500
actttcccca gaggagcctg cagcaccagc tccctcagcc tggagctcag cgttttgcca   1560 cgagggcta tcccatggag gacatgaagc tgcaaggtgt accgatgcct ccgggggacc    1620
tgtgtggtcc gacgctgctg ctagatgtgt ccatcaagat ggagaaggac tctgggtgtg   1680
agggtgctgc agacggctgt gtgcccagcc aggtgtggct gggggccagt gacaggagcc   1740
acccagccac cttccctacc aggatgcacc tgaaaacaga gccagactct cggcaacagg   1800
tgtacatctc gcacctgggg cacggcgtgc gggggctca gccccatggg agggccactg    1860
ctgggcgcag cagggagctg accccttttcc accctgcaca ctgtgcctgc ctggagccca   1920
cagacggcct tccccagtcg gagcctcccc accagctctg tgcacgggc cgaggtgaac    1980 agtcctgcac ctgcagagct gctgaggccg cccctgtggt caagcgggag cccttggact   2040
caccccagtg ggctactcac agccagggaa tggtgcccgg gatgttgccc aaaagtgcct   2100
tggccacgct ggtcccgccc caagcttcgg ggtgcacatt cctgccatag cgcagtgacc   2160
accatccaag ctcagatctg tgtgtctacg ctcagatgcg tcggtggctg ggctgccctg   2220
ctcctggtca ggccggagcc cgtcctaaga cacacgcttt gcagagctgt gcatgcgcag   2280
tctgctagtg tgtgtgtgca gcatacgcag gagcctatcc tgaatttgt aaaatatccc    2340 aacagttctt aaatgaaaac tggccttaag tctattcaag catgacagca tttctctttg   2400
aggaattaaa atctttagga aagtgatcat ggctggacag cttcatgccc cagaggcagc   2460
gagcacccgt cccatggctg ccaagtccac agtcggggat gaagcagtcg ggtgatgctc   2520
ccaagtccgc agtcggggat gaagcggtcg ggtgatgctc ccaagtccgc agtcggggat   2580
gaagcggtcg ggtgacacac ctagctcagc cctcccaggc cacctgcagc tcccagcctg   2640
tgctgtgcag gcagggtcag cccatcgcca cagtgcactg tagaggccag cacacggcaa   2700
attagaaata caacacgcgg agaaaggggt ccgtgagccc actcatagag gaatctagaa   2760
cgttccaggc agcagaggct ggcagcgtgg gtcccacact gccccacacc gtgcggcagg   2820
tgctccatgg cgccatgaca gagtctgagg ccagacctgg actggaattg acagcataac   2880
ccctgttcct tctggacatc tcccgagttc tcagtgggtc tctgcggacg gttcttccta   2940
```

```
atctgcctct tggtacatca cgtaatacag agttcacaga ctccgggttt ggaagtacag    3000
agaaacacac aacgtagaga gaagacacag gaaactgcgc tgcctgtggg ggtttctctc    3060
tggctggctg tacagttcac tcaaatgagg gttcccattg ccatcctagg agaataatta    3120
gggacaagac agacaagtat taatagcatt aaaacagttg taaaggcgat attttctgag    3180
agtaggaaat ttggatacaa aagcataagt cagaaagtga aggtcaccaa tccaccaacc    3240
cgagaaccta cagctgatgg tgcatttcag gcttcttcca cggtctggcc tggaacccca    3300
cccggctggt gcaggcatca gatcagggtg tagaagtcac cccaagcaag aggaagccag    3360
gcagtgaggc cctggggtgt ggctgcagct gggcccacct gtgcggggt gggaaggccc     3420 catcctcagg gagagggcat cggcgccctg acgtcagctc cactgggagt ggcaggagct    3480
gtgggagccc atgggtgagg gacccaccac cccgctgcac tgtgcattgt gcctcccgtg    3540
tggacgccct ctctgttgtt ggcccgcggg tgagggaccc accaccccta gggacccacc    3600
accccgccgc actgtgcatt ctgcctcctg tgtggacgcc ctctctgttg tcagtggctt    3660
tgaggtgtca gtgcttactt agatgctggt ttaatgctgg acccatttgt taaacgcacc    3720
ttcactttgt caaacccag gtttggttgg caggactggg tcttctgccc aatgccaggt     3780
gcctgcgcct ctcagtggcc tggttcttgg acagtttgcc cccatgtggc agggataggg    3840
ataaggatct cctctcagta ctggaagaga acagccaacc atctgagccc agagtcacag    3900
atccatcgtg gcccctatg accccaagc cctaccgagg gggcactcac tctctgctta      3960 gccaggggc gtctttcaaa aggtgacctc catgctgtgc tgtcgtgggt gtgagacgtg     4020
ctcatggcct tccactgcca tctctccctt atctgatgcc taaagtcacg atggggacag    4080
agctacccag gggccagcca tggggtgacc agccacctga gggtcagtca cctgtggaga    4140
gcaggcacct gtgaagacca ggcacctgag gactggcgcc tacttccac tttggcccta    4200 cactggcaca gagcccctct ttattcattt ctcatgctga gcatggcaca cttctggcct    4260
ctgggcattt atggatttaa gaccaggatg gtatttcaga agcttcccac ttccttccta    4320
ttctaaccga gtgcccagct cctttgctga tcatggaaag acccttaata attaggcctg    4380
caggccaggc gcagtggctc atgcctataa tcccagcact ttaggaggtc aaggtaggag    4440
gatcgcttaa gcccaggagt tcaagaccag cctgggcaac acaggaagaa tgtgtctcta    4500
caaaaaataa ttaaaaatca gatctgctgt atccctgaaa aagtctcaat caacatgcat    4560
gttccactct tggagttccc tgttctgagg gccagccacg tcctgtgtcc tggagcttag    4620
ccctcagcag ctcccttcag cctgggcgcc gcctgggtcc caaacgtggc agctgctctt    4680
ccagtctcgg ggccgaggag ggcagggagc tcagtgactg agagtcttgt gtatcacatg    4740
tcttgagtgt cctggagcca acggctgtca ctgggaaaaa caccaggccc caaagatcga    4800
atcagagacg tggctgcgtg tttgcgattg tagccaggcc cttcagtgtc atcaaaggag    4860
cactggggcc tccttaagca cagacggcag cccctgccca ggaggcttct tcaccacgtc    4920
ctgccctgca gcctcccaga cctttagatg cgccctgcc caaggccctc ctggtgacag     4980
gtgccagatt gagtggtggg ttgctgccag gcaggccacg ctgtgttgac gctgcactca    5040
gcacgtgggt gttggctctg ccggttttgt ggtgtgggga ccctacagga ggctgcggcc    5100
ctgagagcct gggatcagcg aggtgtccga catcccttcc tcaacggcaa caaaaactcc    5160
ccaagtcagc actttggtta tttttatagcc acaaccctct tggaaaacag tggggaagac    5220
tatggaacat agaaagtgtg gatgtatcac ttctctctaa aatgtcattg ttagcactaa    5280
ttacaggttc atgttttct gtgtatgtag cttttcccta tatagctgaa aaagtattaa      5340
```

```
agtcaaatat aaggtgggaa tgggatggaa gggaggagat caatacaact tatattttg     5400 cagtttctac tggaagaaaa aagttttcaa tacctagacc aacttgttga attttttaaaa   5460 cttatgcact ataaatgcaa ctttctctac tgctttctca gtgcctttag gaagctttca    5520 aattttttg tactgtggtt tgtattaaat ttgcaatatt gatgtaaaat acatgacatg     5580
ctagtacatg tttaacaaaa atttaaaaaa aaaaaaaaaa aa                       5622
```

<210> SEQ ID NO 18
<211> LENGTH: 2039
<212> TYPE: DNA
<213> ORGANISM: Homo sapiens

<400> SEQUENCE: 18

```
gtaggtgtca cttatatcac aaggctacag gtgtctttat ttccactgca cgctggtgct      60
gggagcgcct gccttctctt gccttgaaag cctcctcttt ggacctagcc accgctgccc    120
tcacggtaat gttggactcg gtgacacaca gcaccttcct gcctaatgca tccttctgcg    180 atccctgat gtcgtggact gatctgttca gcaatgaaga gtactaccct gcctttgagc     240
atcagacaga tgctgattcc aactgcttga aaacaagtgg catcaaaagt caagactgtc    300
acagtcatag tagaacaagc ctccaaagtt ctcatctatg ggaatttgta cgagacctgc    360
ttctatctcc tgaagaaaac tgtggcattc tggaatggga agatagggaa caaggaattt    420
ttcgggtggt taaatcggaa gccctggcaa agatgtgggg acaaaggaag aaaaatgaca    480
gaatgacata tgaaaagttg agcagagccc tgagatacta ctataaaaca ggaattttgg    540
agcgggttga ccgaaggtta gtgtacaaat ttggaaaaaa tgcacacggg tggcaggaag    600
acaagctatg atctgctcca ggcatcaagc tcattttatg gatttctgtc ttttaaaaca    660
atcagattgc aatagacatt cgaaaggctt cattttcttc tctttttttt taacctgcaa    720
acatgctgat aaaatttctc cacatctcag cttacatttg gattcagagt tgttgtctac    780
ggagggtgag agcagaaact cttaagaaat cctttcttct ccctaagggg atgaggggat    840
gatcttttgt ggtgtcttga tcaaacttta ttttcctaga gttgtggaat gacaacagcc    900
catgccattg atgctgatca gagaaaaact attcaattct gccattagag acacatccaa    960
tgctcccatc ccaaaggttc aaaagttttc aaataactgt ggcagctcac caaaggtggg   1020
ggaaagcatg attagtttgc aggttatggt aggagagggt gagatataag acatacatac   1080
tttagatttt aaattattaa agtcaaaaat ccatagaaaa gtatcccttt ttttttttt    1140 gagacgggtt ctcactatgt tgcccagggc tggtcttgaa ctcctatgct caagtgatcc   1200
tcccacctcg gcctcccaaa gtactgtgat tacaagcgtg agccacggca cctgggcaga   1260
aaagtatctt aattaatgaa agagctaagc catcaagctg ggacttaatt ggatttaaca   1320
taggttcaca gaaagtttcc taaccagagc atctttttga ccactcagca aaacttccac   1380
agacatcctt ctggacttaa acacttaaca ttaaccacat tattaattgt tgctgagttt   1440
attccccctt ctaactgatg gctggcatct gatatgcaga gttagtcaac agacactggc   1500
atcaattaca aaatcactgc tgtttctgtg attcaagctg tcaacacaat aaaatcgaaa   1560
ttcattgatt ccatctctgg tccagatgtt aaacgtttat aaaaccggaa atgtcctaac   1620
aactctgtaa tggcaaatta aattgtgtgt cttttttgtt ttgtctttct acctgatgtg   1680
tattcaagcg ctataacacg tatttccttg acaaaaatag tgcagtgaa ttcacactaa    1740 taaatgttca taggttaaag tctgcactga cattttctca tcaatcactg gtatgtaagt   1800
```

| | |
|---|---|
| tatcagtgac tgacagctag gtggactgcc cctaggactt ctgtttcacc agagcaggaa | 1860 |
| tcaagtggtg aggcactgaa tcgctgtaca ggctgaagac ctccttatta gagttgaact | 1920 |
| tcaaagtaac ttgttttaaa aaatgtgaat tactgtaaaa taatctattt tggattcatg | 1980 |
| tgttttccag gtggatatag tttgtaaaca atgtgaataa agtatttaac atgtaaaaa | 2039 |

<210> SEQ ID NO 19
<211> LENGTH: 2222
<212> TYPE: DNA
<213> ORGANISM: Homo sapiens

<400> SEQUENCE: 19

| | |
|---|---|
| ggctgagtgg tttgctcctt cccctctctc tgggaggctg agcaggggtg ccgggttgct | 60 |
| caggccatgg gagccacacc tgttattgct gcctctgatt tgtgtgacac tgagaagccc | 120 |
| acaggcctgt ccctccaact cggtggaccc tctctgtgtg catttggtgt gtgagccagc | 180 |
| tctgagaagg gttcagaagc cactggaggc atctggggac ctcagcttcc atgccatctc | 240 |
| tgcctcactc ccacagggta atgttggact cggtgacaca cagcaccttc ctgcctaatg | 300 |
| catccttctg cgatcccctg atgtcgtgga ctgatctgtt cagcaatgaa gagtactacc | 360 |
| ctgcctttga gcatcagaca ggttactcct tttttaatga cgctgaagaa agcaaggcca | 420 |
| ccatcaaaga ctatgctgat tccaactgct tgaaaacaag tggcatcaaa agtcaagact | 480 |
| gtcacagtca tagtagaaca agcctccaaa gttctcatct atgggaattt gtacgagacc | 540 |
| tgcttctatc tcctgaagaa aactgtggca ttctggaatg ggaagatagg gaacaaggaa | 600 |
| ttttcgggt ggttaaatcg gaagccctgg caaagatgtg gggacaaagg aagaaaaatg | 660 |
| acagaatgac atatgaaaag ttgagcagag ccctgagata ctactataaa acaggaattt | 720 |
| tggagcgggt tgaccgaagg ttagtgtaca aatttggaaa aaatgcacac gggtggcagg | 780 |
| aagacaagct atgatctgct ccaggcatca agctcatttt atggatttct gtcttttaaa | 840 |
| acaatcagat tgcaatagac attcgaaagg cttcattttc ttctcttttt ttttaacctg | 900 |
| caaacatgct gataaaattt ctccacatct cagcttacat ttggattcag agttgttgtc | 960 |
| tacggagggt gagagcagaa actcttaaga aatcctttct tctccctaag gggatgaggg | 1020 |
| gatgatcttt tgtggtgtct tgatcaaact ttattttcct agagttgtgg aatgacaaca | 1080 |
| gcccatgcca ttgatgctga tcagagaaaa actattcaat tctgccatta gagacacatc | 1140 |
| caatgctccc atcccaaagg ttcaaaagtt ttcaaataac tgtggcagct caccaaaggt | 1200 |
| ggggaaagc atgattagtt tgcaggttat ggtaggagag ggtgagatat aagacataca | 1260 |
| tactttagat tttaaattat taaagtcaaa aatccataga aaagtatccc ttttttttt | 1320 |
| tttgagacgg gttctcacta tgttgcccag gctggtcttg aactcctat gctcaagtga | 1380 |
| tcctcccacc tcggcctccc aaagtactgt gattacaagc gtgagccacg gcacctgggc | 1440 |
| agaaaagtat cttaattaat gaaagagcta agccatcaag ctgggactta attggattta | 1500 |
| acataggttc acagaaagtt tcctaaccag agcatctttt tgaccactca gcaaaacttc | 1560 |
| cacagacatc cttctggact taaacactta acattaacca cattattaat tgttgctgag | 1620 |
| tttattcccc cttctaactg atggctggca tctgatatgc agagttagtc aacagacact | 1680 |
| ggcatcaatt acaaaatcac tgctgtttct gtgattcaag ctgtcaacac aataaaatcg | 1740 |
| aaattcattg attccatctc tggtccagat gttaaacgtt tataaaaccg gaaatgtcct | 1800 |
| aacaactctg taatggcaaa ttaaattgtg tgtcttttt gttttgtctt tctacctgat | 1860 |
| gtgtattcaa gcgctataac acgtatttcc ttgacaaaaa tagtgacagt gaattcacac | 1920 |

| | |
|---|---|
| taataaatgt tcataggtta aagtctgcac tgacattttc tcatcaatca ctggtatgta | 1980 |
| agttatcagt gactgacagc taggtggact gccccctagga cttctgtttc accagagcag | 2040 |
| gaatcaagtg gtgaggcact gaatcgctgt acaggctgaa gacctcctta ttagagttga | 2100 |
| acttcaaagt aacttgtttt aaaaaatgtg aattactgta aataatcta ttttggattc | 2160 |
| atgtgttttc caggtggata tagtttgtaa acaatgtgaa taaagtattt aacatgtaaa | 2220 |
| aa | 2222 |

<210> SEQ ID NO 20
<211> LENGTH: 1214
<212> TYPE: DNA
<213> ORGANISM: Homo sapiens

<400> SEQUENCE: 20

| | |
|---|---|
| agaaggttta aggccggaaa gggaaatgaa ggggcccggc gctaaccctc taaggacctg | 60 |
| ttttgcttct gtttaaacca aatgggcagt ctgtcattac acacaccctg ggtcttcata | 120 |
| tgtggccgcc aggtaggagc atcacagtca agctacggga gaaaacagtt tccaggaaac | 180 |
| tggaaatgaa cggcccgagt gctttccagg ggctcatctg tgggaagtat aatggaatgt | 240 |
| gcttacaagg gccagcagga gtgcctggtc gagacgggag ccctggggcc aatggcattc | 300 |
| cgggtacacc tgggatccca ggtcgggatg gattcaaagg agaaaagggg gaatgtctga | 360 |
| gggaaagctt tgaggagtcc tggacaccca actacaagca gtgttcatgg agttcattga | 420 |
| attatggcat agatcttggg aaaattgcgg agtgtacatt tacaaagatg cgttcaaata | 480 |
| gtgctctaag agttttgttc agtggctcac ttcggctaaa atgcagaaat gcatgctgtc | 540 |
| agcgttggta tttcacattc aatggagctg aatgttcagg acctcttccc attgaagcta | 600 |
| taatttattt ggaccaagga agccctgaaa tgaattcaac aattaatatt catcgcactt | 660 |
| cttctgtgga aggactttgt gaaggaattg gtgctggatt agtggatgtt gctatctggg | 720 |
| ttggtacttg ttcagattac ccaaaaggag atgcttctac tggatggaat tcagtttctc | 780 |
| gcatcattat tgaagaacta ccaaaataaa tgctttaatt ttcatttgct acctcttttt | 840 |
| ttattatgcc ttggaatggt tcacttaaat gacattttaa ataagtttat gtatacatct | 900 |
| gaatgaaaag caaagctaaa tatgttaca gaccaaagtg tgatttcaca ctgtttttaa | 960 |
| atctagcatt attcattttg cttcaatcaa agtggtttc aatattttttt ttagttggtt | 1020 |
| agaatacttt cttcatagtc acattctctc aacctataat ttggaatatt gttgtggtct | 1080 |
| tttgtttttt ctcttagtat agcattttta aaaaatata aaagctacca atctttgtac | 1140 |
| aatttgtaaa tgttaagaat ttttttttata tctgttaaat aaaaattatt tccaacaacc | 1200 |
| ttaatatctt taaa | 1214 |

<210> SEQ ID NO 21
<211> LENGTH: 618
<212> TYPE: DNA
<213> ORGANISM: Homo sapiens

<400> SEQUENCE: 21

| | |
|---|---|
| gcggccgcaa gctcggcact cacggctctg agggctccga cggcactgac ggccatggcg | 60 |
| cgttcgaacc tcccgctggc gctgggcctg gccctggtcg cattctgcct cctggcgctg | 120 |
| ccacgcgacg cccgggcccg gccgcaggag cgcatggtcg gagaactccg ggacctgtcg | 180 |
| cccgacgacc cgcaggtgca gaaggcggcg caggcggccg tggccagcta caacatgggc | 240 |

| | |
|---|---|
| agcaacagca tctactactt ccgagacacg cacatcatca aggcgcagag ccagctggtg | 300 |
| gccggcatca agtacttcct gacgatggag atggggagca cagactgccg caagaccagg | 360 |
| gtcactggag accacgtcga cctcaccact tgccccctgg cagcaggggc gcagcaggag | 420 |
| aagctgcgct gtgactttga ggtccttgtg gttccctggc agaactcctc tcagctccta | 480 |
| aagcacaact gtgtgcagat gtgataagtc cccgagggcg aaggccattg ggtttggggc | 540 |
| catggtggag ggcacttcag gtccgtgggc cgtatctgtc acaataaatg gccagtgctg | 600 |
| cttcttgcaa aaaaaaaa | 618 |

<210> SEQ ID NO 22
<211> LENGTH: 2324
<212> TYPE: DNA
<213> ORGANISM: Homo sapiens

<400> SEQUENCE: 22

| | |
|---|---|
| gtaggtgtca cttatatcac aaggctacag gtgtctttat ttccactgca cgctggtgct | 60 |
| gggagcgcct gccttctctt gccttgaaag cctcctcttt ggacctagcc accgctgccc | 120 |
| tcacggtaat gttggactcg gtgacacaca gcaccttcct gcctaatgca tccttctgcg | 180 |
| atcccctgat gtcgtggact gatctgttca gcaatgaaga gtactaccct gcctttgagc | 240 |
| atcagacagc ctgtgactca tactggacat cagtccaccc tgaatactgg actaagcgcc | 300 |
| atgtgtggga gtggctccag ttctgctgcg accagtacaa gttggacacc aattgcatct | 360 |
| ccttctgcaa cttcaacatc agtggcctgc agctgtgcag catgacacag gaggagttcg | 420 |
| tcgaggcagc tggcctctgc ggcgagtacc tgtacttcat cctccagaac atccgcacac | 480 |
| aaggttactc cttttttaat gacgctgaag aaagcaaggc caccatcaaa gactatgctg | 540 |
| attccaactg cttgaaaaca gtggcatca aaagtcaaga ctgtcacagt catagtagaa | 600 |
| caagcctcca aagttctcat ctatgggaat ttgtacgaga cctgcttcta tctcctgaag | 660 |
| aaaactgtgg cattctggaa tgggaagata gggaacaagg aatttttcgg gtggttaaat | 720 |
| cggaagccct ggcaaagatg tggggacaaa ggaagaaaaa tgacagaatg acatatgaaa | 780 |
| agttgagcag agccctgaga tactactata aacaggaat tttggagcgg ttgaccgaa | 840 |
| ggttagtgta caaatttgga aaaaatgcac acgggtggca ggaagacaag ctatgatctg | 900 |
| ctccaggcat caagctcatt ttatggattt ctgtctttta aaacaatcag attgcaatag | 960 |
| acattcgaaa ggcttcattt tcttctcttt ttttttaacc tgcaaacatg ctgataaaat | 1020 |
| ttctccacat ctcagcttac atttggattc agagttgttg tctacggagg gtgagagcag | 1080 |
| aaactcttaa gaaatccttt cttctcccta aggggatgag gggatgatct tttgtggtgt | 1140 |
| cttgatcaaa ctttattttc ctagagttgt ggaatgacaa cagcccatgc cattgatgct | 1200 |
| gatcagagaa aaactattca attctgccat tagagacaca tccaatgctc ccatcccaaa | 1260 |
| ggttcaaaag ttttcaaata actgtggcag ctcaccaaag gtgggggaaa gcatgattag | 1320 |
| tttgcaggtt atggtaggag agggtgagat ataagacata catactttag atttaaatt | 1380 |
| attaaagtca aaatccata gaaaagtatc ctttttttt tttttgagac gggttctcac | 1440 |
| tatgttgccc agggctggtc ttgaactcct atgctcaagt gatcctccca cctcggcctc | 1500 |
| ccaaagtact gtgattacaa gcgtgagcca cggcacctgg gcagaaaagt atcttaatta | 1560 |
| atgaaagagc taagccatca agctgggact taattggatt taacataggt tcacagaaag | 1620 |
| tttcctaacc agagcatctt tttgaccact cagcaaaact tccacagaca tccttctgga | 1680 |
| cttaaacact taacattaac cacattatta attgttgctg agtttattcc cccttctaac | 1740 |

| | | | |
|---|---|---|---|
| tgatggctgg | catctgatat | gcagagttag tcaacagaca ctggcatcaa ttacaaaatc | 1800 |
| actgctgttt | ctgtgattca | agctgtcaac acaataaaat cgaaattcat tgattccatc | 1860 |
| tctggtccag | atgttaaacg | tttataaaac cggaaatgtc ctaacaactc tgtaatggca | 1920 |
| aattaaattg | tgtgtctttt | ttgttttgtc tttctacctg atgtgtattc aagcgctata | 1980 |
| acacgtattt | ccttgacaaa | aatagtgaca gtgaattcac actaataaat gttcataggt | 2040 |
| taaagtctgc | actgacattt | tctcatcaat cactggtatg taagttatca gtgactgaca | 2100 |
| gctaggtgga | ctgcccctag | gacttctgtt tcaccagagc aggaatcaag tggtgaggca | 2160 |
| ctgaatcgct | gtacaggctg | aagacctcct tattagagtt gaacttcaaa gtaacttgtt | 2220 |
| ttaaaaaatg | tgaattactg | taaaataatc tattttggat tcatgtgttt tccaggtgga | 2280 |
| tatagtttgt | aaacaatgtg | aataaagtat ttaacatgta aaaa | 2324 |

<210> SEQ ID NO 23
<211> LENGTH: 1166
<212> TYPE: DNA
<213> ORGANISM: Homo sapiens

<400> SEQUENCE: 23

| | | | |
|---|---|---|---|
| gctccgggaa | tttccctggc | ccggccgctc cgggctttcc agtctcaacc atgcataaaa | 60 |
| agggttcgcc | gatcttgggg | agccacacag cccgggtcgc aggcacctcc ccgccagctc | 120 |
| tcccgcttct | cgcacagctt | cccgacgcgt ctgctgagcc ccatggccca cgccacgctc | 180 |
| tccgccgccc | ccagcaatcc | ccggctcctg cgggtggcgc tgctgctcct gctcctggtg | 240 |
| gccgccagcc | ggcgcgcagc | aggagcgtcc gtggtcactg aactgcgctg ccagtgcttg | 300 |
| cagacactgc | agggaattca | cctcaagaac atccaaagtg tgaatgtaag gtcccccgga | 360 |
| ccccactgcg | cccaaaccga | agtcatagcc acactcaaga atgggaagaa agcttgtctc | 420 |
| aaccccgcat | cccccatggt | tcagaaaatc atcgaaaaga tactgaacaa ggggagcacc | 480 |
| aactgacagg | agagaagtaa | gaagcttatc agcgtatcat tgacacttcc tgcagggtgg | 540 |
| tccctgccct | taccagagct | gaaaatgaaa aagagaacag cagctttcta gggacagctg | 600 |
| gaaaggactt | aatgtgtttg | actatttctt acgagggttc tacttattta tgtatttatt | 660 |
| tttgaaagct | tgtatttaa | tattttacat gctgttattt aaagatgtga gtgtgtttca | 720 |
| tcaaacatag | ctcagtcctg | attatttaat tggaatatga tgggttttaa atgtgtcatt | 780 |
| aaactaatat | ttagtgggag | accataatgt gtcagccacc ttgataaatg acagggtggg | 840 |
| gaactggagg | tgggggggat | tgaaatgcaa gcaattagtg gatcactgtt agggtaaggg | 900 |
| aatgtatgta | cacatctatt | ttttatactt tttttttaaa aaagaatgt cagttgttat | 960 |
| ttattcaaat | tatctcacat | tatgtgttca acatttttat gctgaagttt cccttagaca | 1020 |
| ttttatgtct | tgcttgtagg | gcataatgcc ttgtttaatg tccattctgc agcgtttctc | 1080 |
| tttcccttgg | aaaagagaat | ttatcattac tgttacatt gtacaaatga catgataata | 1140 |
| aaagttttat | gaaaaaaaaa | aaaaaa | 1166 |

<210> SEQ ID NO 24
<211> LENGTH: 5189
<212> TYPE: DNA
<213> ORGANISM: Homo sapiens

<400> SEQUENCE: 24

| | | | |
|---|---|---|---|
| gggaaagtga | agaaaacaga | aaaggagagg gacagaggcc agaggacttc tcatactgga | 60 |

| | |
|---|---|
| cagaaaccga tcaggcatgg aactcccctt cgtcactcac ctgttcttgc ccctggtgtt | 120 |
| cctgacaggt ctctgctccc cctttaacct ggatgaacat cacccacgcc tattcccagg | 180 |
| gccaccagaa gctgaatttg gatacagtgt cttacaacat gttgggggtg gacagcgatg | 240 |
| gatgctggtg ggcgcccct gggatgggcc ttcaggcgac cggagggggg acgtttatcg | 300 |
| ctgccctgta gggggggccc acaatgcccc atgtgccaag gccacttag gtgactacca | 360 |
| actgggaaat tcatctcatc ctgctgtgaa tatgcacctg ggatgtctc tgttagagac | 420 |
| agatggtgat gggggattca tggcctgtgc ccctctctgg tctcgtgctt gtggcagctc | 480 |
| tgtcttcagt tctgggatat gtgcccgtgt ggatgcttca ttccagcctc agggaagcct | 540 |
| ggcacccact gcccaacgct gcccaacata catggatgtt gtcattgtct tggatggctc | 600 |
| caacagcatc taccctggt ctgaagttca gaccttccta cgaagactgg tagggaaact | 660 |
| gtttattgac ccagaacaga tacaggtggg actggtacag tatggggaga gccctgtaca | 720 |
| tgagtggtcc ctgggagatt ccgaacgaa ggaagaagtg gtgagagcag caaagaacct | 780 |
| cagtcggcgg gagggacgag aaacaaagac tgcccaagca ataatggtgg cctgcacaga | 840 |
| agggttcagt cagtcccatg ggggccgacc cgaggctgcc aggctactgg tggttgtcac | 900 |
| tgatggagag tccatgatg gagaggagct tcctgcagca ctaaaggcct gtgaggctgg | 960 |
| aagagtgaca cgctatggga ttgcagtcct tggtcactac ctccggcggc agcgagatcc | 1020 |
| cagctctttc ctgagagaaa ttagaactat tgccagtgat ccagatgagc gattcttctt | 1080 |
| caatgtcaca gatgaggctg ctctgactga cattgtggat gcactaggag atcggatttt | 1140 |
| tggccttgaa gggtcccatg cagaaaacga aagctccttt gggctggaaa tgtctcagat | 1200 |
| tggtttctcc actcatcggc taaggatgg gattctttt gggatggtgg gggcctatga | 1260 |
| ctggggaggc tctgtgctat ggcttgaagg aggccaccgc ctttcccccc cacgaatggc | 1320 |
| actggaagac gagttccccc ctgcactgca gaaccatgca gcctacctgg ttactctgt | 1380 |
| ttcttccatg cttttgcggg gtggacgccg cctgttctc tctggggctc ctcgatttag | 1440 |
| acatcgagga aaagtcatcg ccttccagct taagaaagat ggggctgtga gggttgccca | 1500 |
| gagcctccag ggggagcaga ttggttcata ctttggcagt gagctctgcc cattggatac | 1560 |
| agatagggat ggaacaactg atgtcttact tgtggctgcc cccatgttcc tgggaccca | 1620 |
| gaacaaggaa acaggacgtg tttatgtgta tctggtaggc cagcagtcct tgctgaccct | 1680 |
| ccaaggaaca cttcagccag aaccccccca ggatgctcgg tttggctttg ccatgggagc | 1740 |
| tcttcctgat ctgaaccaag atggttttgc tgatgtggct gtgggggcgc tctggaaga | 1800 |
| tgggcaccag ggagcactgt acctgtacca tggaacccag agtggagtca ggccccatcc | 1860 |
| tgcccagagt attgctgctg cctccatgcc acatgccctc agctactttg gccgaagtgt | 1920 |
| ggatggtcgg ctagatctgg atggagatga tctggtcgat gtggctgtgg gtgcccaggg | 1980 |
| ggcagccatc ctgctcagct cccggcccat tgtccatctg accccatcac tggaggtgac | 2040 |
| cccacaggcc atcagtgtgg ttcagaggga ctgtaggcgg cgaggccaag aggcagtctg | 2100 |
| tctgactgca gcccttgct tccaagtgac ctcccgtact cctggtcgct gggatcacca | 2160 |
| attctacatg aggttcaccg catcactgga tgaatggact gctggggcac gtgcagcatt | 2220 |
| tgatggctct ggccagaggt gtccctcg gaggctccgg ctcagtgtgg ggaatgtcac | 2280 |
| ttgtgagcag ctacacttcc atgtgctgga tacatcagat tacctccggc cagtggcctt | 2340 |
| gactgtgacc tttgccttgg acaatactac aaagccaggg cctgtgctga atgagggctc | 2400 |
| acccacctct atacaaaagc tggtcccctt ctcaaaggat tgtggccctg acaatgaatg | 2460 |

-continued

```
tgtcacagac ctggtgcttc aagtgaatat ggacatcaga ggctccagga aggccccatt    2520
tgtggttcga ggtggccggc ggaaagtgct ggtatctaca actctggaga acagaaagga    2580
aaatgcttac aatacgagcc tgagtctcat cttctctaga aacctccacc tggccagtct    2640
cactcctcag agagagagcc caataaaggt ggaatgtgcc gccccttctg ctcatgcccg    2700
gctctgcagt gtggggcatc ctgtcttcca gactggagcc aaggtgacct ttctgctaga    2760
gtttgagttt agctgctcct ctctcctgag ccaggtcttc gtgaagctga ctgccagcag    2820
tgacagcctg gagagaaatg ggaccccttca agataacaca gcccagacct cagcctacat    2880
ccaatatgag ccccacctcc tgttctctag tgagtctacc ctgcaccgct atgaggttca    2940
cccatatggg accctcccag tgggtcctgg cccagaattc aaaaccactc tcagggttca    3000
gaacctaggc tgctatgtgg tcagtggcct catcatctca gccctccttc cagctgtggc    3060
ccatgggggc aattacttcc tatcactgtc tcaagtcatc actaacaatg caagctgcat    3120
agtgcagaac ctgactgaac ccccaggccc acctgtgcat ccagaggagc ttcaacacac    3180
aaacagactg aatgggagca atactcagtg tcaggtggtg aggtgccacc ttgggcagct    3240
ggcaaagggg actgaggtct ctgttggact attgaggctg gttcacaatg aattttttccg    3300 aagagccaag ttcaagtccc tgacggtggt cagcaccttt gagctgggaa ccgaagaggg    3360
cagtgtccta cagctgactg aagcctcccg ttggagtgag agcctcttgg aggtggttca    3420
gacccggcct atcctcatct ccctgtggat cctcataggc agtgtcctgg gagggttgct    3480
cctgcttgct ctccttgtct tctgcctgtg gaagcttggc ttctttgccc ataagaaaat    3540
ccctgaggaa gaaaaagag aagagaagtt ggagcaatga atgtagaata agggtctaga    3600
aagtcctccc tggcagcttc ttcaagagac ttgcataaaa gcagaggttt gggggctcag    3660
atgggacaag aagccgcctc tggactatct ccccagacca gcagcctgac ttgacttttg    3720
agtcctaggg atgctgctgg ctagagatga ggctttacct cagacaagaa gagctggcac    3780
caaaactagc catgctccca ccctctgctt ccctcctcct cgtgatcctg gttccatagc    3840
caacactggg gcttttgttt ggggtccttt tatccccagg aatcaataat ttttttgcct    3900
aggtgcctga ctcctttcag attccctctt tatcttccct cacagtttgg aaaggatgag    3960
ggttatcttc ctcgattctt ccaccctctc actttcctgc ctgttcccca ctccacagga    4020
gggagctgac gttggcttga aaggagtaaa gtcaacatct gctgctttcc tgtggactct    4080
ggtgattcat agagccggat ggggagagtc aacaggaaaa aaggagggag gaggaaaagc    4140
cacaagagac attctgtaca attccaagga acagagaagc ctttagacag gcaactgcca    4200
tcccccctga aacctgagac ctgtagtgca ctcgaccgcc ctcaggtgtt ggtgaaacag    4260
agctgccccc aggctcgctg gcataggctt cctgattcc aagcctttttc tgggagcaaa    4320 gccagggcct ggtgcctgat tttctgaagc caggagccct caggtggctg gagctggaat    4380
agcagggagg actgggtgta cctaggcagt attttctcta cttctctcaa gtcttatact    4440
cactcttgag ccctccttgg ggcctgctta gaaagcagac aggagagaga gtactgctac    4500
ttgatgatgg gaaatgcttt cactttacca gctttgggaa gcagcagccc catgggatct    4560
aaaagtgtgg agtctgcatt aagaaaccta catggtggc atgggctct ggggagcaag    4620 cccttacttg ctcagcactg gttatgtagc acaaatagct cctaggaaaa tgtttctggg    4680
gcaaccctag aaccctggtc atattttgca gggtttctct ggtggaatca gtttgccagc    4740
ccttgcttga tgcttactgg aaatctccag gttaatttct atctctgatc cctccccaac    4800
```

| | |
|---|---:|
| ccactccata tttgggtcat ggacagtaaa ggcagttgga ttctcataga caactgggta | 4860 |
| acttatattt ctttgtaatc aagacttgag atatcgaagt cagttattgg tctccagagt | 4920 |
| gcagctctgg gagccttttg aagaatcagc actcattaag agctgagaag agagaagacc | 4980 |
| tgattgggtg gttgactagc agtcacagaa cctgtcctcc caggctgttc ctgaggcctg | 5040 |
| accacagtat ttattttggc atgtctctgg ccttctgcag aggcccaccc tcatgggcat | 5100 |
| tgtctctgtt tcccagtggg gtggacagta tatcagatgg tcagaacaaa taaagttcag | 5160 |
| tgtcaaatga aaaaaaaaaa aaaaaaaa | 5189 |

<210> SEQ ID NO 25
<211> LENGTH: 2005
<212> TYPE: DNA
<213> ORGANISM: Homo sapiens

<400> SEQUENCE: 25

| | |
|---|---:|
| tttcctctca gggggcagca ggaagtgagg agaaagggct gggatgggag gcgggagcgg | 60 |
| atgggaggga atggggttta tcaagtcctc ggcgagctgc ccaacgggca gcagctggcg | 120 |
| caagtagcct agctggagag gctcacccca ggaaggaggg aggccaccga cctactgggc | 180 |
| cgacggactc ccacacagtt cctgagctgg tgccaggcag gtgacacctc ctgcagcccc | 240 |
| cagcatgcgg gcaggcccag gccccaccgt tacattggcc ctggtgctgg cggtgtcatg | 300 |
| ggccatggag ctcaagccca cagcaccacc catcttcact ggccggccct tgtggtagc | 360 |
| gtgggacgtg cccacacagg actgtggccc acgcctcaag gtgccactgg acctgaatgc | 420 |
| cttttgatgtg caggcctcac ctaatgaggg ttttgtgaac cagaatatta ccatcttcta | 480 |
| ccgcgaccgt ctaggcctgt atccacgctt cgattctgcc ggaaggtctg tgcatggtgg | 540 |
| tgtgccacag aatgtcagcc tttgggcaca ccggaagatg ctgcagaaac gtgtggagca | 600 |
| ctacattcgg acacaggagt ctgcggggct ggcggtcatc gactgggagg actggcgacc | 660 |
| tgtgtgggtc cgcaactggc aggacaaaga tgtgtatcgc cggttatcac gccagctagt | 720 |
| ggccagtcgt caccctgact ggcctccaga ccgcatagtc aaacaggcac aatatgagtt | 780 |
| tgagttcgca gcacagcagt tcatgctgga gacactgcgt tatgtcaagg cagtgcggcc | 840 |
| ccggcacctc tggggcttct acctctttcc tgactgctac aatcatgatt atgtgcagaa | 900 |
| ctgggagagc tacacaggcc gctgccctga tgttgaggtg gcccgcaatg accagctggc | 960 |
| ctggctgtgg gctgagagca cggccctctt cccgtctgtc tacctggacg agacacttgc | 1020 |
| ttcctcccgc catggccgca actttgtgag cttccgtgtt caggaggccc ttcgtgtggc | 1080 |
| tcgcacccac catgccaacc atgcactccc agtctacgtc ttcacacgac ccacctacag | 1140 |
| ccgcaggctc acgggctta gtgagatgga cctcatctct accattggcg agagtgcggc | 1200 |
| cctgggcgca gctggtgtca tcctctgggg tgacgcgggg tacaccacaa gcacggagac | 1260 |
| ctgccagtac ctcaaagatt acctgacacg gctgctggtc ccctacgtgg tcaatgtgtc | 1320 |
| ctgggccacc caatattgca gccgggccca gtgccatggc catgggcgct gtgtgcgccg | 1380 |
| caaccccagt gccagtacct tcctgcatct cagcaccaac agtttccgcc tagtgcctgg | 1440 |
| ccatgcacct ggtgaacccc agctgcgacc tgtgggggag ctcagttggg ccgacattga | 1500 |
| ccacctgcag acacacttcc gctgccagtg ctacttgggc tggagtggtg agcaatgcca | 1560 |
| gtggaccat aggcaggcag ctggaggtgc cagcgaggcc tggctgggt cccacctcac | 1620 |
| cagtctgctg gctctggcag ccctggcctt tacctggacc ttgtaggggt ctcctgccta | 1680 |
| gctgcctagc aagctggcct ctaccacaag ggctctctta ggcatgtagg accctgcagg | 1740 |

| | |
|---|---|
| gggtggacaa actggagtct ggagtgggca gagcccccag gaagcccagg agggcatcca | 1800 |
| taccagctcg cacccccctg ttctaagggg gaggggaagt ccctgggagg cccttctct | 1860 |
| ccctgccaga ggggaaggag ggtacagctg ggctggggag gacctgaccc tactcccttg | 1920 |
| ccctagatag tttattatta ttattatttt ggggtctctt ttgtaaatta aacataaaac | 1980 |
| aattgcttct ctgcttggat tttgt | 2005 |

<210> SEQ ID NO 26
<211> LENGTH: 5802
<212> TYPE: DNA
<213> ORGANISM: Homo sapiens

<400> SEQUENCE: 26

| | |
|---|---|
| tttatagcag cagtagaaat ataccaccct agaggacaca cctccttta gctaggtacc | 60 |
| tataaatgtc caggattttc tattcaattg agaagaaccc agcaaaatgg ggatctccac | 120 |
| agtcatcctt gaaatgtgtc ttttatgggg acaagttcta tctacaggtg ggtggatccc | 180 |
| aaggactaca gactacgctt cactgattcc ctcggaggtg cccttggatc caactgtagc | 240 |
| agaaggttct ccatttccct cggagtcgac cctggagtca actgtagcag aaggttctcc | 300 |
| gatttccttg gagtcaaccc tggagtcaac cgtagcagaa ggttctctga ttccctcaga | 360 |
| gtcaaccctg gagtcaactg tagcagaagg atctgattct ggtttggccc tgaggctggt | 420 |
| gaatggagat ggcaggtgtc agggccgagt ggagatccta taccgaggct cctggggcac | 480 |
| cgtgtgtgat gacagctggg acaccaatga tgccaacgtg gtctgtaggc agctgggttg | 540 |
| tggctgggcc atgtcagctc caggaaatgc ctggtttggc cagggctcag gacccattgc | 600 |
| cctggatgat gtgcgctgct caggacacga atcctacctg tggagctgcc ccacaatgg | 660 |
| ctggctctcc cataactgtg gccatggtga agatgctggt gttatctgct cagctgccca | 720 |
| gcctcagtca acactcaggc cagaaagttg gcctgtcagg atatcaccac ctgtacccac | 780 |
| agaaggatct gaatccagtt tggccctgag gctggtgaat ggaggcgaca ggtgtcgagg | 840 |
| ccgagtggag gtcctatacc gaggctcctg gggcaccgtg tgtgatgact actgggacac | 900 |
| caatgatgcc aatgtggtct gcaggcagct gggctgtggc tgggccatgt cagccccagg | 960 |
| aaatgcccag tttggccagg gctcaggacc cattgtcctg gatgatgtgc gctgctcagg | 1020 |
| acatgagtcc tacctgtgga gctgcccca caatggctgg ctcacccaca actgtggcca | 1080 |
| tagtgaagac gctggtgtca tctgctcagc tccccagtcc cggccgacac ccagcccaga | 1140 |
| tacttggccc acctcacatg catcaacagc aggacctgaa tccagtttgg ccctgaggct | 1200 |
| ggtgaatgga ggtgacaggt gtcagggccg agtggaggtc ctataccgag gctcctgggg | 1260 |
| caccgtgtgt gatgatagct gggacaccag tgacgccaat gtggtctgcc ggcagctggg | 1320 |
| ctgtggctgg gccacgtcag ccccaggaaa tgcccggttt ggccagggtt caggacccat | 1380 |
| tgtcctggat gacgtgcgct gctcaggcta tgagtcctac ctgtggagct gccccacaa | 1440 |
| tggctggctc tcccataact gtcagcacag tgaagacgct ggtgtcatct gctcagctgc | 1500 |
| ccactcctgg tcgacgccca gtccagacac attgccgacc atcaccttgc ctgcatcgac | 1560 |
| agtaggatct gaatccagtt tggccctgag gctggtgaat ggaggtgaca ggtgtcaggg | 1620 |
| ccgagtggag gtcctatacc aaggctcctg gggcaccgtg tgcgatgaca gctgggacac | 1680 |
| caatgatgcc aatgtcgtct gcaggcaact gggctgtggc tgggccatgt cagccccagg | 1740 |
| aaatgcccgg tttggtcagg gctcaggacc cattgtcctg gatgatgtgc gctgctcagg | 1800 |

```
acacgagtct tacctgtgga gctgccccca caatggctgg ctctcccaca actgtggcca    1860
tagtgaagac gctggtgtca tctgctcagc ttcccagtcc cggccaacac ctagtccaga    1920
cacttggcca acctcacatg catcaacagc aggatctgaa tccagtttgg ccctgaggct    1980
ggtgaatgga ggtgacaggt gtcagggccg agtggaggtc ctataccgag gctcctgggg    2040
caccgtgtgt gatgactact gggacaccaa tgatgccaat gtggtttgca ggcagctggg    2100
ctgtggctgg gccatgtcag ccccaggaaa tgcccggttt ggccagggtt caggacccat    2160
tgtcctggat gatgtgcgct gctcaggaca tgagtcctat ctgtggagct gcccccacaa    2220
tggctggctc tcccacaact gtggccatca tgaagacgct ggtgtcatct gctcagcttc    2280
ccagtcccag ccgacaccca gcccagacac ttggccaacc tcacatgcat caacagcagg    2340
atctgaatcc agtttggccc tgaggctggt gaatggaggt gacaggtgtc agggccgagt    2400
ggaggtccta taccgaggct cctggggcac cgtgtgtgat gactactggg acaccaatga    2460
tgccaatgtg gtttgcaggc agctgggctg tggctgggcc acgtcagccc aggaaatgc    2520
ccggtttggc cagggttcag gacccattgt cctggatgat gtgcgctgct caggacatga    2580
gtcctatctg tggagctgcc ccacaatggg ctggctctcc cacaactgtg gccatcatga    2640
agacgctggt gtcatctgct cagcttccca gtcccagccg acacccagcc cagacacttg    2700
gccaacctct cgtgcatcaa cagcaggatc tgaatccact ttggccctga ctggtgaa    2760
tggaggtgac aggtgtcgag gccgagtgga ggtcctatac caaggctcct ggggcaccgt    2820
gtgtgatgac tactgggaca ccaatgatgc caacgtggtc tgcaggcagc tgggctgtgg    2880
ctgggccatg tcagccccag gaaatgccca gtttggccag gctcaggac ccattgtcct    2940
ggatgatgtg cgctgctcag gacacgagtc ttacctgtgg agctgccccc acaatggctg    3000
gctctcccac aactgtggcc atcatgaaga tgctggtgtc atctgctcag ctgctcagtc    3060
ccagtcaacg cccaggccag atacttggct gaccaccaac ttaccggcat tgacagtagg    3120
atctgaatcc agtttggctc tgaggctggt gaatggaggt gacaggtgtc gaggccgagt    3180
ggaggtcctg tatcgaggct cctggggaac cgtgtgtgat gacagctggg accaatga    3240
tgccaatgtg gtctgcaggc agctgggctg tggctgggcc atgtcggccc aggaaatgc    3300
ccggtttggc cagggctcag gacccattgt cctggatgat gtgcgctgct cagggaatga    3360
gtcctacctg tggagctgcc ccacaaaggc tggctcacc cacaactgtg gccatcacga    3420
agacgctggt gtcatctgct cagccaccca aataaattct actacgacag attggtggca    3480
tccaacaact acaaccactg caagaccctc ttcaaattgt ggtggcttct tattctatgc    3540
cagtgggaca ttctccagcc catcctaccc tgcatactac cccaacaatg ctaagtgtgt    3600
ttggaaaata gaagtgaatt ctggttatcg cataaacctg gcttcagta atctgaaatt    3660
ggaggcacac cataactgca gttttgatta tgttgaaatc tttgatggat cattgaatag    3720
cagtctcctg ctggggaaaa tctgtaatga taccaggcaa atatttacat cttcttacaa    3780
ccgaatgacc attcactttc gaagtgacat cagtttccaa acactggct ttttggcttg    3840
gtataactcc ttcccaagcg atgccacctt gaggttggtc aatttaaatt catcctatgg    3900
tctatgtgcc gggcgtgtag aaatttacca tggtggcacc tggggacag tttgtgatga    3960
ctcctggacc attcaggaag ctgaggtggt ctgcagacag ctagggtgtg acgtgcagt    4020
ttcagccctt ggaaatgcat attttggctc tggctctggc cccatcaccc tggacgatgt    4080
agagtgctca gggacggaat ccactctctg gcagtgccgg aaccgaggct ggttctccca    4140
caactgtaat catcgtgaag atgctggtgt catctgctca ggaaaccatc tatcgacacc    4200
```

```
tgctcctttt ctcaacatca cccgtccaaa cacagattat tcctgcggag gcttcctatc    4260
ccaaccatca ggggactttt ccagcccatt ctatcccggg aactatccaa acaatgccaa    4320
gtgtgtgtgg gacattgagg tgcaaaacaa ctaccgtgtg actgtgatct tcagagatgt    4380
ccagcttgaa ggtggctgca actatgatta tattgaagtt ttcgatggcc cctaccgcag    4440
ttcccctctc attgctcgag tttgtgatgg ggccagaggc tccttcactt cttcctccaa    4500
cttcatgtcc attcgcttca tcagtgacca cagcatcaca aggagagggt tccgggctga    4560
gtactactcc agtccctcca atgacagcac caacctgctc tgtctgccaa atcacatgca    4620
agccagtgtg agcaggagct atctccaatc cttgggcttt tctgccagtg accttgtcat    4680
ttccacctgg aatggatact acgagtgtcg gccccagata acgccgaacc tggtgatatt    4740
cacaattccc tactcaggct gcggcacctt caagcaggca gacaatgaca ccatcgacta    4800
ttccaacttc ctcacagcag ctgtctcagg tggcatcatc aagaggagga cagacctccg    4860
tattcacgtc agctgcagaa tgcttcagaa cacctgggtc gacaccatgt acattgctaa    4920
tgacaccatc cacgttgcta ataacaccat ccaggtcgag gaagtccagt atggcaattt    4980
tgacgtgaac atttcctttt atacttcctc atctttcttg tatcctgtga ccagccgccc    5040
ttactacgtg gacctgaacc aggacttgta cgttcaggct gaaatcctcc attctgatgc    5100
tgtactgacc ttgtttgtgg acacctgcgt ggcatcacca tactcaatg acttcacgtc    5160
tttgacttat gatctaatcc ggagtggatg cgtgagggat gacacctacg accctactc    5220
ctcgccatct cttcgcattg cccgcttccg gttcagggcc ttccacttcc tgaaccgctt    5280
cccctccgtg tacctgcgtt gtaaaatggt ggtgtgcaga gcgtatgacc cctcttcccg    5340
ctgctaccga ggctgtgtgt tgaggtcgaa gagggatgtg ggctcctacc aggaaaaggt    5400
ggacgtcgtc ctgggtccca tccagctgca gaccccccca cgccgagaag aggagcctcg    5460
gtaggtggtc gctctcagac cccactgtcc accggggcgc agaccctga ctcggggact    5520
tgggatgttc ctcttggtgt catattccaa ctcagattga gccctacatt gtgctgcacc    5580
tggtcatacg gagttgaatc agaccctggtt cccgcctccc ccaaggctca tggtccttgg    5640
aggacccgtt gcagggtgag gtcaagagag ttctgacctg gatggcccat agacctgacg    5700
tcccagaatc catgcttctc atctgcaaaa tgaaaatgtc aatacttact tcttagcact    5760
gttgagaggg ttacttacat aaaggaattt tggtgaaact gc                       5802
```

<210> SEQ ID NO 27
<211> LENGTH: 1220
<212> TYPE: DNA
<213> ORGANISM: Homo sapiens

<400> SEQUENCE: 27

```
agtcccagct cagagccgca acctgcacag ccatgcccgg gcaagaactc aggacggtga      60
atggctctca gatgctcctg gtgttgctgg tgctctcgtg gctgccgcat gggggcgccc     120
tgtctctggc cgaggcgagc cgcgcaagtt tcccgggacc ctcagagttg cactccgaag     180
actccagatt ccgagagttg cggaaacgct acgaggacct gctaaccagg ctgcgggcca     240
accagagctg ggaagattcg aacaccgacc tcgtcccggc cctgcagtc cggatactca     300
cgccagaagt gcggctggga tccggcggcc acctgcacct gcgtatctct cgggccgccc     360
ttcccgaggg gctccccgag gcctcccgcc ttcaccgggc tctgttccgg ctgtcccga     420
cggcgtcaag gtcgtgggac gtgacacgac cgctgcggcg tcagctcagc cttgcaagac     480
```

```
cccaggcgcc cgcgctgcac ctgcgactgt cgccgccgcc gtcgcagtcg gaccaactgc      540
tggcagaatc ttcgtccgca cggccccagc tggagttgca cttgcggccg caagccgcca      600
gggggcgccg cagagcgcgt gcgcgcaacg gggaccactg tccgctcggg cccgggcgtt      660
gctgccgtct gcacacggtc cgcgcgtcgc tggaagacct gggctgggcc gattgggtgc      720
tgtcgccacg ggaggtgcaa gtgaccatgt gcatcggcgc gtgcccgagc cagttccggg      780
cggcaaacat gcacgcgcag atcaagacga gcctgcaccg cctgaagccc gacacggtgc      840
cagcgccctg ctgcgtgccc gccagctaca atcccatggt gctcattcaa aagaccgaca      900
ccggggtgtc gctccagacc tatgatgact tgttagccaa agactgccac tgcatatgag      960
cagtcctggt ccttccactg tgcacctgcg cggaggacgc gacctcagtt gtcctgccct     1020
gtggaatggg ctcaaggttc ctgagacacc cgattcctgc ccaaacagct gtatttatat     1080
aagtctgtta tttattatta atttattggg gtgaccttct tggggactcg ggggctggtc     1140
tgatggaact gtgtatttat ttaaaactct ggtgataaaa ataaagctgt ctgaactgtt     1200
aaaaaaaaaa aaaaaaaaaa                                                 1220

<210> SEQ ID NO 28
<211> LENGTH: 1882
<212> TYPE: DNA
<213> ORGANISM: Homo sapiens

<400> SEQUENCE: 28
agcgctccta taagggagc caccagcgct ggaggccgct gctcgctgcg ccaccgcctc       60
ccgccacccc tgcccgcccg acagcgccgc cgcctgcccc gccatgggtc gacagaagga      120
gctggtgtcc cgctgcgggg agatgctcca catccgctac cggctgctcc gacaggcgct      180
ggccgagtgc ctggggaccc tcatcctggt gatgtttggc gtggctccg tggcccaggt      240 tgtgctcagc cggggcaccc acggtggttt cctcaccatc aacctggcct ttggcttttgc     300 tgtcactctg ggcatcctca tcgctggcca ggtctctggg gcccacctga accctgccgt      360 gaccttttgcc atgtgcttcc tggctcgtga gccctggatc aagctgccca tctacaccct      420
ggcacagacg ctgggagcct tcttgggtgc tggaatagtt tttgggctgt attatgatgc      480
aatctggcac ttcgccgaca accagctttt tgtttcgggc cccaatggca cagccggcat      540 cttttgctacc taccccctctg gacacttgga tatgatcaat ggcttctttg accagttcat      600
aggcacagcc tcccttatcg tgtgtgtgct ggccattgtt gaccctctca caacccccgt      660
cccccgaggc ctggaggcct tcaccgtggg cctggtggtc ctggtcattg gcacctccat      720
gggcttcaac tccggctatg ccgtcaaccc tgcccgggac tttggccccc gcttttttac      780
agcccttgcg ggctgggct ctgcagtctt cacgaccggc cagcattggt ggtgggtgcc      840
catcgtgtcc ccactcctgg gctccattgc gggtgtcttc gtgtaccagc tgatgatcgg      900
ctgccacctg gagcagcccc caccctccaa cgaggaagag aatgtgaagc tgcccatgt      960 gaagcacaag gagcagatct gagtgggcag gggccatctc cccactccgc tgccctggcc     1020
ttgagcatcc actgactgtc caagggccac tcccaagaag ccccctcac gatccacct     1080 ttcaggctaa ggagctccct atctaccctc accccacgag acagccccttcaggatttcc     1140 actggacctt gcccaaatag caccttaggc cactgcccct aagctgggt ggaaccggaa     1200 tttgggtcaa tacatccttt tgtctcccaa gggaagagaa tggcagcag gtatgtgtgt      1260 gtgtgcatgt gtgtgcatgt gtgtgcatgt gtgtgcaggg gtgtgtgtgt gtgggggggg     1320
ttcccagata ttcagggcaa gggaccagtc ggaagggatt ctggctattg ggggagccca     1380
```

| gagacagggg aaggcagcct gtccatctgt gcataaggag aggaaagttc cagggtgtgt | 1440 |
| atgtttcagg ggcttcacat ggaggagctg cagatagata tgtgtttctg tgtatgtgta | 1500 |
| tgtctgcctt tttttctaag tgggggcttc tacaggcttt tgggaagtag ggtggatgtg | 1560 |
| ggtagggctg ggaggagggg gccacagctt aggtttggag ctctggatgt acatacataa | 1620 |
| gtaggagcag tgggacgtgt ttctgtcata atgcaggcat aagggtgga gtgaagtcag | 1680 |
| gtcataagtt tcatgtttgc ttttgttttg ttttgttttt aatgtatgta gcagatgtta | 1740 |
| cagtcttagg gatccgggat gggagacccc actttagaaa gggtcgtcac tcctttaatc | 1800 |
| ctctactcaa caatgtactc ttttacttttt atattaaaaa aaataaaata aatatgtgcc | 1860 |
| taaaacctcc aaaaaaaaaa aa | 1882 |

```
<210> SEQ ID NO 29
<211> LENGTH: 1336
<212> TYPE: DNA
<213> ORGANISM: Homo sapiens

<400> SEQUENCE: 29
```

| gagagacaca gagtccggca ttggtcccag gcagcagtta gcccgccgcc cgcctgtgtg | 60 |
| tccccagagc catggagaga gccagtctga tccagaaggc caagctggca gagcaggccg | 120 |
| aacgctatga ggacatggca gccttcatga aaggcgccgt ggagaagggc gaggagctct | 180 |
| cctgcgaaga gcgaaacctg ctctcagtag cctataagaa cgtggtgggc ggccagaggg | 240 |
| ctgcctggag ggtgctgtcc agtattgagc agaaaagcaa cgaggagggc tcggaggaga | 300 |
| aggggcccga ggtgcgtgag taccgggaga aggtggagac tgagctccag ggcgtgtgcg | 360 |
| acaccgtgct gggcctgctg gacagccacc tcatcaagga ggccggggac gccgagagcc | 420 |
| gggtcttcta cctgaagatg aagggtgact actaccgcta cctggccgag gtggccaccg | 480 |
| gtgacgacaa gaagcgcatc attgactcag cccggtcagc ctaccaggag gccatggaca | 540 |
| tcagcaagaa ggagatgccg cccaccaacc ccatccgcct gggcctggcc ctgaactttt | 600 |
| ccgtcttcca ctacgagatc gccaacagcc ccgaggaggc catctctctg gccaagacca | 660 |
| cttttcgacga ggccatggct gatctgcaca ccctcagcga ggactcctac aaagacagca | 720 |
| ccctcatcat gcagctgctg cgagacaacc tgacactgtg gacggccgac aacgccgggg | 780 |
| aagagggggg cgaggctccc caggagcccc agagctgagt gttgcccgcc accgccccgc | 840 |
| cctgccccct ccagtccccc accctgccga gaggactagt atgggtgg aggcccacc | 900 |
| cttctcccct aggcgctgtt cttgctccaa agggctccgt ggagagggac tggcagagct | 960 |
| gaggccacct ggggctgggg atcccactct tcttgcagct gttgagcgca cctaaccact | 1020 |
| ggtcatgccc ccaccctgc tctccgcacc cgcttcctcc cgaccccagg accaggctac | 1080 |
| ttctcccctc ctcttgcctc cctcctgccc ctgctgcctc tgatcgtagg aattgaggag | 1140 |
| tgtcccgcct gtggctgag aactggacag tggcagggc tggagatggg tgtgtgtgtg | 1200 |
| tgtgtgtgtg tgtgtgtgtg tgtgcgcgcg cgccagtgca agaccgagat tgagggaaag | 1260 |
| catgtctgct gggtgtgacc atgtttcctc tcaataaagt tccctgtga cactcaaaaa | 1320 |
| aaaaaaaaaa aaaaaa | 1336 |

```
<210> SEQ ID NO 30
<211> LENGTH: 8171
<212> TYPE: DNA
<213> ORGANISM: Homo sapiens
```

```
<400> SEQUENCE: 30
gaggcagggg tgagaccggc ggccacccgt gagccctccg cacccgcacc atgcagaaga      60
gcgtgcgcta caacgagggg cacgccctgt acctggcctt tctggcgcgc aaggagggca     120
ccaagcgcgg cttcctgagt aagaagacgg ccgaggcgag ccgctggcac gagaagtggt     180
tcgccctcta ccagaatgtg ctcttctact tcgagggcga gcagagctgc cgcccggcgg     240
gcatgtacct cctggagggc tgcagctgcg aacgaacgcc cgcgccaccc agggccggcg     300
ccgggcaggg aggcgtccga gacgcgctgg acaagcagta ttactttact gttcttttttg    360 gccatgaagg tcagaagcca ctggagctgc gctgtgagga ggagcaggat ggtaaagagt     420
ggatggaggc cattcaccaa gccagttatg cagacatttt gattgagagg gaagtattaa     480
tgcagaagta cattcatcta gttcagatcg tagagacaga aaaaattgca gctaaccaac     540
tccgacatca acttgaagat caagacacag aaatcgaaag gcttaaatca gagattattg     600
ctcttaataa aaccaaagaa cgaatgcgac cttaccaaag caaccaagaa gacgaagatc     660
cagacatcaa gaagattaaa aaggttcaga gcttcatgcg aggatggttg tgcagaagga     720
aatggaagac catcgtgcag gattacattt gttctcctca tgctgaaagt atgaggaaga     780
gaaaccagat tgtgttcacc atggtggagg cagagtcaga gtacgttcac cagctctaca     840
tcctggtcaa tggctttctc cggccctgc gtatggccgc cagctccaag aagcccccca      900
tcagccacga cgacgtcagc agtatttttc ttaacagtaa aacaatcatg tttcttcatg     960
aaatatttca tcaaggacta aaggcaagga tagcaaactg gcccactttta attttagctg    1020 atctgtttga tattttgctc cccatgctga acatttatca agaatttgtg cgtaatcacc     1080
agtacagcct gcaagttctc gccaattgta agcaaaacag gattttgac aaaactcttaa     1140 aacagtatga agccaatcca gcctgtgagg ggaggatgct ggagacattc ttgacctatc     1200
ccatgtttca gatccccaga tatatcatca cactccatga gctccttgct cacacacccc     1260
atgagcatgt ggaaaggaaa agcctggagt ttgccaaatc aaagctagag gaactatcca     1320
gagtaatgca cgatgaagtc agcgacactg aaaacataag gaaaaacctt gccatcgaaa     1380
gaatgatcgt ggagggctgt gacatcttgc tggacaccag ccaaacgttc atccgccaag     1440
gttctcttat tcaagtacct tccgttgaga gggggaaact tagtaaagtt cgcctgggtt     1500
cgttgtcttt gaaaaaggaa ggagagagac aatgcttctt atttacaaaa cacttttttaa    1560 tatgtacaag aagttcagga gggaagcttc atctgctcaa gacaggtggg gttctgtctc     1620
taatagactg cacattgatt gaggagccag atgcaagcga tgatgactct aaaggttctg     1680
ggcaagtgtt tgggcacctg gattttaaaa tagtggtgga gcctcctgac gctgccgcct     1740
tcactgttgt cttgttagca ccctcacgcc aggagaaagc tgcctggatg agtgacatca     1800
gtcagtgtgt ggacaatata cgatgtaatg gtttaatgac tatagtgttt gaagagaatt     1860
ccaaagtcac tgtgccacat atgattaagt ctgatgcccg tcttcataaa gacgacactg     1920
acatttgctt cagtaaaaca ctcaactcct gcaaagtgcc ccagatccgt tatgccagcg     1980
tggagcgcct cttggaacga ctgacagact tgcggtttct tagtattgat ttcctcaaca     2040
cctttctgca cacctatcgt attttcacta ctgccgctgt ggtgctgggg aaactctccg     2100
acatatacaa gaggcctttc acctccatcc ctgtcaggtc attggaattg tttttttgcta    2160 ccagccagaa caacagaggt gaacatttgg tggatggcaa atccccacgt ctgtgtcgca     2220
aattctcttc cccgccacca ctggctgtgt ccagaacatc ttccccagtg agggccagaa     2280 agctgtctttt gacttctccc ttgaactcaa agataggagc attggacctg acaacttcca    2340
```

```
gcagtcccac caccaccacc cagagtcccg ctgcgtctcc accaccacac actggtcaga    2400
taccactgga tctcagcaga ggcctctctt ctccagagca aagcccggga acggtagaag    2460
agaatgtcga taacccacgc gtggatctgt gtaacaagct aaaacgaagt attcaaaaag    2520
cagtcctaga gtctgcacca gcggaccgag caggagtgga aagctcccct gcagcggaca    2580
ccacagaact ttcaccttgc agatccccct caactcctcg gcacctccgc tatcgacagc    2640
ctggaggaca gacggcggac aatgcccact gctctgtttc accggcttct gcttttgcaa    2700
tagccacagc tgcagcagga catgggagtc caccaggctt aacaacacc  gagagaacat    2760 gtgataaaga gtttattata cggagaacgg ctaccaatcg agttctgaac gtcctccgtc    2820
actgggtctc aaagcacgca caggatttcg aactcaacaa tgaactaaag atgaatgtcc    2880
taaatttgct agaagaagtt ttgcgagacc cagaccttct tccccaagaa aggaaagccg    2940
ccgcgaatat cctcagggcc ctttcacaag atgaccaaga tgacatccac ctaaaattag    3000
aggatataat tcaaatgact gactgcatga aggccgaatg ctttgagtcc ttgtcggcca    3060
tggagctggc agaacagatc accctcctgg accatgtcat tttcagaagc attccctacg    3120
aggagtttct tgggcagggg tggatgaagc tggataaaaa cgaaagaact ccttacatta    3180
tgaaaaccag ccaacacttc aatgacatga gtaacctggt ggcctcccag ataatgaact    3240
atgctgatgt cagctcccgt gccaacgcca tcgagaaatg ggtggcagtg gcggacatct    3300
gccgatgcct gcacaactac aacggcgtgc tggagatcac ctcggcctta aacagaagtg    3360
ccatctacag gctgaagaaa acctgggcca aggtctctaa gcagacaaaa gctctaatgg    3420
acaaacttca aaagactgtt tcctctgaag gaagatttaa aaatcttaga gaaacccta    3480 aaaattgtaa ccctcctgca gttccttatc ttgggatgta cttgacagac ctggcattta    3540
ttgaagaagg aacaccaaac tttactgagg aaggccttgt caatttctcc aaaatgagaa    3600
tgatatcaca catcatcaga gagatacgcc agttccagca gcttcctac  agaatagatc    3660 atcagccaaa ggtcgcacag tacttgcttg acaaagacct tatcatagat gaagatacgc    3720
tatatgagct gtcactaaaa attgaacctc gactccctgc ttgaagatct ggccttgccc    3780
ctgagtccac gggatgttca tggaaagcag gacagacaga attgtgtatg ccttgcctat    3840
cacggtacag cacgaagcca ggctcctttc tccaccaaag aagatggaac cagactggaa    3900
ttctgtctcc agagagaaac ccagctgttt gggtcaaaga cagatgcttc agacttgggt    3960
gggaaggtga agatggcta  tttagaaagc tggtggcacg ttttacataa gggaatgtca    4020
gatgggagat gctagttgcc attttaacaa agcaggtaaa tcggtaaatt ttaaactctg    4080
tccatgttct gttagaactc agggacaagg atccatgaaa aagacctgtg atgtttctct    4140
ggcgctttac tggcctgggc acacctacca atccttctagg atttgactgg ttccattaca    4200
tttccttttg gtataagctt cacagaaaag ctgacacttc ctctacagag atggaccaaa    4260
acataagcaa tttcagtcta cagcatgtgc atggttgtca gtgcattcta aatatttcta    4320
tgtgaggaat ggtaccttct gaaactgcct ttccagtctt taggcaatgg gataggaaag    4380
aaagaatgaa acacaaatgg atttgtatgt aacatttcct taattaaatg cagtaggctg    4440
tgccccagag gattccagac agtggctggc tgaggtgggt ggggagcttt ccttgagac     4500 tgttggtcct aagaagccag ccctttggga gaggcagctg caaaaaggtg cacgcccatc    4560
tcaccgacaa aactgtggaa cagaaggcca ccaagtgctg tggggaatca tgggtttcag    4620
tgctgagtga aaatctatac ctaaaaatca tctctgcacc ttgctttgtt tgttttcttt    4680
```

```
ccccactcat agtactgcag gaatctattc tcatttacac agaccttttt ttaggcttac    4740
tatgaacatt ggctgtatt tttttaaaca gtttagtgaa attttctttt caaaacccac    4800
acttccatat gctgttcgta gatctctttc tttaaaaact gatgttgaga gatctctgag    4860
aatattataa gtgcatggga aatgggccca accaccgaac agctcttaca ttacaaaacc    4920
aaatgcaagg gttagtcctg ctacctgagg ctggggaagt gaccttcctt ttcccaagat    4980
tgtcagttgt tgaagaaata gggctatctc attgtttacc tccctcttct cttctcaggg    5040
agactgctgc tttaaaagaa ggaagagaaa aaatatagtt ctatttccct gaacctgttg    5100
cacctgacat tttctcttag cagcatgaaa cttattgatg ctgacaatga aaaatggatc    5160
tgtctggctg ctttccctct ttccttgcac tttaattatg ttgctagagc taacagacta    5220
ataaattcca cctgctggct cttaagactc agtgaaagag ctagcattgg taatgcacca    5280
tagaggtaga gaatgtacac tttctgcacg gtaagtgcca tctctgtatg taactatata    5340
gtgaaatatc aactaagtaa aagaaaatat aatatttgaa gaccattccc aaaatatttt    5400
caatagttca tattagccaa cagtgtagca ctcaacccaa ggagggttcc ttatggatgc    5460 tttcttttc tttttaaag ttgcttgttt gttctcttta gtttcaaata agaggttgac     5520
gcatcttgat gcatgatgag aagcatgggc tgtttggatc ctaacaacgc ataacttgtg    5580
atttatttct cagtgctcca gaaactgagg gtttgaaata atatgtatca gttgcaccaa    5640
acacctcaag gtcttgcaga agaaaagtaa aggttagctt tcatggctca aaagcatagt    5700
cctgaagggt gaactaaaac cgggacaaat ctgtgagagg accacacaca tactagtttc    5760
gggccaaaca cacgtggaa aggtgcatgc attctactct gccttggagt tgccagagtc     5820
cttcagaggg aaagggatgg ttctgtgtgc acttttctg gaagttcgga ctcatttctt     5880
tgacccaaat gttccagaga cactgcagcc attcttatta acaaaaaata agacaggagt    5940
ttccaaatgc tccttccctt ttggatcgca gcttttcttc aactagtgac aaagcttttg    6000
cgcctatttc ctgcaggatg ttggaactgc cccgcactgg tcatattagg cactgtcaat    6060
tgctatgctg acttttaggg ggttttgtt tgtttgaaaa acagggtctc accatgttgc     6120
ccaggctggt ctcgaactcc tggactcaag caatcttcct gcctcagcct ctcaagcagc    6180
tgggactgca ggggtgtgcc actcactagc cttcgcatt tttgtttgag aattacacca     6240
ctttctggag tctgcagcct tcctggagct gcaagagggc aagagagaga gctccacctc    6300
tgagggagtg tctgttgatg acctgcacta ttcgtgtgcc agctgggaga ggaatgcaca    6360
ttttaaaatc ccttcaattt ggtcaaatta aaaatcccca agagcaattt gcagtgtttt    6420
ttctggtcgt taaagtaccc atcctcttct gcctacacac aaagcatgca ttcccagctg    6480
catctgcctc tagtccatta tggagaccca tttctaagag gagatgggag gtcaacctct    6540
aacagccaag tagcgaacat gtatactgta aaattaacct agaaaatcag aagaaaaatc    6600
caatttcatg ctttcgaatg aatgcccaca ttttgtactg tcaacgaaat tatcttggag    6660
cttttagggg atgccttttc gttattaact gagacatcta gttttgctac agggacaaat    6720
ctcttaccta atccaatata ttatttgaca gattcaggca tgaagtaaaa cgtcgtcact    6780
tttccttagt gcttttctga aggaatttaa agacggaatt ttaaacggcc attgcaatat    6840
tttcaagtgg ctctcatacc aagtcccatt actgtttgtt aaatttcagt acgtcttaaa    6900
gtactactta taaacaaatg aaactcagag aaactgaatc acctggaaga gaaaaatcca    6960
ttatggtccc atgtggagtg aataatgatg gatcagcacc ctttctctca tgttattgta    7020
taagacgaga cttttgggcc agcagcgatt gggcagcttt taaattctta actgaaaaga    7080
```

```
gtaatgcaat acagggatta ttcccaataa aattaacttt tatttaaaag caagagattt    7140
tacttagctt ttttttttca agtttgatt ttatcccctt gaaaaaaaat ctcttcactt    7200
taaagtataa aggttttta aaatccaatt gcaaaatgta ttatttttac aactatcgaa    7260
aaggcataaa agagaacata ctatttatgg ctgaagggta tagccaggct aatgtgcaca    7320
gagggaatca ataaataaaa ctcttttca tttcagtaag aaatcagatt gtaagtttaa    7380
tggctccatt atagatacca ccgtgtaata aagacttaa gtcaatgaaa tctaatcagt    7440
gtgtcatttc tcagcggcca ttggtgactt aaaattaaga tgaggcagag ccaaaatgga    7500
aaacagtcat tttgttgtag gtataaacac atgaacgatt cagaaaatta ttcatctcag    7560
ctgccatgca gcatgacatt aacattagga ttgatagcac tagtctgatc tgctcaagga    7620
aaataatagt tctattatac ttaatgatgt tggtttttac acagctcatt tcattttca    7680 ctagaaagcc agttatgaaa gagagctggc ctaggcatcc cggccctgag tcctaggccc    7740
agtctccaac tggaaaacct taggctggtg tttacacatc cctgagcctc agtttcctca    7800
tctgcaaaac ggtgtgaata gtaatccctg tgctgcttat ctcacagggc tattgtgagg    7860
accaaatgga ttagactgta aactgcaaag tgctgtccgc acatgaggtc atctgattac    7920
tgtcctcaga tctcttttgt agaggatttc aatgtatttc tttatcattt gagtgtgtgt    7980
gtgatggacg aatatgtgtg tgagtttgag aagcatatcg ttcgtgtcca gttactttgc    8040
aaatttgtgg acatttgtga ttggacagag gggtttgtgc tgtggcctaa cacttgccaa    8100
gtgaggtgta ggttatgcct atatgcaaat taaacttcac cttcttgaa tattcaaaaa    8160 aaaaaaaaaa a                                                         8171

<210> SEQ ID NO 31
<211> LENGTH: 2089
<212> TYPE: DNA
<213> ORGANISM: Homo sapiens

<400> SEQUENCE: 31
agtttggacg gctgcttccc accagcaaag accacgactg gagagccgag ccggaggcag      60
ctgggaaaca tgaagagcgt cttgctgctg accacgctcc tcgtgcctgc acacctggtg     120
gccgcctgga gcaataatta tgcggtggac tgccctcaac actgtgacag cagtgagtgc     180
aaaagcagcc cgcgctgcaa gaggacagtg ctcgacgact gtggctgctg ccgagtgtgc     240
gctgcagggc ggggagaaac ttgctaccgc acagtctcag gcatggatgg catgaagtgt     300
ggcccggggc tgaggtgtca gccttctaat ggggaggatc cttttggtga agagtttggt     360
atctgcaaag actgtcccta cggcaccttc gggatggatt gcagagagac ctgcaactgc     420
cagtcaggca tctgtgacag ggggacggga aaatgcctga aattccccct cttccaatat     480
tcagtaacca agtcttccaa cagatttgtt tctctcacgg agcatgacat ggcatctgga     540
gatggcaata ttgtgagaga agaagttgtg aaagagaatg ctgccgggtc tcccgtaatg     600
aggaaatggt taaatccacg ctgatcccgg ctgtgatttc tgagagaagg ctctattttc     660
gtgattgttc aacacacagc caacatttta ggaactttct agattatagc ataaggacat     720 gtaattttg aagaccaaat gtgatgcatg gtggatccaa aaacaaaaa gtaggatact     780 tacaatccat aacatccata tgactgaaca cttgtatgtg tttgttaaat attcgaatgc     840
atgtagattt gttaaatgtg tgtgtatagt aacactgaag aactaaaaat gcaatttagg     900
taatcttacg tggagacagg tcaaccaaag agggagctag gcaaagctga agaccgcagt     960
```

```
gagtcaaatt agttctttga cttttgatgta cattaatgtt gggatatgga atgaagactt    1020
aagagcagga gaagatgggg aggggtggga agtgggaaat aaaatattta gcccttcctt    1080
ggtaggtagc ttctctagaa tttaattgtg ctttttttt ttttttggc tttgggaaaa    1140 gtcaaaataa aacaaccaga aaaccctga aggaagtaag atgtttgaag cttatggaaa    1200
tttgagtaac aaacagcttt gaactgagag caatttcaaa aggctgctga tgtagttccc    1260
gggttacctg tatctgaagg acggttctgg ggcataggaa acacatacac ttccataaat    1320
agctttaacg tatgccacct cagagataaa tctaagaagt attttaccca ctggtggttt    1380
gtgtgtgtat gaaggtaaat atttatatat tttataaat aaatgtgtta gtgcaagtca    1440
tcttccctac ccatatttat catcctcttg aggaaagaaa tctagtatta tttgttgaaa    1500
atggttagaa taaaactatg actctataag gttttcaaac atctgaggca tgataaattt    1560
attatccata attatagtaa taataacctt aataagcata agaaaaacag agtcactctg    1620
gatttcaaaa atgtcaaaaa atgagcaaca gagggtcctt atttaaacat aagtgctgtg    1680
acttaggtga attttcaatt taaggtagaa aataagtttt taggaggttt gtaaaagaag    1740
aatcaatttt cagcagaaaa catgtcaact ttaaaatata gtttattttc atatttttt    1800 cttttaaact tggttgataa gtggaattag gagtatattt gaaagaatct tagcacaaac    1860
aggactgttg tactagatgt tcttaggaaa tatctcagaa gtattttatt tgaagtgaag    1920
aacttattta agaattattt cagtatttac ctgtatttta ttcttgaagt tggccaacag    1980
agttgtgaat gtgtgtggga aggcctttga atgtaaagct gcataagctg ttaggttttg    2040
tttttaaagg acatgtttat tattgttcaa taaaaaagaa caagataca    2089

<210> SEQ ID NO 32
<211> LENGTH: 7686
<212> TYPE: DNA
<213> ORGANISM: Homo sapiens

<400> SEQUENCE: 32
tttatagcag cagtagaaat ataccaccct agaggacaca cctcctttta gctaggtacc      60
tataaatgtc caggattttc tattcaattg agaagaaccc agcaaaatgg ggatctccac     120
agtcatcctt gaaatgtgtc tttatgggg acaagttcta tctacaggtg ggtggatccc     180
aaggactaca gactacgctt cactgattcc ctcggaggtg cccttggatc caactgtagc     240
agaaggttct ccatttccct cggagtcgac cctggagtca actgtagcag aaggttctcc     300
gatttccttg gagtcaaccc tggagtcaac cgtagcagaa ggttctctga ttccctcaga     360
gtcaaccctg gagtcaactg tagcagaagg atctgattct ggtttggccc tgaggctggt     420
gaatggagat ggcaggtgtc agggccgagt ggagatccta taccgaggct cctggggcac     480
cgtgtgtgat gacagctggg acaccaatga tgccaacgtg gtctgtaggc agctgggttg     540
tggctgggcc atgtcagctc caggaaatgc ctggtttggc cagggctcag gacccattgc     600
cctggatgat gtgcgctgct caggacacga atcctacctg tggagctgcc cccacaatgg     660
ctggctctcc cataactgtg gccatggtga agatgctggt gttatctgct cagctgccca     720
gcctcagtca acactcaggc cagaaagttg gcctgtcagg atatcaccac ctgtacccac     780
agaaggatct gaatccagtt tggccctgag gctggtgaat ggaggcgaca ggtgtcgagg     840
ccgagtggag gtcctatacc gaggctcctg gggcaccgtg tgtgatgact actgggacac     900
caatgatgcc aatgtggtct gcaggcagct gggctgtggc tgggccatgt cagccccagg     960
aaatgcccag tttggccagg gctcaggacc cattgtcctg gatgatgtgc gctgctcagg    1020
```

```
acatgagtcc tacctgtgga gctgccccca caatggctgg ctcacccaca actgtggcca      1080
tagtgaagac gctggtgtca tctgctcagc tccccagtcc cggccgacac ccagcccaga      1140
tacttggccg acctcacatg catcaacagc aggacctgaa tccagtttgg ccctgaggct      1200
ggtgaatgga ggtgacaggt gtcagggccg agtggaggtc ctataccgag ctcctgggg      1260 caccgtgtgt gatgatagct gggacaccag tgacgccaat gtggtctgcc ggcagctggg      1320
ctgtggctgg gccacgtcag ccccaggaaa tgcccggttt ggccagggtt caggacccat      1380
tgtcctggat gacgtgcgct gctcaggcta tgagtcctac ctgtggagct gcccccacaa      1440
tggctggctc tcccataact gtcagcacag tgaagacgct ggtgtcatct gctcagctgc      1500
ccactcctgg tcgacgccca gtccagacac gttgccgacc atcaccttac ctgcatcgac      1560
agtaggatct gaatccagtt tggccctgag gctggtgaat ggaggtgaca ggtgtcaggg      1620
ccgagtggag gtcctatacc gaggctcctg ggcaccgtg tgtgatgaca gctgggacac      1680
caatgatgcc aatgtggtct gcaggcagct gggctgtggc tgggccatgt tggccccagg      1740
aaatgcccgg tttggtcagg gctcaggacc cattgtcctg gatgacgtgc gctgctcagg      1800
gaatgagtcc tacttgtgga gctgccccca caatggctgg ctctcccata actgtggcca      1860
tagtgaagac gctggtgtca tctgctcagg acctgaatcc agtttggccc tgaggctggt      1920
gaatggaggt gacaggtgtc agggccgagt ggaggtccta taccgaggct cttggggcac      1980
cgtgtgtgat gacagctggg acaccaatga tgccaatgtg gtctgcaggc agctgggctg      2040
tggctgggcc acgtcagccc caggaaatgc ccggtttggt cagggctcag gacccattgt      2100
cctggatgat gtgcgctgct caggacatga gtcctacctg tggagctgcc ccaacaatgg      2160
ctggctctcc cacaactgtg gccatcatga agatgctggt gtcatctgct cagctgccca      2220
gtcccggtcg acgccaggc cagacacgtt gtcgaccatc acgttacctc catcgacagt      2280
aggatctgaa tccagtttga ccctgaggct ggtgaatgga agtgacaggt gtcagggccg      2340
agtagaggtc ctataccgag ctcctgggg caccgtgtgt gatgacagct gggataccaa      2400
tgatgccaat gtggtctgca ggcagctggg ctgtggctgg gccacgtcgg ccccaggaaa      2460
tgcccggttt ggccagggct caggacccat tgttctggat gatgtgcgct gctcaggaca      2520
cgagtcctac ctgtggagct gcccccacaa tggctggctc tcccacaact gtggccatca      2580
tgaagatgct ggtgtcatct gctcagtttc ccagtcccgg ccgacaccca gtccagatac      2640
ttggccgacc tcacatgcat caacagcagg acctgaatcc agtttggccc tgaggctggt      2700
gaatggaggt gacaggtgtc agggccgagt ggaggtccta taccgaggct cctggggcac      2760
cgtgtgtgat gatagctggg acaccagtga cgccaatgtg gtctgccggc agctgggctg      2820
tggctgggcc acgtcagccc caggaaatgc ccggtttggc cagggttcag gacccattgt      2880
cctggatgac gtgcgctgct caggctatga gtcctacctg tggagctgcc cccacaatgg      2940
ctggctctcc cataactgtc agcacagtga agacgctggt gtcatctgct cagctgccca      3000
ctcctggtcg acgccagtc cagacacatt gccgaccatc accttgcctg catcgacagt      3060
aggatctgaa tccagtttgg ccctgaggct ggtgaatgga ggtgacaggt gtcagggccg      3120
agtggaggtc ctataccaag ctcctgggg caccgtgtgc gatgacagct gggacaccaa      3180
tgatgccaat gtcgtctgca ggcaactggg ctgtggctgg ccatgtcag ccccaggaaa      3240 tgcccggttt ggtcagggct caggacccat tgtcctggat gatgtgcgct gctcaggaca      3300
cgagtcttac ctgtggagct gcccccacaa tggctggctc tcccacaact gtggccatag      3360
```

```
tgaagacgct ggtgtcatct gctcagcttc ccagtcccgg ccaacaccta gtccagacac   3420
ttggccaacc tcacatgcat caacagcagg atctgaatcc agtttggccc tgaggctggt   3480
gaatggaggt gacaggtgtc agggccgagt ggaggtccta taccgaggct cctggggcac   3540
cgtgtgtgat gactactggg acaccaatga tgccaatgtg gtttgcaggc agctgggctg   3600
tggctgggcc atgtcagccc aggaaatgc ccggtttggc cagggttcag gacccattgt    3660
cctggatgat gtgcgctgct caggacatga gtcctatctg tggagctgcc ccacaatgg    3720
ctggctctcc cacaactgtg gccatcatga agacgctggt gtcatctgct cagcttcca    3780
gtcccagccg acacccagcc cagacacttg gccaacctca catgcatcaa cagcaggatc   3840
tgaatccagt ttggccctga ggctggtgaa tggaggtgac aggtgtcagg gccgagtgga   3900
ggtcctatac cgaggctcct ggggcaccgt gtgtgatgac tactgggaca ccaatgatgc   3960
caatgtggtt tgcaggcagc tgggctgtgg ctggccacg tcagcccag gaaatgcccg     4020
gtttggccag ggttcaggac ccattgtcct ggatgatgtg cgctgctcag gacatgagtc   4080
ctatctgtgg agctgccccc acaatggctg gctctcccac aactgtggcc atcatgaaga   4140
cgctggtgtc atctgctcag cttcccagtc cagccgaca cccagcccag acacttggcc    4200
aacctcacat gcatcaacag caggatctga atccagtttg ccctgaggc tgtgaatgg     4260
aggtgacagg tgtcagggcc gagtggaggt cctataccga ggctcctggg caccgtgtg   4320
tgatgactac tgggacacca atgatgccaa tgtggtttgc aggcagctgg gctgtggctg   4380
ggccacgtca gccccaggaa atgcccggtt tggccaggggt tcaggaccca ttgtcctgga  4440
tgatgtgcgc tgctcaggac atgagtccta tctgtggagc tgcccccaca atggctggct   4500
ctcccacaac tgtggccatc atgaagacgc tggtgtcatc tgctcagctt cccagtccca   4560
gccgacaccc agcccagaca cttggccaac ctctcgtgca tcaacagcag gatctgaatc   4620
cactttggcc ctgagactgg tgaatggagg tgacaggtgt cgaggccgag tggaggtcct   4680
ataccaaggc tcctggggca ccgtgtgtga tgactactgg gacaccaatg atgccaacgt   4740
ggtctgcagg cagctgggct gtggctgggc catgtcagcc ccaggaaatg cccagtttgg   4800
ccagggctca ggacccattg tcctggatga tgtgcgctgc tcaggacacg agtcttacct   4860
gtggagctgc ccccacaatg gctggctctc ccacaactgt ggccatcatg aagatgctgg   4920
tgtcatctgc tcagctgctc agtcccagtc aacgccagg ccagatactt ggctgaccac    4980
caacttaccg gcattgacag taggatctga atccagtttg gctctgaggc tggtgaatgg   5040
aggtgacagg tgtcgaggcc gagtggaggt cctgtatcga ggctcctggg aaccgtgtg    5100
tgatgacagc tgggacacca atgatgccaa tgtggtctgc aggcagctgg gctgtggctg   5160
ggccatgtcg gccccaggaa atgcccggtt tggccagggc tcaggaccca ttgtcctgga   5220
tgatgtgcgc tgctcaggga tgagtcctac ctgtggagc tgcccccaca aggctggct    5280
cacccacaac tgtggccatc acgaagacgc tggtgtcatc tgctcagcca cccaaataaa   5340
ttctactacg acagattggt ggcatccaac aactacaacc actgcaagac cctcttcaaa   5400
ttgtggtggc ttcttattct atgccagtgg gacattctcc agcccatcct accctgcata   5460
ctaccccaac aatgctaagt gtgtttggga atagaagtg aattctggtt atcgcataaa     5520
cctgggcttc agtaatctga aattggaggc acaccataac tgcagttttg attatgttga   5580
aatctttgat ggatcattga atagcagtct cctgctgggg aaaatctgta atgataccag   5640
gcaaatattt acatcttctt acaaccgaat gaccattcac tttcgaagtg acatcagttt   5700
ccaaaacact ggcttttggg cttggtataa ctccttccca agcgatgcca ccttgaggtt   5760
```

```
ggtcaattta aattcatcct atggtctatg tgccgggcgt gtagaaattt accatggtgg      5820
cacctggggg acagtttgtg atgactcctg gaccattcag gaagctgagg tggtctgcag      5880
acagctaggg tgtggacgtg cagtttcagc ccttggaaat gcatattttg gctctggctc      5940
tggccccatc accctggacg atgtagagtg ctcaggacg gaatccactc tctggcagtg      6000
ccggaaccga ggctggttct cccacaactg taatcatcgt gaagatgctg gtgtcatctg      6060
ctcaggaaac catctatcga cacctgctcc ttttctcaac atcacccgtc caaacacaga      6120
ttattcctgc ggaggcttcc tatcccaacc atcaggggac ttttccagcc cattctatcc      6180
cgggaactat ccaaacaatg ccaagtgtgt gtgggacatt gaggtgcaaa acaactaccg      6240
tgtgactgtg atcttcagag atgtccagct tgaaggtggc tgcaactatg attatattga      6300
agttttcgat ggcccctacc gcagttcccc tctcattgct cgagtttgtg atggggccag      6360
aggctccttc acttcttcct ccaacttcat gtccattcgc ttcatcagtg accacagcat      6420
cacaaggaga gggttccggg ctgagtacta ctccagtccc tccaatgaca gcaccaacct      6480
gctctgtctg ccaaatcaca tgcaagccag tgtgagcagg agctatctcc aatccttggg      6540
cttttctgcc agtgaccttg tcatttccac ctggaatgga tactacgagt gtcggcccca      6600
gataacgccg aacctggtga tattcacaat tccctactca ggctgcggca ccttcaagca      6660
ggcagacaat gacaccatcg actattccaa cttcctcaca gcagctgtct caggtggcat      6720
catcaagagg aggacagacc tccgtattca cgtcagctgc agaatgcttc agaacacctg      6780
ggtcgacacc atgtacattg ctaatgacac catccacgtt gctaataaca ccatccaggt      6840
cgaggaagtc cagtatggca attttgacgt gaacatttcc ttttatactt cctcatcttt      6900
cttgtatcct gtgaccagcc gcccttacta cgtggacctg aaccaggact tgtacgttca      6960
ggctgaaatc ctccattctg atgctgtact gaccttgttt gtggacacct gcgtggcatc      7020
accatactcc aatgacttca cgtctttgac ttatgatcta atccggagtg gatgcgtgag      7080
ggatgacacc tacggaccct actcctcgcc atctcttcgc attgcccgct tccggttcag      7140
ggccttccac ttcctgaacc gcttccccctc cgtgtacctg cgttgtaaaa tggtggtgtg      7200
cagagcgtat gaccccctctt cccgctgcta ccgaggctgt gtgttgaggt cgaagaggga      7260
tgtgggctcc taccaggaaa aggtggacgt cgtcctgggt cccatccagc tgcagacccc      7320
cccacgccga gaagaggagc ctcggtaggt ggtcgctctc agaccccact gtccaccggg      7380
gcgcagaccc ctgactcggg gacttgggat gttcctcttg gtgtcatatt ccaactcaga      7440
ttgagcccta cattgtgctg cacctggtca tacggagttg aatcagacct ggttcccgcc      7500
tcccccaagg ctcatggtcc ttggaggacc cgttgcaggg tgaggtcaag agagttctga      7560
cctggatggc ccatagacct gacgtccag aatccatgct tctcatctgc aaaatgaaaa      7620
tgtcaatact tacttcttag cactgttgag agggttactt acataaagga atttggtga      7680 aactgc                                                                 7686

<210> SEQ ID NO 33
<211> LENGTH: 1665
<212> TYPE: DNA
<213> ORGANISM: Homo sapiens

<400> SEQUENCE: 33
agttggaggg aggcagggaa tctggcttga ttggcgtgct gagacgcacc tggcgcaacc        60
ctcccttctg aatcgaagtt caagtcccgc ggacactgca accatgaagg agagacgggc       120
```

-continued

```
cccccagcca gtcgtggcca gatgtaagct cgttctggtc ggggacgtgc agtgtgggaa      180
gaccgcgatg ttgcaagtgt tagcgaagga ttgctatcca gagacctatg tgcccaccgt      240
gttcgaaaat tacacagcct gtttggagac agaggaacag agggtggagc ttagtctctg      300
ggatacctca ggatctccct actacgataa tgtccgtcca ctctgctaca gcgactcgga      360
tgcagtatta ctatgttttg acatcagccg tccagagaca gtggacagcg cactcaagaa      420
gtggaggaca gaaatcctag attattgtcc cagcacccgc gttttgctca ttggctgcaa      480
gacagacctg cgaacagacc tgagtactct gatggagctg tcccaccaga agcaggcgcc      540
catctcctat gagcagggtt gtgcaatagc aaagcagctg ggtgcagaaa tctacctgga      600
aggctcagct ttcacctcag aaaagagcat ccacagcatc tttcggacgg catccatgct      660
gtgtctgaac aagcctagcc cactgcccca aagagccct gtccgaagcc tctccaaacg       720
actgctccac ctccccagtc gctctgaact catctcttct accttcaaga aggaaaaggc      780
caaaagctgt tccattatgt gaagtggaaa ttgaggggg gagacaaccc cctacttcct       840
cccttggggt gcagaggcac ggggagaggg aggatgagac aatttaggac actgacatg       900
agttttttcag atggccacgg tgagggcttg gaaggagaca ggaatggggc gaggaaggag    960
ccaggcccgg catgaggacc tgacgctgag agagaaccat catacccca gccaggcact     1020
agattttgga gggggcgact accccagtgc ccccccgct ccagaggaag gaaagctgtg     1080
ggggacgggg ggcatgctgg cctcatgggc ttggggggcct acagcagcct caccttcagc    1140
ttcatgcctc ttccacacag cgtttccatg caggtcaggg gatgggaggg gtccctgagc     1200
ccttcccttc ccctctaagg aggcagcaac ggagagtggg gaagtggagc ggcagctccc     1260
ttgggggctt agcccaggtg cttcgtaact gcaatcggaa gtgcaggagc tggtcagagc     1320
caatgagaag gaaacctcat ctttgcatag cccatgcctc atggagaggt gacatcatac     1380
attcacatgc ttctcaccta agtccccagg gtccaaggga gaagccccag accccttct     1440
cttgcagagt gtggggtgg tgtgctgca ggggcagggc tgggtgggg tcaccagact        1500
ttttctgccc ttagggtagt acagctggca tttgtttat agactcttgt ctttggaatt     1560
gggggagggg gggagtgtt tcaatctgtt atatgttctg tgtttaatga agaaaaccta     1620
tttattaatg aaaaatataa tacatataaa gaatttggct ccgta                    1665
```

<210> SEQ ID NO 34
<211> LENGTH: 1849
<212> TYPE: DNA
<213> ORGANISM: Homo sapiens

<400> SEQUENCE: 34

```
gggttatatg atctctttgg ctttagggaa ttactccata ccagctctga gatttccagc       60
tcagcgatgc ccccaggtcc ctgggagagc tgcttctggg tgggggggcct cattttgtgg     120
ctcagcgttg gaagttcagg ggatgcacct cctaccccac agccaaagtg cgctgacttc      180
cagagcgcca accttttga aggcaccgat ctcaaagtcc agtttctcct ctttgtccct       240
tcgaatccta gctgtgggca gctagtagaa ggaagcagtg acctccaaaa ctctgggttc      300
aatgccactc tgggaaccaa actaattatc catggattca gggttttagg aacaaagcct      360
tcctggattg acacatttat tagaacccttt ctgcgtgcaa cgaatgctaa tgtgattgcc     420
gtggactgga tttatgggtc tacaggagtc tacttctcag ctgtgaaaaa tgtgattaag      480
ttgagcctcg agatctccct tttcctcaat aaactcctgg tgctgggtgt gtcggaatcc      540
tcaatccaca tcattggtgt tagcctgggg gcccacgttg ggggcatggt gggacagctc      600
```

```
ttcggaggcc agctgggaca gatcacaggc ctggaccccg ctggacctga gtacaccagg      660
gccagtgtgg aagagcgctt ggatgctgga gatgccctct tcgtggaagc catccacaca      720
gacaccgaca atttgggtat tcggattccc gttggacatg tggactactt cgtcaacgga      780
ggccaagacc aacctggctg ccccaccttc ttttacgcag gttatagtta tctgatctgt      840
gatcacatga gggctgtgca cctctacatc agcgccctgg agaattcctg tccactgatg      900
gcctttccct gtgccagcta caaggccttc cttgctggac gctgtctgga ttgctttaac      960
ccttttctgc tttcctgccc aaggatagga ctggtggaac aaggtggtgt caagatagag     1020
ccgctcccca aggaagtgaa agtctacctc ctgactactt ccagtgctcc gtactgcatg     1080
catcacagcc tcgtggagtt tcacttgaag gaactgagaa acaaggacac caacatcgag     1140
gttaccttcc ttagcagtaa catcacctct tcatctaaga tcaccatacc taagcagcaa     1200
cgctatggga aggaatcat agcccatgcc accccacaat gccagataaa ccaagtgaaa      1260
ttcaagtttc agtcttccaa ccgagtttgg aaaaaagacc ggactaccat tattgggaag     1320
ttctgcactg cccttttgcc tgtcaatgac agagaaaaga tggtctgctt acctgaacca     1380
gtgaacttac aagcaagtgt gactgtttcc tgtgacctga agatagcctg tgtgtagttt     1440
aacctgggca ggacacatct ccctgcattt ttttttttt tttgagagag aggtgtgatg     1500
agggatgtgt gtgtgcagct tattgtagac cattactact aaggagaaaa gcaaagctct     1560
ttcttatttt cctcataatc agctaccctg gaggggaggg agaactcatt ttacagaact     1620
tggtttcctt tgccgatctt atgtacatac ccattttagc tttcccatgc atacttaact     1680
gcacttgctt tatctccttg ggcattcgta cttaggattc aatagaaaca tgtacagggt     1740
aaacaatttt ttaaaaataa aacttcatgg agtatctgaa aaaaaaaaa aaaaaaaaa      1800 aaaaaaaaa aaaaaaaaa aaaaaaaaa aaaaaaaa                               1849
```

<210> SEQ ID NO 35
<211> LENGTH: 7656
<212> TYPE: DNA
<213> ORGANISM: Homo sapiens

<400> SEQUENCE: 35

```
tttatagcag cagtagaaat ataccaccct agaggacaca cctccttta gctaggtacc       60 tataaatgtc caggattttc tattcaattg agaagaaccc agcaaaatgg ggatctccac      120
agtcatcctt gaaatgtgtc ttttatgggg acaagttcta tctacaggtg ggtggatccc      180
aaggactaca gactacgctt cactgattcc ctcggaggtg cccttggatc caactgtagc      240
agaaggttct ccatttccct cggagtcgac cctggagtca actgtagcag aaggttctcc      300
gatttccttg gagtcaaccc tggagtcaac cgtagcagaa ggttctctga ttccctcaga      360
gtcaaccctg gagtcaactg tagcagaagg atctgattct ggtttggccc tgaggctggt      420
gaatggagat ggcaggtgtc agggccgagt ggagatccta taccgaggct cctggggcac      480
cgtgtgtgat gacagctggg acaccaatga tgccaacgtg gtctgtaggc agctgggttg      540
tggctgggcc atgtcagctc caggaaatgc ctggtttggc cagggctcag gacccattgc      600
cctggatgat gtgcgctgct caggacacga atcctacctg tggagctgcc cccacaatgg      660
ctggctctcc cataactgtg gccatggtga agatgctggt gttatctgct cagctgccca      720
gcctcagtca acactcaggc cagaaagttg gcctgtcagg atatcaccac ctgtacccac      780
agaaggatct gaatccagtt tggccctgag gctggtgaat ggaggcgaca ggtgtcgagg      840
```

```
ccgagtggag gtcctatacc gaggctcctg gggcaccgtg tgtgatgact actgggacac    900
caatgatgcc aatgtggtct gcaggcagct gggctgtggc tgggccatgt cagccccagg    960
aaatgcccag tttggccagg ctcaggacc cattgtcctg gatgatgtgc gctgctcagg    1020
acatgagtcc tacctgtgga gctgccccca caatggctgg ctcacccaca actgtggcca    1080
tagtgaagac gctggtgtca tctgctcagc tccccagtcc cggccgacac ccagcccaga    1140
tacttggccg acctcacatg catcaacagc aggacctgaa tccagtttgg ccctgaggct    1200
ggtgaatgga ggtgacaggt gtcagggccg agtggaggtc ctataccgag gctcctgggg    1260
caccgtgtgt gatgatagct gggacaccag tgacgccaat gtggtctgcc ggcagctggg    1320
ctgtggctgg gccacgtcag ccccaggaaa tgcccggttt ggccagggtt caggacccat    1380
tgtcctggat gacgtgcgct gctcaggcta tgagtcctac ctgtggagct gccccacaa    1440 tggctggctc tcccataact gtcagcacag tgaagacgct ggtgtcatct gctcagacac    1500
gttgccgacc atcaccttac ctgcatcgac agtaggatct gaatccagtt tggccctgag    1560
gctggtgaat ggaggtgaca ggtgtcaggg ccgagtggag gtcctatacc gaggctcctg    1620
gggcaccgtg tgtgatgaca gctgggacac caatgatgcc aatgtggtct gcaggcagct    1680
gggctgtggc tgggccatgt tggccccagg aaatgcccgg tttggtcagg ctcaggacc    1740 cattgtcctg gatgacgtgc gctgctcagg gaatgagtcc tacttgtgga gctgcccca    1800 caatggctgg ctctcccata actgtggcca tagtgaagac gctggtgtca tctgctcagg    1860
acctgaatcc agtttggccc tgaggctggt gaatggaggt gacaggtgtc agggccgagt    1920
ggaggtccta taccgaggct cttggggcac cgtgtgtgat gacagctggg acaccaatga    1980
tgccaatgtg gtctgcaggc agctgggctg tggctgggcc acgtcagccc aggaaatgc    2040 ccggtttggt cagggctcag gacccattgt cctggatgat gtgcgctgct caggacatga    2100
gtcctacctg tggagctgcc caacaatgg ctggctctcc cacaactgtg gccatcatga    2160
agatgctggt gtcatctgct cagctgccca gtcccggtcg acgcccaggc cagacacgtt    2220
gtcgaccatc acgttacctc catcgacagt aggatctgaa tccagtttga ccctgaggct    2280
ggtgaatgga agtgacaggt gtcagggccg agtagaggtc ctataccgag gctcctgggg    2340
caccgtgtgt gatgacagct gggataccaa tgatgccaat gtggtctgca ggcagctggg    2400
ctgtggctgg gccacgtcgg ccccaggaaa tgcccggttt ggccagggct caggacccat    2460
tgttctggat gatgtgcgct gctcaggaca cgagtcctac ctgtggagct gccccacaa    2520 tggctggctc tcccacaact gtggccatca tgaagatgct ggtgtcatct gctcagtttc    2580
ccagtcccgg ccgacaccca gtccagatac ttggccgacc tcacatgcat caacagcagg    2640
acctgaatcc agtttggccc tgaggctggt gaatggaggt gacaggtgtc agggccgagt    2700
ggaggtccta taccgaggct cctggggcac cgtgtgtgat gatagctggg acaccagtga    2760
cgccaatgtg gtctgccggc agctgggctg tggctgggcc acgtcagccc aggaaatgc    2820 ccggtttggc cagggttcag gacccattgt cctggatgac gtgcgctgct caggctatga    2880
gtcctacctg tggagctgcc ccacaatgg ctggctctcc cataactgtc agcacagtga    2940
agacgctggt gtcatctgct cagctgccca ctcctggtcg acgcccagtc cagacacatt    3000
gccgaccatc accttgcctg catcgacagt aggatctgaa tccagtttgg ccctgaggct    3060
ggtgaatgga ggtgacaggt gtcagggccg agtggaggtc ctataccaag gctcctgggg    3120
caccgtgtgc gatgacagct gggacaccaa tgatgccaat gtcgtctgca ggcaactggg    3180
ctgtggctgg gccatgtcag ccccaggaaa tgcccggttt ggtcagggct caggacccat    3240
```

```
tgtcctggat gatgtgcgct gctcaggaca cgagtcttac ctgtggagct gcccccacaa    3300
tggctggctc tcccacaact gtggccatag tgaagacgct ggtgtcatct gctcagcttc    3360
ccagtcccgg ccaacaccta gtccagacac ttggccaacc tcacatgcat caacagcagg    3420
atctgaatcc agtttggccc tgaggctggt gaatggaggt gacaggtgtc agggccgagt    3480
ggaggtccta taccgaggct cctggggcac cgtgtgtgat gactactggg acaccaatga    3540
tgccaatgtg gtttgcaggc agctgggctg tggctgggcc atgtcagccc aggaaatgc    3600
ccggtttggc cagggttcag gacccattgt cctggatgat gtgcgctgct caggacatga    3660
gtcctatctg tggagctgcc ccacaatggc tggctctcc cacaactgtg gccatcatga    3720
agacgctggt gtcatctgct cagcttccca gtcccagccg acacccagcc agacacttg    3780
gccaacctca catgcatcaa cagcaggatc tgaatccagt ttggccctga ggctggtgaa    3840
tggaggtgac aggtgtcagg gccgagtgga ggtcctatac cgaggctcct ggggcaccgt    3900
gtgtgatgac tactgggaca ccaatgatgc caatgtggtt gcaggcagc tgggctgtgg    3960
ctgggccacg tcagccccag gaaatgcccg gtttggccag ggttcaggac ccattgtcct    4020
ggatgatgtg cgctgctcag gacatgagtc ctatctgtgg agctgcccc acaatggctg    4080
gctctcccac aactgtggcc atcatgaaga cgctggtgtc atctgctcag cttcccagtc    4140
ccagccgaca cccagcccag acacttggcc aacctcacat gcatcaacag caggatctga    4200
atccagtttg ccctgaggc tggtgaatgg aggtgacagg tgtcagggcc gagtggaggt    4260
cctataccga ggctcctggg gcaccgtgtg tgatgactac tgggacacca atgatgccaa    4320
tgtggtttgc aggcagctgg gctgtggctg gccacgtca gccccaggaa atgcccggtt    4380
tggccagggt tcaggaccca ttgtcctgga tgatgtgcgc tgctcaggac atgagtccta    4440
tctgtggagc tgcccccaca atggctggct ctcccacaac tgtggccatc atgaagacgc    4500
tggtgtcatc tgctcagctt cccagtccca gccgacaccc agcccagaca cttggccaac    4560
ctctcgtgca tcaacagcag gatctgaatc cactttggcc ctgagactgg tgaatggagg    4620
tgacaggtgt cgaggccgag tggaggtcct ataccaaggc tctggggca cgtgtgtga    4680
tgactactgg gacaccaatg atgccaacgt ggtctgcagg cagctgggct gtggctgggc    4740
catgtcagcc caggaaatg cccagtttgg ccagggctca ggaccccattg tcctggatga    4800
tgtgcgctgc tcaggacacg agtcttacct gtggagctgc ccccacaatg ctggctctc    4860
ccacaactgt ggccatcatg aagatgctgg tgtcatctgc tcagctgctc agtcccagtc    4920
aacgcccagg ccagatactt ggctgaccac caacttaccg gcattgacag taggatctga    4980
atccagtttg gctctgaggc tggtgaatgg aggtgacagg tgtcgaggcc gagtggaggt    5040
cctgtatcga ggctcctggg gaaccgtgtg tgatgacagc tgggcacca atgatgccaa    5100
tgtggtctgc aggcagctgg gctgtggctg gccatgtcg gccccaggaa atgcccggtt    5160
tggccagggt tcaggaccca ttgtcctgga tgatgtgcgc tgctcaggga tgagtccta    5220
cctgtggagc tgcccccaca aaggctggct cacccacaac tgtggccatc acgaagacgc    5280
tggtgtcatc tgctcagcca cccaaataaa ttctactacg acagattggt ggcatccaac    5340
aactacaacc actgcaagac cctcttcaaa ttgtggtggc ttcttattct atgccagtgg    5400
gacattctcc agcccatcct accctgcata ctaccccaac aatgctaagt gtgtttggga    5460
aatagaagtg aattctggtt atcgcataaa cctgggcttc agtaatctga aattggaggc    5520
acaccataac tgcagttttg attatgttga aatctttgat ggatcattga atagcagtct    5580
```

| | |
|---|---|
| cctgctgggg aaaatctgta atgataccag gcaaatattt acatcttctt acaaccgaat | 5640 |
| gaccattcac tttcgaagtg acatcagttt ccaaaacact ggcttttggg cttggtataa | 5700 |
| ctccttccca agcgatgcca ccttgaggtt ggtcaattta aattcatcct atggtctatg | 5760 |
| tgccgggcgt gtagaaattt accatggtgg cacctggggg acagtttgtg atgactcctg | 5820 |
| gaccattcag gaagctgagg tggtctgcag acagctaggg tgtggacgtg cagtttcagc | 5880 |
| ccttggaaat gcatattttg gctctggctc tggccccatc accctggacg atgtagagtg | 5940 |
| ctcagggacg gaatccactc tctggcagtg ccggaaccga ggctggttct cccacaactg | 6000 |
| taatcatcgt gaagatgctg gtgtcatctg ctcaggaaac catctatcga cacctgctcc | 6060 |
| ttttctcaac atcacccgtc caaacacaga ttattcctgc ggaggcttcc tatcccaacc | 6120 |
| atcaggggac ttttccagcc cattctatcc cgggaactat ccaaacaatg ccaagtgtgt | 6180 |
| gtgggacatt gaggtgcaaa acaactaccg tgtgactgtg atcttcagag atgtccagct | 6240 |
| tgaaggtggc tgcaactatg attatattga agttttcgat ggccctaccc gcagttcccc | 6300 |
| tctcattgct cgagtttgtg atggggccag aggctccttc acttcttcct ccaacttcat | 6360 |
| gtccattcgc ttcatcagtg accacagcat cacaaggaga gggttccggg ctgagtacta | 6420 |
| ctccagtccc tccaatgaca gcaccaacct gctctgtctg ccaaatcaca tgcaagccag | 6480 |
| tgtgagcagg agctatctcc aatccttggg cttttctgcc agtgaccttg tcatttccac | 6540 |
| ctggaatgga tactacgagt gtcggcccca gataacgccg aacctggtga tattcacaat | 6600 |
| tccctactca ggctgcggca ccttcaagca ggcagacaat gacaccatcg actattccaa | 6660 |
| cttcctcaca gcagctgtct caggtggcat catcaagagg aggacagacc tccgtattca | 6720 |
| cgtcagctgc agaatgcttc agaacacctg ggtcgacacc atgtacattg ctaatgacac | 6780 |
| catccacgtt gctaataaca ccatccaggt cgaggaagtc cagtatggca attttgacgt | 6840 |
| gaacatttcc ttttatactt cctcatcttt cttgtatcct gtgaccagcc gcccttacta | 6900 |
| cgtgacctg aaccaggact tgtacgttca ggctgaaatc ctccattctg atgctgtact | 6960 |
| gaccttgttt gtggacacct gcgtggcatc accatactcc aatgacttca cgtctttgac | 7020 |
| ttatgatcta atccggagtg gatgcgtgag ggatgacacc tacggaccct actcctcgcc | 7080 |
| atctcttcgc attgcccgct tccggttcag ggccttccac ttcctgaacc gcttcccctc | 7140 |
| cgtgtacctg cgttgtaaaa tggtggtgtg cagagcgtat gaccctctt cccgctgcta | 7200 |
| ccgaggctgt gtgttgaggt cgaagaggga tgtgggctcc taccaggaaa aggtggacgt | 7260 |
| cgtcctgggt cccatccagc tgcagacccc ccacgccga gaagaggagc ctcggtaggt | 7320 |
| ggtcgctctc agaccccact gtccaccggg gcgcagaccc ctgactcggg gacttgggat | 7380 |
| gttcctcttg gtgtcatatt ccaactcaga ttgagcccta cattgtgctg cacctggtca | 7440 |
| tacggagttg aatcagacct ggttcccgcc tcccccaagg ctcatggtcc ttggaggacc | 7500 |
| cgttgcaggg tgaggtcaag agagttctga cctggatggc ccatagacct gacgtcccag | 7560 |
| aatccatgct tctcatctgc aaaatgaaaa tgtcaatact tacttcttag cactgttgag | 7620 |
| agggttactt acataaagga attttggtga aactgc | 7656 |

<210> SEQ ID NO 36
<211> LENGTH: 2413
<212> TYPE: DNA
<213> ORGANISM: Homo sapiens

<400> SEQUENCE: 36

| | |
|---|---|
| cccgggctcg cgggcagacg gaggcgcctc tctttccccg cccctcgcct cggcccttc | 60 |

```
tcttcccagc acctcggctg ttccccggcg gcggcagcgg cagcggcggc ccacacagca    120
gcgagaggcg agaggaggct gcctcgagga ggctgcctcg aggatgaagt gcaaacccaa    180
ccagacgcgg acctacgacc ccgagggggtt caagaagcgg gcggcgtgcc tgtgcttccg    240
gagcgaacgc gaggacgagg tcctgttagt gagtagcagc cggtacccgg accgctggat    300
cgtgccgggc gggggcatgg agcccgagga ggagccgggc ggtgcggcgg tccgagaggt    360
gtacgaagaa gcgggagtca aggggaagtt aggccggctc ctgggcgtct tcgaacagaa    420
ccaggatcgc aagcacagaa cgtacgtgta tgtactgact gtcacggagc tgctggagga    480
ttgggaagat tcggttagca ttgggaggaa gcgagagtgg ttcaaagtcg aagatgccat    540
caaggttctc cagtgccaca agcccgtgca cgccgaatat ctggagaaac taaagctggg    600
cggttcccca accaatggaa actccatggc cccatcctcg ccagatagcg atccctaatg    660
aacagcaaag atgttcagta ttgtgctgaa agaaacattg atgtgaaccc agtgatcagt    720
ggaattgtca agtacaggtg agcacttctg tgttcccaag aagacagctc atctggtttc    780
ttcctgcatc ttgggacact ccttccctgt ctataccact gactcttgct ctggttgttg    840
tactcttata cgtgaataga ctcttaattc agcacctata gccttttgtt gtgctttttt    900
gatgtgtctg ccttcattag actatgatgt ctttgagagc aaagactatt tttccttact    960
ctttgcatat tctgcatctg agacactact tgaaatatgg ttggcatcac tgaaggttct   1020
ttgattcaat taatatttg taatcaccgt gtggcaaaac attcccttc caatctggtg     1080 ctagtagagt atatgctatc taggcaccat gtgtgtggct tttgtgtatc aggtgtttca   1140
gaaatatttc aagacagttg taagatgttt gaggacaaga attattactc ctatttctat   1200
gtcataccac acagtagctg cacagtttta agattatgcc atcacctagg gtaatgtttt   1260
gtagaatcag tccttcgtgt aacaactcta gtgtttttgt actgttgatg atttgcttaa   1320 atttattca aaactatca cttgctataa aggtaattgt aaaaataaat acagtggacg      1380
caaaataatg ttgtgagttt ttataaaaat aaattttaaa atgatatata agacattttt   1440
ttgcaatgcc tgccctaacc acttcttaca tgtcatctta acatctcttt gaggaaacac   1500
tgtttcctca ttttacagat ttaacatact gtattatttg atgccagagc caacaggcta   1560
tatcataggc agtttccaaa cttaattatg ccatttagtt tgtctagatt tcttttgcct   1620
ctctcactga tccatttggc tgtagttttc atccctttc cagtacacac agctagctcc    1680
tcatcctacc tggtttctgc atatgagaat gcagagggct gagagagggc aaaattgttg   1740
tcatttagaa aaggcattta ggaaagaggc tgctattaga ggggaacaca agtgaaggt    1800 tttttaaaa aagaggactt gcatcagctg cctccagaac aatttttaaga aaataacaaa   1860 gatgtttaga agaaatctta cggagtttgc catgggatgt gtgatatcag cagtcttcag   1920
ctccttacaa attaccaaaa gtggttctaa tatgctagtt tgtttgattt tttctttat    1980 attataaagc aattgcatcg ataaaagctt ggactccatt ttagtgtgac actcttcctc   2040
atgataccag tgaaatgtat tgattgtgtc cccagttgtt acataatttg aaataaaaat   2100
ataacttctt gatttattgt tttttaagat gtgatatggt actgtggtta tgttgtttta   2160
aaaaatgatt atcttttaga gaagtatact gaaaaatgta caggtgaaat gatatgttac   2220
tggtattcgc ttcaaaatca tctgagtgtg gggtaattga gtacatagat gaaacaagat   2280
tggccataaa ttggtaattg ctgaagctgt gtgatggatg tttgagagtt cattatacta   2340
ttctctatac ttttgtatat gtttgaaatt ttccataata aaaattgaaa aaagtaaaaa   2400
```

| | |
|---|---:|
| aaaaaaaaaa aaa | 2413 |

<210> SEQ ID NO 37
<211> LENGTH: 862
<212> TYPE: DNA
<213> ORGANISM: Homo sapiens

<400> SEQUENCE: 37

| | |
|---|---:|
| cttggcggtg acgcacggcc ctcacgtgac cgggagctgc agagctacgc agccttcggt | 60 |
| gcagtcgtca ctcgtgtctc gctaccagct ccccgctgcc ctgcgctcgg cgggctggca | 120 |
| tccggcccgg gggaaagcgg accagcccctt ctgcaggtct gcggggccaa gtgtcccggc | 180 |
| ggcgcacctc gtggcgagaa tcgggagaag gaggagacta caaggatagg cccaggagta | 240 |
| atggagtcca agagaaacg agcagtaaac agtctcagca tggaaaatgc caaccaagaa | 300 |
| aatgaagaaa aggagcaagt tgctaataaa ggggagcccct tggccctccc tttggatgct | 360 |
| ggtgaatact gtgtgcctag aggaaatcgt aggcggttcc gcgttaggca gcccatcctg | 420 |
| cagtatagat gggatatgat gcataggctt ggagaaccac aggcaaggat gagagaagag | 480 |
| aatatggaaa ggattgggga ggaggtgaga cagctgatgg aaaagctgag ggaaaagcag | 540 |
| ttgagtcata gtctgcgggc agtcagcact gacccccctc accatgacca tcatgatgag | 600 |
| ttttgcctta tgccctgaat cctgatggtt tccctaaagt tattacggaa acagacccct | 660 |
| gctttcgaat ttacatgttc atgatgtgcc cttgttgtaa acctttacct gtcacttgtt | 720 |
| tacgtgggtc tcctattacc agcttctaat tgaatattgt gttttttgaac cagtctgtaa | 780 |
| gattttttgtt agcagaagaa ttttacctat tgcatggaaa gatgctcatt atagtgaagt | 840 |
| taataaagca cctttaaaaa gc | 862 |

<210> SEQ ID NO 38
<211> LENGTH: 7080
<212> TYPE: DNA
<213> ORGANISM: Homo sapiens

<400> SEQUENCE: 38

| | |
|---|---:|
| gagctagcgc tcaagcagag cccagcgcgg tgctatcgga cagagcctgg cgagcgcaag | 60 |
| cggcgcgggg agccagcggg gctgagcgcg gccagggtct gaacccagat ttcccagact | 120 |
| agctaccact ccgcttgccc acgccccggg agctcgcggc gcctggcggt cagcgaccag | 180 |
| acgtccgggg ccgctgcgct cctggcccgc gaggcgtgac actgtctcgg ctacagaccc | 240 |
| agagggagca cactgccagg atgggagctg ctgggaggca ggacttcctc ttcaaggcca | 300 |
| tgctgaccat cagctggctc actctgacct gcttccctgg ggccacatcc acagtggctg | 360 |
| ctgggtgccc tgaccagagc cctgagttgc aaccctggaa ccctggccat gaccaagacc | 420 |
| accatgtgca tatcggccag ggcaagacac tgctgctcac ctcttctgcc acggtctatt | 480 |
| ccatccacat ctcagaggga ggcaagctgg tcattaaaga ccacgacgag ccgattgttt | 540 |
| tgcgaacccg gcacatcctg attgacaacg gaggagagct gcatgctggg agtgccctct | 600 |
| gcccttttcca gggcaatttc accatcattt tgtatggaag ggctgatgaa ggtattcagc | 660 |
| cggatcctta ctatggtctg aagtacattg gggttggtaa aggaggcgct cttgagttgc | 720 |
| atggacagaa aaagctctcc tggacatttc tgaacaagac ccttcaccca ggtggcatgg | 780 |
| cagaaggagg ctatttttt gaaaggagct ggggccaccg tggagttatt gttcatgtca | 840 |
| tcgaccccaa atcaggcaca gtcatccatt ctgaccggtt tgacacctat agatccaaga | 900 |
| aagagagtga acgtctggtc cagtatttga acgcggtgcc cgatggcagg atccttttctg | 960 |

-continued

```
ttgcagtgaa tgatgaaggt tctcgaaatc tggatgacat ggccaggaag gcgatgacca   1020
aattgggaag caaacacttc ctgcaccttg gatttagaca cccttggagt tttctaactg   1080
tgaaaggaaa tccatcatct tcagtggaag accatattga atatcatgga catcgaggct   1140
ctgctgctgc ccgggtattc aaattgttcc agacagagca tggcgaatat ttcaatgttt   1200
ctttgtccag tgagtgggtt caagacgtgg agtggacgga gtggttcgat catgataaag   1260
tatctcagac taaaggtggg gagaaaattt cagacctctg aaagctcac ccaggaaaaa    1320 tatgcaatcg tcccattgat atacaggcca ctacaatgga tggagttaac ctcagcaccg   1380
aggttgtcta caaaaaaggc caggattata ggtttgcttg ctacgaccgg ggcagagcct   1440
gccggagcta ccgtgtacgg ttcctctgtg ggaagcctgt gaggcccaaa ctcacagtca   1500
ccattgacac caatgtgaac agcaccattc tgaacttgga ggataatgta cagtcatgga   1560
aacctggaga taccctggtc attgccagta ctgattactc catgtaccag gcagaagagt   1620
tccaggtgct tccctgcaga tcctgcgccc caaccaggt caaagtggca gggaaaccaa    1680
tgtacctgca catcggggag gagatagacg gcgtggacat gcggcggag gttgggcttc    1740 tgagccggaa catcatagtg atgggggaga tggaggacaa atgctacccc tacagaaacc   1800
acatctgcaa tttctttgac ttcgatacct ttggggcca catcaagttt gctctgggat    1860
ttaaggcagc acacttggag ggcacggagc tgaagcatat gggacagcag ctggtgggtc   1920
agtacccgat tcacttccac ctggccggtg atgtagacga aggggaggt tatgacccac    1980 ccacatacat cagggacctc tccatccatc atacattctc tcgctgcgtc acagtccatg   2040
gctccaatgg cttgttgatc aaggacgttg tgggctataa ctctttgggc cactgcttct   2100
tcacggaaga tgggccggag gaacgcaaca cttttgacca ctgtcttggc ctccttgtca   2160
agtctggaac cctcctcccc tcggaccgtg acagcaagat gtgcaagatg atcacagagg   2220
actcctaccc ggggtacatc cccaagccca ggcaagactg caatgctgtg tccaccttct   2280
ggatggccaa tcccaacaac aacctcatca actgtgccgc tgcaggatct gaggaaactg   2340
gattttggtt tattttttcac cacgtaccaa cgggcccctc cgtgggaatg tactccccag   2400
gttattcaga gcacattcca ctgggaaaat tctataacaa ccgagcacat tccaactacc   2460
gggctggcat gatcatagac aacggagtca aaaccaccga ggcctctgcc aaggacaagc   2520
ggccgttcct ctcaatcatc tctgccagat acagccctca ccaggacgcc gacccgctga   2580
agccccggga gccggccatc atcagacact tcattgccta caagaaccag gaccacgggg   2640
cctggctgcg cggcggggat gtgtggctgg acagctgccg gtttgctgac aatggcattg   2700 gcctgacccct ggccagtggt ggaaccttcc cgtatgacga cggctccaag caagagataa   2760
agaacagctg gtttgttggc gagagtgca acgtggggac ggaaatgatg gacaatagga   2820 tctgggccc tggcggcttg gaccatagcg gaaggaccct ccctataggc cagaatttc    2880 caattagagg aattcagtta tatgatggcc ccatcaacat ccaaaactgc actttccgaa   2940
agtttgtggc cctggagggc cggcacacca gcgccctggc cttccgcctg aataatgcct   3000
ggcagagctg ccccccataac aacgtgaccg gcattgcctt tgaggacgtt ccgattactt   3060
ccagagtgtt cttcggagag cctgggccct ggttcaacca gctggacatg gatgggata    3120 agacatctgt gttccatgac gtcgacggct ccgtgtccga gtaccctggc tcctacctca   3180
cgaagaatga caactggctg gtccggcacc cagactgcat caatgttccc gactggagag   3240
gggccatttg cagtgggtgc tatgcacaga tgtacattca agcctacaag accagtaacc   3300
```

```
tgcgaatgaa gatcatcaag aatgacttcc ccagccaccc tctttacctg gagggggcgc    3360
tcaccaggag cacccattac cagcaatacc aaccggttgt caccctgcag aagggctaca    3420
ccatccactg ggaccagacg gcccccgccg aactcgccat ctggctcatc aacttcaaca    3480
agggcgactg gatccgagtg gggctctgct acccgcgagg caccacattc tccatcctct    3540
cggatgttca caatcgcctg ctgaagcaaa cgtccaagac gggcgtcttc gtgaggacct    3600
tgcagatgga caaagtggag cagagctacc ctggcaggag ccactactac tgggacgagg    3660
actcagggct gttgttcctg aagctgaaag ctcagaacga gagagagaag tttgctttct    3720
gctccatgaa aggctgtgag aggataaaga ttaaagctct gattccaaag aacgcaggcg    3780
tcagtgactg cacagccaca gcttacccca agttcaccga gagggctgtc gtagacgtgc    3840
cgatgcccaa gaagctcttt ggttctcagc tgaaaacaaa ggaccatttc ttggaggtga    3900
agatggagag ttccaagcag cacttcttcc acctctggaa cgacttcgct tacattgaag    3960
tggatgggaa gaagtacccc agttcggagg atggcatcca ggtggtggtg attgacggga    4020
accaagggcg cgtggtgagc cacacagagct tcaggaactc cattctgcaa ggcataccat    4080
ggcagctttt caactatgtg gcgaccatcc ctgacaattc catagtgctt atggcatcaa    4140
agggaagata cgtctccaga ggcccatgga ccagagtgct ggaaaagctt ggggcagaca    4200
ggggtctcaa gttgaaagag caaatggcat cgttggcttc aaaggcagc ttccggccca    4260
tctgggtgac actggacact gaggatcaca agccaaaat cttccaagtt gtgcccatcc    4320
ctgtggtgaa gaagaagaag ttgtgaggac agctgccgcc cggtgccacc tcgtggtaga    4380
ctatgacggt gactcttggc agcagaccag tgggggatgg ctgggtcccc cagcccctgc    4440
cagcagctgc ctgggaaggc cgtgtttcag ccctgatggg ccaagggaag gctatcagag    4500
accctggtgc tgccacctgc ccctactcaa gtgtctacct ggagcccctg gggcggtgct    4560
ggccaatgct ggaaacattc actttcctgc agcctcttgg gtgcttctct cctatctgtg    4620
cctcttcagt gggggtttgg ggaccatatc aggagacctg ggttgtgctg acagcaaaga    4680
tccactttgg caggagccct gacccagcta ggaggtagtc tggagggctg gtcattcaca    4740
gatccccatg gtcttcagca gacaagtgag ggtggtaaat gtaggagaaa gagccttggc    4800
cttaaggaaa tctttactcc tgtaagcaag agccaacctc acaggattag gagctggggt    4860
agaactggct atccttgggg aagaggcaag ccctgcctct ggccgtgtcc acctttcagg    4920
agactttgag tggcaggttt ggacttggac tagatgactc tcaaaggccc ttttagttct    4980
gagattccag aaatctgctg catttcacat ggtacctgga acccaacagt tcatggatat    5040
ccactgatat ccatgatgct gggtgcccca gcgcacacgg gatggagagg tgagaactaa    5100
tgcctagctt gaggggtctg cagtccagta gggcaggcag tcaggtccat gtgcactgca    5160
atgccaggtg gagaaatcac agagaggtaa aatggaggcc agtgccattt cagaggggag    5220
gctcaggaag gcttcttgct tacaggaatg aaggctgggg cattttgct gggggagat     5280
gaggcagcct ctggaatggc tcagggattc agccctccct gccgctgcct gctgaagctg    5340
gtgactacgg ggtcgccctt tgctcacgtc tctctggccc actcatgatg gagaagtgtg    5400
gtcagagggg agcaatgggc tttgctgctt atgagcacag aggaattcag tccccaggca    5460
gccctgcctc tgactccaag agggtgaagt ccacagaagt gagctcctgc cttagggcct    5520
catttgctct tcatccaggg aactgagcac agggggcctc caggagaccc tagatgtgct    5580
cgtactccct cggcctggga tttcagagct ggaaatatag aaaatatcta gcccaaagcc    5640
ttcattttaa cagatgggga aagtgagccc ccaagatggg aaagaaccac acagctaagg    5700
```

```
gagggcctgg ggagccccac cctagcccett getgccacac cacattgcct caacaaccgg   5760
ccccagagtg cccaggcact cctgaggtag cttctggaaa tggggacaag tccctcgaa    5820
ggaaaggaaa tgactagagt agaatgacag ctagcagatc tcttccctcc tgctcccagc    5880
gcacacaaac ccgccctccc cttggtgttg gcggtccctg tggccttcac tttgttcact    5940
acctgtcagc ccagcctggg tgcacagtag ctgcaactcc ccattggtgc tacctggctc    6000
tcctgtctct gcagctctac aggtgaggcc cagcagaggg agtagggctc gccatgtttc    6060
tggtgagcca atttggctga tcttgggtgt ctgaacagct attgggtcca ccccagtccc    6120
tttcagctgc tgcttaatgc cctgctctct ccctggccca ccttatagag agcccaaaga   6180
gctcctgtaa gagggagaac tctatctgtg gtttataatc ttgcacgagg caccagagtc    6240
tccctgggtc ttgtgatgaa ctacatttat cccctttcct gccccaacca caaactcttt    6300
ccttcaaaga gggcctgcct ggctccctcc acccaactgc acccatgaga ctcggtccaa    6360
gagtccattc cccaggtggg agccaactgt cagggaggtc tttcccacca aacatctttc    6420
agctgctggg aggtgaccat agggctctgc ttttaaagat atggctgctt caaaggccag    6480
agtcacagga aggacttctt ccagggagat tagtggtgat ggagaggaga gttaaaatga    6540
cctcatgtcc ttcttgtcca cggttttgtt gagttttcac tcttctaatg caagggtctc    6600
acactgtgaa ccacttagga tgtgatcact ttcaggtggc caggaatgtt gaatgtcttt    6660
ggctcagttc atttaaaaaa gatatctatt tgaaagttct cagagttgta catatgtttc    6720
acagtacagg atctgtacat aaaagtttct ttcctaaacc attccaccaag agccaatatc    6780
taggcatttt cttggtagca caaattttct tattgcttag aaaattgtcc tccttgttat    6840
ttctgtttgt aagacttaag tgagttaggt ctttaaggaa agcaacgctc ctctgaaatg    6900
cttgtcttt ttctgttgcc gaaatagctg gtcctttttc gggagttaga tgtatagagt     6960
gtttgtatgt aaacatttct tgtaggcatc accatgaaca aagatatatt ttctatttat    7020
ttattatatg tgcacttcaa gaagtcactg tcagagaaat aaagaattgt cttaaatgtc    7080
```

<210> SEQ ID NO 39
<211> LENGTH: 5676
<212> TYPE: DNA
<213> ORGANISM: Homo sapiens

<400> SEQUENCE: 39

```
ggcacgtgga ctcccttaa tccagtgact gtcaggtcga tcatatgccg aggacgatga       60
tcccgccggg ggagtgcacg tacgcgggcc ggaagcggag gaggccctg cagaaacaga    120
ggcccgccgt gggggcagag aagtccaacc cctccaagcg acaccgggac cgcctcaacg     180
ccgagttgga ccacctggcc agcctgctgc cgttcccgcc tgcatcatc tccaagctgg     240
acaagctttc tgtcctgcgc ctcagtgtca gttacctccg ggtgaagagc ttcttccaag    300
tcgtgcagga gcagagctca cggcagcctg cggccggcgc cccctcgccc ggagacagct    360
gtcctcttgc agggtctgcc gtgctggagg aaggctgct gttggagtct cttaatggct     420
ttgctctggt cgtgagtgca gaagggacga tattttatgc atcagcaacg atcgtggact    480
atctgggctt ccatcagacg gatgtaatgc accagaacat ttatgactac atccacgtgg    540
acgaccgcca ggacttctgc cggcagctcc actgggccat ggaccctccc caggtggtgt    600
ttgggcagcc ccgcccttg gagacaggag atgatgctat cctggggagg ctgctcaggg    660
cccaggagtg gggcacaggc acgcccaccg agtactcggc cttcctgacc cgctgcttca    720
```

-continued

| | |
|---|---|
| tctgccgtgt gcgctgcctg ctggacagca cctcgggctt cctggcccgg gggtcacagg | 780 |
| cttggcagct gcggctctgc tgtcccgagc cactcatgac gatgcagttt caaggaaaac | 840 |
| taaaattcct gtttggacag aagaagaagg cgccgtcagg agccatgctc ccgccgcggc | 900 |
| tgtcgctgtt ctgcattgcg gcacccgttc tcctcccctc cgcagcggag atgaaaatga | 960 |
| ggagcgcgct cctgagggca aacccagag cagacaccgc agccaccgcg gatgcaaaag | 1020 |
| taaaagccac caccagtctg tgcgaatcgg aactgcatgg aaaacccaat tactcagcag | 1080 |
| gaaggagcag cagagagagc ggcgttttgg tgctcaggga acagactgac gctggccgat | 1140 |
| gggcacaggt tcccgccagg gccccatgcc tgtgcctccg gggtggccct gaccttgtcc | 1200 |
| ttgaccccaa gggggggctca ggggacaggg aggaggagca gcacaggatg ctgagcaggg | 1260 |
| cctctggagt gacagggcgg agggagactc caggacccac aaagccctg ccctggacag | 1320 |
| cgggaaagca cagtgaggat ggtgccaggc cgaggctgca gcccagcaag aatgacccgc | 1380 |
| cctccctgcg ccccatgccc cgcggctcct gcctgccctg cccgtgtgtc cagggcactt | 1440 |
| tcaggaactc gcccatctct cacccgccga gcccgtcccc cagtgcctac tccagccgga | 1500 |
| ccagcagacc catgcgggat gtcggtgagg accaggtgca ccctcccctc tgccactttc | 1560 |
| cccagaggag cctgcagcac cagctccctc agcctggagc tcagcgtttt gccacgaggg | 1620 |
| gctatcccat ggaggacatg aagctgcaag gtgtaccgat gcctccgggg gacctgtgtg | 1680 |
| gtccgacgct gctgctagat gtgtccatca agatggagaa ggactctggg tgtgagggtg | 1740 |
| ctgcagacgg ctgtgtgccc agccaggtgt ggctgggggc cagtgacagg agccacccag | 1800 |
| ccaccttccc taccaggatg cacctgaaaa cagagccaga ctctcggcaa caggtgtaca | 1860 |
| tctcgcacct ggggcacggc gtgcgggggg ctcagcccca tgggagggcc actgctgggc | 1920 |
| gcagcaggga gctgacccct ttccaccctg cacactgtgc ctgcctggag cccacagacg | 1980 |
| gccttcccca gtcggagcct ccccaccagc tctgtgcacg gggccgaggt gaacagtcct | 2040 |
| gcacctgcag agctgctgag gccgcccctg tggtcaagcg ggagcccttg gactcacccc | 2100 |
| agtgggctac tcacagccag ggaatggtgc ccgggatgtt gcccaaaagt gccttggcca | 2160 |
| cgctggtccc gccccaagct tcggggtgca cattcctgcc atagcgcagt gaccaccatc | 2220 |
| caagctcaga tctgtgtgtc tacgctcaga tgcgtcggtg gctgggctgc cctgctcctg | 2280 |
| gtcaggccgg agcccgtcct aagacacacg ctttgcagag ctgtgcatgc gcagtctgct | 2340 |
| agtgtgtgtg tgcagcatac gcaggagcct atcctgaatt ttgtaaaata tcccaacagt | 2400 |
| tcttaaatga aaactggcct taagtctatt caagcatgac agcatttctc tttgaggaat | 2460 |
| taaaatcttt aggaaagtga tcatggctgg acagcttcat gccccagagg cagcgagcac | 2520 |
| ccgtcccatg gctgccaagt ccacagtcgg ggatgaagca gtcgggtgat gctcccaagt | 2580 |
| ccgcagtcgg ggatgaagcg gtcgggtgat gctcccaagt ccgcagtcgg ggatgaagcg | 2640 |
| gtcgggtgac acacctagct cagccctccc aggccacctg cagctcccag cctgtgctgt | 2700 |
| gcaggcaggg tcagcccatc gccacagtgc actgtagagg ccagcacacg gcaaattaga | 2760 |
| aatacaacac gcggagaaag gggtccgtga gcccactcat agaggaatct agaacgttcc | 2820 |
| aggcagcaga ggctggcagc gtgggtccca cactgcccca caccgtgcgg caggtgctcc | 2880 |
| atggcgccat gacagagtct gaggccagac ctggactgga attgacagca taacccctgt | 2940 |
| tccttctgga catctcccga gttctcagtg gtgtctctgcg gacggttctt cctaatctgc | 3000 |
| ctcttggtac atcacgtaat acagagttca cagactccgg gtttggaagt acagagaaac | 3060 |
| acacaacgta gagagaagac acaggaaact gcgctgcctg tgggggtttc tctctggctg | 3120 |

```
gctgtacagt tcactcaaat gagggttccc attgccatcc taggagaata attagggaca    3180
agacagacaa gtattaatag cattaaaaca gttgtaaagg cgatattttc tgagagtagg    3240
aaatttggat acaaaagcat aagtcagaaa gtgaaggtca ccaatccacc aacccgagaa    3300
cctacagctg atggtgcatt tcaggcttct tccacggtct ggcctggaac cccacccggc    3360
tggtgcaggc atcagatcag ggtgtagaag tcaccccaag caagaggaag ccaggcagtg    3420
aggccctggg gtgtggctgc agctgggccc acctgtgcgg gggtgggaag ccccatcct    3480 cagggagagg gcatcggcgc cctgacgtca gctccactgg gagtggcagg agctgtggga    3540
gcccatgggt gagggaccca ccaccccgct gcactgtgca ttgtgcctcc cgtgtggacg    3600
ccctctctgt tgttggcccg cgggtgaggg acccaccacc cctagggacc caccaccccg    3660
ccgcactgtg cattctgcct cctgtgtgga cgccctctct gttgtcagtg gctttgaggt    3720
gtcagtgctt acttagatgc tggtttaatg ctggacccat ttgttaaacg caccttcact    3780
ttgtcaaaac ccaggtttgg ttggcaggac tgggtcttct gcccaatgcc aggtgcctgc    3840
gcctctcagt ggcctggttc ttggacagtt tgcccccatg tggcagggat agggataagg    3900
atctcctctc agtactggaa gagaacagcc aaccatctga gcccagagtc acagatccat    3960
cgtggccccc tatgaccccc aagccctacc gaggggcac tcactctctg cttagccagg    4020
gggcgtcttt caaaaggtga cctccatgct gtgctgtcgt gggtgtgaga cgtgctcatg    4080
gccttccact gccatctctc ccttatctga tgcctaaagt cacgatgggg acagagctac    4140
ccaggggcca gccatggggt gaccagccac ctgagggtca gtcacctgtg gagagcaggc    4200
acctgtgaag accaggcacc tgaggactgg cgcctacttc ccactttggc cctacactgg    4260
cacagagccc ctctttattc atttctcatg ctgagcatgg cacacttctg gcctctgggc    4320
atttatggat ttaagaccag gatggtattt cagaagcttc ccacttcctt cctattctaa    4380
ccgagtgccc agctcctttg ctgatcatgg aaagacccct aataattagg cctgcaggcc    4440
aggcgcagtg gctcatgcct ataatcccag cactttagga ggtcaaggta ggaggatcgc    4500
ttaagcccag gagttcaaga ccagcctggg caacacagga gaatgtgtc tctacaaaaa    4560 ataattaaaa atcagatctg ctgtatccct gaaaagtct caatcaacat gcatgttcca    4620
ctcttggagt tccctgttct gagggccagc cacgtcctgt gtcctggagc ttagccctca    4680
gcagctccct tcagcctggg cgccgcctgg gtcccaaacg tggcagctgc tcttccagtc    4740
tcggggccga ggagggcagg gagctcagtg actgagagtc ttgtgtatca catgtcttga    4800
gtgtcctgga gccaacggct gtcactggga aaaacaccag gccccaaaga tcgaatcaga    4860
gacgtggctg cgtgtttgcg attgtagcca ggcccttcag tgtcatcaaa ggagcactgg    4920
ggcctcctta agcacagacg gcagccctg cccaggagc ttcttcacca cgtcctgccc    4980
tgcagcctcc cagacctta gatgcgcccc tgcccaaggc cctcctggtg acaggtgcca    5040
gattgagtgg tgggttgctg ccaggcaggc cacgctgtgt tgacgctgca ctcagcacgt    5100
gggtgttggc tctgccggtt ttgtggtgtg ggaccctac aggaggctgc ggccctgaga    5160
gcctgggatc agcgaggtgt ccgacatccc ttcctcaacg gcaacaaaaa ctccccaagt    5220
cagcactttg gttattttat agccacaacc ctcttggaaa acagtgggga agactatgga    5280
acatagaaag tgtggatgta tcacttctct ctaaaatgtc attgttagca ctaattacag    5340
gttcatgttt ttctgtgtat gtagcttttc cctatatagc tgaaaagta ttaaagtcaa    5400 atataaggtg ggaatgggat ggaagggagg agatcaatac aacttatatt tttgcagttt    5460
```

| | |
|---|---|
| ctactggaag aaaaaagttt tcaatacctg gaccaacttg ttgaattttt aaaacttatg | 5520 |
| cactataaat gcaactttct ctactgcttt ctcagtgcct ttaggaagct ttcaaatttt | 5580 |
| tttgtactgt ggtttgtatt aaatttgcaa tattgatgta aaatacatga catgctagta | 5640 |
| catgtttaac aaaaatttaa aaaaaaaaaa aaaaaa | 5676 |

<210> SEQ ID NO 40
<211> LENGTH: 1763
<212> TYPE: DNA
<213> ORGANISM: Homo sapiens

<400> SEQUENCE: 40

| | |
|---|---|
| cttctggtaa ggaggccccg tgatcagctc cagccatttg cagtcctggc tatcccagga | 60 |
| gcttacataa agggacaatt ggagcctgag aggtgacagt gctgacacta caaggctcgg | 120 |
| agctccgggc actcagacat catgagttgg tccttgcacc cccggaattt aattctctac | 180 |
| ttctatgctc ttttatttct ctcttcaaca tgtgtagcat atgttgctac cagagacaac | 240 |
| tgctgcatct tagatgaaag attcggtagt tattgtccaa ctacctgtgg cattgcagat | 300 |
| ttcctgtcta cttatcaaac caaagtagac aaggatctac agtctttgga agacatctta | 360 |
| catcaagttg aaaacaaaac atcagaagtc aaacagctga taaaagcaat ccaactcact | 420 |
| tataatcctg atgaatcatc aaaaccaaat atgatagacg ctgctacttt gaagtccagg | 480 |
| aaaatgttag aagaaattat gaaatatgaa gcatcgattt taacacatga ctcaagtatt | 540 |
| cgatatttgc aggaaatata taattcaaat aatcaaaaga ttgttaacct gaaagagaag | 600 |
| gtagcccagc ttgaagcaca gtgccaggaa ccttgcaaag acacggtgca aatccatgat | 660 |
| atcactggga aagattgtca agacattgcc aataagggag ctaaacagag cgggctttac | 720 |
| tttattaaac ctctgaaagc taaccagcaa ttccttagtct actgtgaaat cgatgggtct | 780 |
| ggaaatggat ggactgtgtt tcagaagaga cttgatggca gtgtagattt caagaaaaac | 840 |
| tggattcaat ataagaagg atttggacat ctgtctccta ctggcacaac agaattttgg | 900 |
| ctgggaaatg agaagattca tttgataagc acacagtctg ccatcccata tgcattaaga | 960 |
| gtggaactgg aagactggaa tggcagaacc agtactgcag actatgccat gttcaaggtg | 1020 |
| ggacctgaag ctgacaagta ccgcctaaca tatgcctact cgctggtgg ggatgctgga | 1080 |
| gatgcctttg atggctttga ttttggcgat gatcctagtg acaagttttt cacatcccat | 1140 |
| aatggcatgc agttcagtac ctgggacaat gacaatgata agtttgaagg caactgtgct | 1200 |
| gaacaggatg gatctggttg gtggatgaac aagtgtcacg ctggccatct caatggagtt | 1260 |
| tattaccaag gtggcactta ctcaaaagca tctactccta atggttatga taatggcatt | 1320 |
| atttgggcca cttggaaaac ccggtggtat tccatgaaga aaccactat gaagataatc | 1380 |
| ccattcaaca gactcacaat tggagaagga cagcaacacc acctgggggg agccaaacag | 1440 |
| gtcagaccag agcaccctgc ggaaacagaa tatgactcac tttaccctga ggatgatttg | 1500 |
| tagaaaatta actgctaact tctattgacc cacaaagttt cagaaattct ctgaaagttt | 1560 |
| cttcctttt tctcttacta tatttattga tttcaagtct tctattaagg acatttagcc | 1620 |
| ttcaatggaa attaaaactc atttaggact gtatttccaa attactgata tcagagttat | 1680 |
| ttaaaaattg tttatttgag gagataacat ttcaactttg ttcctaaata tataataata | 1740 |
| aaatgattga ctttatttgc aaa | 1763 |

<210> SEQ ID NO 41
<211> LENGTH: 666

```
<212> TYPE: DNA
<213> ORGANISM: Homo sapiens

<400> SEQUENCE: 41
gggtggctta gcactgcagg gctctgcgcg ggaacgctaa cctggtccgg agcgagtctg      60
ggtctcagcc ccgcgaacag cctttcacga gtcttcaagc tttcaggcta tcttctagtc     120
aagatgagtg ataagccaga cttgtcggaa gtggagaagt ttgacaggtc aaaactgaag     180
aaaactaata ctgaagaaaa aaatactctt ccctcaaagg aaactatcca gcaagagaaa     240
gagtgtgttc aaacatcata aaatggggat cgcctcccaa cagcagattt cgacattacc     300
tgagagtctt gattttaggc ttgttttttg taaacccatg tgtttgtaga gattttaggc     360
gtcttcggat atcttctcac ctatgttccc tggctaagaa gtcagaggta gccaatgttt     420
ccttaaattc attttaaac ttaccattgg tgcatatgtt ccagatggca gatgctgtca     480
ataatctcac cattgatgac ctttgtgtat gtagttcttg catcctatac tggataagcc     540
tgttttaacc tgctatgatg ggtgcttcca ttgcttcata atcttcatga agttgcatgc     600
ttttgcagct tttcacagtt tatttgcatt tctaatgtag taataaagta accaatataa     660
tcatta                                                                666

<210> SEQ ID NO 42
<211> LENGTH: 1437
<212> TYPE: DNA
<213> ORGANISM: Homo sapiens

<400> SEQUENCE: 42
attgctgatg gatcagtgag cctgtgttca tgccagtgag ctgctgtggc tcagatactg      60
atactttctt tccaaacagc ataagaagtg attgagccac aagtatactg aaggaagggc     120
tccctcgagt tctggtgtga agagataaat caccagtcac agactatgca cccgactgct     180
gctgttcagt ccagggaaaa tgaaagttgg agtgctgtgg ctcatttctt tcttcacctt     240
cactgacggc cacggtggct tcctggggaa aaatgatggc atcaaaacaa aaaagaact      300
cattgtgaat aagaaaaaac atctaggccc agtcgaagaa tatcagctgc tgcttcaggt     360
gacctataga gattccaagg agaaagaga tttgagaaat ttctgaagc tcttgaagcc      420
tccattatta tggtcacatg ggctaattag aattatcaga gcaaaggcta ccacagactg     480
caacagcctg aatggagtcc tgcagtgtac ctgtgaagac agctacacct ggtttcctcc     540
ctcatgcctt gatccccaga actgctacct tcacacggct ggagcactcc caagctgtga     600
atgtcatctc aacaacctca gccagagtgt caatttctgt gagagaacaa agatttgggg     660
cactttcaaa attaatgaaa ggtttacaaa tgaccttttg aattcatctt ctgctatata     720
ctccaaatat gcaaatggaa ttgaaattca acttaaaaaa gcatatgaaa gaattcaagg     780
ttttgagtcg gttcaggtca cccaatttcg aatgtcactc ttgtcgccca gttggagtg      840
caatggcaca atctaggctc actgcaaccc tgcaacctct gcctaccggg ttcaagagat     900
tcccctgcct cagcctccca gtagctgga attacaggca cctgccacca catccagcta     960
acttttttg tattttact agagacaggg tttcaccatg ttggccacac tggtctcaaa     1020
ctcctgacct caggtgatcc gcctgcctcg gccccaaag tgctgggatt acaggcatga     1080
gccaccacat ctggcctagg accttaaata ttggaaagca tcctcaaaac tgtgggtcag     1140
tgagtagaac tacaaaacaa tagcagtagg gcagaaactt gaagaaggc aggagatcat     1200
ggtgacagtg gatgggaaaa agtgaggggtt ggggataagg gttgcgggtt gtcgaagggt     1260
```

| | | |
|---|---|---|
| ggattttctc cttcagcaac tacaggagat atgatgcctc ataattcgga gccagaagtg | 1320 | |
| gggctttggg tgagatatct ttgcacagat aacatgtata catcatagtt caaaacccag | 1380 | |
| tagtcattgt ttacagcaaa taaagaaata tttagtaaat taaaaaaaaa aaaaaaa | 1437 | |

<210> SEQ ID NO 43
<211> LENGTH: 2413
<212> TYPE: DNA
<213> ORGANISM: Homo sapiens

<400> SEQUENCE: 43

| | |
|---|---|
| tttcctctca gggggcagca ggaagtgagg agaaagggct gggatgggag gcgggagcgg | 60 |
| atgggaggga atggggttta tcaagtcctc ggcgagctgc ccaacgggca gcagctggcg | 120 |
| caagtagcct agctggagag gctcacccca ggaaggaggg aggccaccga cctactgggc | 180 |
| cgacggactc ccacacaggg ctggcggcgc gcgggagctg ggaggactga accaccggcc | 240 |
| tcgggctgca ggggaaacat ttcaggctga ctggcgctcg tggctgagac tcccatagaa | 300 |
| agcccggctc agagggcat tagggtccta aatgggcggc cacgtccctc tgcagaggac | 360 |
| ctggggctct tcgagcccga aacgaggcac cggcaccgag aaaggtggac cacaccttcc | 420 |
| cgccccgtcc gcaagtccaa tcccgggccc acctccgcac tggagtctta aagggccagc | 480 |
| gtgcctgggg gcggagccag cagaggcgct gagccgggcc gcgcctgggc gaacggccgg | 540 |
| agcgggctgg gctgggcccg ggatggcggt ggccctggcg ccgtcccgg tggcgccccg | 600 |
| cgcgagttcc tgagctggtg ccaggcaggt gacacctcct gcagccccca gcatgcgggc | 660 |
| aggcccaggc cccaccgtta cattggccct ggtgctggcg tgtcatggg ccatggagct | 720 |
| caagcccaca gcaccaccca tcttcactgg ccggcccttt gtggtagcgt gggacgtgcc | 780 |
| cacacaggac tgtggcccac gcctcaaggt gccactggac ctgaatgcct ttgatgtgca | 840 |
| ggcctcacct aatgagggtt ttgtgaacca gaatattacc atcttctacc gcgaccgtct | 900 |
| aggcctgtat ccacgcttcg attctgccgg aaggtctgtg catggtggtg tgccacagaa | 960 |
| tgtcagcctt tgggcacacc ggaagatgct gcagaaacgt gtggagcact acattcggac | 1020 |
| acaggagtct gcggggctgg cggtcatcga ctgggaggac tggcgacctg tgtgggtgcg | 1080 |
| caactggcag gacaaagatg tgtatcgccg gttatcacgc cagctagtgg ccagtcgtca | 1140 |
| ccctgactgg cctccagacc gcatagtcaa acaggcacaa tatgagtttg agttcgcagc | 1200 |
| acagcagttc atgctggaga cactgcgtta tgtcaaggca gtgcggcccc ggcacctctg | 1260 |
| gggcttctac ctctttcctg actgctacaa tcatgattat gtgcagaact gggagagcta | 1320 |
| cacaggccgc tgccctgatg ttgaggtggc ccgcaatgac cagctggcct ggctgtgggc | 1380 |
| tgagagcacg gccctcttcc cgtctgtcta cctggacgag acacttgctt cctcccgcca | 1440 |
| tggccgcaac tttgtgagct ccgtgttca ggaggccctt cgtgtggctc gcacccacca | 1500 |
| tgccaaccat gcactcccag tctacgtctt cacacgaccc acctacagcc gcaggctcac | 1560 |
| ggggcttagt gagatggacc tcatctctac cattggcgag agtgcggccc tgggcgcagc | 1620 |
| tggtgtcatc ctctggggtg acgcggggta caccacaagc acggagacct gccagtacct | 1680 |
| caaagattac ctgacacggc tgctggtccc ctacgtggtc aatgtgtcct gggccaccca | 1740 |
| atattgcagc cgggcccagt gccatggcca tgggcgctgt gtgcgccgca accccagtgc | 1800 |
| cagtaccttc ctgcatctca gcaccaacag tttccgccta gtgcctggcc atgcacctgg | 1860 |
| tgaaccccag ctgcgacctg tggggagct cagttgggcc gacattgacc acctgcagac | 1920 |
| acacttccgc tgccagtgct acttgggctg gagtggtgag caatgccagt gggaccatag | 1980 |

```
gcaggcagct ggaggtgcca gcgaggcctg ggctgggtcc cacctcacca gtctgctggc    2040
tctggcagcc ctggccttta cctggacctt gtagggtct cctgcctagc tgcctagcaa    2100
gctggcctct accacaaggg ctctcttagg catgtaggac cctgcagggg gtggacaaac    2160
tggagtctgg agtgggcaga gcccccagga agcccaggag ggcatccata ccagctcgca    2220
cccccctgtt ctaaggggga ggggaagtcc ctgggaggcc ccttctctcc ctgccagagg    2280
ggaaggaggg tacagctggg ctggggagga cctgacccta ctcccttgcc ctagatagtt    2340
tattattatt attattttgg ggtctctttt gtaaattaaa cataaaacaa ttgcttctct    2400
gcttggattt tgt                                                      2413

<210> SEQ ID NO 44
<211> LENGTH: 1279
<212> TYPE: DNA
<213> ORGANISM: Homo sapiens

<400> SEQUENCE: 44
gggagggaga gaggcgcgcg ggtgaaaggc gcattgatgc agcctgcggc ggcctcggag      60
cgcggcggag ccagacgctg accacgttcc tctcctcggt ctcctccgcc tccagctccg     120
cgctgcccgg cagccgggag ccatgcgacc ccagggcccc gccgcctccc cgcagcggct     180
ccgcggcctc ctgctgctcc tgctgctgca gctgccgcg ccgtcgagcg cctctgagat     240
ccccaagggg aagcaaaagg cgcagctccg gcagagggag gtggtggacc tgtataatgg     300
aatgtgctta caagggccag caggagtgcc tggtcgagac gggagccctg ggccaatgg     360 cattccgggt acacctggga tcccaggtcg ggatggattc aaaggagaaa aggggaatg     420 tctgagggaa agctttgagg agtcctggac acccaactac aagcagtgtt catggagttc     480
attgaattat ggcatagatc ttgggaaaat tgcggagtgt acatttacaa agatgcgttc     540
aaatagtgct ctaagagttt tgttcagtgg ctcacttcgg ctaaaatgca gaaatgcatg     600
ctgtcagcgt tggtatttca cattcaatgg agctgaatgt tcaggacctc ttcccattga     660
agctataatt tatttggacc aaggaagccc tgaaatgaat tcaacaatta atattcatcg     720
cacttcttct gtggaaggac tttgtgaagg aattggtgct ggattagtgg atgttgctat     780
ctgggttggt acttgttcag attacccaaa aggagatgct tctactggat ggaattcagt     840
ttctcgcatc attattgaag aactaccaaa ataaatgctt taattttcat ttgctacctc     900
tttttttatt atgccttgga atggttcact taaatgacat tttaaataag tttatgtata     960
catctgaatg aaaagcaaag ctaaatatgt ttacagacca aagtgtgatt tcacactgtt    1020
tttaaatcta gcattattca ttttgcttca atcaaaagtg gtttcaatat tttttttagt    1080
tggttagaat actttcttca tagtcacatt ctctcaacct ataatttgga atattgttgt    1140
ggtcttttgt tttttctctt agtatagcat ttttaaaaaa atataaaagc taccaatctt    1200
tgtacaattt gtaaatgtta agaatttttt ttatatctgt taaataaaaa ttatttccaa    1260
caaccttaat atctttaaa                                                 1279

<210> SEQ ID NO 45
<211> LENGTH: 4571
<212> TYPE: DNA
<213> ORGANISM: Homo sapiens

<400> SEQUENCE: 45
gcagtcagag ctgcctctcg ccctcgctag ctgggctcgc agcctcttcc tccctccctg      60
```

-continued

```
gctcctggct ttttgtttaa agcaacaccc accctccatc caggcttttt ttctttcttt    120
ctttattggt agcggccaaa aagagttgat tgctattggg atccgctgag taaagacacg    180
ggcaggggtg cgcggaggtg agaaaactga agacctggaa gatttttttt tccttcaaaa    240
acccgtttcc atccagtctt cagccagtcc agtctacttt aatcctcacc aggacaatgg    300
attaagtttc tcttccctgg accagaagtc gggttcggac ttggggcaaa atgaaggaaa    360
aggccatgat caagaccgct aagatgcagg ggaacgtgat ggagctggtg gggagtaacc    420
ctccgcagag gaattggaaa ggaatagcaa ttgcactgct tgtcattctg gtcatctgct    480
ccttgatcgt cacctcggtc atacttctga caccagcgga agataatagt ctgtctcaaa    540
agaagaaggt cactgtagaa gatctcttca gtgaagactt caaaattcat gaccccgagg    600
ctaagtggat aagtgataca gaattcatct acagagaaca gaaaggaaca gtgagactgt    660
ggaatgttga aacaaatact tctactgtct taatagaagg caaaaaaatt gaatcattaa    720
gagccatcag atatgaaata tctccagata gagagtatgc acttttttca tacaatgtgg    780
aacccatata tcaacactcg tatactggat attacgtcct gagcaaaatt cctcatgggg    840
atcctcaaag tctggaccca ccagaagtca gcaatgcaaa acttcagtat gcaggatggg    900
gccctaaagg ccaacagctg atatttattt ttgaaaacaa tatctactac tgtgcacatg    960
tcgggaaaca ggccatccgt gtggtctcca ctggcaagga aggtgtgatt tacaatggcc    1020
tcagtgactg gctgtatgaa gaggagattt tgaagacaca catcgcacac tggtggtctc    1080
cggatggcac gagactcgcc tacgccgcca tcaatgattc ccgtgtcccc atcatggagc    1140
tcccaactta caccggctcc atctacccca ccgtgaagcc ctaccactat cccaaggctg    1200
gaagtgagaa ccccagcatt tccctacacg ttattggctt aaatggaccc acccatgatc    1260
tggagatgat gccgcctgat gatccacgga tgagggagta ctacatcacc atggtgaagt    1320
gggccaccag caccaaggtc gccgtgacct ggctgaaccg ggcgcagaac gtgtccatcc    1380
tcaccctctg cgacgccacc acgggggtct gcacgaagaa acacgaggat gaaagtgagg    1440
cctggctcca cagacagaat gaagaacctg tgttctccaa ggatggccga agttttttct    1500
tcatcagagc catcccccag ggaggacgag ggaaattcta tcacatcacg gtgtcctcgt    1560
cccagcccaa cagcagcaac gacaacatcc agtccatcac ctccggggac tgggacgtga    1620
ccaagatcct agcctacgat gagaagggga ataagatcta cttcctgagc acggaggacc    1680
tgcctcggag acgacaactc tacagtgcca acacggtggg caacttcaac aggcagtgcc    1740
tctcctgtga cctggttgag aactgcacct acttcagcgc ttccttcagc catagcatgg    1800
acttcttcct gctcaagtgc gaaggtcctg tgttcctat ggtgacggtg cacaacacaa    1860
cagataagaa aaaaatgttt gacctagaaa caaatgaaca tgtcaagaag gccataaatg    1920
accgacagat gcctaaagtg aatacaggg acattgagat tgatgattac aacctgccca    1980
tgcagatact gaagccagca accttcaccg acaccaccca ctaccctctg ctcctggtgg    2040
tggatggcac cccaggcagc cagagtgtgg ctgagaagtt cgaggtgagc tgggagacgg    2100
tgatggtgag cagccacggc gcggtggtgg taaagtgtga cggccgtggc agcggcttcc    2160
aagggaccaa gctcctgcac gaagtgaggc ggcggctggg cttgctggag gagaaggacc    2220
agatggaggc cgtgcggacg atgctgaagg agcagtacat tgacaggacg cgcgtggccg    2280
tgtttgggaa ggattacggt ggctacctga gcacctacat cctcccagca aagggagaaa    2340
atcaaggcca gacattcacc tgcggctctg ctctctctcc aataacagac ttcaaactct    2400
atgcctctgc gttttccgag aggtacttgg gcctccatgg acttgacaac agagcatacg    2460
```

```
agatgaccaa ggtagcccat cgagtctccg cgctggaaga acagcagttc ctgatcattc    2520
atcccactgc cgatgaaaaa attcatttcc agcacacagc agaactcatt acacaactaa    2580
ttaggggaaa ggctaattac agcttacaga tttacccgga cgaaagccat tactttacca    2640
gctccagcct caaacagcat ctgtaccggt ccatcatcaa cttcttcgtg gaatgcttca    2700
ggatccagga caaactgctg acagtcacag cgaaagagga cgaggaggag gactaagctc    2760
aggtcgctct aagcacaaac gtggctcttt ctacaaccag atgcaaccga gggatttccc    2820
tgccctccct cttccctcgg aggggcgggg cggggcgggg ccgggtgttc catagcatgt    2880
gtgtctcgga tgcggaaggc agttttgctt gggaaacaag ctccttcccc ggggtcatca    2940
ctcacggcct ccatggcacc agggacaacg ctgtccccgc agcagcgcct cctcccggcg    3000
cccgagagac cggcacgcca cggcccctcc ccaaggaac agagcaaagg atggtggccg    3060
caggccccac gcgagcccac aggacaccgg cccctagatt ccagccacca agcggaagca    3120
tgagacccgc ccacactagc ctctgtgttc ccgttaggga catcacaccc tgtctcacgt    3180
cgcagtgcca tggacgcagc agttacagca ccattgtttt agcagtgcgt gttcatatat    3240
gggcttgcta cttcctgtaa tgaggacgtt caacatggtg aggggctaca agaaaacgct    3300
tttctgtaca gagtcttact gtagctacgc taatggttaa cctgatagaa ttaactcgta    3360
tttttctatg gttttaacct gatgctccac tgtctccgtc atggggttgt tttgctgttt    3420
ggggttgggc cttgtttccc tttcctttct ccagtccacg tgtagacttt gcgcttgatg    3480
aagaagcaga tcggaagtaa ctgctccctc ctcaaggttg tcttcagacg tcttggggac    3540
gttcctaaac actgagggg aagacagcca atagcaccca ttaaaagaaa tacctaaata    3600
aaacctctct cccactcagc tatgctaggg cttggctgta ggtgtgcact gtctatttac    3660
atccgtcctt acaaccatcc ttgtcctcct tggtaccgta tcaagctctt tcccatgaca    3720
tttggtttaa aaaaaaaaa aaaaaaaaa aaaaacaga aaaaagacaa agcgtcaact    3780
ccacccacag gcccgctgtg tgtgctcggg ccacgggagt cctgagggtt ctgtgggcct    3840
gcgcgcatcc ctctcccatc gtggggtgg ctccgtgacc ttcctgccac gagcaggagg    3900
ttgatgatgt gctacgttag ccttgtaaga tacacccca ccaaatgtgc agccggtgtt    3960
cccagtgtat atttcattct cttgtatata aaggaagcaa tgtgtgtcag gcctctgtgc    4020
agtcaaccca gcctcctccc gccagtgcta accccgtgtt gagcctgcat gctgacactg    4080
tggccgatct ggactctaga agtgctagtt tgaaatatat ccattactgt catttccttt    4140
tgagcttgtg gacaagctga atgtcaggac tgacttcgcc agctcccagc cctgcggggg    4200
tgtccttggc atcccatcag cagaggagat gcgtccctgt tgcattttgg cgtttggggc    4260
tttgggttta tccacatgag ctctgaacgt ccgttatagt tagggtgatt ggaaggtctc    4320
catcactggg tgttttaaag gtgattcacc accatttgtg aaaggaccaa cgtgctgata    4380
aacaggaccg atccgagtgc tacatgactg tgcgtttgct atttcaatgg gcctgaacga    4440
ctacaaagcc agctaggtct ggaagggaa gccagctctg gccacgacat ctggtcggag    4500
ggaagtgggg atgtggcatg gtagcgtctg ttcatccatg gaataaaaca ttatttacc    4560 aaaaaaaaa a                                                          4571
```

<210> SEQ ID NO 46
<211> LENGTH: 4460
<212> TYPE: DNA
<213> ORGANISM: Homo sapiens

```
<400> SEQUENCE: 46
actaagcagc ggcagcttcc tgcttcggat cctctctctg ctgcttgcat ttaaagagca    60
aactcgtctt gtctacccac cctccctccc ccatcctccc caaaatagcc ttgtgatttc   120
ggaagtatgg actaaaatca cactcctcct taccttaccg cttggactct ggtggctccc   180
aactcgccgt cagacccac ctgccccggt ggtgggaagc gcctggacag accatgacca   240
cagccaagga gccaagcgct tcggggaaat ccgtgcagca gcaggaacag gagctggtgg   300
ggagtaaccc tccgcagagg aattggaaag gaatagcaat tgcactgctt gtcattctgg   360
tcatctgctc cttgatcgtc acctcggtca tacttctgac accagcggaa gataatagtc   420
tgtctcaaaa gaagaaggtc actgtagaag atctcttcag tgaagacttc aaaattcatg   480
accccgaggc taagtggata agtgatacag aattcatcta cagagaacag aaaggaacag   540
tgagactgtg gaatgttgaa acaaatactt ctactgtctt aatagaaggc aaaaaaattg   600
aatcattaag agccatcaga tatgaaatat ctccagatag agagtatgca ctttttttcat   660
acaatgtgga acccatatat caacactcgt atactggata ttacgtcctg agcaaaattc   720
ctcatgggga tcctcaaagt ctggacccac cagaagtcag caatgcaaaa cttcagtatg   780
caggatgggg ccctaaaggc caacagctga tatttatttt tgaaaacaat atctactact   840
gtgcacatgt cgggaaacag gccatccgtg tggtctccac tggcaaggaa ggtgtgattt   900
acaatggcct cagtgactgg ctgtatgaag aggagatttt gaagacacac atcgcacact   960
ggtggtctcc ggatggcacg agactcgcct acgccgccat caatgattcc cgtgtcccca  1020
tcatggagct cccaacttac accggctcca tctaccccac cgtgaagccc taccactatc  1080
ccaaggctgg aagtgagaac cccagcattt ccctacacgt tattggctta aatggaccca  1140
cccatgatct ggagatgatg ccgcctgatg atccacggat gagggagtac tacatccaca  1200
tggtgaagtg ggccaccagc accaaggtcg ccgtgacctg gctgaaccgg gcgcagaacg  1260
tgtccatcct caccctctgc gacgccacca cgggggtctg cacgaagaaa cacgaggatg  1320
aaagtgaggc ctggctccac agacagaatg aagaacctgt gttctccaag gatggccgaa  1380
agttttttctt catcagagcc atcccccagg gaggacgagg gaaattctat cacatcacgg  1440
tgtcctcgtc ccagcccaac agcagcaacg acaacatcca gtccatcacc tccggggact  1500
gggacgtgac caagatccta gcctacgatg agaaggggaa taagatctac ttcctgagca  1560
cggaggacct gcctcggaga cgacaactct acagtgccaa cacggtgggc aacttcaaca  1620
ggcagtgcct ctcctgtgac ctggttgaga actgcaccta cttcagcgct tccttcagcc  1680
atagcatgga cttcttcctg ctcaagtgcg aaggtcctgg tgttcctatg gtgacggtgc  1740
acaacacaac agataagaaa aaaatgtttg acctagaaac aaatgaacat gtcaagaagg  1800
ccataaatga ccgacagatg cctaaagtgg aatacaggga cattgagatt gatgattaca  1860
acctgcccat gcagatactg aagccagcaa ccttcaccga caccacccac taccctctgc  1920
tcctggtggt ggatggcacc ccaggcagcc agagtgtggc tgagaagttc gaggtgagct  1980
gggagacggt gatggtgagc agccacggcg cggtggtggt aaagtgtgac ggccgtggca  2040
gcggcttcca agggaccaag ctcctgcacg aagtgaggcg gcggctgggc ttgctggagg  2100
agaaggacca gatggaggcc gtgcggacga tgctgaagga gcagtacatt gacaggacgc  2160
gcgtggccgt gtttgggaag gattacggtg gctacctgag cacctacatc ctcccagcaa  2220
agggagaaaa tcaaggccag acattcacct gcggctctgc tctctctcca ataacagact  2280
tcaaactcta tgcctctgcg ttttccgaga ggtacttggg cctccatgga cttgacaaca  2340
```

```
gagcatacga gatgaccaag gtagcccatc gagtctccgc gctggaagaa cagcagttcc    2400
tgatcattca tcccactgcc gatgaaaaaa ttcatttcca gcacacagca gaactcatta    2460
cacaactaat taggggaaag gctaattaca gcttacagat ttacccggac gaaagccatt    2520
actttaccag ctccagcctc aaacagcatc tgtaccggtc catcatcaac ttcttcgtgg    2580
aatgcttcag gatccaggac aaactgctga cagtcacagc gaaagaggac gaggaggagg    2640
actaagctca ggtcgctcta agcacaaacg tggctctttc tacaaccaga tgcaaccgag    2700
ggatttccct gccctccctc ttccctcgga ggggcggggc ggggcggggc cgggtgttcc    2760
atagcatgtg tgtctcggat gcggaaggca gttttgcttg ggaaacaagc tccttccccg    2820
gggtcatcac tcacggcctc catggcacca gggacaacgc tgtccccgca gcagcgcctc    2880
ctcccggcgc ccgagagacc ggcacgccac ggccccctcc ccaaggaaca gagcaaagga    2940
tggtggccgc aggccccacg cgagcccaca ggacaccggc ccctagattc cagccaccaa    3000
gcggaagcat gagacccgcc cacactagcc tctgtgttcc cgttagggac atcacaccct    3060
gtctcacgtc gcagtgccat ggacgcagca gttacagcac cattgtttta gcagtgcgtg    3120
ttcatatatg ggcttgctac ttcctgtaat gaggacgttc aacatggtga ggggctacaa    3180
gaaaacgctt ttctgtacag agtcttactg tagctacgct aatggttaac ctgatagaat    3240
taactcgtat ttttctatgg ttttaacctg atgctccact gtctccgtca tggggttgtt    3300
ttgctgtttg gggttgggcc ttgtttccct ttcctttctc cagtccacgt gtagactttg    3360
cgcttgatga agaagcagat cggaagtaac tgctccctcc tcaaggttgt cttcagacgt    3420
cttggggacg ttcctaaaca ctgaggggga agacagccaa tagcacccat taaaagaaat    3480
acctaaataa aacctctctc ccactcagct atgctagggc ttggctgtag gtgtgcactg    3540
tctatttaca tccgtcctta caaccatcct tgtcctcctt ggtaccgtat caagctcttt    3600
cccatgacat ttggtttaaa aaaaaaaaaa aaaaaaaaa aaaaacagaa aaaagacaaa    3660
gcgtcaactc cacccacagg cccgctgtgt gtgctcgggc cacgggagtc ctgagggttc    3720
tgtgggcctg cgcgcatccc tctcccatcg tgggggtggc tccgtgacct tcctgccacg    3780
agcaggaggt tgatgatgtg ctacgttagc cttgtaagat acaccccac caaatgtgca    3840 gccggtgttc ccagtgtata tttcattctc ttgtatataa aggaagcaat gtgtgtcagg    3900
cctctgtgca gtcaacccag cctcctcccg ccagtgctaa ccccgtgttg agcctgcatg    3960
ctgacactgt ggccgatctg gactctagaa gtgctagttt gaaatatatc cattactgtc    4020
atttcctttt gagcttgtgg acaagctgaa tgtcaggact gacttcgcca gctcccagcc    4080 ctgcggggt gtccttggca tcccatcagc agaggagatg cgtccctgtt gcattttggc    4140 gtttgggct tgggtttat ccacatgagc tctgaacgtc cgttatagtt agggtgattg    4200
gaaggtctcc atcactgggt gttttaaagg tgattcacca ccatttgtga aaggaccaac    4260
gtgctgataa acaggaccga tccgagtgct acatgactgt gcgtttgcta tttcaatggg    4320
cctgaacgac tacaaagcca gctaggtctg gaaggggaag ccagctctgg ccacgacatc    4380
tggtcggagg gaagtgggga tgtggcatgg tagcgtctgt tcatccatgg aataaaacat    4440
tattttacca aaaaaaaaaa                                                4460
```

<210> SEQ ID NO 47
<211> LENGTH: 4542
<212> TYPE: DNA
<213> ORGANISM: Homo sapiens

<400> SEQUENCE: 47

```
gctgctgctg ctgctgcctc cccaccgcct ttttttttt ttaatctgga gcggggtggg     60
gagtgggaac cggagagaaa gcaaaatatt aaaaagcccc aaagacagcc agcaggagcg    120
cggtgcccga tggcttcgct gtaccagagg ttcactggca agatcaacac ctcgaggtcc    180
ttccccgcgc ccccggaggc gagtcacctc ctgggcggcc aggggcccga ggaggacggc    240
ggcgcaggag ccaagcccct cggcccgcgg gcgcaggcgg cggcgccccg ggagcgcggc    300
ggcggcggcg gcggcgcggg tggccggccc cggttccagt accaggcgcg gagcgatggt    360
gacgaggagg acgagctggt ggggagtaac cctccgcaga ggaattggaa aggaatagca    420
attgcactgc ttgtcattct ggtcatctgc tccttgatcg tcacctcggt catacttctg    480
acaccagcgg aagataatag tctgtctcaa aagaagaagg tcactgtaga agatctcttc    540
agtgaagact tcaaaattca tgaccccgag gctaagtgga taagtgatac agaattcatc    600
tacagagaac agaaaggaac agtgagactg tggaatgttg aaacaaatac ttctactgtc    660
ttaatagaag gcaaaaaaat tgaatcatta agagccatca gatatgaaat atctccagat    720
agagagtatg cacttttttc atacaatgtg gaacccatat atcaacactc gtatactgga    780
tattacgtcc tgagcaaaat tcctcatggg gatcctcaaa gtctggaccc accagaagtc    840
agcaatgcaa aacttcagta tgcaggatgg ggccctaaag ccaacagct gatatttatt    900
tttgaaaaca atatctacta ctgtgcacat gtcggggaaac aggccatccg tgtggtctcc    960
actggcaagg aaggtgtgat ttacaatggc ctcagtgact ggctgtatga gaggagatt   1020
ttgaagacac acatcgcaca ctggtggtct ccggatggca cgagactcgc ctacgccgcc   1080
atcaatgatt cccgtgtccc catcatggag ctcccaactt acaccggctc catctacccc   1140
accgtgaagc cctaccacta tcccaaggct ggaagtgaga ccccagcat ttccctacac   1200
gttattggct taaatggacc cacccatgat ctggagatga tgccgcctga tgatccacgg   1260
atgagggagt actacatcac catggtgaag tgggccacca gcaccaaggt cgccgtgacc   1320
tggctgaacc gggcgcagaa cgtgtccatc ctcaccctct gcgacgccac cacggggtc   1380
tgcacgaaga acacgagga tgaaagtgag gcctggctcc acagacagaa tgaagaacct   1440
gtgttctcca aggatggccg aaagttttttc ttcatcagag ccatccccca gggaggacga   1500
gggaaattct atcacatcac ggtgtcctcg tcccagccca acagcagcaa cgacaacatc   1560
cagtccatca cctccgggga ctgggacgtg accaagatcc tagcctacga tgagaagggg   1620
aataagatct acttcctgag cacggaggac ctgcctcgga gacgacaact ctacagtgcc   1680
aacacggtgg gcaacttcaa caggcagtgc ctctcctgtg acctggttga gaactgcacc   1740
tacttcagcg cttccttcag ccatagcatg gacttcttcc tgctcaagtg cgaaggtcct   1800
ggtgttccta tggtgacggt gcacaacaca acagataaga aaaaaatgtt tgacctagaa   1860
acaaatgaac atgtcaagaa ggccataaat gaccgacaga tgcctaaagt ggaatacagg   1920
gacattgaga ttgatgatta caacctgccc atgcagatac tgaagccagc aaccttcacc   1980
gacaccaccc actaccctct gctcctggtg gtggatggca ccccaggcag ccagagtgtg   2040
gctgagaagt tcgaggtgag ctgggagacg gtgatggtga gcagccacgg cgcggtggtg   2100
gtaaagtgtg acggccgtgg cagcggcttc caagggacca agctcctgca cgaagtgagg   2160
cggcggctgg gcttgctgga ggagaaggac cagatggagg ccgtgcggac gatgctgaag   2220
gagcagtaca ttgacaggac gcgcgtggcc gtgtttggga aggattacgg tggctacctg   2280
agcacctaca tcctcccagc aaagggagaa aatcaaggcc agacattcac ctgcggctct   2340
```

```
gctctctctc caataacaga cttcaaactc tatgcctctg cgttttccga gaggtacttg    2400
ggcctccatg gacttgacaa cagagcatac gagatgacca aggtagccca tcgagtctcc    2460
gcgctggaag aacagcagtt cctgatcatt catcccactg ccgatgaaaa aattcatttc    2520
cagcacacag cagaactcat tacacaacta attaggggaa aggctaatta cagcttacag    2580
atttacccgg acgaaagcca ttactttacc agctccagcc tcaaacagca tctgtaccgg    2640
tccatcatca acttcttcgt ggaatgcttc aggatccagg acaaactgct gacagtcaca    2700
gcgaaagagg acgaggagga ggactaagct caggtcgctc taagcacaaa cgtggctctt    2760
tctacaacca gatgcaaccg agggatttcc ctgccctccc tcttccctcg gaggggcggg    2820
gcggggcggg gccgggtgtt ccatagcatg tgtgtctcgg atgcggaagg cagttttgct    2880
tgggaaacaa gctccttccc cggggtcatc actcacggcc tccatggcac cagggacaac    2940
gctgtccccg cagcagcgcc tcctcccggc gcccgagaga ccggcacgcc acggcccctc    3000
ccccaaggaa cagagcaaag gatggtggcc gcaggcccca cgcgagccca caggacaccg    3060
gcccctagat tccagccacc aagcggaagc atgagacccg cccacactag cctctgtgtt    3120
cccgttaggg acatcacacc ctgtctcacg tcgcagtgcc atggacgcag cagttacagc    3180
accattgttt tagcagtgcg tgttcatata tgggcttgct acttcctgta atgaggacgt    3240
tcaacatggt gaggggctac aagaaaacgc ttttctgtac agagtcttac tgtagctacg    3300
ctaatggtta acctgataga attaactcgt attttttctat ggttttaacc tgatgctcca    3360
ctgtctccgt catggggttg ttttgctgtt tggggttggg ccttgtttcc ctttcctttc    3420
tccagtccac gtgtagactt tgcgcttgat gaagaagcag atcggaagta actgctccct    3480
cctcaaggtt gtcttcagac gtcttgggga cgttcctaaa cactgagggg gaagacagcc    3540
aatagcaccc attaaaagaa atacctaaat aaaacctctc tcccactcag ctatgctagg    3600
gcttggctgt aggtgtgcac tgtctatttta catccgtcct tacaaccatc cttgtcctcc    3660
ttggtaccgt atcaagctct ttcccatgac atttggttta aaaaaaaaaa aaaaaaaaaa    3720
aaaaaaacag aaaaaagaca aagcgtcaac tccacccaca ggcccgctgt gtgtgctcgg    3780
gccacgggag tcctgagggt tctgtgggcc tgcgcgcatc cctctcccat cgtggggtg     3840 gctccgtgac cttcctgcca cgagcaggag gttgatgatg tgctacgtta gccttgtaag    3900
atacaccccc accaaatgtg cagccggtgt tcccagtgta tatttcattc tcttgtatat    3960
aaaggaagca atgtgtgtca ggcctctgtg cagtcaaccc agcctcctcc cgccagtgct    4020
aaccccgtgt tgagcctgca tgctgacact gtggccgatc tggactctag aagtgctagt    4080
ttgaaatata tccattactg tcatttcctt ttgagcttgt ggacaagctg aatgtcagga    4140
ctgacttcgc cagctcccag ccctgcgggg gtgtccttgg catcccatca gcagaggaga    4200
tgcgtccctg ttgcattttg gcgtttgggg ctttgggttt atccacatga gctctgaacg    4260
tccgttatag ttagggtgat tggaaggtct ccatcactgg gtgttttaaa ggtgattcac    4320
caccatttgt gaaaggacca acgtgctgat aaacaggacc gatccgagtg ctacatgact    4380
gtgcgtttgc tatttcaatg ggcctgaacg actacaaagc cagctaggtc tggaagggga    4440
agccagctct ggccacgaca tctggtcgga gggaagtggg gatgtggcat ggtagcgtct    4500
gttcatccat ggaataaaac attattttac caaaaaaaaa aa                      4542
```

<210> SEQ ID NO 48
<211> LENGTH: 940
<212> TYPE: DNA

<213> ORGANISM: Homo sapiens

<400> SEQUENCE: 48

```
cctgggcgtg tgctaaggcc agagctacca gatgggtcca gctgccgcag gctctccagg      60
cactgtcccc taagtgacag ctgttactgc ctgggagagc tcaagtgcaa agactatcct     120
gttctcccat aaagaggagg aaaaggaaga tacagaaatc ggtgctgctc ccaacagcag     180
atcaaggcag tcgtcaggaa ctcaggatcc gggggtctt cacggcttct ctgcccaggg     240
gccagaaccg aggaggccag agggctgct ggggctaagg ggtctaagga cctcgttgca     300
cacgctacca ggagcagggg catggagcac agtgagggg ctcccggaga cccagccggt     360
actgtggtac cccaggagct gctggaagag atgctttggt tttttcgtgt ggaagatgca     420
tctccctgga atcattccat ccttgccctg gcagctgtgg tggtcattat aagcatggtc     480
ctcctgggaa gaagcatcca ggcaagcaga aagaaaaga tgcagccacc agaaaaagaa     540
actccagaag tcctgcattt ggatgaggcc aaggatcaca acagcctaaa caacctaaga     600
gaaactttgc tctcagaaaa gccaaacttg cccaggtgg aacttgagtt aaaagagaga     660
gatgtgctgt cagttttcct tccggatgta ccagaaactg agagctagtg agggttcaga     720
gaagccccat cctaagccag acacatgatg tgggctcagc tcagtggcct gaaacctctc     780
aggttttaga gtctctccca agaagccgct ttttt ctttt tctttctttc tttttttttt     840
tcttagcaga tacaatgaat gaactgcaag caaactaaaa ttctgttatt aaaaaaaatc     900
ttttattaaa atgctcctgg aagggagcag gtggtattgc                           940
```

<210> SEQ ID NO 49
<211> LENGTH: 5018
<212> TYPE: DNA
<213> ORGANISM: Homo sapiens

<400> SEQUENCE: 49

```
gcccgggact atcccttcgc ggtgtagcgg cagccggaga cctggctgag gaggcaaccg      60
cgtagacacc tccctgctta gaaaacaaac actgaaccag accgatccca gttggagggt     120
tcgaaaatgt tccagacagc ctgtcgggag gggttgttgt tgctgttgga ctaaatagct     180
attcctgatt ggtcatgtat agggtttttt aaggcgggtg gggggaggag ggggtagagg     240
aaaggctcca acacctgca ggttggggc ggaaagctgt ttgcgattcc ctggactggt      300
tggtcgggga caggaggtaa ttcccagcca ttgaccccca tttctctctc tccctccctc     360
ttgccctgcc tctttctctc caccccatc tttcctggaa actcgctttg ggcgcggcag     420
atcgcccagg accacaccgc agcgtaactg caggcctctc agcgaaaaag ggggaaagca     480
aagacccggg tgtgcatcct cttcctcggc ttccgcccct ttccggcgga gtggagatcc     540
tattcagagg ggccggtctc tctaaatatg ccccaggatg accgagcggc cgccgagcga     600
ggcggctcgc agtgaccccc agctagaggg acgggacgcg gccgaggcca gcatggcccc     660
cccgcacctg gtcctgctga acggcgtcgc caaggagacg agccgcgcgg ccgcagcgga     720
gccccagtc atcgaactgg gcgcgcgcgg aggcccgggg ggcggccctg ccggtgggg      780
cggcgccgcg agagacttaa agggccgcga cgcggcgacg gccgaagcgc gccatcgggt     840
gcccaccacc gagctgtgca gacctcccgg gcccgcccg gccccgcgc ccgcctcggt      900
tacagcggag ctgcccggcg acggccgcat ggtgcagctg agtcctcccg cgctggctgc     960
ccccgccgcc cccggccgcg cgctgctcta cagcctcagc cagccgctgg cctctctcgg    1020
cagcgggttc tttggggagc cggatgcctt ccctatgttc accaccaaca atcgagtgaa    1080
```

```
gaggagacct tccccctatg agatggagat tactgatggt ccccacacca aagttgtgcg    1140
gcgtatcttc accaacagcc gggagcgatg gcggcagcag aatgtgaacg gggcctttgc    1200
cgagctccgc aagctgatcc ccacacatcc cccggacaag aagctcagca agaatgagat    1260
cctccgcctg gccatgaagt atatcaactt cttggccaag ctgctcaatg accaggagga    1320
ggagggcacc cagcgggcca agactggcaa ggaccctgtg gtgggggctg gtggggtgg    1380 aggtggggga ggggcggcg cgccccaga tgacctcctg caagacgtgc tttcccccaa    1440
ctccagctgc ggcagctccc tggatggggc agccagcccg acagctaca cggaggagcc    1500 cgcgcccaaa cacacggccc gcagcctcca tcctgccatg ctgcctgccg ccgatggagc    1560
cggccctcgg tgatgggtct gggccaccag gatcagccag gagggcgttc ttaggctgct    1620
gggatggtgg gcttcagggc aagtgggtg agaattgggc ggctctgaag caaggcggtg    1680
gacttgaact ttcctggatg tctgaactt gggaagcctt tactgaccct ggggctggct    1740
tttctgtttc ctgtaccagt aggagatcag aaaaatggag caaagtggta ggtactttt    1800 gtgaagacgg cacggtcttc cctcttccct cagtcccaaa tccttcccaa gtaagaggct    1860
ggagttgtca ctgcttttgg cctggagttt gggatccctg tctttcctaa gacctggggt    1920
tgtcagctct catctgaggc atccagcagt ctctgccttg cctttagccc ctcccaagct    1980
ggctggggtg gcctgtgtgg ccacttctgt ccatatttat aggtacccaa tagctgccca    2040
tttcgtgagc cccatcttca cccaggccta tgttgatcca tccagcttgc cagatgctgc    2100
agagtcacaa gcctcgaggt gccttcttca gggcctggtt gaagaagatg atcagtggac    2160
agtctgctct agatgagctg ggccggaggg tcaggaaacc cagtcgccct tacttcttgc    2220
cctggggatc aaagttctgc tttctcccca atgagacttg ccttcctaag cctgtggctg    2280
tggagacaat gtctgcagcc ctgagaaagc cctgtcgggc tttgtgtgaa ggcagagaaa    2340
gggacaatga tagtagagtg atatggagca agagatattt tgggcatgtg ggcttcaact    2400
cctcgacatc actgttcatg ctggcgagtg aatgccagtg tgctgatggg cgtacgctgg    2460
tgctgagtag atgcgcagcc ccatctgtgc attctcctgg atgcttagag ggatttcttt    2520
gctgtaagat gtctgttttgc tgatggtctg gtctatgttc cgaattgagc acaaaacctg    2580
tcctatgaat gctttgcatt tggaattttt gcttgacttc agttattggt ggaatcttta    2640
gcgctcaata ggaccaggat ccagcctcac ttctagggta tgggaaatcc aatcagagac    2700
caggccctgg ctaagaccca aacatatgca cattcactta gcagaacctt aaacacccct    2760
cagttgtgca gcttttggtc atcaagggtg cgtctgggag gttggtttaa tgcaatagaa    2820
gtgctcccct ctgaaagttg tacatgaaat ttttgtaaat cacatcctta tccttcatct    2880
tttaaagaaa taaccactgc aagtcctttt gtaaagtgaa gaatcctttt gtagaatgaa    2940
ccactgcccc ttcattgatt tcctgtgtca atccagatgg tgggatgtgg ttttcttaag    3000
gtgaggcctg tctgtgacct gcatctaagc ccatgggaca aattgcacag aagtcctgta    3060
tgtctgtcat tgtacccta agtcacccta gccctctccc tctaggctct gccttcgagg    3120
tcagaggaga gatagcctgt ggccctgtcc tgccatgcaa gaactcatca ctgtggctgt    3180
ctggaaagcc ccccttata gtttgggctt cagcctagtg gcttgtcctc accatgatgg    3240
ggccctaatt cagccatgta cagacagaga atatgtctgc tcctttcccc ttccttttaa    3300
gtaaggtcca attctcgagc ttggggcaac attgttcacc tttgtagcac tcaggctctc    3360
cattcaattt caggctcccc agatcatgtt ttggtgaaaa ttagggttgg ttcctttcca    3420
```

```
acgtttggaa gatcctgtga ggagcccat ctgtctaaag atagagtcat tgctgtagga    3480
tctaaggctg tttgcttcac cgtggattcg cttgagttag gaatgagaag tagccacagt    3540
atggatgggt ggatgggttt tatgagatgg atcacatatt ttattaagaa ctcaaacttc    3600
tggctccctc ttctttcaga cttgccatgt gactctggct tggcctatct cctagggcta    3660
tggtgtggac tgaatgggat catgaaagta gacagttttg agaacgtaaa gaacttttc     3720
ttttccctca atctcaatcc tgcagtgggg tttcgcagcc tgagtccacg acctaggcag    3780
taggccggtg tgcctgactg cccagcattt gggtaattta gattgtaaac cgctttggcc    3840
tgagttattg agattgtcct catttctcca gattatctat ttgtgtgtgt gtgtgtgtgt    3900
gtgtgagaga cggtgtcttg ttctgtcact caggctggag tacagtggtg ccatcattgc    3960
tgtctgcagc cttgaactct gggctcaagc aatcctctca cctcagcctc ccgagtaggg    4020
aggaccacag gtgtgagcca ccacacctgg ctaatttta ctttttttt ttttggtag      4080
agatggagtc ttgctatatt gcccaggctg gtcttgaagt cctggcttca ggcaattctc    4140
ctgcctttgc ctccagaagc actgggatca caggtgtcag ccattgcacc cagcccagat    4200
tgtcttaatt tctatcttgt tccaaggcca gggacagtaa taagaatgga aaagagatat    4260
gggaacactg gcagactgtg taaaatgtaa tgcaactacc caaacaagc ctggtaggaa     4320
agggcaagtc tttaggtctt tgtaagaact aaagaagatc tgtaattttt attttcaccc   4380
tctgtacccc atgaccttat ccttcctctc cttccttgtt acccatgaaa aactggcaac    4440
attccaagaa tagcatctgt acaaagggga agaacataa aggtaaaaca aaacaaaaca    4500
acattttgag aacaaagatg accataacca ctgaagggaa tcacatcttt taagacaaat    4560
tcatattctt ttatttgtta tggcagatga caagatggta caacctttat tcttttccaa   4620
aataaaacaa agggcacagc atctgtagtc agccgacaac tatttcggcc ttttgggggt    4680
gggtctggcc gtacttgtga tttcgatggt acgtgaccct ctgctgaaga cttgccccct    4740
gcccgtgtac atagtgcatt gtttctgtgg gcgggcccag cactttccgt caacgttgta    4800
ctgtatgtga tgaattgcgt tggtctctgc attttttctgc agaagaggag taaccgctcc   4860
aggtaccttg acctttgtac agcccagagg ccaacactgt gggtgtgtga ctctttagca    4920
aaaaaaccc atgtggtgat gatgtgtata tatatgtgag gatgtatcgg gaagatttct     4980
aaataaaagt tttacaaagg ggaaaaaaaa aaaaaaa                             5018

<210> SEQ ID NO 50
<211> LENGTH: 3024
<212> TYPE: DNA
<213> ORGANISM: Homo sapiens

<400> SEQUENCE: 50
aggatatctt tagccaaagg aaaagctccg cattcccacc cagtccagaa attgaaatac      60
tatcagggg caagagcctt tctctccagc tacacactcc atctcccggg agcaagggga     120
aactccgaga ggagggcaac agagccagca tcttgccagg ccccggagg aggggttccc     180
cgctacgcct gtgccggagg agttccagtc accgagcgag gggcgcaagg gtgggtgcat    240
cctgcgctgc ggcgggcgcg ctacccagac gctggtgtgc agagccacat gaagcctgct    300
ggggactggg ggccagggag cagcaagcca gctgggactg aggcggacgc tgtctcaggg    360
agacgctgac tcgcaaagac actcccttcc ttgtgcctgg gtaaaaagtc tcctcctggg    420
gtccctggcc atcctgaata tccagaatgg tgttctgaa gttcttctgc atgagtttct     480
tctgccacct gtgtcaaggc tacttcgatg gccccctcta cccagagatg tccaatggga    540
```

```
ctctgcacca ctacttcgtg cccgatgggg actatgagga gaacgatgac cccgagaagt      600
gccagctgct cttcagggtg agtgaccaca ggcgctgctc ccaggggag gggagccagg       660 ttggcagcct gctgagcctc accctgcggg aggagttcac cgtgctgggc cgccaggtgg     720
aggatgctgg gcgcgtgctg gagggcatca gcaaaagcat ctcctacgac ctagacgggg     780
aagagagcta tggcaagtac ctgcggcggg agtcccacca gatcggggat gcctactcca     840
actcggacaa atccctcact gagctggaga gcaagttcaa gcagggccag gaacaggaca     900
gccggcagga gagcaggctc aacgaggact ttctgggaat gctggtccac accaggtccc     960
tgctgaagga gacactggac atctctgtgg ggctcaggga caaatacgag ctgctggccc    1020
tcaccattag gagccatggg acccgactag gtcggctgaa aaatgattat cttaaagtat    1080
aggtggaaga atacaaatgc tagaaagagg gaatcaaatc agccccgttt tggagggtgg    1140
gggacagaag atgggctac atttccccca tacctactat ttttttatat cccgatttgc     1200
actttgagaa tacatctaag gtcatctttc aaaagagaaa aattggacac ttgagtgact    1260
ttgtttttag ttttgttttt gtacattatt tatgtgattg ttatggaatt gtcacctgga    1320
aagaacaatt ttaagcaatg tcatttctag atgggtttct aattctgcag agacacccgt    1380
ttcagccaca tctaaaagag cacagtttat gtggtgcgga attaaacttc cccatcctgc    1440
agattatgtg gaaatacccca aagataatag tgcatagctc ctttcagcct ctagccttca    1500
ctcctgggct ccaaaagcta tcccagttgc ctgtttttca aatgaggttc aaggtgctgc    1560
tttgcatgcc tgccaaccca tggaagttgt ttcttacttc ttttctctct tatttattaa    1620
ccatggtctg agagttgttt tgttctatg taacagtatt gccacaaaac tataggcaaa      1680
tcgtgtttgc agggagattt ctgatgcctc tgtgggtgtg tgtaagttaa agtggccaca    1740
tttaagaagg ccaagctttg tagtggttgc acagtcacac tgatatgctg atttgctctt    1800
tctcattgta tgtctatgct ttgtcatcag tgctatagta aattacaaag aaataggtag    1860
attgtatgaa catacccaca aatgcctatg atttaggtta ccaatgtatt ctttctcatt    1920
tggggttttg cttctgtctg tctgtttatt ggaaacttgt acttcaagta gggggaatcc    1980
taattctaat aactccttag ctaagtttta ttattcaggc aataaacatg ttttcatgta    2040
atactggctt actttgtaat ttacatctgt aactttcata tttctaaaag gggccaatgc    2100
aaaaggagag agaaggactg gatttaagcc agtttactta gagtatatga taaagaaggc    2160
agaggaatag ctacatattt ggcaattctc ctctctgtag tcaccctgac atcctcacaa    2220
gaaaacaaat ctagccattg cccaaacttt aaatttgatc tctataggtc tgcttaaaga    2280
ctcaaatttt ctccagtttc tctcataaat tcaattgcaa agtttctga caaggctcat     2340 accctgtacc cttatgcaga gcaagcattc catcctaagt tataaactac agtgatgttt    2400
aattttgaag ccaggtctac attatttaat taatggcttc aaaaggtgga gatgcacttt    2460
atttaatgtc tttccctagc taattcttac tctcaccta aatatgcttt cttgttgcat      2520
atatgcacag atacacacac acacacacac gaaaataaat aaatgttcat attcttctgt    2580
tcaacagaca tttatttct cctctccctt gaataagaaa ataagttttc cattcctatg      2640
aactgtctaa tatctttcta ttacagaagg ggaaactgag gctgggaaag gctaaatgac    2700
ttatcctcca tcagttataa cagcccctgg tcttcttaaa tttaaacacg ggacttcccg    2760
aactaatttt tttaaggata ctgaaaaatg agagagagtg gtcgaatgcc tgaaattttg    2820
cttaacttac tgtacttaaa atcaattata acttcttttt gttactcagg gcccccacttt   2880
```

| | |
|---|---|
| ttgttgcttt ctagacttgt gtgtagaaag aagattaatg atcacttaaa gtagtttcct | 2940 |
| tctttattct gaaaaaatga ggaaaaaata acaacagtgg caaataaaat catatttggt | 3000 |
| actaaaaaaa aaaaaaaaaa aaaa | 3024 |

<210> SEQ ID NO 51
<211> LENGTH: 7111
<212> TYPE: DNA
<213> ORGANISM: Homo sapiens

<400> SEQUENCE: 51

| | |
|---|---|
| gcgtcagccc tcacgtcact tcgccagcag tagcagaggc ggcggcggcg gctcccggaa | 60 |
| ttgggttgga gcaggagcct cgctggctgc ttcgctcgcg ctctacgcgc tcagtccccg | 120 |
| gcggtagcag gagcctggac ccaggcgccg ccggcgggcg tgaggcgccg agcccggcc | 180 |
| tcgaggtgca taccggaccc ccattcgcat ctaacaagga atctgcgccc cagagagtcc | 240 |
| cgggagcgcc gccggtcggt gcccggcgcg ccgggccatg cagcgacggc cgccgcggag | 300 |
| ctccgagcag cggtagcgcc cccctgtaaa gcggttcgct atgccgggc cactgtgaac | 360 |
| cctgccgcct gccggaacac tcttcgctcc ggaccagctc agcctctgat aagctggact | 420 |
| cggcacgccc gcaacaagca ccgaggagtt aagagagccg caagcgcagg gaaggcctcc | 480 |
| ccgcacgggt gggggaaagc ggccggtgca gcgcggggac aggcactcgg gctggcactg | 540 |
| gctgctaggg atgtcgtcct ggataaggtg gcatggaccc ccatggcgc ggctctgggg | 600 |
| cttctgctgg ctggttgtgg gcttctggag ggccgctttc gcctgtccca cgtcctgcaa | 660 |
| atgcagtgcc tctcggatct ggtgcagcga cccttctcct ggcatcgtgg catttccgag | 720 |
| attggagcct aacagtgtag atcctgagaa catcaccgaa attttcatcg caaaccagaa | 780 |
| aaggttagaa atcatcaacg aagatgatgt tgaagcttat gtgggactga aaatctgac | 840 |
| aattgtggat tctggattaa aatttgtggc tcataaagca tttctgaaaa acagcaacct | 900 |
| gcagcacatc aattttaccc gaaacaaact gacgagtttg tctaggaaac atttccgtca | 960 |
| ccttgacttg tctgaactga tcctggtggg caatccattt acatgctcct gtgacattat | 1020 |
| gtggatcaag actctccaag aggctaaatc cagtccagac actcaggatt tgtactgcct | 1080 |
| gaatgaaagc agcaagaata ttcccctggc aaacctgcag atacccaatt gtggtttgcc | 1140 |
| atctgcaaat ctggccgcac ctaacctcac tgtggaggaa ggaaagtcta tcacattatc | 1200 |
| ctgtagtgtg gcaggtgatc cggttcctaa tatgtattgg gatgttggta acctggttc | 1260 |
| caaacatatg aatgaaacaa gccacacaca gggctcctta aggataacta acatttcatc | 1320 |
| cgatgacagt gggaagcaga tctcttgtgt ggcggaaaat cttgtaggag aagatcaaga | 1380 |
| ttctgtcaac ctcactgtgc attttgcacc aactatcaca tttctcgaat ctccaacctc | 1440 |
| agaccaccac tggtgcattc cattcactgt gaaaggcaac cccaaaccag cgcttcagtg | 1500 |
| gttctataac gggcaatat tgaatgagtc caaatacatc tgtactaaaa tacatgttac | 1560 |
| caatcacacg gagtaccacg gctgcctcca gctggataat cccactcaca tgaacaatgg | 1620 |
| ggactacact ctaatagcca agaatgagta tgggaaggat gagaaacaga tttctgctca | 1680 |
| cttcatgggc tggcctggaa ttgacgatgg tgcaaaccca aattatcctg atgtaattta | 1740 |
| tgaagattat ggaactgcag cgaatgacat cggggacacc acgaacagaa gtaatgaaat | 1800 |
| cccttccaca gacgtcactg ataaaaccgg tcgggaacat ctctcggtct atgctgtggt | 1860 |
| ggtgattgcg tctgtggtgg gattttgcct tttggtaatg ctgtttctgc ttaagttggc | 1920 |
| aagacactcc aagtttggca tgaaaggttt tgttttgttt cataagatcc cactggatgg | 1980 |

```
gtagctgaaa taaaggaaaa gacagagaaa ggggctgtgg tgcttgttgg ttgatgctgc   2040
catgtaagct ggactcctgg gactgctgtt ggcttatccc gggaagtgct gcttatctgg   2100
ggttttctgg tagatgtggg cggtgtttgg aggctgtact atatgaagcc tgcatatact   2160
gtgagctgtg attggggaac accaatgcag aggtaactct caggcagcta agcagcacct   2220
caagaaaaca tgttaaatta atgcttctct tcttacagta gttcaaatac aaaactgaaa   2280
tgaaatccca ttggattgta cttctcttct gaaaagtgtg cttttttgacc ctactggaca   2340 tttattgact taattgcttc tgtttattaa aattgacctg caaagttaaa aaaaaattaa   2400
agttgagaac aggtataagt gcacactgaa tagtctaatc tacatgtaac acatatttta   2460
gtgtgatttt ctatactcta atcagcactg aattcagagg gtttgacttt ttcatctata   2520
acacagtgac taaagagtt aagggtatat ataccatcac tttgggactt ggtagtatta   2580
ttaaaaggtt atttccttca ctgtcaataa aagtccaaat gtttagctta ggtctgagag   2640
tcaaacaatg ttaaggattg tcttaaagtt ccttagccag caaacaaaa caaacaaaa   2700 caaacaaatg aaaaacgttt aaaaagaaga agaagaaaaa aacaagaac aagcagcaac   2760 agctgttttg ttggggctat agatttaagt taggcatagt caatttcaga ataactaaga   2820
gtggaatata tgcatatggt gaaattataa ccttgcccct ttttatttgc cctctgcgat   2880
ccacctgctt tttagaagtc tgccgagtga aaggccaca gtatctcatg ctgtttgcat   2940
tacagaactg cagcttttct actctgaaaa ggcctgggag cagaatggct ggcctgctgt   3000
gagcaggaga ggagattcta agaaggatag tccccctac aacatactgt catactgctg   3060
ggttttcatg ggtaggaaag cttgtcctga ccccagcagc aaagaggtgg caggtcgcta   3120
atgaatatat gctttataat gtccttcttc attgctgaga gggcagcctt agagctgtgg   3180
atttctgcat ccccctgag tctgacccat ggacacctgt tcattcact ttagcatcac   3240 agtgaccttt gtatgctctg ttcagtctgt gtcaggcagt atgcttgtcc tgaagagagg   3300
tttggctatc cccaccccac cccacccac cctgttcctt ttttatcagg aggacttcag   3360
agccaggcct gcagcatttt gtttgaaaac acaatcagct ctgacagtta gacatgcaca   3420
cagacgccat agctggattg gaaacattga tgttttaaaa atttatttt tttggaaata   3480 gttgcacaaa tgctgcaatt tagctttaag gttctataga tttttaacta gtccaacaca   3540
gtcagaaaca ttgtttttgaa tcctctgtaa accaaggcat taatcttaat aaaccaggat   3600
ccatttaggt accacttgat ataaaaagga tatccataat gaatatttta tactgcatcc   3660
tttacattag ccactaaata cgttattgct tgatgaagac ctttcacaga atcctatgga   3720
ttgcagcatt tcacttggct acttcatacc catgccttaa agaggggcag tttctcaaaa   3780
gcagaaacat gccgccagtt ctcaagttttt cctcctaact ccatttgaat gtaagggcag   3840
ctggccccca atgtggggag gtccgaacat tttctgaatt cccattttct tgttcgcggc   3900
taaatgacag tttctgtcat tacttagatt ccgatcttc ccaaaggtgt tgatttacaa   3960
agaggccagc taatagcaga aatcatgacc ctgaaagaga gatgaaattc aagctgtgag   4020
ccaggcagga gctcagtatg gcaaaggttc ttgagaatca gccatttggt acaaaaaaga   4080 ttttaaagc ttttatgtta taccatggag ccatagaaag gctatggatt gtttaagaac   4140
tattttaaag tgttccagac ccaaaaagga aaaataaaaa aaaggaata tttgtaccca   4200 acagctagaa ggattgcaag gtagatttt gttttaaaat ggagagaagt ggacagataa   4260
ggccatttaa tatatcaaag atcagttgac atctcctagg gaatgatgaa aacagcaggc   4320
```

```
tattagaaaa ttatttcata tagttctcgt gttcttttct tttttttaat ccctgaaggg    4380
atgatcagta acatagcttc tcttttctgt actctagacc accccttttc atcatttgc    4440 tttttatgtc tcccataaga aatgtgcttt ttagagcttc ctaatgcatg tgttgcatta    4500
ttgcagcatt agaaaaggag aggtagcatt tttgctgaaa tcgggcctgt cactctccaa    4560
taaaggttct ggcacttcaa tgccaggcag gtctcctaaa tgaacagaat gatctgtgtg    4620
agccgatgcc tgcccttcca gaggggccac tgtcccagc cgcagccaac tgtgtcccac     4680
aggaatggga gcctaggttt ccaaatcttg tgattcttta ggagaaacat gaaacctgga    4740
tttcgtgtga aatgtcccga ttgttaaaaa gttggctcaa ttatttttaa aacattttgt    4800
aagccaacaa aagtctgtgg gctgccagtt tattacttttt gtcttaaaac atgatcattg   4860
ttctctcacg gtatccttct gtcttcccgt tgcaaattca ctttctttc ttcctgacat     4920 tgccattgag ggctttgtta ccacaagcta agaaactgag tttaacagcc cagttatctg    4980
caacatgtca attacctttg ctcctctcct gtgattccca ccatgctgtg accctcagct    5040
gtctcccttt gctgggaatt ctgcaccaat gtctcccctc aacccattcc ctggttggtc    5100
ctactcccgt gtggccagag acatcctagc aaatccttcc tcctattata tctgacacta    5160
atttcttttc aacagcgctc atgtctcttg gcccagtcag gtgctgccag gtttagatag    5220
gaaagtacat gtcccatttt catgggtgcc cttaatgtgg tccacgtcct atatcttatt    5280
atatttactc atggctcaat gggggcctcc agagaccctc tcaggctgct gagctagact    5340
aaggaatgca tccaccgtca tcacatgaga cactgactct gtgacgacaa aagtacaaac    5400
agtctgaggc taagaaaggt tcatctcaca acaggaaaaa caaatctcaa cacacattag    5460
agataattga ttcaggggtt ttctctccca gtctcccagc agggactgat ttcatttctg    5520
acccactagg ttttctttcc agaaataggt agcaaggaca agaactaaac aatcccagcc    5580
ccacccagca acacagaaca caggagtttg cttttggctt ctcactctcc aagtaaccct    5640
gaattaggcc cagaatggct gaggcttgga gcatctcctc agacagagca gaggcgacac    5700
ctcttcaggg gtgtgtggag taaatagctc gaagagctga agacagaaaa ccagtttcac    5760
gccaggtgcg agagagagca taatggaggg aagcccgctt tctctctcct cttcttttct    5820
cttttattct ttagagcact tgactttttt ttctctctct ctctagtatt ctaaactgac    5880
cccatgacca actgagaatt tattttttgtt tcattggttg tttcacagaa ttagaacaca    5940
cacgactttt tattcctcca ttgcaaaatg gaatcaagat actacacaag acctgtgctt    6000
tcttcctttg catgatttac acctccgcct gttttggtgc tagctgtcta gaacttctct    6060
cttggtttga atctgattcc ttcacactac actagaagtt tatttcatct tgttttgtct    6120
agactccaga tacagaggga cagctggact gaggacaagc aattccatct agcataggggt   6180 ctctcagggt tggtgcatcc agccacatgg gcagggccag tcacatctag tctatgtccc    6240
cagagccctt ggagttgcgc agcttagctg acttgactcc aaggaaatta gtacagaagt    6300
aaccactcta ttaagtgtgt tctgctatgt tcacatgcct gtagtacctg caaaccatgc    6360
caggttcatc taaagacata ggggaagatt aaggactctt ttggacagac catgaattga    6420
atttgctgcc aggtgctgcc agactgaatt tggctgacag aactcccagc ccaggaaagt    6480
tccatgacaa tgactgtcgc agaaggaaat ttcccactaa agtcagtcca ttttcaagtt    6540
ttggtcttca gagacaaaag aacgtcccag ccacctgatt ttgatggtga ggtaactcta    6600
agttgaattc aggctagtgt tgcagtatag ctttggcatg ttcatgagtg agcacccaga    6660
atgtgttgaa ccaaccccca cccctaacta ctgactatga ctgcagtggg tttttatggg    6720
```

```
gaaaaaaagt gtgaaaagca aaagaaagg aacagagatt ttttatcacc tttattgtaa    6780
gacagtccat ttatgaattg agtataaaca catacaaagt aacaagagat tcctaagaaa    6840
cgcaaatcct tgagtttcac gcacttcatg ttcaaccatt tgctgtaatc cagaggcagc    6900
ctgtgaatca ttctcatgcc ctgttttttt ttttttttc ctataatgtt ctgggtttaa    6960
aagccatctt ttccacattt tctgtaaata atggataatc attttaaaaa ttttatttt    7020 tagtgctgtt ttaacaatgt agatagatca taaatgtact tgctgaattc aatcatttt    7080 aacaagccaa taaagtttga taattcatct c                                  7111
```

<210> SEQ ID NO 52
<211> LENGTH: 5560
<212> TYPE: DNA
<213> ORGANISM: Homo sapiens

<400> SEQUENCE: 52

```
aagacggatt ctcagacaag gcttgcaaat gccccgcagc catcatttaa ctgcacccgc      60
agaatagtta cggtttgtca cccgaccctc ccggatcgcc taatttgtcc ctagtgagac     120
cccgaggctc tgcccgcgcc tggcttcttc gtagctggat gcatatcgtg ctccgggcag     180
cgcgggcgca gggcacgcgt tcgcgcacac cctagcacac atgaacacgc gcaagagctg     240
aaccaagcac ggtttccatt tcaaaaaggg agacagcctc taccgcgatt gtagaagaga     300
ctgtggtgtg aattagggac cgggaggcgt cgaacggagg aacggttcat cttagagact     360
aattttctgg agtttctgcc cctgctctgc gtcagccctc acgtcacttc gccagcagta     420
gcagaggcgg cggcggcggc tcccggaatt gggttggagc aggagcctcg ctggctgctt     480
cgctcgcgct ctacgcgctc agtccccggc ggtagcagga gcctggaccc aggcgccgcc     540
ggcgggcgtg aggcgccgga gcccggcctc gaggtgcata ccggaccccc attcgcatct     600
aacaaggaat ctgcgcccca gagagtcccg ggagcgccgc cggtcggtgc ccggcgcgcc     660
gggccatgca gcgacggccg ccgcggagct ccgagcagcg gtagcgcccc cctgtaaagc     720
ggttcgctat gccggggcca ctgtgaaccc tgccgcctgc cggaacactc ttcgctccgg     780
accagctcag cctctgataa gctggactcg gcacgcccga acaagcacc gaggagttaa      840 gagagccgca agcgcaggga aggcctcccc gcacgggtgg gggaaagcgg ccggtgcagc     900
gcggggacag gcactcgggc tggcactggc tgctagggat gtcgtcctgg ataaggtggc     960
atggacccgc catggcgcgg ctctggggct tctgctggct ggttgtgggc ttctggaggg    1020
ccgctttcgc ctgtcccacg tcctgcaaat gcagtgcctc tcggatctgg tgcagcgacc    1080
cttctcctgg catcgtggca tttccgagat tggagcctaa cagtgtagat cctgagaaca    1140
tcaccgaaat tttcatcgca aaccagaaaa ggttagaaat catcaacgaa gatgatgttg    1200
aagcttatgt gggactgaga aatctgacaa ttgtggattc tggattaaaa tttgtggctc    1260
ataaagcatt tctgaaaaac agcaacctgc agcacatcaa ttttacccga aacaaactga    1320
cgagtttgtc taggaaacat ttccgtcacc ttgacttgtc tgaactgatc ctggtgggca    1380
atccatttac atgctcctgt gacattatgt ggatcaagac tctccaagag gctaaatcca    1440
gtccagacac tcaggatttg tactgcctga atgaaagcag caagaatatt cccctggcaa    1500
acctgcagat acccaattgt ggtttgccat ctgcaaatct ggccgcacct aacctcactg    1560
tggaggaagg aaagtctatc acattatcct gtagtgtggc aggtgatccg gttcctaata    1620
tgtattggga tgttggtaac ctggtttcca acatatgaa tgaaacaagc cacacacagg    1680
```

```
gctccttaag gataactaac atttcatccg atgacagtgg gaagcagatc tcttgtgtgg      1740
cggaaaatct tgtaggagaa gatcaagatt ctgtcaacct cactgtgcat tttgcaccaa      1800
ctatcacatt tctcgaatct ccaacctcag accaccactg gtgcattcca ttcactgtga      1860
aaggcaaccc caaaccagcg cttcagtggt tctataacgg ggcaatattg aatgagtcca      1920
aatacatctg tactaaaata catgttacca atcacacgga gtaccacggc tgcctccagc      1980
tggataatcc cactcacatg aacaatgggg actacactct aatagccaag aatgagtatg      2040
ggaaggatga gaaacagatt tctgctcact tcatgggctg gcctggaatt gacgatggtg      2100
caaacccaaa ttatcctgat gtaatttatg aagattatgg aactgcagcg aatgacatcg      2160
gggacaccac gaacagaagt aatgaaatcc cttccacaga cgtcactgat aaaaccggtc      2220
gggaacatct ctcggtctat gctgtggtgg tgattgcgtc tgtggtggga ttttgccttt      2280
tggtaatgct gtttctgctt aagttggcaa gacactccaa gtttggcatg aaaggcccag      2340
cctccgttat cagcaatgat gatgactctg ccagcccact ccatcacatc tccaatggga      2400
gtaacactcc atcttcttcg gaaggtggcc cagatgctgt cattattgga atgaccaaga      2460
tccctgtcat tgaaaatccc cagtactttg gcatcaccaa cagtcagctc aagccagaca      2520
catttgttca gcacatcaag cgacataaca ttgttctgaa agggagcta ggcgaaggag       2580 cctttggaaa agtgttccta gctgaatgct ataacctctg tcctgagcag gacaagatct      2640
tggtggcagt gaagaccctg aaggatgcca gtgacaatgc acgcaaggac ttccaccgtg      2700
aggccgagct cctgaccaac ctccagcatg agcacatcgt caagttctat ggcgtctgcg      2760
tggagggcga ccccctcatc atggtctttg agtacatgaa gcatggggac ctcaacaagt      2820
tcctcagggc acacggccct gatgccgtgc tgatggctga gggcaacccg cccacggaac      2880
tgacgcagtc gcagatgctg catatagccc agcagatcgc cgcgggcatg gtctacctgg      2940
cgtcccagca cttcgtgcac cgcgatttgg ccaccaggaa ctgcctggtc ggggagaact      3000
tgctggtgaa aatcggggac tttgggatgt cccgggacgt gtacagcact gactactaca      3060
gggtcggtgg ccacacaatg ctgcccattc gctggatgcc tccagagagc atcatgtaca      3120
ggaaattcac gacggaaagc gacgtctgga gcctgggggt cgtgttgtgg gagattttca      3180
cctatggcaa acagccctgg taccagctgt caaacaatga ggtgatagag tgtatcactc      3240
agggccgagt cctgcagcga ccccgcacgt gcccccagga ggtgtatgag ctgatgctgg      3300
ggtgctggca gcgagagccc cacatgagga gaacatcaa gggcatccat accctccttc       3360
agaacttggc caaggcatct ccggtctacc tggacattct aggctagggc cttttcccc      3420 agaccgatcc ttcccaacgt actcctcaga cgggctgaga ggatgaacat cttttaactg      3480
ccgctggagg ccaccaagct gctctccttc actctgacag tattaacatc aaagactccg      3540
agaagctctc gagggaagca gtgtgtactt cttcatccat agacacagta ttgacttctt      3600
tttggcatta tctctttctc tctttccatc tccttggtt gttccttttt cttttttaa       3660 atttctttt tctttttttt ttcgtcttcc ctgcttcacg attcttaccc tttctttga       3720 atcaatctgg cttctgcatt actattaact ctgcatagac aaaggcctta acaaacgtaa      3780
tttgttatat cagcagacac tccagtttgc ccaccacaac taacaatgcc ttgttgtatt      3840
cctgcctttg atgtggatga aaaaaggga aaacaaatat tcacttaaa ctttgtcact       3900 tctgctgtac agatatcgag agtttctatg gattcacttc tatttattta ttattattac     3960
tgttcttatt gttttggat ggcttaagcc tgtgtataaa aagaaaact tgtgttcaat       4020 ctgtgaagcc tttatctatg ggagattaaa accagagaga aagaagattt attatgaacc     4080
```

| | | | | | |
|---|---|---|---|---|---|
| gcaatatggg | aggaacaaag | acaaccactg | ggatcagctg | gtgtcagtcc | ctacttagga | 4140 |
| aatactcagc | aactgttagc | tgggaagaat | gtattcggca | ccttccctg | aggacctttc | 4200 |
| tgaggagtaa | aaagactact | ggcctctgtg | ccatggatga | ttcttttccc | atcaccagaa | 4260 |
| atgatagcgt | gcagtagaga | gcaaagatgg | cttccgtgag | acacaagatg | gcgcatagtg | 4320 |
| tgctcggaca | cagttttgtc | ttcgtaggtt | gtgatgatag | cactggtttg | tttctcaagc | 4380 |
| gctatccaca | gaacctttgt | caacttcagt | tgaaaagagg | tggattcatg | tccagagctc | 4440 |
| atttcgggt | caggtgggaa | agccaagaac | ttggaaaaga | taagacaagc | tataaattcg | 4500 |
| gaggcaagtt | tcttttacaa | tgaacttttc | agatctcact | tccctccgac | ccctaacttc | 4560 |
| catgcccacc | cgtccttta | actgtgcaag | caaaattgtg | catggtcttc | gtcgattaat | 4620 |
| accttgtgtg | cagacactac | tgctccagac | gtcgtttccc | tgataggtag | agcagatcca | 4680 |
| taaaaggta | tgacttatac | aattagggga | agctaatgga | gtttattagc | tgagtatcaa | 4740 |
| tgtctctgcg | ttgtacggtg | gtgatgggtt | ttaatgaata | tggaccctga | agcctggaaa | 4800 |
| tcctcatcca | cgtcgaaccc | acaggactgt | gggaagggca | gaatcaatcc | ctaagggaaa | 4860 |
| ggaaacctca | ccctgagggc | atcacatgca | ctcatgttca | gtgtacacag | gtcaagtccc | 4920 |
| ttgctctggg | ctctagttgg | gagagtggtt | tcattccaag | tgtactccat | tgtcagtatg | 4980 |
| ctgttttgt | ttccttcact | ccattcaaaa | agtcaaaata | caaatttgg | cacagcatgc | 5040 |
| caacgggagg | ctgtgcccag | accaagcact | ggaagtgtgc | ttctaggcat | agtcattggt | 5100 |
| tttgcaaaaa | gagggctcaa | atttaaatag | aaatttacag | ctatttgaat | ggtcagatat | 5160 |
| accaagaaag | aaaatatttt | ctgttcctca | agaaaacttg | ctaccctctg | tgagggaat | 5220 |
| tttgctaaac | ttgacatctt | tataacatga | gccagattga | aagggagtga | ttttcattca | 5280 |
| tcttaggtca | tgttatttca | tatttgtttc | tgaaggtgcg | atagctctgt | tttaggtttt | 5340 |
| gcttgcgcct | gttaattact | ggaacaccctt | attttcatt | aaaggctttg | aaagccaatt | 5400 |
| ctcaaaaatt | caaaagtgca | aattaacaga | acaaaaggaa | atccagtagc | aactgcagtc | 5460 |
| aagcgaggga | gttgacaaga | taaaccttac | gtccattcaa | gttatatgct | ggcctatgag | 5520 |
| agatgagagt | tgggtcgttt | gttctctttg | ttgatgattt | | | 5560 |

<210> SEQ ID NO 53
<211> LENGTH: 5608
<212> TYPE: DNA
<213> ORGANISM: Homo sapiens

<400> SEQUENCE: 53

| | | | | | |
|---|---|---|---|---|---|
| aagacggatt | ctcagacaag | gcttgcaaat | gccccgcagc | catcatttaa | ctgcacccgc | 60 |
| agaatagtta | cggtttgtca | cccgaccctc | ccggatcgcc | taatttgtcc | ctagtgagac | 120 |
| cccgaggctc | tgcccgcgcc | tggcttcttc | gtagctggat | gcatatcgtg | ctccgggcag | 180 |
| cgcgggcgca | gggcacgcgt | tcgcgcacac | cctagcacac | atgaacacgc | gcaagagctg | 240 |
| aaccaagcac | ggtttccatt | tcaaaaaggg | agacagcctc | taccgcgatt | gtagaagaga | 300 |
| ctgtggtgtg | aattagggac | cgggaggcgt | cgaacggagg | aacggttcat | cttagagact | 360 |
| aatttttctgg | agtttctgcc | cctgtctctgc | gtcagccctc | acgtcacttc | gccagcagta | 420 |
| gcagaggcgg | cggcggcggc | tcccggaatt | gggttggagc | aggagcctcg | ctggctgctt | 480 |
| cgctcgcgct | ctacgcgctc | agtccccggc | ggtagcagga | gcctggaccc | aggcgccgcc | 540 |
| ggcgggcgtg | aggcgccgga | gcccggcctc | gaggtgcata | ccggaccccc | attcgcatct | 600 |

```
aacaaggaat ctgcgcccca gagagtcccg ggagcgccgc cggtcggtgc ccggcgcgcc    660
gggccatgca gcgacggccg ccgcggagct ccgagcagcg gtagcgcccc cctgtaaagc    720
ggttcgctat gccggggcca ctgtgaaccc tgccgcctgc cggaacactc ttcgctccgg    780
accagctcag cctctgataa gctggactcg gcacgcccgc aacaagcacc gaggagttaa    840
gagagccgca agcgcaggga aggcctcccc gcacgggtgg gggaaagcgg ccggtgcagc    900
gcggggacag gcactcgggc tggcactggc tgctagggat gtcgtcctgg ataaggtggc    960
atggacccgc catggcgcgg ctctggggct tctgctggct ggttgtgggc ttctggaggg   1020
ccgctttcgc ctgtcccacg tcctgcaaat gcagtgcctc tcggatctgg tgcagcgacc   1080
cttctcctgg catcgtggca tttccgagat tggagcctaa cagtgtagat cctgagaaca   1140
tcaccgaaat tttcatcgca aaccagaaaa ggttagaaat catcaacgaa gatgatgttg   1200
aagcttatgt gggactgaga aatctgacaa ttgtggattc tggattaaaa tttgtggctc   1260
ataaagcatt tctgaaaaac agcaacctgc agcacatcaa ttttacccga aacaaactga   1320
cgagtttgtc taggaaacat ttccgtcacc ttgacttgtc tgaactgatc ctggtgggca   1380
atccatttac atgctcctgt gacattatgt ggatcaagac tctccaagag gctaaatcca   1440
gtccagacac tcaggatttg tactgcctga atgaaagcag caagaatatt cccctggcaa   1500
acctgcagat acccaattgt ggtttgccat ctgcaaatct ggccgcacct aacctcactg   1560
tggaggaagg aaagtctatc acattatcct gtagtgtggc aggtgatccg gttcctaata   1620
tgtattggga tgttggtaac ctggtttcca acatatgaa tgaaacaagc cacacacagg   1680
gctccttaag gataactaac atttcatccg atgcagtgg gaagcagatc tcttgtgtgg   1740
cggaaaatct tgtaggagaa gatcaagatt ctgtcaacct cactgtgcat tttgcaccaa   1800
ctatcacatt tctcgaatct ccaacctcag accaccactg gtgcattcca ttcactgtga   1860
aaggcaaccc caaaccagcg cttcagtggt tctataacgg gcaatattg aatgagtcca   1920
aatacatctg tactaaaaata catgttacca atcacacgga gtaccacggc tgcctccagc   1980
tggataatcc cactcacatg aacaatgggg actacactct aatagccaag aatgagtatg   2040
ggaaggatga gaaacagatt tctgctcact tcatgggctg gcctggaatt gacgatggtg   2100
caaacccaaa ttatcctgat gtaatttatg aagattatgg aactgcagcg aatgacatcg   2160
gggcaccac gaacagaagt aatgaaatcc cttccacaga cgtcactgat aaaaccggtc   2220
gggaacatct ctcggtctat gctgtggtgg tgattgcgtc tgtggtggga ttttgccttt   2280
tggtaatgct gtttctgctt aagttggcaa gacactccaa gtttggcatg aaagatttct   2340
catggtttgg atttgggaaa gtaaaatcaa gacaaggtgt tggcccagcc tccgttatca   2400
gcaatgatga tgactctgcc agcccactcc atcacatctc caatgggagt aacactccat   2460
cttcttcgga aggtggccca gatgctgtca ttattggaat gaccaagatc cctgtcattg   2520
aaaatcccca gtactttggc atcaccaaca gtcagctcaa gccagacaca tttgttcagc   2580
acatcaagcg acataacatt gttctgaaaa gggagctagg cgaaggagcc tttggaaaag   2640
tgttcctagc tgaatgctat aacctctgtc ctgagcagga caagatcttg gtggcagtga   2700
agacccctgaa ggatgccagt gacaatgcac gcaaggactt ccaccgtgag gccgagctcc   2760
tgaccaacct ccagcatgag cacatcgtca gttctatgg cgtctgcgtg gagggcgacc   2820
ccctcatcat ggtctttgag tacatgaagc atgggaccct caacaagttc ctcagggcac   2880
acggccctga tgccgtgctg atggctgagg gcaacccgcc cacggaactg acgcagtcgc   2940
agatgctgca tatagcccag cagatcgccg cgggcatggt ctacctggcg tcccagcact   3000
```

```
tcgtgcaccg cgatttggcc accaggaact gcctggtcgg ggagaacttg ctggtgaaaa    3060
tcggggactt tgggatgtcc cgggacgtgt acagcactga ctactacagg gtcggtggcc    3120
acacaatgct gcccattcgc tggatgcctc cagagagcat catgtacagg aaattcacga    3180
cggaaagcga cgtctggagc ctgggggtcg tgttgtggga gattttcacc tatggcaaac    3240
agccctggta ccagctgtca acaatgagg tgatagagtg tatcactcag ggccgagtcc    3300
tgcagcgacc ccgcacgtgc ccccaggagg tgtatgagct gatgctgggg tgctggcagc    3360
gagagcccca catgaggaag aacatcaagg gcatccatac cctccttcag aacttggcca    3420
aggcatctcc ggtctacctg gacattctag gctagggccc ttttccccag accgatcctt    3480
cccaacgtac tcctcagacg ggctgagagg atgaacatct tttaactgcc gctggaggcc    3540
accaagctgc tctccttcac tctgacagta ttaacatcaa agactccgag aagctctcga    3600
gggaagcagt gtgtacttct tcatccatag acacagtatt gacttctttt tggcattatc    3660
tctttctctc tttccatctc ccttggttgt tcctttttct tttttaaat tttctttttc    3720
tttttttttt cgtcttccct gcttcacgat tcttacccct tcttttgaat caatctggct    3780
tctgcattac tattaactct gcatagacaa aggccttaac aaacgtaatt tgttatatca    3840
gcagacactc cagtttgccc accacaacta acaatgcctt gttgtattcc tgcctttgat    3900
gtggatgaaa aaagggaaa acaaatattt cacttaaact ttgtcacttc tgctgtacag    3960
atatcgagag tttctatgga ttcacttcta tttatttatt attattactg ttcttattgt    4020
ttttggatgg cttaagcctg tgtataaaaa agaaaacttg tgttcaatct gtgaagcctt    4080
tatctatggg agattaaaac cagagagaaa gaagatttat tatgaaccgc aatatgggag    4140
gaacaaagac aaccactggg atcagctggt gtcagtccct acttaggaaa tactcagcaa    4200
ctgttagctg ggaagaatgt attcggcacc ttcccctgag gaccttttctg aggagtaaaa    4260
agactactgg cctctgtgcc atggatgatt cttttcccat caccagaaat gatagcgtgc    4320
agtagagagc aaagatggct tccgtgagac acaagatggc gcatagtgtg ctcggacaca    4380
gttttgtctt cgtaggttgt gatgatagca ctggtttgtt tctcaagcgc tatccacaga    4440
acctttgtca acttcagttg aaaagaggtg gattcatgtc cagagctcat ttcggggtca    4500
ggtgggaaag ccaagaactt ggaaaagata agacaagcta taaattcgga ggcaagtttc    4560
ttttacaatg aacttttcag atctcacttc cctccgaccc ctaacttcca tgcccacccg    4620
tccttttaac tgtgcaagca aaattgtgca tggtcttcgt cgattaatac cttgtgtgca    4680
gacactactg ctccagacgt cgtttccctg ataggtagag cagatccata aaaaggtatg    4740
acttatacaa ttaggggaag ctaatggagt ttattagctg agtatcaatg tctctgcgtt    4800
gtacggtggt gatgggtttt aatgaatatg gaccctgaag cctggaaatc ctcatccacg    4860
tcgaacccac aggactgtgg gaagggcaga atcaatccct aagggaaagg aaacctcacc    4920
ctgagggcat cacatgcact catgttcagt gtacacaggt caagtccctt gctctgggct    4980
ctagttggga gagtggtttc attccaagtg tactccattg tcagtatgct gtttttgttt    5040
ccttcactcc attcaaaaag tcaaaataca aaatttggca cagcatgcca acggaggct    5100
gtgcccagac caagcactgg aagtgtgctt ctaggcatag tcattggttt tgcaaaaga    5160
gggctcaaat ttaaatagaa atttacagct atttgaatgg tcagatatac caagaaagaa    5220
aaatatttct gttcctcaag aaaacttgct accctctgtg aggggaattt tgctaaactt    5280
gacatcttta taacatgagc cagattgaaa gggagtgatt ttcattcatc ttaggtcatg    5340
```

| | |
|---|---:|
| ttatttcata tttgtttctg aaggtgcgat agctctgttt taggttttgc ttgcgcctgt | 5400 |
| taattactgg aacaccttat ttttcattaa aggctttgaa agccaattct caaaaattca | 5460 |
| aaagtgcaaa ttaacagaac aaaaggaaat ccagtagcaa ctgcagtcaa gcgagggagt | 5520 |
| tgacaagata aaccttacgt ccattcaagt tatatgctgg cctatgagag atgagagttg | 5580 |
| ggtcgtttgt tctctttgtt gatgattt | 5608 |

```
<210> SEQ ID NO 54
<211> LENGTH: 3600
<212> TYPE: DNA
<213> ORGANISM: Homo sapiens

<400> SEQUENCE: 54
```

| | |
|---|---:|
| gaagagactc agggcagagg gaggaaggac agcagaccag acagtcacag cagccttgac | 60 |
| aaaacgttcc tggaactcaa gctcttctcc acagaggagg acagagcaga cagcagagac | 120 |
| catggagtct ccctcggccc ctccccacag atggtgcatc ccctggcaga ggctcctgct | 180 |
| cacagcctca cttctaacct tctggaaccc gcccaccact gccaagctca ctattgaatc | 240 |
| cacgccgttc aatgtcgcag aggggaagga ggtgcttcta cttgtccaca atctgcccca | 300 |
| gcatcttttt ggctacagct ggtacaaagg tgaaagagtg gatggcaacc gtcaaattat | 360 |
| aggatatgta ataggaactc aacaagctac cccagggccc gcatacagtg gtcgagagat | 420 |
| aatataccccc aatgcatccc tgctgatcca gaacatcatc agaatgaca caggattcta | 480 |
| caccctacac gtcataaagt cagatcttgt gaatgaagaa gcaactggcc agttccgggt | 540 |
| atacccggag ctgcccaagc cctccatctc cagcaacaac tccaaacccg tggaggacaa | 600 |
| ggatgctgtg gccttcacct gtgaacctga gactcaggac gcaacctacc tgtggtgggt | 660 |
| aaacaatcag agcctcccgg tcagtccag gctgcagctg tccaatggca acaggaccct | 720 |
| cactctattc aatgtcacaa gaaatgacac agcaagctac aaatgtgaaa cccagaaccc | 780 |
| agtgagtgcc aggcgcagtg attcagtcat cctgaatgtc ctctatggcc cggatgcccc | 840 |
| caccatttcc cctctaaaca tcttacag atcagggaa atctgaacc tctcctgcca | 900 |
| cgcagcctct aacccacctg cacagtactc ttggtttgtc aatgggactt tccagcaatc | 960 |
| cacccaagag ctctttatcc ccaacatcac tgtgaataat agtggatcct atacgtgcca | 1020 |
| agcccataac tcagacactg gcctcaatag gaccacagtc acgacgatca cagtctatgc | 1080 |
| agagccaccc aaaccttca tcaccagcaa caactccaac cccgtggagg atgaggatgc | 1140 |
| tgtagcctta acctgtgaac ctgagattca gaacacaacc tacctgtggt gggtaaataa | 1200 |
| tcagagcctc ccggtcagtc ccaggctgca gctgtccaat gacaacagga ccctcactct | 1260 |
| actcagtgtc acaaggaatg atgtaggacc ctatgagtgt ggaatccaga acaaattaag | 1320 |
| tgttgaccac agcgacccag tcatcctgaa tgtcctctat ggcccagacg accccaccat | 1380 |
| ttcccctca tacacctatt accgtccagg ggtgaacctc agcctctcct gccatgcagc | 1440 |
| ctctaaccca cctgcacagt attcttggct gattgatggg aacatccagc aacacacaca | 1500 |
| agagctcttt atctccaaca tcactgagaa gaacagcgga ctctatacct gccaggccaa | 1560 |
| taactcagcc agtggccaca gcaggactac agtcaagaca atcacagtct ctgcggagct | 1620 |
| gcccaagccc tccatctcca gcaacaactc caaacccgtg gaggacaagg atgctgtggc | 1680 |
| cttcacctgt gaacctgagg ctcagaacac aacctacctg tgggtgggtaa atggtcagag | 1740 |
| cctcccagtc agtcccaggc tgcagctgtc caatggcaac aggaccctca ctctattcaa | 1800 |
| tgtcacaaga aatgacgcaa gagcctatgt atgtggaatc cagaactcag tgagtgcaaa | 1860 |

| | |
|---|---|
| ccgcagtgac ccagtcaccc tggatgtcct ctatgggccg gacaccccca tcatttcccc | 1920 |
| cccagactcg tcttaccttt cgggagcgaa cctcaacctc tcctgccact cggcctctaa | 1980 |
| cccatccccg cagtattctt ggcgtatcaa tgggataccg cagcaacaca cacaagttct | 2040 |
| ctttatcgcc aaaatcacgc caaataataa cgggacctat gcctgttttg tctctaactt | 2100 |
| ggctactggc cgcaataatt ccatagtcaa gagcatcaca gtctctgcat ctggaacttc | 2160 |
| tcctggtctc tcagctgggg ccactgtcgg catcatgatt ggagtgctgg ttggggttgc | 2220 |
| tctgatatag cagccctggt gtagtttctt catttcagga agactgacag ttgttttgct | 2280 |
| tcttccttaa agcatttgca acagctacag tctaaaattg cttctttacc aaggatattt | 2340 |
| acagaaaaga ctctgaccag agatcgagac catcctagcc aacatcgtga aaccccatct | 2400 |
| ctactaaaaa tacaaaaatg agctgggctt ggtggcgcgc acctgtagtc ccagttactc | 2460 |
| gggaggctga ggcaggagaa tcgcttgaac ccggaggtg gagattgcag tgagcccaga | 2520 |
| tcgcaccact gcactccagt ctggcaacag agcaagactc catctcaaaa agaaaagaaa | 2580 |
| agaagactct gacctgtact cttgaataca agtttctgat accactgcac tgtctgagaa | 2640 |
| tttccaaaac tttaatgaac taactgacag cttcatgaaa ctgtccacca agatcaagca | 2700 |
| gagaaaataa ttaatttcat gggactaaat gaactaatga ggataatatt ttcataattt | 2760 |
| tttatttgaa attttgctga ttcttaaat gtcttgtttc ccagatttca ggaaactttt | 2820 |
| tttcttttaa gctatccaca gcttacagca atttgataaa atatactttt gtgaacaaaa | 2880 |
| attgagacat ttacattttc tccctatgtg gtcgctccag acttgggaaa ctattcatga | 2940 |
| atatttatat tgtatggtaa tatagttatt gcacaagttc aataaaaatc tgctctttgt | 3000 |
| atgcacagaat acatttgaaa acattggtta tattaccaag actttgacta gaatgtcgta | 3060 |
| tttgaggata taaacccata ggtaataaac ccacaggtac tacaaacaaa gtctgaagtc | 3120 |
| agccttggtt tggcttccta gtgtcaatta aacttctaaa agtttaatct gagattcctt | 3180 |
| ataaaaactt ccagcaaagc aactttaaaa aagtctgtgt gggccgggcg cggtggctca | 3240 |
| cgcctgtaat cccagcactt tgatccgccg aggcgggcgg atcacgaggt caggagatcc | 3300 |
| agaccatcct ggctaacaca gtgaaacccc gtctctacta aaaatacaaa aaagttagc | 3360 |
| cgggcgtggt ggtgggggcc tgtagtccca gctactcagg aggctgaggc aggagaacgg | 3420 |
| catgaacccg ggaggcaggg cttgcagtga gccaagatca tgccgctgca ctccagcctg | 3480 |
| ggagacaaag tgagactccg tcaaaaaaaa aaaaagtct atgtggtcag tcactactct | 3540 |
| tgctgcagtt atgaaaagaa tgaggccaag tctgatgaaa ataaacttat tttgaaaaca | 3600 |

<210> SEQ ID NO 55
<211> LENGTH: 3095
<212> TYPE: DNA
<213> ORGANISM: Homo sapiens

<400> SEQUENCE: 55

| | |
|---|---|
| attgctgatg gatcagtgag cctgtgttca tgccagtgag ctgctgtggc tcagatactg | 60 |
| atactttctt tccaaacagc ataagaagtg attgagccac aagtatactg aaggaagggc | 120 |
| tccctcgagt tctggtgtga agagataaat caccagtcac agactatgca cccgactgct | 180 |
| gctgttcagt ccagggaaaa tgaaagttgg agtgctgtgg ctcatttctt tcttcacctt | 240 |
| cactgacggc cacggtggct tcctggggaa aaatgatggc atcaaaacaa aaaagaact | 300 |
| cattgtgaat aagaaaaaac atctaggccc agtcgaagaa tatcagctgc tgcttcaggt | 360 |

-continued

```
gacctataga gattccaagg agaaaagaga tttgagaaat tttctgaagc tcttgaagcc    420
tccattatta tggtcacatg ggctaattag aattatcaga gcaaaggcta ccacagactg    480
caacagcctg aatggagtcc tgcagtgtac ctgtgaagac agctacacct ggtttcctcc    540
ctcatgcctt gatccccaga actgctacct tcacacggct ggagcactcc caagctgtga    600
atgtcatctc aacaacctca gccagagtgt caatttctgt gagagaacaa agatttgggg    660
cactttcaaa attaatgaaa ggtttacaaa tgacctttg aattcatctt ctgctatata     720
ctccaaatat gcaaatggaa ttgaaattca acttaaaaaa gcatatgaaa gaattcaagg    780
ttttgagtcg gttcaggtca cccaatttcg aaatggaagc atcgttgctg ggtatgaagt    840
tgttggctcc agcagtgcat ctgaactgct gtcagccatt gaacatgttg ccgagaaggc    900
taagacagcc cttcacaagc tgtttccatt agaagacggc tctttcagag tgttcggaaa    960
agcccagtgt aatgacattg tctttggatt tgggtccaag gatgatgaat atacccctgcc   1020 ctgcagcagt ggctacaggg gaaacatcac agccaagtgt gagtcctctg ggtggcaggt   1080
catcagggag acttgtgtgc tctctctgct gaagaactg aacaagaatt tcagtatgat    1140
tgtaggcaat gccactgagg cagctgtgtc atccttcgtg caaaatcttt ctgtcatcat   1200
tcggcaaaac ccatcaacca cagtggggaa tctggcttcg gtggtgtcga ttctgagcaa   1260
tatttcatct ctgtcactgg ccagccattt cagggtgtcc aattcaacaa tggaggatgt   1320
catcagtata gctgacaata tccttaattc agcctcagta accaactgga cagtcttact   1380
gcgggaagaa aagtatgcca gctcacggtt actagagaca ttagaaaaca tcagcactct   1440
ggtgcctccg acagctcttc ctctgaattt ttctcggaaa ttcattgact ggaaagggat   1500
tccagtgaac aaaagccaac tcaaaagggg ttacagctat cagattaaaa tgtgtcccca   1560
aaatacatct attcccatca gaggccgtgt gttaattggg tcagaccaat tccagagatc   1620
ccttccagaa actattatca gcatggcctc gttgactctg gggaacattc tacccgtttc   1680
caaaaatgga aatgctcagg tcaatggacc tgtgatatcc acggttattc aaaactattc   1740
cataaatgaa gttttcctat tttttccaa gatagagtca aacctgagcc agcctcattg    1800
tgtgttttgg gatttcagtc atttgcagtg gaacgatgca ggctgccacc tagtgaatga   1860
aactcaagac atcgtgacgt gccaatgtac tcacttgacc tccttctcca tattgatgtc   1920
accttttgtc ccctctacaa tcttccccgt tgtaaaatgg atcacctatg tgggactggg   1980
tatctccatt ggaagtctca ttttatgcct gatcatcgag gctttgtttt ggaagcagat   2040 taaaaaagc caaacctctc acacgctcg tatttgcatg gtgaacatag ccctgtccct     2100
cttgattgct gatgtctggt ttattgttgg tgccacagtg gacaccacgg tgaaccttc    2160 tggagtctgc acagctgctg tgttctttac acacttcttc tacctctctt tgttcttctg   2220
gatgctcatg cttggcatcc tgctggctta ccggatcatc ctcgtgttcc atcacatggc   2280
ccagcatttg atgatggctg ttggatttg cctgggttat gggtgccctc tcattatatc    2340
tgtcattacc attgctgtca cgcaacctag caatacctac aaaaggaaag atgtgtgttg   2400
gcttaactgg tccaatggaa gcaaaccact cctggctttt gttgtccctg cactggctat   2460
tgtggctgtg aacttcgttg tggtgctgct agttctcaca aagctctgga ggccgactgt   2520
tggggaaaga ctgagtcggg atgacaaggc caccatcatc cgcgtgggga agagcctcct   2580
cattctgacc cctctgctag ggctcaccctg gggctttgga ataggaacaa tagtggacag   2640
ccagaatctg gcttggcatg ttattttgc tttactcaat gcattccagg attttttat     2700 cttatgcttt ggaatactct tggacagtaa gctgcgacaa cttctgttca acaagttgtc   2760
```

```
tgccttaagt tcttggaagc aaacagaaaa gcaaaactca tcagatttat ctgccaaacc    2820
caaattctca aagcctttca acccactgca aacaaaggc cattatgcat tttctcatac     2880
tggagattcc tccgacaaca tcatgctaac tcagtttgtc tcaaatgaat aaggcaagga    2940
atcataaaat caagaaaaaa tttccagaac aacttgacat ttagagacaa atgtcaatga    3000
agaaattatg ctcagtattc gatcgggttt tctgatttag gggtctggga ataaaacaag    3060
aatgtctcag tggcttcaaa aaaaaaaaaa aaaaa                               3095
```

<210> SEQ ID NO 56
<211> LENGTH: 4071
<212> TYPE: DNA
<213> ORGANISM: Homo sapiens

<400> SEQUENCE: 56

```
tgattcgagc gggaagaggg gggtgggtgg gatcggtggg ggagaccatg acctccagct     60
acgggcacgt tctggagcgg caaccggcgc tgggcggccg cttggacagc ccggcaacc     120 tcgacaccct gcaggcgaaa agaacttct ccgtcagtca cctgctagac ctggaggaag     180
ccggggacat ggtggcggca caggcggatg agaacgtggg cgaggctggc cggagcctgc    240
tggagtcgcc gggactcacc agcggcagcg acacccccgca gcaggacaat gaccagctga   300
actcagaaga aaaaagaag agaaagcagc aaggaatag acaaccttc aatagcagcc       360 agctgcaggc tttggagcgt gtctttgagc ggacacacta tcctgatgct tttgtgcgag    420
aagaccttgc ccgccgggtg aacctcaccg aggcgagagt gcaggtgtgg tttcagaacc    480
gaagagccaa gttccgcagg aatgagagag ccatgctagc caataaaaac gcttccctcc    540
tcaaatccta ctcaggagac gtgactgctg tggagcagcc catcgtacct cgtcctgctc    600
cgagacccac cgattatctc tcctgggggga cagcgtctcc gtacagatcc tcgtccctcc   660
caagatgttg tttacacgag gggcttcata acgattcta acggaagaca ctgaaaagcg     720
ccatggctac ttattctgcc acatgtgcca acaatagccc tgcacagggc atcaacatgg    780
ccaacagcat tgccaacctg agactgaagg ccaaggaata tagtttacag aggaaccagg    840
tgccaacagt caactgagga aaaaaaataa ttaaacaggc taagaagaa atcaaaaacc     900 ataagacacc tatcctgctc tgttatttct tcatctgctg gggggaaaaa gtaaattaca    960
aacaaacaaa caaagcagaa ctaaaatatt gggaccatgg cagagaaaag caggagagga   1020
gcaaaatgaa aattagttaa caaatgttcc tcctcccctct gggataccac caccacttgt   1080
ttctgtgtgt gtttatttg ttttctttc attcatgctt tgcttaatgt actccaggct     1140
tcttcagata ggttcagccc acccaccccc atgattgtat gaagttttaa aaaaaactac    1200
agcagccaaa gaactatat atatatat atatatatat atccagaatg attgcctcta     1260
ctgtcctcat tgacttgttt gaaccttagt gccttaccct gtcctcttcc cagttctctt   1320
tatagaagct ctaggagctt tcgaaaagcc aaagtctttc tgaagaatct gtgctggaca   1380
gacataattc cctttctcat tgtctccatc tttgttggtc atggtaaggt ttttccatca   1440
gcctctgaaa aaatagttgt gcacaacatc tgctcactgg actgtctgat ccaatgtaat   1500
tggctgcgtc tggctaattc taagcactaa agtctacatc taagctatag atttaagctt   1560
gaagctacag attatatcac tatcaccacc acccctcacc ctatgcaatc aatcaatcaa   1620
tcatcttaag ttaaagatat ttgttgtctt tgaatgattt gctgtcacag actatttggt   1680
agaagaaata ttttttcacct gagagaggaa gagaaatttc tctagtaaca caaagagtga   1740
```

-continued

```
gttctaaaag gcatgcccac atctctttcg tgccttaagg atagtgagat gcacacttat    1800
atatatactg tatatattta tatatttata tatatatttc atatatatat ataatattgc    1860
aagcttaagt ttgcaatttc ccaaacaata caaaaagcaa attacacacc ctcaccactg    1920
ttcttatctc tatagtgatg aaacattaat tagggatctt gctgcttttc ttttctaca    1980
cgaagttttc attaaagcca cagaataatt gataggcag ctgtttgaga acaggtccca    2040
ttttcacatt agggctttaa atgaattaga aactatttga ggctataaaa atgtccttga    2100
gtttggagcc tgagctctgg tgaaatgctg atacatctga tctatcatgg gaattgcagt    2160
tagagagagt aaggaatacc atttagtcat ctatccgttc ttcacttagc aggaatatga    2220
aagaaaggca catgtttaag aggaatacct aaaggttttt ctaaattcca acatttaaaa    2280
ggcaattgtg ggctattttt attttttaat attttgaaat aaagtttagt gtctagggct    2340
gggagccagg actgatcttc catttctttt tctttgttcc cagccatgct tttgtaactt    2400
gccaggtgga cttgaccaac tacattacca tgctgtgcct cagtttaccc atttgtaaaa    2460
tgggattaat aatacttacc tacctcacag gggtgttgtg aggctctatt catttgctcc    2520
tttattcttt cctgtattct ctgtatgtcc agcactttgt agccatggga ggaaagggac    2580
tataaaagtg tacaatgtta atggaatgat acggtacctg aaagccttgt ttctagtaa    2640
gaaaatgcta ccttgctgta catacttata accttgtatt tggaaatgag aaataggttt    2700
atattttcag atctctcaaa aatcacatca tttgaccaaa gaataattta agacacatag    2760
aacagatttt tttaatttat attttcatcc tgaccagctt agttctaata atttttagtt    2820
gtgagtgatt aaaaaacttt ggatcaattt tggtcaaaca tgccaacttt gtagtctgag    2880
tgacaggcaa ggattttggg gtttaagatg cacttttagc acacatttgt atttcccttg    2940
gcatatcaga ttgagctaat ggtgatgtta tttcaatcta acagccacca atctgaaatt    3000
gtatttcaaa tgttgattct gtagttcttt aaataataat gaagctcatc ttatacattt    3060
tgctttcacc aattgattcc ttcttctttt agcccactat aaaacatttt cttactgaat    3120
ggttcatgta ggcttgctga acagcacgca ttacttgctt cctgaagagt tcccccattc    3180
atccatttgt cccattagtt gctgtggatt atcaagtttt gaaggaactg tacatcccaa    3240
cagactgaaa cattctaagt gaaatgagta taatccaagt aactggtgaa ctttggaggt    3300
ttggagcttg aagagaatgg ctaagaagat ttgaattata gggagggaac agaaatcata    3360
catgaaaagg ttttactgag aaggggaaaa ccttagatag agggacatgt gaaacaaaat    3420
catttgaaat tttgattcag acatccattt ccagtggcaa acagcaaagc ctgaacccat    3480
aaacccaaat gataggtgaa gttgggtggt tttatccaat gtctcaagca agcaatgtct    3540
gggaatatca tagagtaaca agtgctggtc agccaaagaa acattcactg ctggtgaacc    3600
aataccataa gcatgtatta tctaagcact tgatcaagaa atatacatgt tgtacaagct    3660
ctcaattttg ttcatttatt atcaaatttt taaatacaa gtttggtatg tgatttggaa    3720
aagatgcctt ctggatctta agccagttgt cagtggaggt cctcagggct gcaaatgtca    3780
agacataacc ctgttcctca ccatcatgat accagataca ggtgaataca taggaactat    3840
ctgcctgtgt cctcaatctc ccttcaaaca agatgctgat ttgtagggta cttggcaggt    3900
taaattaaac cagaagaggt gacttaataa aaaagggaat gacatttagg gtataaagat    3960
ctcataagaa atgtaatatg taaattatat cttgctttat gttgtaaaat atacattgtt    4020
tgcgctagaa tagaaatgat ttcttttcaa taaaaagaaa gaaggactct a              4071
```

<210> SEQ ID NO 57
<211> LENGTH: 3999
<212> TYPE: DNA
<213> ORGANISM: Homo sapiens

<400> SEQUENCE: 57

| | | | | | |
|---|---|---|---|---|---|
| tgattcgagc | gggaagaggg | gggtgggtgg | gatcggtggg | ggagaccatg | acctccagct | 60 |
| acgggcacgt | tctggagcgg | caaccggcgc | tgggcggccg | cttggacagc | ccgggcaacc | 120 |
| tcgacaccct | gcaggcgaaa | aagaacttct | ccgtcagtca | cctgctagac | ctggaggaag | 180 |
| ccggggacat | ggtggcggca | caggcggatg | agaacgtggg | cgaggctggc | cggagcctgc | 240 |
| tggagtcgcc | gggactcacc | agcggcagcg | acaccccgca | gcaggacaat | gaccagctga | 300 |
| actcagaaga | aaaaagaag | agaaagcagc | gaaggaatag | gacaaccttc | aatagcagcc | 360 |
| agctgcaggc | tttggagcgt | gtctttgagc | ggacacacta | tcctgatgct | tttgtgcgag | 420 |
| aagaccttgc | ccgccgggtg | aacctcaccg | aggcgagagt | gcaggtgtgg | tttcagaacc | 480 |
| gaagagccaa | gttccgcagg | aatgagagag | ccatgctagc | caataaaaac | gcttccctcc | 540 |
| tcaaatccta | ctcaggagac | gtgactgctg | tggagcagcc | catcgtacct | cgtcctgctc | 600 |
| cgagacccac | cgattatctc | tcctggggga | cagcgtctcc | gtacagcgcc | atggctactt | 660 |
| attctgccac | atgtgccaac | aatagccctg | cacagggcat | caacatggcc | aacagcattg | 720 |
| ccaacctgag | actgaaggcc | aaggaatata | gtttacagag | gaaccaggtg | ccaacagtca | 780 |
| actgaggaaa | aaaaataatt | aaacaggcct | aagaagaaat | caaaaaccat | aagcaccta | 840 |
| tcctgctctg | ttatttcttc | atctgctggg | gggaaaagt | aaattacaaa | caaacaaaca | 900 |
| aagcagaact | aaaatattgg | gaccatggca | gagaaaagca | ggagaggagc | aaaatgaaaa | 960 |
| ttagttaaca | aatgttcctc | ctccctctgg | gataccacca | ccacttgttt | ctgtgtgtgt | 1020 |
| ttattttgtt | tttctttcat | tcatgctttg | cttaatgtac | tccaggcttc | ttcagatagg | 1080 |
| ttcagcccac | ccaccccat | gattgtatga | agtttaaaa | aaaactacag | cagccaaaga | 1140 |
| aactatatat | atatatatat | atatatatat | ccagaatgat | tgcctctact | gtcctcattg | 1200 |
| acttgtttga | accttagtgc | cttaccctgt | cctcttccca | gttctcttta | tagaagctct | 1260 |
| aggagctttc | gaaaagccaa | agtctttctg | aagaatctgt | gctggacaga | cataattccc | 1320 |
| tttctcattg | tctccatctt | tgttggtcat | ggtaaggttt | ttccatcagc | ctctgaaaaa | 1380 |
| atagttgtgc | acaacatctg | ctcactggac | tgtctgatcc | aatgtaattg | gctgcgtctg | 1440 |
| gctaattcta | agcactaaag | tctacatcta | agctatagat | ttaagcttga | agctacagat | 1500 |
| tatatcacta | tcaccaccac | ccctcaccct | atgcaatcaa | tcaatcaatc | atcttaagtt | 1560 |
| aaagatattt | gttgtctttg | aatgatttgc | tgtcacagac | tatttggtag | aagaaatatt | 1620 |
| tttcacctga | gagaggaaga | gaaatttctc | tagtaacaca | aagagtgagt | tctaaaaggc | 1680 |
| atgcccacat | ctctttcgtg | ccttaaggat | agtgagatgc | acacttatat | atatactgta | 1740 |
| tatatttata | tatttatata | tatatttcat | atatatatat | aatattgcaa | gcttaagttt | 1800 |
| gcaatttccc | aaacaataca | aaaagcaaat | tacacaccct | caccactgtt | cttatctcta | 1860 |
| tagtgatgaa | acattaatta | gggatcttgc | tgcttttctt | tttctacacg | aagttttcat | 1920 |
| taaagccaca | gaataattga | tagggcagct | gtttgagaac | aggtcccatt | ttcacattag | 1980 |
| ggctttaaat | gaattagaaa | ctatttgagg | ctataaaaat | gtccttgagt | ttggagcctg | 2040 |
| agctctggtg | aaatgctgat | acatctgatc | tatcatggga | attgcagtta | gagagagtaa | 2100 |
| ggaataccat | ttagtcatct | atccgttctt | cacttagcag | gaatatgaaa | gaaaggcaca | 2160 |

```
tgtttaagag gaatacctaa aggttttttct aaattccaac atttaaaagg caattgtggg    2220
ctatttttat ttttaatat tttgaaataa agtttagtgt ctagggctgg gagccaggac     2280
tgatcttcca tttcttttttc tttgttccca gccatgcttt tgtaacttgc caggtggact   2340
tgaccaacta cattaccatg ctgtgcctca gtttacccat ttgtaaaatg ggattaataa    2400
tacttaccta cctcacaggg gtgttgtgag gctctattca tttgctcctt tattctttcc   2460
tgtattctct gtatgtccag cactttgtag ccatgggagg aaagggacta taaaagtgta    2520
caatgttaat ggaatgatac ggtacctgaa agccttgttt tctagtaaga aaatgctacc   2580
ttgctgtaca tacttataac cttgtatttg gaaatgagaa ataggtttat attttcagat   2640
ctctcaaaaa tcacatcatt tgaccaaaga ataatttaag acacatagaa cagattttttt 2700
taattttatat tttcatcctg accagcttag ttctaataat ttttagttgt gagtgattaa   2760
aaaactttgg atcaattttg gtcaaacatg ccaactttgt agtctgagtg acaggcaagg    2820
attttttgggt ttaagatgca cttttagcac acatttgtat ttcccttggc atatcagatt  2880
gagctaatgg tgatgttatt tcaatctaac agccaccaat ctgaaattgt atttcaaatg   2940
ttgattctgt agttctttaa ataataatga agctcatctt atacatttttg ctttcaccaa  3000
ttgattcctt cttcttttag cccactatta aaacatttct tactgaatgg ttcatgtagg   3060
cttgctgaac agcacgcatt acttgcttcc tgaagagttc ccccattcat ccatttgtcc   3120
cattagttgc tgtggattat caagtttga aggaactgta catcccaaca gactgaaaca    3180
ttctaagtga aatgagtata atccaagtaa ctggtgaact ttggaggttt ggagcttgaa   3240
gagaatggct aagaagattt gaattatagg gagggaacag aaatcataca tgaaaaggtt  3300
ttactgagaa ggggaaaacc ttagatagag ggacatgtga acaaaatca tttgaaattt    3360
tgattcagac atccatttcc agtggcaaac agcaaagcct gaacccataa acccaaatga  3420
taggtgaagt tgggtggttt tatccaatgt ctcaagcaag caatgtctgg gaatatcata   3480
gagtaacaag tgctggtcag ccaaagaaac attcactgct ggtgaaccaa taccataagc  3540
atgtattatc taagcacttg atcaagaaat atacatgttg tacaagctct caattttgtt   3600
catttattat caaattttta aaatacaagt ttggtatgtg atttggaaaa gatgccttct   3660
ggatcttaag ccagttgtca gtggaggtcc tcagggctgc aaatgtcaag acataaccct   3720
gttcctcacc atcatgatac cagatacagg tgaatacata ggaactatct gcctgtgtcc   3780
tcaatctccc ttcaaacaag atgctgattt gtagggtact tggcaggtta aattaaacca   3840
gaagaggtga cttaataaaa aagggaatga catttagggt ataaagatct cataagaaat  3900
gtaaatatgta aattatatct tgctttatgt tgtaaaatat acattgtttg cgctagaata  3960
gaaatgattt cttttcaata aaagaaaga aggactcta                           3999
```

<210> SEQ ID NO 58
<211> LENGTH: 2466
<212> TYPE: DNA
<213> ORGANISM: Homo sapiens

<400> SEQUENCE: 58

```
ggctgagtgg tttgctcctt cccctctctc tgggaggctg agcagggggtg ccgggttgct    60
caggccatgg gagccacacc tgttattgct gcctctgatt tgtgtgacac tgagaagccc    120
acaggcctgt ccctccaact cggtggaccc tctctgtgtg catttggtgt gtgagccagc   180
tctgagaagg gttcagaagc cactggaggc atctggggac ctcagcttcc atgccatctc   240
tgcctcactc ccacagggta atgttggact cggtgacaca cagcaccttc ctgcctaatg   300
```

```
catccttctg cgatccctg atgtcgtgga ctgatctgtt cagcaatgaa gagtactacc    360
ctgcctttga gcatcagaca gcctgtgact catactggac atcagtccac cctgaatact    420
ggactaagcg ccatgtgtgg gagtggctcc agttctgctg cgaccagtac aagttggaca    480
ccaattgcat ctccttctgc aacttcaaca tcagtggcct gcagctgtgc agcatgacac    540
aggaggagtt cgtcgaggca gctggcctct gcggcgagta cctgtacttc atcctccaga    600
acatccgcac acaaggttac tccttttta atgacgctga agaaagcaag gccaccatca    660
aagactatgc tgattccaac tgcttgaaaa caagtggcat caaaagtcaa gactgtcaca    720
gtcatagtag aacaagcctc caaagttctc atctgtggga attttacga gacctgcttc    780
tatctcctga agaaaactgt ggcattctgg aatgggaaga tagggaacaa ggaattttc    840
gggtggttaa atcggaagcc ctggcaaaga tgtggggaca aggaagaaa atgacagaa    900
tgacatatga aaagttgagc agagccctga gatactacta taaaacagga attttggagc    960
gggttgaccg aaggttagtg tacaaatttg gaaaaaatgc acacgggtgg caggaagaca    1020
agctatgatc tgctccaggc atcaagctca tttttatggat ttctgtcttt taaaacaatc    1080
agattgcaat agacattcga aaggcttcat tttcttctct ttttttttaa cctgcaaaca    1140
tgctgataaa atttctccac atctcagctt acatttggat tcagagttgt tgtctacgga    1200
gggtgagagc agaaactctt aagaaatcct ttcttctccc taaggggatg aggggatgat    1260
cttttgtggt gtcttgatca aactttattt tcctagagtt gtggaatgac aacagcccat    1320
gccattgatg ctgatcagag aaaaactatt caattctgcc attagagaca catccaatgc    1380
tcccatccca aaggttcaaa agttttcaaa taactgtggc agctcaccaa aggtgggga    1440
aagcatgatt agtttgcagg ttatggtagg agagggtgag atataagaca tacatacttt    1500
agattttaaa ttattaaagt caaaaatcca tagaaaagta tccctttttt tttttttgag    1560
acgggtctc actatgttgc ccagggctgg tcttgaactc ctatgctcaa gtgatcctcc    1620
cacctcggcc tcccaaagta ctgtgattac aagcgtgagc cacggcacct gggcagaaaa    1680
gtatcttaat taatgaaaga gctaagccat caagctggga cttaattgga tttaacatag    1740
gttcacagaa agtttcctaa ccagagcatc ttttgacca ctcagcaaaa cttccacaga    1800
catccttctg gacttaaaca cttaacatta accacattat taattgttgc tgagtttatt    1860
ccccttcta actgatggct ggcatctgat atgcagagtt agtcaacaga cactggcatc    1920
aattacaaaa tcactgctgt ttctgtgatt caagctgtca acacaataaa atcgaaattc    1980
attgattcca tctctggtcc agatgttaaa cgtttataaa accggaaatg tcctaacaac    2040
tctgtaatgg caaattaaat tgtgtgtctt ttttgttttg tctttctacc tgatgtgtat    2100
tcaagcgcta taacacgtat ttccttgaca aaaatagtga cagtgaattc acactaataa    2160
atgttcatag gttaaagtct gcactgacat tttctcatca atcactggta tgtaagttat    2220
cagtgactga cagctaggtg gactgcccct aggacttctg tttcaccaga gcaggaatca    2280
agtggtgagg cactgaatcg ctgtacaggc tgaagacctc cttattagag ttgaacttca    2340
aagtaacttg ttttaaaaaa tgtgaattac tgtaaaataa tctattttgg attcatgtgt    2400
tttccaggtg atatagtttt gtaaacaatg tgaataaagt atttaacatg taaaaaaaaa    2460
aaaaaa                                                              2466
```

<210> SEQ ID NO 59
<211> LENGTH: 3127
<212> TYPE: DNA

<213> ORGANISM: Homo sapiens

<400> SEQUENCE: 59

```
gaagctccac accagccatt acaaccctgc caatctcaag cacctgcctc tacagttggt      60
acagatggca ttgtcccagt ctgttcccett ctcggccaca gagcttctcc tggcctctgc    120
catcttctgc ctggtattct gggtgctcaa gggtttgagg cctcgggtcc ccaaaggcct    180
gaaaagtcca ccagagccat ggggctggcc cttgctcggg catgtgctga ccctggggaa    240
gaacccgcac ctggcactgt caaggatgag ccagcgctac ggggacgtcc tgcagatccg    300
cattggctcc acgcccgtgc tggtgctgag ccgcctggac accatccggc aggcctggt    360
gcggcagggc gacgatttca agggccggcc tgacctctac acctccaccc tcatcactga    420
tggccagagc ttgaccttca gcacagactc tggaccggtg tgggctgccc gccgcgcct    480
ggcccagaat gccctcaaca ccttctccat cgcctctgac ccagcttcct catcctcctg    540
ctacctggag gagcatgtga gcaaggaggc taaggccctg atcagcaggt tgcaggagct    600
gatggcaggg cctgggcact tcgacccctta caatcaggtg gtggtgtcag tggccaacgt    660
cattggtgcc atgtgcttcg acagcacttc ccctgagagt agcgatgaga tgctcagcct    720
cgtgaagaac actcatgagt tcgtggagac tgcctcctcc gggaaccccc tggacttctt    780
ccccatcctt cgctacctgc ctaaccctgc cctgcagagg ttcaaggcct tcaaccagag    840
gttcctgtgg ttcctgcaga aacagtcca ggagcactat caggactttg acaagaacag    900
tgtccgggac atcacgggtg ccctgttcaa gcacagcaag aaggggccta gagccagcgg    960
caacctcatc ccacaggaga agattgtcaa ccttgtcaat gacatctttg agcaggatt   1020
tgacacagtc accacagcca tctcctggag cctcatgtac cttgtgacca gcctgagat   1080
acagaggaag atccagaagg agctggacac tgtgattggc agggagcggc ggccccggct   1140
ctctgacaga ccccagctgc cctacttgga ggccttcatc ctggagacct tccgacactc   1200
ctccttcttg cccttcacca tcccccacag cacaacaagg acacaacgc tgaatggctt   1260
ctacatcccc aagaaatgct gtgtcttcgt aaaccagtgg caggtcaacc atgacccaga   1320
gctgtgggag gaccctctg agttccggcc tgagcggttc ctcaccgccg atggcactgc   1380
cattaacaag cccttgagtg agaagatgat gctgtttggc atgggcaagc gccggtgtat   1440
cggggaagtc ctggccaagt gggagatctt cctcttcctg gccatcctgc tacagcaact   1500
ggagttcagc gtgccgccgg gcgtgaaagt cgacctgacc cccatctacg ggctgaccat   1560
gaagcacgcc cgctgtgaac atgtccaggc gcggctgcgc ttctccatca attgaagaag   1620
acaccaccat tctgaggcca gggagcgagt gggggccagc cacggggact cagcccttgt   1680
ttctcttcct ttcttttttt aaaaaatagc agctttagcc aagtgcaggg cctgtaatcc   1740
cagcatttta ggaggccaag gttggaggat catttgagcc caggaattgg aaagcagcct   1800
ggccaacata gtgggaccct gtctctacaa aaaaaaatt tgccaagagc ctgagtgaca   1860
gagcaagacc ccatctcaaa aaaaaaaca aacaaacaaa aaaaaaacca tatatataca   1920
tatatatata gcagctttat ggagatataa ttcttatgcc atataattca ccttctttt   1980
ttttttttgt ctgagacaga atctcagtct gtcacccagg ttggagtgca gtggcgtgat   2040
ctcagctcac tgcaacctcc acctcgcagg ttcaagcaat cctcccactt cagcctccca   2100
agcacctggg attacaagca tgagtcacta cgcctggctg atttttgtag ttttagtgga   2160
gatgggtttt caccatgttg gccaggcttg tctcgaactc ctgaccccaa gttatccacc   2220
tgccttggct tcccaaagtc ctgggattac aggtgtgagc caccacatcc agcctaactt   2280
```

```
acattcttaa agtgtcgaat gacttctagt gtagaattgt gcaaccatca ccagaattaa    2340
ttttattatt cttattattt ttgagacaga gtcttactct gttgccaggc tggagtgcag    2400
tggcgcgatc tcagctcact acaacctccg cctcccatgt tcaagcgatt ctcctgcctc    2460
agcctcccga gtagctggga ctataggcat gcgccaccat ggccagctaa tttttgtatt    2520
tttagtagag acgaggtttc actgtgttgg ccaggatggt ctccatctct tgacctcgtg    2580
atccacccgc ctcagcctcc caaagtgctg ggattaacag gtatgaacca ccgcgcccag    2640 ccttttgtt tttttttttt ttgagacaga gtcttcctct gtctcctaag ctggagtgca     2700
gtggcatcat ctcagctcac tgcaacctct gcctcccagg ttcaagtgct tctccagcct    2760
cagcctccca agtagctgag actacaggca cacaccacca cgcctggcta atttttgtat    2820
ttttagtaga gacgggtttc accatgttgg ctagactagt ctcaaactcc tgacctcaag    2880
tgatctgccc gcctcgacct ctctcaaagt gctggcatta caggtgtgag ccacggtgcc    2940
cggcccacaa ttaattttag aacattttca tcacccctaa aagaaaccct gcacccatta    3000
gcagtccctc cacatttccc cctagcctgc ctcccctgcc tcaccagccc tggcaactgc    3060
taatctactt tctgtgtcta tggatttgcc ttctctaaac atttcatata aatggaatta    3120
cacaatg                                                               3127
```

METHODS OF DIAGNOSING CHRONIC OBSTRUCTIVE PULMONARY DISEASE (COPD) USING NOVEL MOLECULAR BIOMARKERS

This application is a national phase application under 35 U.S.C. § 371 of International Application No. PCT/EP2015/062440, filed Jun. 3, 2015, which claims benefit of European Application No. 14171385.9, filed Jun. 5, 2014, the entire contents of each of which are hereby incorporated by reference.

The present invention relates to in vitro methods for the diagnosis of chronic obstructive pulmonary disease (COPD), wherein the expression of the marker gene KIAA1199 is determined. In particular, the invention relates to an in vitro diagnostic method of assessing the susceptibility of a subject to develop progressive COPD involving the appearance of irreversible lung damage, wherein the expression of the marker gene KIAA1199 and optionally one or more further marker genes selected from DMBT1, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. The invention also relates to an in vitro method of diagnosing stable COPD or assessing the susceptibility of a subject to develop stable COPD, wherein the expression of KIAA1199 and optionally one or more further marker genes selected from DMBT1, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL is determined. Furthermore, the invention relates to the use of primers for transcripts of the aforementioned marker genes, the use of nucleic acid probes to transcripts of these marker genes, the use of microarrays comprising nucleic acid probes to transcripts of these marker genes, and the use of antibodies against the proteins expressed from these marker genes in corresponding in vitro methods. In vitro methods of monitoring the progression of COPD are also provided, in which the expression of marker genes according to the invention is determined.

COPD represents one of the leading pathologies of the world's elderly population. Triggered by long-term exposure to combustion products, climatic conditions and repeated infections, COPD has become the fourth-leading cause of mortality in aged individuals. During the last decades, the worldwide prevalence of COPD has risen by more than 10%, particularly in active smokers beyond the age of 55 (Murray et al., 1997). Given the increasing number of elderly people in the world's population and the world-wide increase of inhalative hazards, both occupational and personal, COPD must be regarded as one of the most challenging threats to the world's health systems (Halbert et al., 2006; US Burden of Disease Collaborators, 2013). However, although the impact of COPD on health conditions is increasingly understood, the mechanisms that cause and maintain the progression of the disease are largely unknown. Based on clinical experience and results of controlled studies, COPD is regarded as a largely inflammatory disease. However, while long-term anti-inflammatory treatment may improve the outcome in COPD, its impact on the overall pathology of the disease is less clear. The TORCH (TOwards a Revolution in COPD Health) study has clearly shown that this unilateral view upon the pathophysiology of COPD is not entirely correct as patients who were under continuous treatment with inhaled corticosteroids did not have a better outcome than those without. In line with this, several well-defined clinical trials have tried to stratify patients according to relevant clinical phenotypes, the ECLIPSE (Evaluation of COPD Longitudinally to Identify Predictive Surrogate Endpoints) study being the latest and most important attempt thus far (Vestbo et al., 2011). While these attempts have proven the remarkable heterogeneity of the clinical manifestations of COPD, they unfortunately failed to improve the understanding of the disease's central driving forces, their mediators, and their hierarchy in evoking the clinical phenotypes of COPD.

Until recently, COPD has been largely defined by the limitation of the maximum volume of air exhaled in one second during forced expiration ($FEV_1$), as well as by the total amount of air exhaled (forced [expiratory] vital capacity, FVC), and their respective relationship (Wedzicha JA, 2000). However, the variability of the clinical presentation of COPD regardless of any individual degree of airflow limitation suggested that the disease comprises different mechanisms related to bronchial and peribronchial pathologies (Hurst et al., 2010; Han et al., 2010). As a consequence, further clinical measures have been added to the diagnostic process in COPD, such as the intensity of bronchial inflammation, the frequency of disease exacerbations or the presence of comorbidities (Vestbo et al., 2013).

Not surprisingly, $FEV_1$ does not correlate well with symptom development. However, many studies have clearly demonstrated that $FEV_1$ is a strong predictor of mortality and morbidity in COPD, suggesting a relevant correlation between the (morphologically fixed) obstruction of the peripheral airways and the pathophysiology of the disease. Given the probability that the morphology of the small airways is going to reflect the pathologic net result of all metabolic events within this lung compartment, including chronic inflammatory and regenerative activities, this is more than plausible. Based on these facts, it still seems appropriate to apply the symptoms of the most established clinical manifestations of COPD, i.e. fixed bronchial obstruction and intensity of bronchitis as the main clinical indicators for a first attempt to delineate mechanisms and mediators capable of driving the pathology of COPD. In view of the well-documented long-term history of COPD often covering periods of more than two decades, any attempt to delineate the pathology of the disease ought to a) cover the earliest phase of pathologic development, the establishment of chronic bronchitis (COPD "at risk" according to the GOLD (Global Initiative on Obstructive Lung Disease) criteria) likely to precede the first manifestation of "irreversible" bronchial obstruction, b) to include both long-term development of the disease preceding the controlled phase of clinical assessment and c) to span a period long enough to allow for the identification of important short-range effects on COPD pathology. Lastly, as the pathology of COPD is focused in the small airways (Hogg JC, et al., 2004 (a)), the initial biological assessment ought to be performed in this compartment, regardless of the fact that some characteristic symptoms, such as the production of phlegm as a sign of intensified bronchitis, will also reflect the metabolic activity of the more central airways.

COPD progressively debilitates patients, resulting in an increasing disability and worsening impact of exacerbations. In particular, the development of irreversible damage to the lungs commences and then gradually worsens when a patient suffering from COPD advances from the stable early disease stage into the progressive stage of COPD. Unfortunately, many patients with COPD remain undiagnosed and potentially unknown to healthcare providers until the more advanced stages of the disease. In such cases, the delayed diagnosis of COPD results in patients suffering from symptoms and limitations that could otherwise be alleviated by treatment (Price et al., 2011). It would therefore be highly desirable to be able to diagnose COPD at an early disease stage and, in particular, to identify patients who are at risk of developing progressive COPD in order to be able to prevent these patients from suffering significant irreversible damage.

It is therefore an object of the present invention to provide novel and/or improved methods that allow to diagnose COPD at an early disease stage or to assess the risk or susceptibility of a subject to develop COPD. It is furthermore an object of the invention to provide novel and/or improved methods that allow to assess the susceptibility of a subject to develop progressive COPD).

The present invention is based on the unexpected finding that the gene KIAA1199 as well as the genes DMBT1, TMSB15A, DPP6, SLC51B, NUDT11, ELFS, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL are differentially expressed in samples from subjects suffering from progressive COPD or subjects at risk/prone to develop progressive COPD on the one hand, and in control samples from healthy subjects on the other hand. In particular, and as also described in Example 1, it has been found that the expression of the genes KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is upregulated in samples from patients suffering from progressive COPD or at risk of developing progressive COPD, while the expression of the genes TMSB15A, DPP6, SLC51B, NUDT11, PLA1A, HYAL2, CST6, ITGA10, CTHRC1, TAL1, FIBIN, BEX5, BEX1, ESM1 and GHRL is downregulated in samples from patients suffering from progressive COPD or at risk of developing progressive COPD, as compared to the expression of the corresponding genes in control samples from healthy patients. Therefore, in accordance with the present invention, these novel molecular biomarkers can advantageously be used for assessing the susceptibility/proneness of a subject to develop progressive COPD. It has further been surprisingly found that the genes KIAA1199, DMBT1, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL are differentially expressed in samples from subjects suffering from stable COPD or subjects at risk/prone to develop stable COPD on the one hand, and in control samples from healthy subjects on the other hand. In this connection, it has particularly been found that the expression of the genes KIAA1199, TMSB15A, DPP6, SLC51B, NUDT11, PLA1A, HYAL2, CST6, ITGA10, CTHRC1, TAL1, FIBIN, BEX5, BEX1, ESM1 and GHRL is downregulated in samples from patients having stable COPD or at risk of developing stable COPD, while the expression of the genes DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is upregulated in samples from patients having stable COPD or at risk of developing stable COPD, as compared to the expression of the corresponding genes in control samples from healthy patients. In accordance with the present invention, these novel molecular biomarkers can thus be used for diagnosing stable COPD and/or assessing the susceptibility/proneness of a subject to develop stable COPD. Moreover, the biomarkers provided herein have excellent sensitivity and/or specificity.

Accordingly, in a first aspect the present invention provides an in vitro method for the diagnosis of COPD, the method comprising determining the level of expression of the gene KIAA1199 in a sample obtained from a subject.

In accordance with this first aspect, the invention also relates to the use of KIAA1199 as a marker for the in vitro diagnosis of COPD.

In a second aspect, the present invention provides an in vitro diagnostic method of assessing the susceptibility of a subject to develop progressive COPD involving the appearance of irreversible lung damage, the method comprising:
  determining the level of expression of the gene KIAA1199 in a sample obtained from the subject;
  comparing the level of expression of KIAA1199 in the sample from the subject to a control expression level of KIAA1199 in a healthy subject; and
  determining whether or not the subject is prone to develop progressive COPD involving the appearance of irreversible lung damage, wherein an increase in the level of expression of KIAA1199 in the sample from the subject as compared to the control expression level of KIAA1199 is indicative of a proneness to develop progressive COPD.

It is preferred that in this second aspect the method further comprises:
  determining the level of expression of one or more further genes selected from DMBT1, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in the sample obtained from the subject;
  comparing the level of expression of the one or more further genes to a control expression level of the corresponding gene(s) in a healthy subject; and
  determining whether or not the subject is prone to develop progressive COPD involving the appearance of irreversible lung damage,
  wherein an increase in the level of expression of KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject as compared to the control expression level of the corresponding gene(s) is indicative of a proneness to develop progressive COPD, and
  wherein a decrease in the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject as compared to the control expression level of the corresponding gene(s) is indicative of a proneness to develop progressive COPD.

In a third aspect, the invention provides an in vitro method of diagnosing stable COPD in a subject or assessing the susceptibility of a subject to develop stable COPD, the method comprising:
  determining the level of expression of the gene KIAA1199 in a sample obtained from the subject;

comparing the level of expression of KIAA1199 in the sample from the subject to a control expression level of KIAA1199 in a healthy subject; and determining whether or not the subject suffers from stable COPD or is prone to suffer from stable COPD, wherein a decrease in the level of expression of KIAA1199 in the sample from the subject as compared to the control expression level of KIAA1199 is indicative of stable COPD or a proneness to stable COPD.

The method according to this third aspect preferably further comprises:

determining the level of expression of one or more further genes selected from DMBT1, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIB1N, BEX5, BEX1, ESM1 and GHRL in the sample obtained from the subject;

comparing the level of expression of the one or more further genes to a control expression level of the corresponding gene(s) in a healthy subject; and determining whether or not the subject suffers from stable COPD or is prone to suffer from stable COPD, wherein an increase in the level of expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or. COMP in the sample from the subject as compared to the control expression level of the corresponding gene(s) is indicative of stable COPD or a proneness to stable COPD, and wherein a decrease in the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject as compared to the control expression level of the corresponding gene(s) is indicative of stable COPD or a proneness to stable COPD.

In a fourth aspect, the invention relates to an in vitro diagnostic method of assessing the susceptibility of a subject suffering from stable COPD to develop progressive COPD involving the appearance of irreversible lung damage, the method comprising:

determining the level of expression of the gene KIAA1199 in a sample obtained from the subject;

comparing the level of expression of KIAA1199 in the sample from the subject to a control expression level of KIAA1199 in a subject suffering from stable COPD; and determining whether or not the subject is prone to develop progressive COPD involving the appearance of irreversible lung damage, wherein an increase in the level of expression of KIAA1199 in the sample from the subject as compared to the control expression level of KIAA1199 is indicative of a proneness to develop progressive COPD.

It is preferred that the method of this fourth aspect further comprises:

determining the level of expression of one or more further genes selected from DMBT1, ELF5, AZGP1, PRRX1, AQP3, GPR110, GDF15, RASGRF2, RND1, FGG, CEACAM5, HYAL2, AHRR, CXCL3, CYP1A1, CYP1B1, CYP1A2, CST6, NTRK2, COMP, ITGA10, CTHRC1, TAL1, BEX1 and GHRL in the sample obtained from the subject;

comparing the level of expression of the one or more further genes to a control expression level of the corresponding gene(s) in a subject suffering from stable COPD; and determining whether or not the subject is prone to develop progressive COPD involving the appearance of irreversible lung damage, wherein an increase in the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAU in the sample from the subject as compared to the control expression level of the corresponding gene(s) is indicative of a proneness to develop progressive COPD, and wherein a decrease in the level of expression of DMBT1, ELF5, AZGP1, PRRX1, AQP3, COMP, ITGA10, CTHRC1, BEX1 and/or GHRL in the sample from the subject as compared to the control expression level of the corresponding gene(s) is indicative of a proneness to develop progressive COPD.

In a fifth aspect, the invention relates to the use of (i) a pair of primers for a transcript of the gene KIAA1199, (ii) a nucleic acid probe to a transcript of the gene KIAA1199, (iii) a microarray comprising a nucleic acid probe to the transcript of KIAA1199 and optionally comprising nucleic acid probes to the transcripts of one or more further genes selected from DMBT1, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL, or (iv) an antibody against the protein KIAA1199, in an in vitro diagnostic method of assessing the susceptibility of a subject to develop progressive COPD involving the appearance of irreversible lung damage.

In a sixth aspect, the invention relates to a drug against COPD for use in treating COPD in a subject that has been identified in a method according to the second aspect of the invention as being prone to develop progressive COPD involving the appearance of irreversible lung damage.

The invention further relates to the use of a drug against COPD in the preparation of a pharmaceutical composition for treating COPD in a subject that has been identified in a method according to the second aspect of the invention as being prone to develop progressive COPD involving the appearance of irreversible lung damage.

Moreover, in accordance with this sixth aspect, the invention also provides a method of treating COPD, the method comprising administering a drug against COPD to a subject that has been identified in a method according to the second aspect of the invention as being prone to develop progressive COPD involving the appearance of irreversible lung damage.

In a seventh aspect, the invention relates to the use of (i) a pair of primers for a transcript of the gene KIAA1199, (ii) a nucleic acid probe to a transcript of the gene KIAA1199, (iii) a microarray comprising a nucleic acid probe to the transcript of KIAA1199 and optionally comprising nucleic acid probes to the transcripts of one or more further genes selected from DMBT1, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL, or (iv) an antibody against the protein KIAA1199, in an in vitro method of diagnosing stable COPD in a subject or assessing the susceptibility of a subject to develop stable COPD.

In an eighth the invention relates to a drug against COPD for use in treating or preventing COPD in a subject that has been identified in a method according to the third aspect of the invention as suffering from stable COPD or as being prone to suffer from stable COPD.

The invention also relates to the use of a drug against COPD in the preparation of a pharmaceutical composition for treating or preventing COPD in a subject that .has been identified in a method according to the third aspect of the invention as suffering from stable COPD or as being prone to suffer from stable COPD.

In this aspect, the invention likewise relates to a method of treating or preventing COPD, the method comprising administering a drug against COPD to a subject that has been identified in a method according to the third aspect of the invention as suffering from stable COPD or as being prone to suffer from stable COPD.

In a ninth aspect, the invention relates to the use of (i) a pair of primers for a transcript of the gene KIAA1199, (ii) a nucleic acid probe to a transcript of the gene KIAA1199, (iii) a microarray comprising a nucleic acid probe to the transcript of KIAA1199 and optionally comprising nucleic acid probes to the transcripts of one or more further genes selected from DMBT1, ELF5, AZGP1, PRRX1, AQP3, GPR110, GDF15, RASGRF2, RND1, FGG, CEACAMS, HYAL2, AHRR, CXCL3, CYP1A1, CYP1B1, CYP1A2, CST6, NTRK2, COMP, ITGA10, CTHRC1, TAL1, BEX1 and GHRL, or (iv) an antibody against the protein KIAA1199, in an in vitro diagnostic method of assessing the susceptibility of a subject suffering from stable COPD to develop progressive COPD involving the appearance of irreversible lung damage.

In a tenth aspect, the invention relates to a drug against COPD for use in treating COPD in a subject suffering from stable COPD, wherein the subject has been identified in a method according to the fourth aspect of the invention as being prone to develop progressive COPD involving the appearance of irreversible lung damage.

The invention further refers to the use of a drug against COPD in the preparation of a pharmaceutical composition for treating COPD in a subject suffering from stable COPD, wherein the subject has been identified in a method according to the fourth aspect of the invention as being prone to develop progressive COPD involving the appearance of irreversible lung damage.

The invention according to this tenth aspect also relates to a method of treating COPD, the method comprising administering a drug against COPD to a subject suffering from stable COPD, wherein the subject has been identified in a method according to the fourth aspect of the invention as being prone to develop progressive COPD involving the appearance of irreversible lung damage.

In an eleventh aspect, the present invention provides an in vitro method of monitoring the progression of COPD in a subject, the method comprising:
determining the level of expression of one or more genes selected from NTRK2 and RASGRF2 in a first sample obtained from the subject;
determining the level of expression of the one or more genes in a second sample obtained from the subject at a later point in time than the first sample;
comparing the level of expression of the one or more genes in the second sample to the level of expression of the corresponding gene(s) in the first sample; and
assessing the progression of COPD in the subject,
wherein a decrease in the level of expression of NTRK2 and/or RASGRF2 in the second sample as compared to the level of expression of the corresponding gene(s) in the first sample is indicative of an amelioration of COPD in the subject, and
wherein an increase in the level of expression of NTRK2 and/or RASGRF2 in the second sample as compared to the level of expression of the corresponding gene(s) in the first sample is indicative of a worsening of COPD in the subject.

The following description of general and preferred features and embodiments relates to each one of the methods, uses and drugs against COPD provided in the present specification, including in particular those according to the above-described first, second, third, fourth, fifth, sixth, seventh, eighth, ninth, tenth and eleventh aspects of the invention, unless explicitly indicated otherwise.

Chronic obstructive pulmonary disease (COPD) is a lung disease characterized by persistent airflow limitation that is usually progressive and associated with an enhanced chronic inflammatory response in the airways and the lung to noxious particles or gases. COPD is typically classified into four different stages based on the extent of non-reversible pulmonary obstruction to be determined by spirometry, as specified by the Global Initiative for Obstructive Lung Disease (GOLD) (see, e.g., Vestbo et al., 2013; and Pauwels et al., 2001). COPD stage I ("mild COPD") is characterized by an $FEV_1/FVC$ ratio of <70% and an $FEV_1$ of ≥80%. At stage I, the patient may not be aware that his/her lung function is abnormal. COPD stage II ("moderate COPD") is characterized by an $FEV_1/FVC$ ratio of <70% and an $FEV_1$ of ≥50% and <80%. This is the stage at which patients typically seek medical attention because of chronic respiratory symptoms or an exacerbation of their disease. COPD stage III ("severe COPD") is characterized by an $FEV_1/FVC$ ratio of <70% and an $FEV_1$ of ≥30% and <50%. COPD stage IV ("very severe COPD") is characterized by an $FEV_1/FVC$ ratio of <70% and an $FEV_1$ of <30%, or chronic respiratory failure and an $FEV_1$ of <50%. The pathological development of COPD may be preceded by chronic respiratory symptoms (particularly chronic bronchitis) without airways obstruction ($FEV_1/FVC$ ratio of ≥70%), which is also referred to as "stage 0" or "at risk for COPD". The terms "stage I", "stage II", "stage III", "stage IV", and "stage 0" as used in the present specification refer to the corresponding GOLD stages, i.e., the corresponding COPD stages according to the above-described GOLD criteria.

As used herein, the term "stable COPD" (used synonymously with "stable early-stage COPD") refers to the initial stages of COPD that precede the development of irreversible lung damage. In particular, "stable COPD" refers to the initial COPD stages from the earliest signs for the onset of the disease through to mild airflow limitation characterized by an $FEV_1/FVC$ ratio of <70% and an $FEV_1$ of ≥80%. "Stable COPD" thus preferably refers to COPD stage 0 (i.e., the COPD "at risk" stage) and COPD stage I (according to GOLD criteria), and more preferably refers to COPD stage I.

The terms "progressive COPD" and "progressive COPD involving the appearance of irreversible lung damage" are used herein synonymously/interchangeably, and refer to the disease stage of COPD in which irreversible damage to the lungs occurs and progressively worsens. In particular, "progressive COPD" refers to the COPD disease stage characterized by moderate airflow limitation, i.e., an $FEV_1/FVC$ ratio of <70% and an $FEV_1$ of ≥50% and <80%. Accordingly, it is particularly preferred that "progressive COPD" refers to COPD stage II (according to GOLD criteria).

As used herein, the terms "KIAA1199", "DMBT1", "TMSB15A", "DPP6", "SLC51B", "NUDT11", "ITGA10", "CST6", "TAL1", "FIBIN", "BEXS", "BEX1", "ESM1", "GHRL", "NTRK2", "SFN", "GPR110", "FGG", "CEACAMS", "AZGP1", "COMP", "PRRX1", "AHRR", "CYP1A1", "CYP1A2", "CYP1B1", "GDF15", "ELF5", "AQP3", "RASGRF2", "PLA1A", "HYAL2", "CTHRC1", "RND1" and "CXCL3" each refer to the respective human gene, the corresponding mRNA (including all possible transcripts/splice variants), and the corresponding protein (including all possible isoforms). These terms also refer to homologs and/or orthologs of the corresponding human genes that are found in other (non-human) species, particularly other mammalian species, as well as their corresponding mRNAs and their corresponding proteins. It is to be understood that, if the subject to be tested in the methods of the present invention is a non-human (particularly a non-human mammal), then the one or more marker genes (the level of expression of which is to be determined) will be the homologs/orthologs of the indicated human genes that are found in the non-human animal to be tested. Preferably, the subject is a human and, accordingly, the above-mentioned terms preferably refer to the respective human genes and the corresponding mRNAs and proteins.

The full names of the human forms of the above-mentioned marker genes, their Entrez Gene ID, and NCBI reference sequences of their mRNAs and proteins are listed in the following Table 1:

TABLE 1

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| KIAA1199 | KIAA1199 | 57214 | NM_018689.1 (preferably as indicated in SEQ ID NO: 38) | NP_061159.1 |
| DMBT1 | deleted in malignant brain tumors 1 | 1755 | NM_004406.2 (preferably as indicated in SEQ ID NO: 26) NM_007329.2 (preferably as indicated in SEQ ID NO: 32) NM_017579.2 (preferably as indicated in SEQ ID NO: 35) | NP_004397.2 NP_015568.2 NP_060049.2 |
| TMSB15A | thymosin beta 15a | 11013 | NM_021992.2 (preferably as indicated in SEQ ID NO: 41) | NP_068832.1 |
| DPP6 | dipeptidyl-peptidase 6 | 1804 | NM_001039350.1 (preferably as indicated in SEQ ID NO: 45) NM_001936.3 (preferably as indicated in SEQ ID NO: 46) NM_130797.2 (preferably as indicated in SEQ ID NO: 47) | NP_001034439.1 NP_001927.3 NP_570629.2 |
| SLC51B | solute carrier family 51, beta subunit | 123264 | NM_178859.3 (preferably as indicated in SEQ ID NO: 48) | NP_849190.2 |
| NUDT11 | nudix (nucleoside diphosphate linked moiety X)-type motif 11 | 55190 | NM_018159.3 (preferably as indicated in SEQ ID NO: 36) | NP_060629 |
| ITGA10 | integrin, alpha 10 | 8515 | NM_003637.3 (preferably as indicated in SEQ ID NO: 24) | NP_003628.2 |
| CST6 | cystatin E/M | 1474 | NM_001323.3 (preferably as indicated in SEQ ID NO: 21) | NP_001314.1 |
| TAL1 | T-cell acute lymphocytic leukemia 1 | 6886 | NM_003189.2 (preferably as indicated in SEQ ID NO: 49) | NP_003180.1 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| FIBIN | fin bud initiation factor homolog (zebrafish) | 387758 | NM_203371.1 (preferably as indicated in SEQ ID NO: 50) | NP_976249.1 |
| BEX5 | brain expressed, X-linked 5 | 340542 | NM_001012978.2 (preferably as indicated in SEQ ID NO: 5) NM_001159560.1 (preferably as indicated in SEQ ID NO: 13) | NP_001012996.1 NP_001153032.1 |
| BEX1 | brain expressed, X-linked 1 | 55859 | NM_018476.3 (preferably as indicated in SEQ ID NO: 37) | NP_060946.3 |
| ESM1 | endothelial cell-specific molecule 1 | 11082 | NM_001135604.1 (preferably as indicated in SEQ ID NO: 12) NM_007036.4 (preferably as indicated in SEQ ID NO: 31) | NP_001129076.1 NP_008967.1 |
| GHRL | ghrelin/obestatin prepropeptide | 51738 | NM_001134941.1 (preferably as indicated in SEQ ID NO: 8) NM_001134944.1 (preferably as indicated in SEQ ID NO: 9) NM_001134945.1 (preferably as indicated in SEQ ID NO: 10) NM_001134946.1 (preferably as indicated in SEQ ID NO: 11) | NP_001128413.1 NP_001128416.1 NP_001128417.1 NP_001128418.1 NP_001128418.1 |
| NTRK2 | neurotrophic tyrosine kinase, receptor, type 2 | 4915 | NM_001007097.1 (preferably as indicated in SEQ ID NO: 51) NM_001018064.1 (preferably as indicated in SEQ ID NO: 52) NM_001018065.2 (preferably as indicated in SEQ ID NO: 6) NM_001018066.2 (preferably as indicated in SEQ ID NO: 7) NM_006180.3 (preferably as indicated in SEQ ID NO: 53) | NP_001007098.1 NP_001018074.1 NP_001018075.1 NP_001018076.1 NP_006171.2 |
| SFN | stratifin | 2810 | NM_006142.3 (preferably as indicated in SEQ ID NO: 29) | NP_006133.1 |
| GPR110 | G protein-coupled receptor 110 | 266977 | NM_025048.2 (preferably as indicated in SEQ ID NO: 42) NM_153840.2 (preferably as | NP_079324.2 NP_722582.2 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| | | | indicated in SEQ ID NO: 55) | |
| CYP1B1 | cytochrome P450, family 1, subfamily B, polypeptide 1 | 1545 | NM_000104.3 (preferably as indicated in SEQ ID NO: 2) | NP_000095.2 |
| FGG | fibrinogen gamma chain | 2266 | NM_000509.4 (preferably as indicated in SEQ ID NO: 4) NM_021870.2 (preferably as indicated in SEQ ID NO: 40) | NP_000500.2 NP_068656.2 |
| CEACAM5 | carcinoembryonic antigen-related cell adhesion molecule 5 | 1048 | NM_004363.2 (preferably as indicated in SEQ ID NO: 54) | NP_004354.2 |
| AZGP1 | alpha-2-glycoprotein 1, zinc-binding | 563 | NM_001185.3 (preferably as indicated in SEQ ID NO: 14) | NP_001176.1 |
| COMP | cartilage oligomeric matrix protein | 1311 | NM_000095.2 (preferably as indicated in SEQ ID NO: 1) | NP_000086.2 |
| PRRX1 | paired related homeobox 1 | 5396 | NM_006902.3 (preferably as indicated in SEQ ID NO: 56) NM_022716.2 (preferably as indicated in SEQ ID NO: 57) | NP_008833.1 NP_073207.1 |
| AHRR | aryl-hydrocarbon receptor repressor | 57491 | NM_001242412.1 (preferably as indicated in SEQ ID NO: 17) NM_020731.4 (preferably as indicated in SEQ ID NO: 39) | NP_001229341.1 NP_065782.2 |
| GDF15 | growth differentiation factor 15 | 9518 | NM_004864.2 (preferably as indicated in SEQ ID NO: 27) | NP_004855.2 |
| ELF5 | E74-like factor 5 (ets domain transcription factor) | 2001 | NM_001243080.1 (preferably as indicated in SEQ ID NO: 18) NM_001243081.1 (preferably as indicated in SEQ ID NO: 19) NM_001422.3 (preferably as indicated in SEQ ID NO: 22) NM_198381.1 (preferably as indicated in SEQ ID NO: 58) | NP_001230009.1 NP_001230010.1 NP_001413.1 NP_938195.1 |
| AQP3 | aquaporin 3 (Gill blood group) | 360 | NM_004925.4 (preferably as indicated in SEQ ID NO: 28) | NP_004916.1 |
| RASGRF2 | Ras protein-specific guanine nucleotide-releasing factor 2 | 5924 | NM_006909.2 (preferably as indicated in SEQ ID NO: 30) | NP_008840.1 |

TABLE 1-continued

Overview of the marker genes provided herein (human forms), including their full names, their Entrez Gene ID, and NCBI reference sequences of their mRNAs and their proteins (where applicable, different mRNA transcripts/splice variants and the corresponding protein isoforms are indicated; further possible mRNA variants and protein isoforms of the indicated genes may also be used to determine the corresponding levels of marker gene expression in accordance with the invention).

| Marker gene | Full name | Gene ID | mRNA (NCBI ref. seq.) | Protein (NCBI ref. seq.) |
|---|---|---|---|---|
| PLA1A | phospholipase A1 member A | 51365 | NM_001206960.1 (preferably as indicated in SEQ ID NO: 15) NM_001206961.1 (preferably as indicated in SEQ ID NO: 16) NM_015900.3 (preferably as indicated in SEQ ID NO: 34) | NP_001193889.1 NP_001193890.1 NP_056984.1 |
| HYAL2 | hyaluronoglucosaminidase 2 | 8692 | NM_003773.4 (preferably as indicated in SEQ ID NO: 25) NM_033158.4 (preferably as indicated in SEQ ID NO: 43) | NP_003764.3 NP_149348.2 |
| CTHRC1 | collagen triple helix repeat containing 1 | 115908 | NM_001256099.1 (preferably as indicated in SEQ ID NO: 20) NM_138455.3 (preferably as indicated in SEQ ID NO: 44) | NP_001243028.1 NP_612464.1 |
| RND1 | Rho family GTPase 1 | 27289 | NM_014470.3 (preferably as indicated in SEQ ID NO: 33) | NP_055285.1 |
| CXCL3 | chemokine (C—X—C motif) ligand 3 | 2921 | NM_002090.2 (preferably as indicated in SEQ ID NO: 23) | NP_002081.2 |
| CYP1A1 | cytochrome P450, family 1, subfamily A, polypeptide 1 | 1543 | NM_000499.3 (preferably as indicated in SEQ ID NO: 3) | NP_000490.1 |
| CYP1A2 | cytochrome P450, family 1, subfamily A, polypeptide 2 | 1544 | NM_000761.4 (preferably as indicated in SEQ ID NO: 59) | NP_000752.2 |

In the methods according to the present invention, including in particular the methods according to the first, second, third, fourth and eleventh aspect of the invention, the level of expression of one or more genes is determined in a sample obtained from the subject to be tested.

The level of expression can be determined, e.g., by determining the level of transcription or the level of translation of the corresponding marker gene(s). Thus, the amount of mRNA of these gene(s) in the sample can be measured or the amount of the corresponding protein(s) can be measured in order to determine the level of expression of the respective genes. This can be accomplished using methods known in the art, as described, e.g., in Green et al., 2012. The level of transcription of these gene(s) can, for example, be determined using a quantitative (real-time) reverse transcriptase polymerase chain reaction ("qRT-PCR") or using a microarray (see, e.g., Ding et al., 2004). The use of a microarray can be advantageous, e.g., if the level of transcription of a number of different marker genes is to be determined. Using a microarray can also be advantageous if various different diseases/disorders or the susceptibility to various diseases/disorders is to be tested or diagnosed simultaneously. If the level of transcription is to be determined, it may further be advantageous to include one or more RNase inhibitors in the sample from the subject. The level of translation of the corresponding marker gene(s) can, for example, be determined using antibody-based assays, such as an enzyme-linked immunosorbent assay (ELISA) or a radioimmunoassay (RIA), wherein antibodies directed specifically against the protein(s) to be quantified are employed, or mass spectrometry, a gel-based or blot-based assay, or flow cytometry (e.g., FACS). If the level of translation is to be determined, it may be advantageous to include one or more protease inhibitors in the sample from the subject. Since mRNA can be isolated and quantified more easily and in a more cost-effective manner than proteins, it is preferred in the methods of the present invention that the level of expression of the one or more genes is determined by determining the level of transcription of the corresponding gene(s). The level of transcription is preferably determined using qRT-PCR or a microarray.

The subject to be tested in accordance with the present invention may be an animal and is preferably a mammal. The mammal to be tested in accordance with the invention may be, e.g., a rodent (such as, e.g., a guinea pig, a hamster, a rat or a mouse), a murine (such as, e.g., a mouse), a canine (such as, e.g., a dog), a feline (such as, e.g., a cat), a porcine (such as, e.g., a pig), an equine (such as, e.g., a horse), a primate, a simian (such as, e.g., a monkey or an ape), a monkey (such as, e.g., a marmoset or a baboon), an ape (such as, e.g., a gorilla, a chimpanzee, an orang-utan or a gibbon), or a human. It is particularly envisaged that non-human mammals are to be tested, which are economically, agronomically or scientifically important. Scientifically important mammals include, e.g., mice, rats and rabbits. Non-limiting examples of agronomically important mammals are sheep, cattle and pigs. Economically important mammals include, e.g., cats and dogs. Most preferably, the subject to be tested in accordance with the present invention is a human.

In the second and the fourth aspect of the invention, it is furthermore preferred that the subject to be tested is a subject (preferably a human) that has been diagnosed as suffering from stable COPD or is suspected of suffering from stable COPD.

In accordance with the third aspect of the invention, it is preferred that the subject to be tested is a subject (preferably a human) that is suspected to suffer from stable COPD or a subject (preferably a human) suspected to be prone to suffer from stable COPD.

The sample obtained from the subject to be tested can, in principle, be any tissue sample or serum from the subject. Preferably, the sample is a lung tissue sample. More preferably, the sample is a transbronchial lung biopsy sample or a bronchoalveolar lavage (BAL) sample.

In some of the methods provided herein, including in particular the methods according to the second and the third aspect of the invention, the level of expression of one or more specific genes is compared to a control expression level of the corresponding gene(s) in a healthy subject. Such control expression levels can be established as part of the respective methods of the invention, which may thus include a further step of determining the level of expression of the corresponding gene(s) in a sample obtained from a healthy subject (i.e., a subject that does not suffer from COPD and does not have an increased risk of developing COPD) or in a mixture of samples from several healthy subjects (e.g., about 10, about 20, about 50, about 100, or about 500 healthy subjects). It is to be understood that the healthy subject(s) will be of the same species as the subject to be tested and should preferably have the same age, gender and ethnicity as the subject to be tested. Alternatively, these control expression levels can also be derived from the medical literature or from experiments conducted before carrying out the methods of the invention. It will be understood that the conditions under which the control expression levels are or were obtained (regardless of whether they are derived from the literature or earlier experiments or whether they are determined in the course of carrying out the methods of the invention), including also the type/origin of the sample (or mixture of samples) from the healthy subject, should be identical or at least similar/comparable to the conditions used for determining the level of expression of the one or more genes in the sample obtained from the subject to be tested.

In the method according to the fourth aspect, the level of expression of one or more specific genes is compared to a control expression level of the corresponding gene(s) in a subject suffering from stable COPD. Such control expression levels can be established as part of the method according to the fourth aspect of the invention, which may thus include a further step of determining the level of expression of the corresponding gene(s) in a sample obtained from a subject suffering from stable COPD (particularly a subject that has been diagnosed as suffering from stable COPD) or in a mixture of samples from several subjects (e.g., about 10, about 20, about 50, about 100, or about 500 subjects) suffering from stable COPD. It is to be understood that these control subject(s) will be of the same species as the subject to be tested and should preferably have the same age, gender and ethnicity as the subject to be tested. Alternatively, the corresponding control expression levels can also be derived from experiments conducted before carrying out the method of the fourth aspect of the invention. It will be understood that the conditions under which the control expression levels are or were obtained (regardless of whether they are derived from earlier experiments or whether they are determined in the course of carrying out the method of the fourth aspect), including also the type/origin of the sample (or mixture of samples) from the control subject, should be identical or at least similar/comparable to the conditions used for determining the level of expression of the one or more genes in the sample obtained from the subject to be tested. The control subject suffering from stable COPD in accordance with the fourth aspect of the invention is preferably a subject suffering from stage I COPD (particularly a subject that has been diagnosed as suffering from stage I COPD).

In the methods according to the second, third and fourth aspect of the present invention, the level of expression of KIAA1199 and optionally of one or more further marker genes is determined. Preferably, the level of expression of KIAA1199 and at least one of the corresponding further marker genes is determined, more preferably the level of expression of KIAA1199 and at least two of these further marker genes is determined, and even more preferably the level of expression of KIAA1199 and at least three of the corresponding further marker genes is determined, whereby the reliability of the diagnosis or assessment can be further improved. In general, the greater the number of marker genes the expression of which is altered (as defined in the corresponding aspect of the invention), and also the more pronounced the upregulation or downregulation of the expression of each of these marker genes, the more likely it will be that the subject tested is prone to develop progressive CORD (in the methods of the second and the fourth aspect) or that the subject tested suffers from stable CORD or is prone to suffer from stable COPD (in the method of the third aspect of the invention).

Thus, both (i) the number of tested marker genes showing an altered expression level as described above and (ii) the extent of alteration of the expression level of each one of the marker genes tested can be taken into consideration when determining whether or not the subject is prone to develop progressive COPD (in accordance with the second or the fourth aspect) or whether or not the subject suffers from stable COPD or is prone to suffer from stable COPD (in accordance with the third aspect of the invention). Further factors, signs and symptoms indicative of COPD, such as, e.g., airflow limitation (as determined, e.g., by spirometry), coughing, expiratory wheezing, further respiratory symptoms, the subject's smoking history, bronchial inflammation and/or further biomarkers (including molecular biomarkers), can additionally be taken into account in order to further improve the accuracy of the determination whether or not the subject is prone to develop progressive COPD (in accordance with the second or the fourth aspect) or whether or not the subject suffers from stable COPD or is prone to suffer from stable COPD (in accordance with the third aspect).

In one embodiment of the method according to the second aspect of the invention, it is preferred that the level of expression of KIAA1199 and at least one further gene selected from FGG, CYP1A1, CEACAM5, CTHRC1, NTRK2 and RASGRF2 is determined in the sample obtained from the subject. In this embodiment, it is furthermore preferred that the level of expression of at least two of the aforementioned further genes is determined. For example, the level of expression of KIAA1199, FGG and CYP1A1 may be determined, or the level of expression of KIAA1199, FGG and CEACAM5 may be determined, or the level of expression of KIAA1199, FGG and CTHRC1 may be determined, or the level of expression of KIAA1199, FGG and NTRK2 may be determined, or the level of expression of KIAA1199, FGG and RASGRF2 may be determined, or the level of expression of KIAA1199, CYP1A1 and CEACAM5 may be determined, or the level of expression of KIAA1199, CYP1A1 and CTHRC1 may be determined, or the level of expression of KIAA1199, CYP1A1 and NTRK2 may be determined, or the level of expression of KIAA1199, CYP1A1 and RASGRF2 may be determined, or the level of expression of KIAA1199, CEACAM5 and CTHRC1 may be determined, or the level of expression of KIAA1199, CEACAM5 and NTRK2 may be determined, or the level of expression of KIAA1199, CEACAM5 and RASGRF2 may be determined, or the level of expression of KIAA1199, CTHRC1 and NTRK2 may be determined, or the level of expression of KIAA1199, CTHRC1 and RASGRF2 may be determined, or the level of expression of KIAA1199, NTRK2 and RASGRF2 may be determined. In addition thereto, the level of expression of at least one further gene selected from ELF5, AZGP1, PRRX1, AQP3, SFN, GPR110, GDF15, RASGRF2 and RND1 and/or the level of expression of at least one further gene selected from DMBT1, TMSB15A, DPP6, SLC51B and NUDT11 (particularly DMBT1 and/or TMSB15A) may also be determined.

In a further embodiment of the method according to the second aspect of the invention, it is preferred that the level of expression of KIAA1199 and at least one further gene selected from ELF5, AZGP1, PRRX1, AQP3, SFN, GPR110, GDF15, RASGRF2 and RND1 is determined in the sample obtained from the subject. In this embodiment, it is furthermore preferred that the level of expression of at least two of the aforementioned further genes is determined. For example, the level of expression of KIAA1199, ELF5 and AZGP1 may be determined, or the level of expression of KIAA1199, ELF5 and PRRX1 may be determined, or the level of expression of KIAA1199, ELF5 and AQP3 may be determined, or the level of expression of KIAA1199, ELF5 and SFN may be determined, or the level of expression of KIAA1199, ELF5 and GPR110 may be determined, or the level of expression of KIAA1199, ELF5 and GDF15 may be determined, or the level of expression of KIAA1199, ELF5 and RASGRF2 may be determined, or the level of expression of KIAA1199, ELF5 and RND1 may be determined, or the level of expression of KIAA1199, AZGP1 and PRRX1 may be determined, or the level of expression of KIAA1199, AZGP1 and AQP3 may be determined, or the level of expression of KIAA1199, AZGP1 and SFN may be determined, or the level of expression of KIAA1199, AZGP1 and GPR110 may be determined, or the level of expression of KIAA1199, AZGP1 and GDF15 may be determined, or the level of expression of KIAA1199, AZGP1 and RASGRF2 may be determined, or the level of expression of KIAA1199, AZGP1 and RND1 may be determined, or the level of expression of KIAA1199, PRRX1 and AQP3 may be determined, or the level of expression of KIAA1199, PRRX1 and SFN may be determined, or the level of expression of KIAA1199, PRRX1 and GPR110 may be determined, or the level of expression of KIAA1199, PRRX1 and GDF15 may be determined, or the level of expression of KIAA1199, PRRX1 and RASGRF2 may be determined, or the level of expression of KIAA1 199, PRRX1 and RND1 may be determined, or the level of expression of KIAA1199, AQP3 and SFN may be determined, or the level of expression of KIAA1199, AQP3 and GPR110 may be determined, or the level of expression of KIAA1199, AQP3 and GDF15 may be determined, or the level of expression of KIAA1199, AQP3 and RASGRF2 may be determined, or the level of expression of KIAA1199, AQP3 and RND1 may be determined, or the level of expression of KIAA1199, SFN and GPR110 may be determined, or the level of expression of KIAA1199, SFN and GDF15 may be determined, or the level of expression of KIAA1199, SFN and RASGRF2 may be determined, or the level of expression of KIAA1199, SFN and RND1 may be determined, or the level of expression of KIAA1199, GPR110 and GDF15 may be determined, or the level of expression of KIAA1199, GPR110 and RASGRF2 may be determined, or the level of expression of KIAA1199, GPR110 and RND1 may be determined, or the level of expression of KIAA1199, GDF15 and RASGRF2 may be determined, or the level of expression of KIAA1199, GDF15 and RND1 may be determined, or the level of expression of KIAA1199, RASGRF2 and RND1 may be determined. In addition thereto, the level of expression of at least one further gene selected from FGG, CYP1A1, CEACAM5, CTHRC1, NTRK2 and RASGRF2 and/or the level of expression of at least one further gene selected from DMBT1, TMSB15A, DPP6, SLC51B and NUDT11 (particularly DMBT1 and/or TMSB15A) may also be determined.

In a further embodiment of the method according to the second aspect of the invention, it is preferred that the level of expression of KIAA1199 and at least one further gene selected from DMBT1, TMSB15A, DPP6, SLC51B and NUDT11 is determined in the sample obtained from the subject. In this embodiment, it is furthermore preferred that the level of expression of at least two of the aforementioned further genes is determined. For example, the level of expression of KIAA1199, DMBT1 and TMSB15A may be determined, or the level of expression of KIAA1199, DMBT1 and DPP6 may be determined, or the level of expression of KIAA1199, DMBT1 and SLC51B may be determined, or the level of expression of KIAA1199, DMBT1 and NUDT11 may be determined, or the level of expression of KIAA1199, TMSB15A and DPP6 may be determined, or the level of expression of KIAA1199, TMSB15A and SLC51B may be determined, or the level of expression of KIAA1199, TMSB15A and NUDT11 may be determined, or the level of expression of KIAA1199, DPP6 and SLC51B may be determined, or the level of expression of KIAA1199, DPP6 and NUDT11 may be determined, or the level of expression of KIAA1199, SLC51B and NUDT11 may be determined. In addition thereto, the level of expression of at least one further gene selected from FGG, CYP1A1, CEACAM5, CTHRC1, NTRK2 and RASGRF2 and/or the level of expression of at least one further gene selected from ELF5, AZGP1, PRRX1, AQP3, SFN, GPR110, GDF15, RASGRF2 and RND1 may also be determined.

In the method according to the second aspect of the invention, it is particularly preferred that the level of expression of KIAA1199 and at least one further gene selected from DMBT1 and TMSB15A is determined in the sample obtained from the subject. Accordingly, it is preferred that the level of expression of KIAA1199 and DMBT1 is determined, or that the level of expression of KIAA1199 and TMSB15A is determined. Most preferably, the level of expression of KIAA1199, DMBT1 and TMSB15A is determined in the sample obtained from the subject. For example, the level of expression of KIAA1199, DMBT1, TMSB15A and at least one further gene selected from FGG, CYP1A1, CEACAM5, CTHRC1, NTRK2, RASGRF2, ELF5, AZGP1, PRRX1, AQP3, SFN, GPR110, GDF15, RASGRF2, RND1, DPP6, SLC51B and NUDT11 may be determined.

In one embodiment of the method according to the third aspect of the invention, it is preferred that the level of expression of KIAA1199 and at least one further gene selected from FGG, CYP1A1, CEACAM5, CTHRC1, NTRK2 and RASGRF2 is determined in the sample obtained from the subject. In this embodiment, it is furthermore preferred that the level of expression of at least two of the aforementioned further genes is determined. For example, the level of expression of KIAA1199, FGG and CYP1A1 may be determined, or the level of expression of KIAA1199, FGG and CEACAM5 may be determined, or the level of expression of KIAA1199, FGG and CTHRC1 may be determined, or the level of expression of KIAA1199, FGG and NTRK2 may be determined, or the level of expression of KIAA1199, FGG and RASGRF2 may be determined, or the level of expression of KIAA1199, CYP1A1 and CEACAM5 may be determined, or the level of expression of KIAA1199, CYP1A1 and CTHRC1 may be determined, or the level of expression of KIAA1199, CYP1A1 and NTRK2 may be determined, or the level of expression of KIAA1199, CYP1A1 and RASGRF2 may be determined, or the level of expression of KIAA1199, CEACAM5 and CTHRC1 may be determined, or the level of expression of KIAA1199, CEACAM5 and NTRK2 may be determined, or the level of expression of KIAA1199, CEACAM5 and RASGRF2 may be determined, or the level of expression of KIAA1199, CTHRC1 and NTRK2 may be determined, or the level of expression of KIAA1199, CTHRC1 and RASGRF2 may be determined, or the level of expression of KIAA1199, NTRK2 and RASGRF2 may be determined. In addition thereto, the level of expression of at least one further gene selected from ELF5, AZGP1, PRRX1, AQP3, GPR110, GDF15, RASGRF2 and RND1 and/or the level of expression of at least one further gene selected from DMBT1, TMSB15A, DPP6, SLC51B and NUDT11 (particularly DMBT1 and/or TMSB15A) may also be determined.

In a further embodiment of the method according to the third aspect of the invention, it is preferred that the level of expression of KIAA1199 and at least one further gene selected from ELF5, AZGP1, PRRX1, AQP3, SFN, GPR110, GDF15, RASGRF2 and RND1 is determined in the sample obtained from the subject. In this embodiment, it is furthermore preferred that the level of expression of at least two of the aforementioned further genes is determined. For example, the level of expression of KIAA1199, ELF5 and AZGP1 may be determined, or the level of expression of KIAA1199, ELF5 and PRRX1 may be determined, or the level of expression of KIAA1199, ELF5 and AQP3 may be determined, or the level of expression of KIAA1199, ELF5 and SFN may be determined, or the level of expression of KIAA1199, ELF5 and GPR110 may be determined, or the level of expression of KIAA1199, ELF5 and GDF15 may be determined, or the level of expression of KIAA1199, ELF5 and RASGRF2 may be determined, or the level of expression of KIAA1199, ELF5 and RND1 may be determined, or the level of expression of KIAA1199, AZGP1 and PRRX1 may be determined, or the level of expression of KIAA1199, AZGP1 and AQP3 may be determined, or the level of expression of KIAA1199, AZGP1 and SFN may be determined, or the level of expression of KIAA1199, AZGP1 and GPR110 may be determined, or the level of expression of KIAA1199, AZGP1 and GDF15 may be determined, or the level of expression of KIAA1199, AZGP1 and RASGRF2 may be determined, or the level of expression of KIAA1199, AZGP1 and RND1 may be determined, or the level of expression of KIAA1199, PRRX1 and AQP3 may be determined, or the level of expression of KIAA1199, PRRX1 and SFN may be determined, or the level of expression of KIAA1199, PRRX1 and GPR110 may be determined, or the level of expression of KIAA1199, PRRX1 and GDF15 may be determined, or the level of expression of KIAA1199, PRRX1 and RASGRF2 may be determined, or the level of expression of KIAA1199, PRRX1 and RND1 may be determined, or the level of expression of KIAA1199, AQP3 and SFN may be determined, or the level of expression of KIAA1199, AQP3 and GPR110 may be determined, or the level of expression of KIAA1199, AQP3 and GDF15 may be determined, or the level of expression of KIAA1199, AQP3 and RASGRF2 may be determined, or the level of expression of KIAA1199, AQP3 and RND1 may be determined, or the level of expression of KIAA1199, SFN and GPR110 may be determined, or the level of expression of KIAA1199, SFN and GDF15 may be determined, or the level of expression of KIAA1199, SFN and RASGRF2 may be determined, or the level of expression of KIAA1199, SFN and RND1 may be determined, or the level of expression of KIAA1199, GPR110 and GDF15 may be determined, or the level of expression of KIAA1199, GPR110 and RASGRF2 may be determined, or the level of expression of KIAA1199, GPR110 and RND1 may be determined, or the level of expression of KIAA1199, GDF15 and RASGRF2 may be determined, or the level of expression of KIAA1199, GDF15 and RND1 may be determined, or the level of expression of KIAA1199, RASGRF2 and RND1 may be determined. In addition thereto, the level of expression of at least one further gene selected from FGG, CYP1A1, CEACAM5, CTHRC1, NTRK2 and RASGRF2 and/or the level of expression of at least one further gene selected from DMBT1, TMSB15A, DPP6, SLC51B and NUDT11 (particularly DMBT1 and/or TMSB15A) may also be determined.

In a further embodiment of the method according to the third aspect of the invention, it is preferred that the level of expression of KIAA1199 and at least one further gene selected from DMBT1, TMSB15A, DPP6, SLC51B and NUDT11 is determined in the sample obtained from the subject. In this embodiment, it is furthermore preferred that the level of expression of at least two of the aforementioned further genes is determined. For example, the level of expression of KIAA1199, DMBT1 and TMSB15A may be determined, or the level of expression of KIAA1199, DMBT1 and DPP6 may be determined, or the level of expression of KIAA1199, DMBT1 and SLC51B may be determined, or the level of expression of KIAA1199, DMBT1 and NUDT11 may be determined, or the level of expression of KIAA1199, TMSB15A and DPP6 may be determined, or the level of expression of K1AA1199, TMSB15A and SLC51B may be determined, or the level of expression of KIAA1199, TMSB15A and NUDT11 may be determined, or the level of expression of KIAA1199, DPP6 and SLC51B may be determined, or the level of expression of KIAA1199, DPP6 and NUDT11 may be determined, or the level of expression of KIAA1199, SLC51B and NUDT11 may be determined. In addition thereto, the level of expression of at least one further gene selected from FGG, CYP1A1, CEACAM5, CTHRC1, NTRK2 and RASGRF2 and/or the level of expression of at least one further gene selected from ELF5, AZGP1, PRRX1, AQP3, SFN, GPR110, GDF15, RASGRF2 and RND1 may also be determined.

In the method according to the third aspect of the invention, it is particularly preferred that the level of expression of KIAA1199 and at least one further gene selected from DMBT1 and TMSB15A is determined in the sample obtained from the subject. AccOrdingly, it is preferred that the level of expression of K1AA1199 and DMBT1 is determined, or that the level of expression of KIAA1199 and TMSB15A is determined. Most preferably, the level of expression of KIAA1199, DMBT1 and TMSB15A is determined in the sample obtained from the subject.

In one embodiment of the method according to the fourth aspect of the invention, it is preferred that the level of expression of KIAA1199 and at least one further gene selected from FGG, CYP1A1, CEACAM5, CTHRC1, NTRK2 and RASGRF2 is determined in the sample obtained from the subject. In this embodiment, it is furthermore preferred that the level of expression of at least two of the aforementioned further genes is determined. For example, the level of expression of KIAA1199, FGG and CYP1A1 may be determined, or the level of expression of KIAA1199, FGG and CEACAM5 may be determined, or the level of expression of KIAA1199, FGG and CTHRC1 may be determined, or the level of expression of K1AA1199, FGG and NTRK2 may be determined, or the level of expression of KIAA1199, FGG and RASGRF2 may be determined, or the level of expression of KIAA1199, CYP1A1 and CEACAM5 may be determined, or the level of expression of KIAA1199, CYP1A1 and CTHRC1 may be determined, or the level of expression of KIAA1199, CYP1A1 and NTRK2 may be determined, or the level of expression of KIAA1199, CYP1A1 and RASGRF2 may be determined, or the level of expression of KIAA1199, CEACAM5 and CTHRC1 may be determined, or the level of expression of KIAA1199, CEACAM5 and NTRK2 may be determined, or the level of expression of KIAA1199, CEACAM5 and RASGRF2 may be determined, or the level of expression of KIAA1199, CTHRC1 and NTRK2 may be determined, or the level of expression of KIAA1199, CTHRC1 and RASGRF2 may be determined, or the level of expression of KIAA1199, NTRK2 and RASGRF2 may be determined. In addition thereto, the level of expression of at least one further gene selected from ELF5, AZGP1, PRRX1, AQP3, GPR110, GDF15, RASGRF2 and RND1 and/or the level of expression of at least one further gene selected from DMBT1 and TMSB15A may also be determined.

In a further embodiment of the method according to the fourth aspect of the invention, it is preferred that the level of expression of KIAA1199 and at least one further gene selected from ELF5, AZGP1, PRRX1, AQP3, GPR110, GDF15, RASGRF2 and RND1 is determined in the sample obtained from the subject. In this embodiment, it is furthermore preferred that the level of expression of at least two of the aforementioned further genes is determined. For example, the level of expression of KIAA1199, ELF5 and AZGP1 may be determined, or the level of expression of KIAA1199, ELF5 and PRRX1 may be determined, or the level of expression of KIAA1199, ELF5 and AQP3 may be determined, or the level of expression of KIAA1199, ELF5 and GPR110 may be determined, or the level of expression of KIAA1199, ELF5 and GDF15 may be determined, or the level of expression of KIAA1199, ELF5 and RASGRF2 may be determined, or the level of expression of KIAA1199. ELF5 and RND1 may be determined, or the level of expression of KIAA1199, AZGP1 and PRRX1 may be determined, or the level of expression of KIAA1199, AZGP1 and AQP3 may be determined, or the level of expression of KIAA1199, AZGP1 and GPR110 may be determined, or the level of expression of KIAA1199, AZGP1 and GDF15 may be determined, or the level of expression of KIAA1199, AZGP1 and RASGRF2 may be determined, or the level of expression of KIAA1199, AZGP1 and RND1 may be determined, or the level of expression of KIAA1199, PRRX1 and AQP3 may be determined, or the level of expression of KIAA1199, PRRX1 and GPR110 may be determined, or the level of expression of KIAA1199, PRRX1 and GDF15 may be determined, or the level of expression of KIAA1199, PRRX1 and RASGRF2 may be determined, or the level of expression of KIAA1199, PRRX1 and RND1 may be determined, or the level of expression of KIAA1199, AQP3 and GPR110 may be determined, or the level of expression of KIAA1199, AQP3 and GDF15 may be determined, or the level of expression of KIAA1199, AQP3 and RASGRF2 may be determined, or the level of expression of KIAA1199, AQP3 and RND1 may be determined, or the level of expression of KIAA1199, GPR110 and GDF15 may be determined, or the level of expression of KIAA1199, GPR110 and RASGRF2 may be determined, or the level of expression of KIAA1199, GPR110 and RND1 may be determined, or the level of expression of KIAA1199, GDF15 and RASGRF2 may be determined, or the level of expression of KIAA1199, GDF15 and RND1 may be determined, or the level of expression of KIAA1199, RASGRF2 and RND1 may be determined. In addition thereto, the level of expression of at least one further gene selected from FGG, CYP1A1, CEACAM5, CTHRC1, NTRK2 and RASGRF2 and/or the level of expression of at least one further gene selected from DMBT1 and TMSB15A may also be determined.

In the method according to the fourth aspect of the invention, it is particularly preferred that the level of expression of KIAA1199 and at least one further gene selected from DMBT1 and TMSB15A is determined in the sample obtained from the subject. Accordingly, it is preferred that the level of expression of KIAA1199 and DMBT1 is determined, or that the level of expression of KIAA1199 and TMSB15A is determined. Most preferably, the level of expression of KIAA1199, DMBT1 and TMSB15A is determined in the sample obtained from the subject.

In the method according to the second aspect of the invention, preferably, it is determined that the subject is prone to develop progressive COPD if the level of expression of a majority of the number of genes tested (i.e., of the number of genes, the expression of which has been tested) is altered in the sense that (i) the level of expression of KIAA1199, DMBT1, ELF5, AZGP1, PRRX1, AQP3, SFN, GPR110, GDF15, RASGRF2, RND1, FGG, CEACAMS, AHRR, CXCL3, CYP1A1, CYP1B1, CYP1A2, NTRK2 and/or COMP in the sample from the subject is increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s). If only one marker gene (i.e., KIAA1199) is tested, then the alteration of the level of expression of this marker gene is decisive for determining whether or not the subject is prone to develop progressive COPD. If two or more marker genes are tested, then a decrease or increase in the level of expression of a majority of the number of these marker genes is required for determining that the subject is prone to develop progressive COPD. The term "majority" (as in the expression "majority of the number of genes tested") means more than 50% of the number of the marker genes tested.

In accordance with the second aspect, it is furthermore preferred that an alteration in the level of expression of at least 60%, more preferably at least 70%, even more preferably at least 80%, and still more preferably at least 90% of the number of genes tested—i.e., an alteration in the sense that (i) the level of expression of KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s)—is required for determining that the subject is prone to develop progressive COPD.

The decrease or increase in the level of expression of the marker gene(s) tested which is required for determining that the subject is prone to develop progressive COPD in accordance with the second aspect is preferably at least a 1.5-fold decrease or increase, more preferably at least a 2-fold decrease or increase, even more preferably at least a 3-fold decrease or increase, even more preferably at least a 5-fold decrease or increase, and yet even more preferably at least a 10-fold decrease or increase.

In a preferred embodiment of the method according to the second aspect of the invention, it is determined that the subject to be tested is prone to develop progressive COPD if the level of expression of a majority of the number of genes tested is altered in the sense that (i) the level of expression of KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In a further preferred embodiment of the method according to the second aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s).

In a further preferred embodiment of the method according to the second aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of TMSB15A, DPP6, SLC51B, NUDT11, PLA1A, HYAL2, CST6, ITGA10, CTHRC1, TAL1, FIBIN, BEXS, BEX1, ESM1 and/or GHRL in the sample from the subject is at least 3-fold (more preferably at least 5-fold, even more preferably at least 10-fold) decreased as compared to the control expression level of the corresponding gene(s).

In the method according to the second aspect of the invention, it is particularly preferred to determine the level of expression of KIAA1199 and DMBT1 since the disease stage of COPD is particularly well reflected by the expression patterns of these marker genes. While an initial decrease in the expression of KIAA1199 and a simultaneous increase in the expression of DMBT1 is observed when a subject develops stable COPD, the ratio between the expression levels of KIAA1199 and DMBT1 changes upon entering the progressive stage of COPD, i.e., the expression of KIAA1199 increases while the expression of DMBT1 decreases. Therefore, in a particularly preferred embodiment of the method according to the second aspect, if the difference between the expression levels of DMBT1 and KIAA1199 (i.e., the expression level of DMBT1 minus the expression level of KIAA1199) in the sample from the subject is increased as compared to the difference between the control expression levels of DMBT1 and KIAA1199 (i.e., as compared to the value obtained when subtracting the control expression level of KIAA1199 from the control expression level of DMBT1) by a factor of more than $2^{3.63}$ (i.e., by a factor of more than 12.38; preferably by a factor of more than $2^{3.8}$, i.e., more than 13.93; and more preferably by a factor of more than $2^4$, i.e., more than 16), then it is determined that the subject is prone to develop progressive COPD. This procedure allows to particularly reliably distinguish between progressive COPD and stable COPD (see also FIG. 6E) and, thus, further improves the accurateness of the method of assessing the susceptibility of a subject to develop progressive COPD in accordance with the second aspect of the invention.

In the method according to the third aspect of the invention, preferably, it is determined that the subject suffers from stable COPD or is prone to suffer from stable COPD if the level of expression of a majority (i.e., more than 50%) of the number of genes tested is altered in the sense that (i) the level of expression of DMBT1, ELF5, AZGP1, PRRX1, AQP3, SFN, GPR110, GDF15, RASGRF2, RND1, FGG, CEACAMS, AHRR, CXCL3, CYP1A1, CYP1B1, CYP1A2, NTRK2 and/or COMP in the sample from the subject is increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s).

In accordance with the third aspect, it is furthermore preferred that an alteration in the level of expression of at least 60%, more preferably at least 70%, even more preferably at least 80%, and still more preferably at least 90% of the number of genes tested—i.e., an alteration in the sense that (i) the level of expression of DMBT1, ELF5, AZGP1, PRRX1, AQP3, SFN, GPR110, GDF15, RASGRF2, RND1, FGG, CEACAMS, AHRR, CXCL3, CYP1A1, CYP1B1, CYP1A2, NTRK2 and/or COMP in the sample from the subject is increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s)—is required for determining that the subject suffers from stable COPD or is prone to suffer from stable COPD.

The decrease or increase in the level of expression of the marker gene(s) tested which is required for determining that the subject suffers from stable COPD or is prone to suffer from stable COPD in accordance with the third aspect is preferably at least a 1.5-fold decrease or increase, more preferably at least a 2-fold decrease or increase, even more preferably at least a 3-fold decrease or increase, even more preferably at least a 5-fold decrease or increase, and yet even more preferably at least a 10-fold decrease or increase.

In a preferred embodiment of the method according to the third aspect of the invention, it is determined that the subject to be tested suffers from stable COPD or is prone to suffer from stable COPD if the level of expression of a majority of the number of genes tested is altered in the sense that (i) the level of expression of DMBT1, ELF5, AZGP1, PRRX1, AQP3, SFN, GPR110, GDF15, RASGRF2, RND1, FGG, CEACAMS, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In a further preferred embodiment of the method according to the third aspect of the invention, it is determined that the subject to be tested suffers from stable COPD or is prone to suffer from stable COPD if the level of expression of at least 70% (more preferably at least 80%, and even more preferably at least 90%) of the number of genes tested is altered in the sense that (i) the level of expression of DMBT1, ELFS, AZGP1, PRRX1, AQP3, SFN, GPR110, GDF15, RASGRF2, RND1, FGG, CEACAMS, AHRR, CXCL3, CYP1A1, CYP1B1, CYP1A2, NTRK2 and/or COMP in the sample from the subject is increased as compared to the control expression level of the corresponding gene(s) and (ii) the level of expression of KIAA1199, TIV1SB15A, DPP6, SL051B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the corresponding gene(s).

In a further preferred embodiment of the method according to the third aspect of the invention, it is determined that the subject to be tested suffers from stable COPD or is prone to suffer from stable COPD if the level of expression of at least 70% (more preferably at least 80%, and even more preferably at least 90%) of the number of genes tested is altered in the sense that (i) the level of expression of DMBT1, ELFS, AZGP1, PRRX1, AQP3, SFN, GPR110, GDF15, RASGRF2, RND1, FGG, CEACAMS, AHRR, CXCL3, CYP1A1, CYP1B1, CYP1A2, NTRK2 and/or COMP in the sample from the subject is at least 3-fold (more preferably at least 5-fold, even more preferably at least 10-fold) increased as compared to the control expression level of the corresponding gene(s) and (ii) the level of expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold (more preferably at least 5-fold, even more preferably at least 10-fold) decreased as compared to the control expression level of the corresponding gene(s).

In the method according to the fourth aspect of the invention, preferably, it is determined that the subject is prone to develop progressive COPD if the level of expression of a majority (i.e., more than 50%) of the number of genes tested is altered in the sense that (i) the level of expression of KIAA1199, GPR110, GDF15, RASGRF2, RND1, FGG, CEACAMS, HYAL2, AHRR, CXCL3, CYP1A1, CYP1B1, CYP1A2, CST6, NTRK2 and/or TALI in the sample from the subject is increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is decreased as compared to the control expression level of the corresponding gene(s).

In accordance with the fourth aspect, it is furthermore preferred that an alteration in the level of expression of at least 60%, more preferably at least 70%, even more preferably at least 80%, and still more preferably at least 90% of the number of genes tested—i.e., an alteration in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAU in the sample from the subject is increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is decreased as compared to the control expression level of the corresponding gene(s)—is required for determining that the subject is prone to develop progressive COPD.

The decrease or increase in the level of expression of the marker gene(s) tested which is required for determining that the subject is prone to develop progressive COPD in accordance with the fourth aspect is preferably at least a 1.5-fold decrease or increase, more preferably at least a 2-fold decrease or increase, even more preferably at least a 3-fold decrease or increase, even more preferably at least a 5-fold decrease or increase, and yet even more preferably at least a 10-fold decrease or increase.

In a preferred embodiment of the method according to the fourth aspect of the invention, it is determined that the subject to be tested is prone to develop progressive COPD if the level of expression of a majority of the number of genes tested is altered in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject is at least 3-fold (more preferably at least 5-fold, even more preferably at least 10-fold) increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is at least 3-fold (more preferably at least 5-fold, even more preferably at least 10-fold) decreased as compared to the control expression level of the corresponding gene(s).

In a further preferred embodiment of the method according to the fourth aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject is increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is decreased as compared to the control expression level of the corresponding gene(s).

In a further preferred embodiment of the method according to the fourth aspect of the invention, it is determined that the subject to be tested is prone to develop progressive COPD if the level of expression of at least 70% (more preferably at least 80%, and even more preferably at least 90%) of the number of genes tested is altered in the sense that (i) the level of expression of KIAA1199, GPR110, GDF15, RASGRF2, RND1, FGG, CEACAM5, HYAL2, AHRR, CXCL3, CYP1A1, CYP1B1, CYP1A2, CST6, NTRK2 and/or TAL1 in the sample from the subject is at least 3-fold (more preferably at least 5-fold, even more preferably at least 10-fold) increased as compared to the control expression level of the corresponding gene(s) and (ii) the level of expression of DMBT1, ELF5, AZGP1, PRRX1, AQP3, COMP, ITGA10, CTHRC1, BEX1 and/or GHRL in the sample from the subject is at least 3-fold (more preferably at least 5-fold, even more preferably at least 10-fold) decreased as compared to the control expression level of the corresponding gene(s).

The present invention furthermore relates to the use of the gene KIAA1199 as a marker in an in vitro diagnostic method of assessing the susceptibility of a subject to develop progressive COPD. In particular, in accordance with the fifth aspect, the invention relates to the use of a pair of primers for (i.e., binding to) a transcript of the gene KIAA1199 in an in vitro diagnostic method of assessing the susceptibility of a subject to develop progressive COPD. Non-limiting examples of such an in vitro method are the methods according to the second aspect of the present invention. The transcript is preferably an mRNA of the gene KIAA1199 (e.g., the specific mRNA of KIAA1199 listed in Table 1 above) or a cDNA synthesized from the mRNA of the gene KIAA1199 (e.g., a cDNA synthesized from the specific mRNA of KIAA1199 listed in Table 1 above). The primers can be designed using methods known in the art (as also described, e.g., in Green et al., 2012) so as to allow the specific amplification/quantification of the transcript of the gene KIAA1199. Furthermore, the primers are preferably DNA primers. The in vitro diagnostic method of assessing the susceptibility of a subject to develop progressive COPD, in which the pair of primers is to be used, preferably comprises a step of determining the expression level of the gene KIAA1199 in a sample obtained from the subject. The preferred features/embodiments of the method according to the second aspect of the present invention as described herein, including in particular the preferred embodiments of determining expression levels, the preferred embodiments of the sample, and the preferred embodiments of the subject, also apply to the method in which the pair of primers is to be used.

In accordance with the fifth aspect, the present invention also relates to the use of a nucleic acid probe to (i.e., binding to) a transcript of the gene KIAA1199 in an in vitro diagnostic method of assessing the susceptibility of a subject to develop progressive COPD. Non-limiting examples of such an in vitro method are the methods according to the second aspect of the present invention. The transcript is preferably an mRNA of the gene KIAA1199 (e.g., the specific mRNA of KIAA1199 listed in Table 1 above) or a cDNA synthesized from the mRNA of the gene KIAA1199 (e.g., a cDNA synthesized from the specific mRNA of KIAA1199 listed in Table 1 above). The nucleic acid probe comprises or consists of a nucleic acid capable of hybridizing with the above-mentioned transcript. The nucleic acid probe is preferably a single-stranded DNA probe or a single-stranded RNA probe, more preferably a single-stranded DNA probe. It is furthermore preferred that the nucleic acid probe (which may be, e.g., a single-stranded DNA or a single-stranded RNA, and is preferably a single-stranded DNA) is an oligonucleotide probe having, e.g., 10 to 80 nucleotides, preferably 15 to 60 nucleotides, more preferably 20 to 35 nucleotides, and even more preferably about 25 nucleotides. Such nucleic acid probes can be designed using methods known in the art (as also described, e.g., in Green et al., 2012) so as to allow the specific detection and quantification of the transcript of the corresponding gene. The in vitro diagnostic method of assessing the susceptibility of a subject to develop progressive COPD, in which the nucleic acid probe is to be used, preferably comprises a step of determining the expression level of the gene KIAA1199 in a sample obtained from the subject, The preferred features/embodiments of the method according to the second aspect of the invention as described herein, including in particular the preferred embodiments of determining expression levels, the preferred embodiments of the sample, and the preferred embodiments of the subject, also apply to the method in which the nucleic acid probe is to be used.

In the fifth aspect, the invention further relates to the use of a microarray comprising a nucleic acid probe to (i.e., binding to) a transcript of the gene KIAA1199 and optionally comprising nucleic acid probes to the transcripts of one or more further genes selected from DMBT1, TMSBI5A, DPP6, SLC51B, NUDT11, ELFS, AZGP1, PRRX1, AQP3, SFN, GPR110, GDF15, RASGRF2, RND1, PLA1A, FGG, CEACAMS, HYAL2, AHRR, CXCL3, CYP1A1, CYP1B1, CYP1A2, CST6, NTRK2, COMP, ITGA10, CTHRC1, TAL1, FIBIN, BEXS, BEX1, ESM1 and GHRL in an in vitro diagnostic method of assessing the susceptibility of a subject to develop progressive COPD. The microarray preferably comprises nucleic acid probes to the transcript of KIAA1199 and to the transcripts of at least one, more preferably at least two, even more preferably at least three of the above-mentioned further genes. Each of the transcripts is preferably an mRNA of the corresponding gene (including, e.g., any one of the corresponding specific mRNAs listed in Table 1 above) or a cDNA synthesized from the mRNA of the gene (including, e.g., a cDNA synthesized from any one of the corresponding specific mRNAs listed in Table 1 above). Each of the nucleic acid probes is preferably a single-stranded DNA probe or a single-stranded RNA probe, more preferably a single-stranded DNA probe. It is furthermore preferred that the nucleic acid probes (which may be, e.g., single-stranded DNA or single-stranded RNA, preferably single-stranded DNA) are oligonucleotide probes having, e.g., 10 to 80 nucleotides, preferably 15 to 60 nucleotides, more preferably 20 to 35 nucleotides, and even more preferably about 25 nucleotides. The in vitro diagnostic method of assessing the susceptibility of a subject to develop progressive COPD, in which the microarray is to be used, preferably comprises a step of determining the expression level of the gene KIAA1199 and optionally of the one or more further genes in a sample obtained from the subject. The preferred features/embodiments of the method according to the second aspect of the invention as described herein, including in particular the preferred embodiments of determining expression levels, the preferred embodiments of the sample, and the preferred embodiments of the subject, also apply to the method in which the microarray is to be used.

In accordance with the fifth aspect, the invention is also directed to the use of an antibody against (i.e., binding to) the protein KIAA1199 in an in vitro diagnostic method of assessing the susceptibility of a subject to develop progressive COPD. The antibody binds specifically to the protein KIAA1199 and may be, e.g., a polyclonal antibody or a monoclonal antibody. Preferably, the antibody is a monoclonal antibody. The antibody may further be a full/intact immunoglobulin molecule or a fragment/part thereof (such as, e.g., a separated light or heavy chain, an Fab fragment, an Fab/c fragment, an Fv fragment, an Fab' fragment, or an F(ab')$_2$ fragment), provided that the fragment/part substantially retains the binding specificity of the corresponding full immunoglobulin molecule. The antibody may also be a modified and/or altered antibody, such as a chimeric or humanized antibody, a bifunctional or trifunctional antibody, or an antibody construct (such as a single-chain variable fragment (scFv) or an antibody-fusion protein). The antibody can be prepared using methods known in the art, as also described, e.g., in Harlow et al., 1998. For example, monoclonal antibodies can be prepared by methods such as the hybridoma technique (see, e.g., Kohler et al., 1975), the trioma technique, the human B-cell hybridoma technique (see, e.g., Kozbor et al., 1983) or the EBV-hybridoma technique (see, e.g., Cole et al., 1985). The protein KIAA1199 may be, e.g., the specific KIAA1199 protein listed in Table 1 above. The in vitro diagnostic method of assessing the susceptibility of a subject to develop progressive COPD, in which the antibody is to be used, preferably comprises a step of determining the amount of the protein KIAA1199 in a sample obtained from the subject. The preferred features/embodiments of the method according to the second aspect of the invention as described herein, including in particular the preferred embodiments of determining the amount of a specific protein in a sample (as discussed in connection with the determination of translation levels), the preferred embodiments of the sample, and the preferred embodiments of the subject, also apply to the method in which the antibody is to be used.

Moreover, in accordance with the seventh aspect, the present invention relates to the use of a pair of primers for (i.e., binding to) a transcript of the gene KIAA1199 in an in vitro method of diagnosing stable COPD in a subject or assessing the susceptibility of a subject to develop stable COPD. Non-limiting examples of such an in vitro method are the methods according to the third aspect of the present invention. The transcript is preferably an mRNA of the gene KIAA1199 (e.g., the specific mRNA of KIAA1199 listed in Table 1 above) or a cDNA synthesized from the mRNA of the gene KIAA1 199 (e.g., a cDNA synthesized from the specific mRNA of KIAA1199 listed in Table 1 above). The primers can be designed using methods known in the art (as also described, e.g., in Green et al., 2012) so as to allow the specific amplification/quantification of the transcript of the gene KIAA1199. Furthermore, the primers are preferably DNA primers. The in vitro method of diagnosing stable COPD in a subject or assessing the susceptibility of a subject to develop stable COPD, in which the pair of primers is to be used, preferably comprises a step of determining the expression level of the gene KIAA1199 in a sample obtained from the subject. The preferred features/embodiments of the method according to the third aspect of the present invention as described herein, including in particular the preferred embodiments of determining expression levels, the preferred embodiments of the sample, and the preferred embodiments of the subject, also apply to the method in which the pair of primers is to be used.

In accordance with the seventh aspect, the present invention also relates to the use of a nucleic acid probe to (i.e., binding to) a transcript of the gene KIAA1199 in an in vitro method of diagnosing stable COPD in a subject or assessing the susceptibility of a subject to develop stable COPD. Non-limiting examples of such an in vitro method are the methods according to the third aspect of the present invention. The transcript is preferably an mRNA of the gene KIAA1199 (e.g., the specific mRNA of KIAA1199 listed in Table 1 above) or a cDNA synthesized from the mRNA of the gene KIAA1199 (e.g., a cDNA synthesized from the specific mRNA of KIAA1199 listed in Table 1 above). The nucleic acid probe comprises or consists of a nucleic acid capable of hybridizing with the above-mentioned transcript. The nucleic acid probe is preferably a single-stranded DNA probe or a single-stranded RNA probe, more preferably a single-stranded DNA probe. It is furthermore preferred that the nucleic acid probe (which may be, e.g., a single-stranded DNA or a single-stranded RNA, and is preferably a single-stranded DNA) is an oligonucleotide probe having, e.g., 10 to 80 nucleotides, preferably 15 to 60 nucleotides, more preferably 20 to 35 nucleotides, and even more preferably about 25 nucleotides. Such nucleic acid probes can be designed using methods known in the art (as also described, e.g., in Green et al., 2012) so as to allow the specific detection and quantification of the transcript of the corresponding gene. The in vitro method of diagnosing stable COPD in a subject or assessing the susceptibility of a subject to develop stable COPD, in which the nucleic acid probe is to be used, preferably comprises a step of determining the expression level of the gene KIAA1199 in a sample obtained from the subject. The preferred features/embodiments of the method according to the third aspect of the invention as described herein, including in particular the preferred embodiments of determining expression levels, the preferred embodiments of the sample, and the preferred embodiments of the subject, also apply to the method in which the nucleic acid probe is to be used.

In the seventh aspect, the invention further relates to the use of a microarray comprising a nucleic acid probe to (i.e., binding to) a transcript of the gene KIAA1199 and optionally comprising nucleic acid probes to the transcripts of one or more further genes selected from DMBT1, TMSB15A, DPP6, SLC51B, NUDT11, ELFS, AZGP1, PRRX1, AQP3, SFN, GPR110, GDF15, RASGRF2, RND1, PLA1A, FGG, CEACAMS, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in an in vitro method of diagnosing stable COPD in a subject or assessing the susceptibility of a subject to develop stable COPD. The microarray preferably comprises nucleic acid probes to the transcript of KIAA1199 and to the transcripts of at least one, more preferably at least two, even more preferably at least three of the above-mentioned further genes. Each of the transcripts is preferably an mRNA of the corresponding gene (including, e.g., any one of the corresponding specific mRNAs listed in Table 1 above) or a cDNA synthesized from the mRNA of the gene (including, e.g., a cDNA synthesized from any one of the corresponding specific mRNAs listed in Table 1 above). Each of the nucleic acid probes is preferably a single-stranded DNA probe or a single-stranded RNA probe, more preferably a single-stranded DNA probe. It is furthermore preferred that the nucleic acid probes (which may be, e.g., single-stranded DNA or single-stranded RNA, preferably single-stranded DNA) are oligonucleotide probes having, e.g., 10 to 80 nucleotides, preferably 15 to 60 nucleotides, more preferably 20 to 35 nucleotides, and even more preferably about 25 nucleotides. The in vitro method of diagnosing stable COPD in a subject or assessing the susceptibility of a subject to develop stable COPD, in which the microarray is to be used, preferably comprises a step of determining the expression level of the gene KIAA1199 and optionally of the one or more further genes in a sample obtained from the subject. The preferred features/embodiments of the method according to the third aspect of the invention as described herein, including in particular the preferred embodiments of determining expression levels, the preferred embodiments of the sample, and the preferred embodiments of the subject, also apply to the method in which the microarray is to be used.

In accordance with the seventh aspect, the invention is also directed to the use of an antibody against (i.e., binding to) the protein KIAA1199 in an in vitro method of diagnosing stable COPD in a subject or assessing the susceptibility of a subject to develop stable COPD. The antibody binds specifically to the protein KIAA1199 and may be, e.g., a polyclonal antibody or a monoclonal antibody. Preferably, the antibody is a monoclonal antibody. The antibody may further be a full/intact immunoglobulin molecule or a fragment/part thereof (such as, e.g., a separated light or heavy chain, an Fab fragment, an Fab/c fragment, an Fv fragment, an Fab' fragment, or an F(ab')$_2$ fragment), provided that the fragment/part substantially retains the binding specificity of the corresponding full immunoglobulin molecule. The antibody may also be a modified and/or altered antibody, such as a chimeric or humanized antibody, a bifunctional or trifunctional antibody, or an antibody construct (such as a single-chain variable fragment (scFv) or an antibody-fusion protein). The antibody can be prepared using methods known in the art, as also described, e.g., in Harlow et al., 1998. For example, monoclonal antibodies can be prepared by methods such as the hybridoma technique (see, e.g., Köhler et al., 1975), the trioma technique, the human B-cell hybridoma technique (see, e.g., Kozbor et al., 1983) or the EBV-hybridoma technique (see, e.g., Cole et al., 1985). The protein KIAA1199 may be, e.g., the specific KIAA1199 protein listed in Table 1 above. The in vitro method of diagnosing stable COPD in a subject or assessing the susceptibility of a subject to develop stable COPD, in which the antibody is to be used, preferably comprises a step of determining the amount of the protein KIAA1199 in a sample obtained from the subject. The preferred features/embodiments of the method according to the third aspect of the invention as described herein, including in particular the preferred embodiments of determining the amount of a specific protein in a sample (as discussed in connection with the determination of translation levels), the preferred embodiments of the sample, and the preferred embodiments of the subject, also apply to the method in which the antibody is to be used.

Furthermore, in accordance with the ninth aspect, the present invention relates to the use of a pair of primers for (i.e., binding to) a transcript of the gene KIAA1199 in an in vitro diagnostic method of assessing the susceptibility of a subject suffering from stable COPD to develop progressive COPD involving the appearance of irreversible lung damage. Non-limiting examples of such an in vitro method are the methods according to the fourth aspect of the present invention. The transcript is preferably an mRNA of the gene KIAA1199 (e.g., the specific mRNA of KIAA1199 listed in Table 1 above) or a cDNA synthesized from the mRNA of the gene KIAA1199 (e.g., a cDNA synthesized from the specific mRNA of KIAA1199 listed in Table 1 above). The primers can be designed using methods known in the art (as also described, e.g., in Green et al., 2012) so as to allow the specific amplification/quantification of the transcript of the gene KIAA1199. Furthermore, the primers are preferably DNA primers. The in vitro diagnostic method of assessing the susceptibility of a subject suffering from stable COPD to develop progressive COPD involving the appearance of irreversible lung damage, in which the pair of primers is to be used, preferably comprises a step of determining the expression level of the gene KIAA1199 in a sample obtained from the subject. The preferred features/embodiments of the method according to the fourth aspect of the present invention as described herein, including in particular the preferred embodiments of determining expression levels, the preferred embodiments of the sample, and the preferred embodiments of the subject, also apply to the method in which the pair of primers is to be used.

In accordance with the ninth aspect, the present invention also relates to the use of a nucleic acid probe to (i.e., binding to) a transcript of the gene KIAA1199 in an in vitro diagnostic method of assessing the susceptibility of a subject suffering from stable COPD to develop progressive COPD involving the appearance of irreversible lung damage. Non-limiting examples of such an in vitro method are the methods according to the fourth aspect of the present invention. The transcript is preferably an mRNA of the gene KIAA1199 (e.g., the specific mRNA of KIAA1199 listed in Table 1 above) or a cDNA synthesized from the mRNA of the gene KIAA1199 (e.g., a cDNA synthesized from the specific mRNA of KIAA1199 listed in Table 1 above). The nucleic acid probe comprises or consists of a nucleic acid capable of hybridizing with the above-mentioned transcript.

The nucleic acid probe is preferably a single-stranded DNA probe or a single-stranded RNA probe, more preferably a single-stranded DNA probe. It is furthermore preferred that the nucleic acid probe (which may be, e.g., a single-stranded DNA or a single-stranded RNA, and is preferably a single-stranded DNA) is an oligonucleotide probe having, e.g., 10 to 80 nucleotides, preferably 15 to 60 nucleotides, more preferably 20 to 35 nucleotides, and even more preferably about 25 nucleotides. Such nucleic acid probes can be designed using methods known in the art (as also described, e.g., in Green et al., 2012) so as to allow the specific detection and quantification of the transcript of the corresponding gene. The in vitro diagnostic method of assessing the susceptibility of a subject suffering from stable COPD to develop progressive COPD involving the appearance of irreversible lung damage, in which the nucleic acid probe is to be used, preferably comprises a step of determining the expression level of the gene KIAA1199 in a sample obtained from the subject. The preferred features/embodiments of the method according to the fourth aspect of the invention as described herein, including in particular the preferred embodiments of determining expression levels, the preferred embodiments of the sample, and the preferred embodiments of the subject, also apply to the method in which the nucleic acid probe is to be used.

In the ninth aspect, the invention further relates to the use of a microarray comprising a nucleic acid probe to (i.e., binding to) a transcript of the gene KIAA1199 and optionally comprising nucleic acid probes to the transcripts of one or more further genes selected from DMBT1, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 and GHRL in an in vitro diagnostic method of assessing the susceptibility of a subject suffering from stable COPD to develop progressive COPD involving the appearance of irreversible lung damage. The microarray preferably comprises nucleic acid probes to the transcript of KIAA1199 and to the transcripts of at least one, more preferably at least two, even more preferably at least three of the above-mentioned further genes. Each of the transcripts is preferably an mRNA of the corresponding gene (including, e.g., any one of the corresponding specific mRNAs listed in Table 1 above) or a cDNA synthesized from the mRNA of the gene (including, e.g., a cDNA synthesized from any one of the corresponding specific mRNAs listed in Table 1 above). Each of the nucleic acid probes is preferably a single-stranded DNA probe or a single-stranded RNA probe, more preferably a single-stranded DNA probe. It is furthermore preferred that the nucleic acid probes (which may be, e.g., single-stranded DNA or single-stranded RNA, preferably single-stranded DNA) are oligonucleotide probes having, e.g., 10 to 80 nucleotides, preferably 15 to 60 nucleotides, more preferably 20 to 35 nucleotides, and even more preferably about 25 nucleotides. The in vitro diagnostic method of assessing the susceptibility of a subject suffering from stable COPD to develop progressive COPD involving the appearance of irreversible lung damage, in which the microarray is to be used, preferably comprises a step of determining the expression level of the gene KIAA1199 and optionally of the one or more further genes in a sample obtained from the subject. The preferred features/embodiments of the method according to the fourth aspect of the invention as described herein, including in particular the preferred embodiments of determining expression levels, the preferred embodiments of the sample, and the preferred embodiments of the subject, also apply to the method in which the microarray is to be used.

In accordance with the ninth aspect, the invention is also directed to the use of an antibody against (i.e., binding to) the protein KIAA1199 in an in vitro diagnostic method of assessing the susceptibility of a subject suffering from stable COPD to develop progressive COPD involving the appearance of irreversible lung damage. The antibody binds specifically to the protein KIAA1199 and may be, e.g., a polyclonal antibody or a monoclonal antibody. Preferably, the antibody is a monoclonal antibody. The antibody may further be a full/intact immunoglobulin molecule or a fragment/part thereof (such as, e.g., a separated light or heavy chain, an Fab/c fragment, an Fab/c fragment, an Fv fragment, an Fab' fragment, or an F(ab')$_2$ fragment), provided that the fragment/part substantially retains the binding specificity of the corresponding full immunoglobulin molecule. The antibody may also be a modified and/or altered antibody, such as a chimeric or humanized antibody, a bifunctional or trifunctional antibody, or an antibody construct (such as a single-chain variable fragment (scFv) or an antibody-fusion protein). The antibody can be prepared using methods known in the art, as also described, e.g., in Harlow et al., 1998. For example, monoclonal antibodies can be prepared by methods such as the hybridoma technique (see, e.g., Köhler et al., 1975), the trioma technique, the human B-cell hybridoma technique (see, e.g., Kozbor et al., 1983) or the EBV-hybridoma technique (see, e.g., Cole et al., 1985). The protein KIAA1199 may be, e.g., the specific KIAA1199 protein listed in Table 1 above. The in vitro diagnostic method of assessing the susceptibility of a subject suffering from stable COPD to develop progressive COPD involving the appearance of irreversible lung damage, in which the antibody is to be used, preferably comprises a step of determining the amount of the protein KIAA1199 in a sample obtained from the subject. The preferred features/embodiments of the method according to the fourth aspect of the invention as described herein, including in particular the preferred embodiments of determining the amount of a specific protein in a sample (as discussed in connection with the determination of translation levels), the preferred embodiments of the sample, and the preferred embodiments of the subject, also apply to the method in which the antibody is to be used, In accordance with the sixth aspect, the present invention provides a method of treating COPD, the method comprising administering a drug against COPD to a subject that has been identified in a method according to the second aspect of the invention as being prone to develop progressive COPD. The invention likewise provides a drug against COPD for use in treating COPD in a subject that has been identified in a method according to the second aspect as being prone to develop progressive COPD. The invention also relates to the use of a drug against COPD in the preparation of a pharmaceutical composition for treating COPD in a subject that has been identified in a method according to the second aspect as being prone to develop progressive COPD. The subject referred to above is as defined in the methods according to the second aspect of the invention and, accordingly, is preferably a human.

Moreover, in accordance with the eighth aspect, the present invention provides a method of treating or preventing COPD, the method comprising administering a drug against COPD to a subject that has been identified in a method according to the third aspect of the invention as suffering from stable COPD or as being prone to suffer from stable COPD. It will be understood that a subject that has been identified as suffering from stable COPD can be treated by administering a drug against COPD, while a subject that has been identified as being prone to suffer from stable COPD can be prevented from developing COPD by administering a drug against COPD. The invention likewise provides a drug against COPD for use in treating or preventing COPD in a subject that has been identified in a method according to the third aspect as suffering from stable COPD or as being prone to suffer from stable COPD. The invention also relates to the use of a drug against COPD in the preparation of a pharmaceutical composition for treating or preventing COPD in a subject that has been identified in a method according to the third aspect as suffering from stable COPD or as being prone to suffer from stable COPD. The subject referred to above is as defined in the methods according to the third aspect of the invention and, accordingly, is preferably a human.

In accordance with the tenth aspect, the present invention provides a method of treating COPD, the method comprising administering a drug against COPD to a subject suffering from stable COPD, wherein the subject has been identified in a method according to the fourth aspect of the invention as being prone to develop progressive COPD. The invention likewise provides a drug against COPD for use in treating COPD in a subject suffering from stable COPD, wherein the subject has been identified in a method according to the fourth aspect as being prone to develop progressive COPD. The invention also relates to the use of a drug against COPD in the preparation of a pharmaceutical composition for treating COPD in a subject suffering from stable COPD, wherein the subject has been identified in a method according to the fourth aspect as being prone to develop progressive COPD. The subject referred to above is as defined in the methods according to the fourth aspect of the invention and, accordingly, is preferably a human.

The drug against COPD to be administered to a subject in accordance with the sixth, eighth or tenth aspect of the invention is not particularly limited and may be, for example, a $\beta_2$-agonist (such as, e.g., bitolterol, carbuterol, fenoterol, pirbuterol, procaterol, reproterol, rimiterol, salbutamol, levosalbutamol, terbutaline, tulobuterol, arformoterol, bambuterol, clenbuterol, formoterol, olodaterol, salmeterol, indacaterol, or a pharmaceutically acceptable salt of any of the aforementioned agents), a glucocorticoid (such as, e.g., beclometasone, betamethasone, budesonide, ciclesonide, flunisolide, fluticasone, mometasone, triamcinolone, or a pharmaceutically acceptable salt of any of the aforementioned agents), an anticholinergic or a muscarinic antagonist (such as, e.g., aclidinium bromide, glycopyrronium bromide, ipratropium bromide, oxitropium bromide, tiotropium bromide, or a pharmaceutically acceptable salt of any of the aforementioned agents), a mast cell stabilizer (such as, e.g., cromoglicate, nedocromil, or a pharmaceutically acceptable salt of any of the aforementioned agents), a xanthine derivative (such as, e.g., acefylline, ambuphylline, bamifylline, doxofylline, enprofylline, etamiphyiline, proxyphylline, theobromine, theophylline, aminophylline, choline theophyllinate, or a pharmaceutically acceptable salt of any of the aforementioned agents), a leukotriene antagonist (such as, e.g., montelukast, pranlukast, zafirlukast, or a pharmaceutically acceptable salt of any of the aforementioned agents), a lipoxygenase inhibitor (such as, e.g., zileuton or a pharmaceutically acceptable salt thereof), a thromboxane receptor antagonist (such as, e.g., ramatroban, seratrodast, or a pharmaceutically acceptable salt of any of the aforementioned agents) a non-xanthine PDE4 inhibitor (such as, e.g., ibudilast, roflumilast, or a pharmaceutically acceptable salt of any of the aforementioned agents), or any other drug against COPD (such as, e.g., amlexanox, eprozinol, fenspiride, omalizumab, epinephrine, hexoprenaline, isoprenaline, isoproterenol, orciprenaline, metaproterenol, atropine, or a pharmaceutically acceptable salt of any of the aforementioned agents), or any combination thereof. A particularly preferred drug against COPD is roflumilast.

In the eleventh aspect, the present invention provides an in vitro method of monitoring the progression of COPD in a subject, the method comprising:
determining the level of expression of one or more genes selected from NTRK2 and RASGRF2 in a first sample obtained from the subject;
determining the level of expression of the one or more genes in a second sample obtained from the subject at a later point in time than the first sample;
comparing the level of expression of the one or more genes in the second sample to the level of expression of the corresponding gene(s) in the first sample; and
assessing (or determining) the progression of COPD in the subject,
wherein a decrease in the level of expression of NTRK2 and/or RASGRF2 in the second sample as compared to the level of expression of the corresponding gene(s) in the first sample is indicative of an amelioration (i.e., an improvement) of COPD in the subject, and
wherein an increase in the level of expression of NTRK2 and/or RASGRF2 in the second sample as compared to the level of expression of the corresponding gene(s) in the first sample is indicative of a worsening of COPD in the subject.

Figure 4:
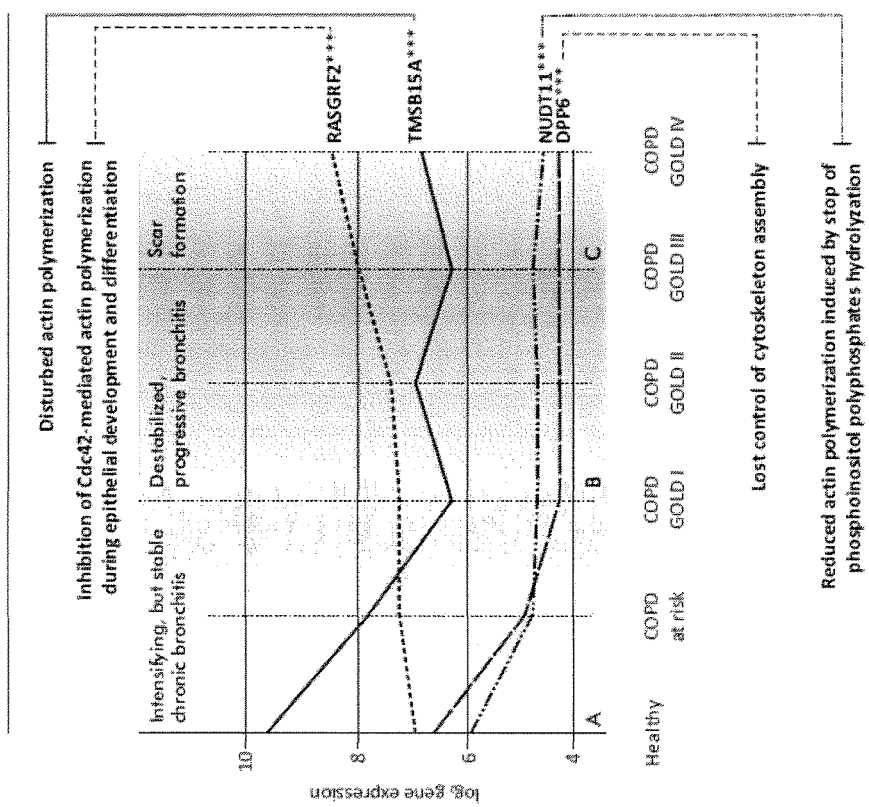
Figure 4:
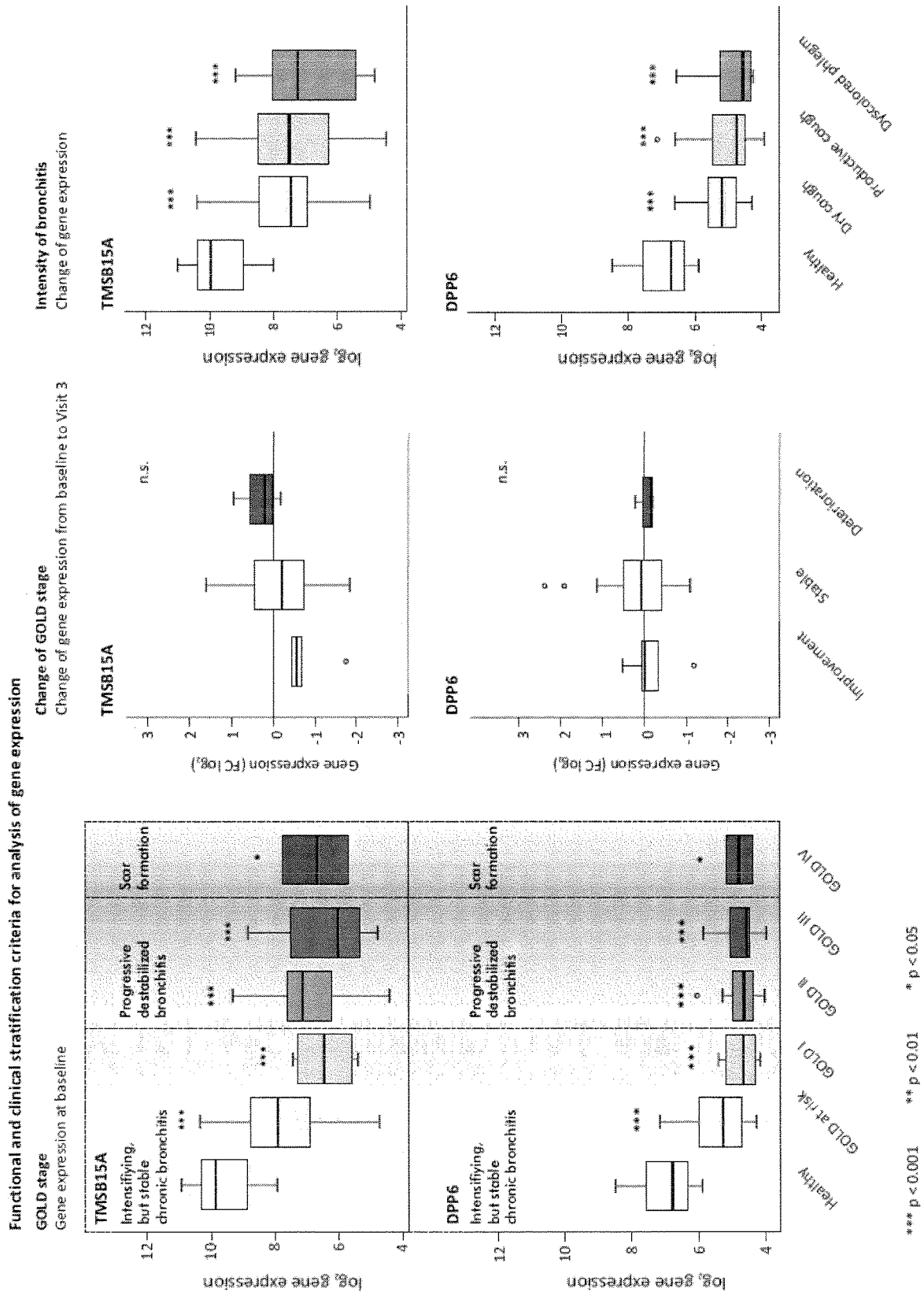
Figure 4:
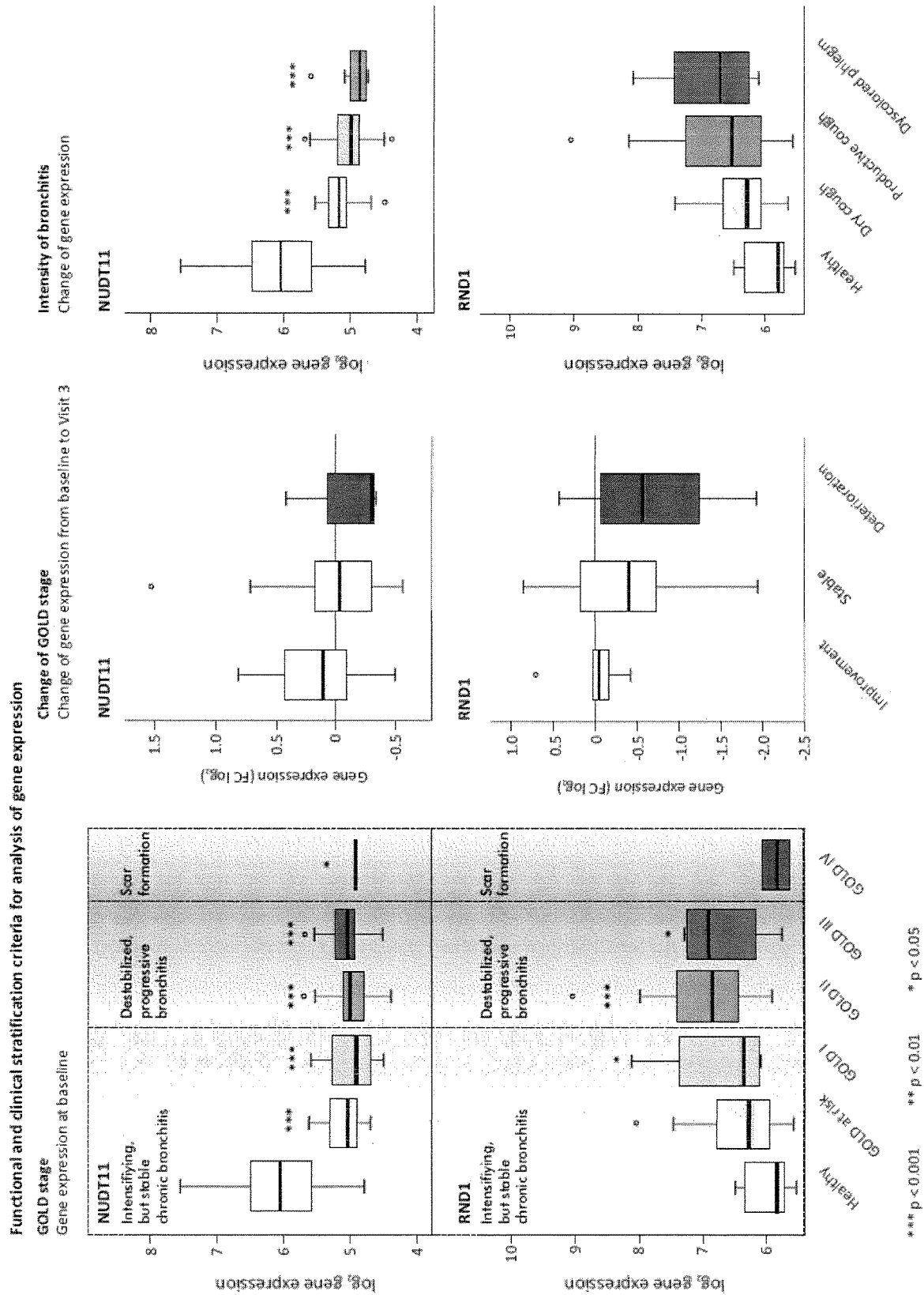
Figure 4:
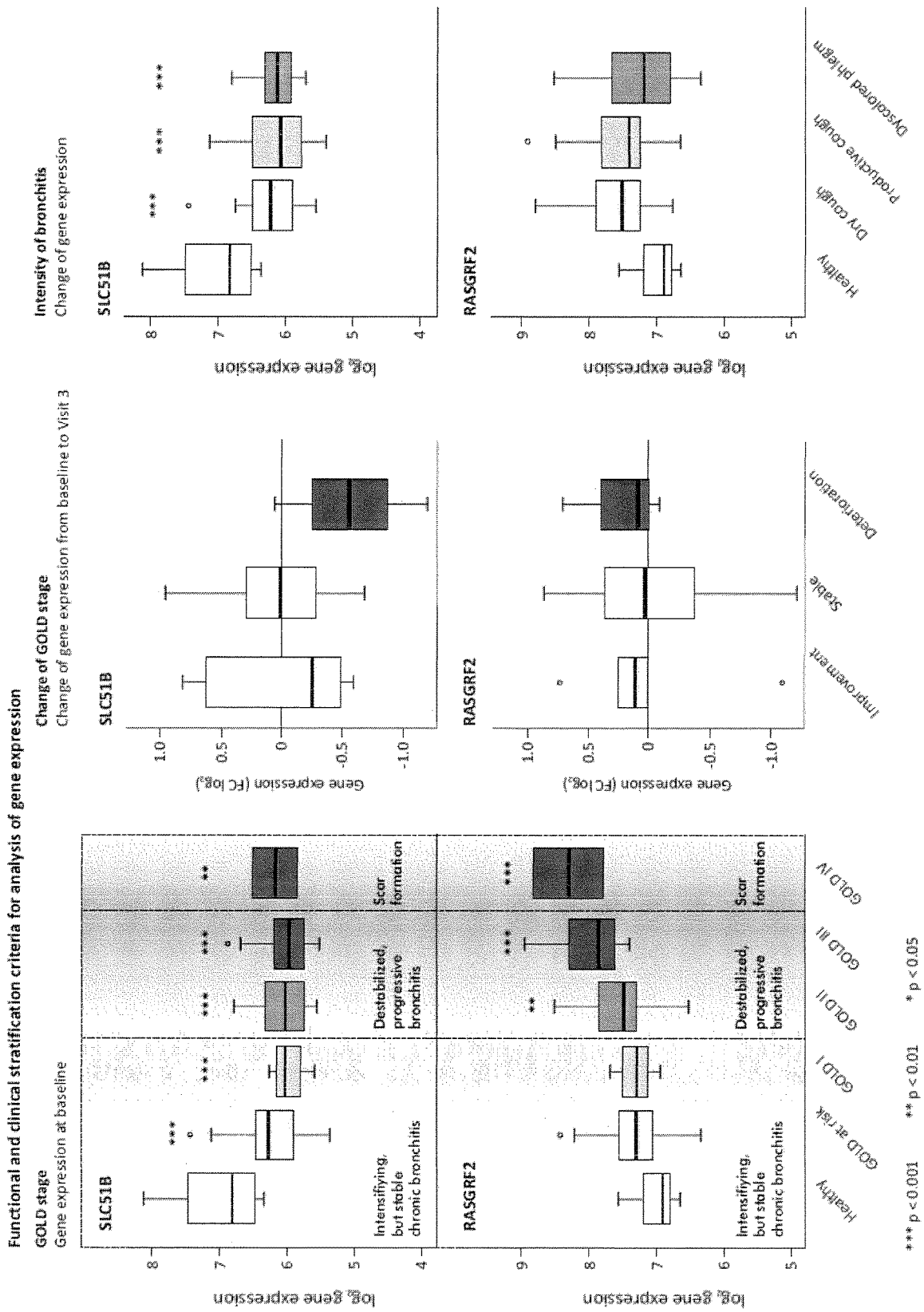
Figure 8:
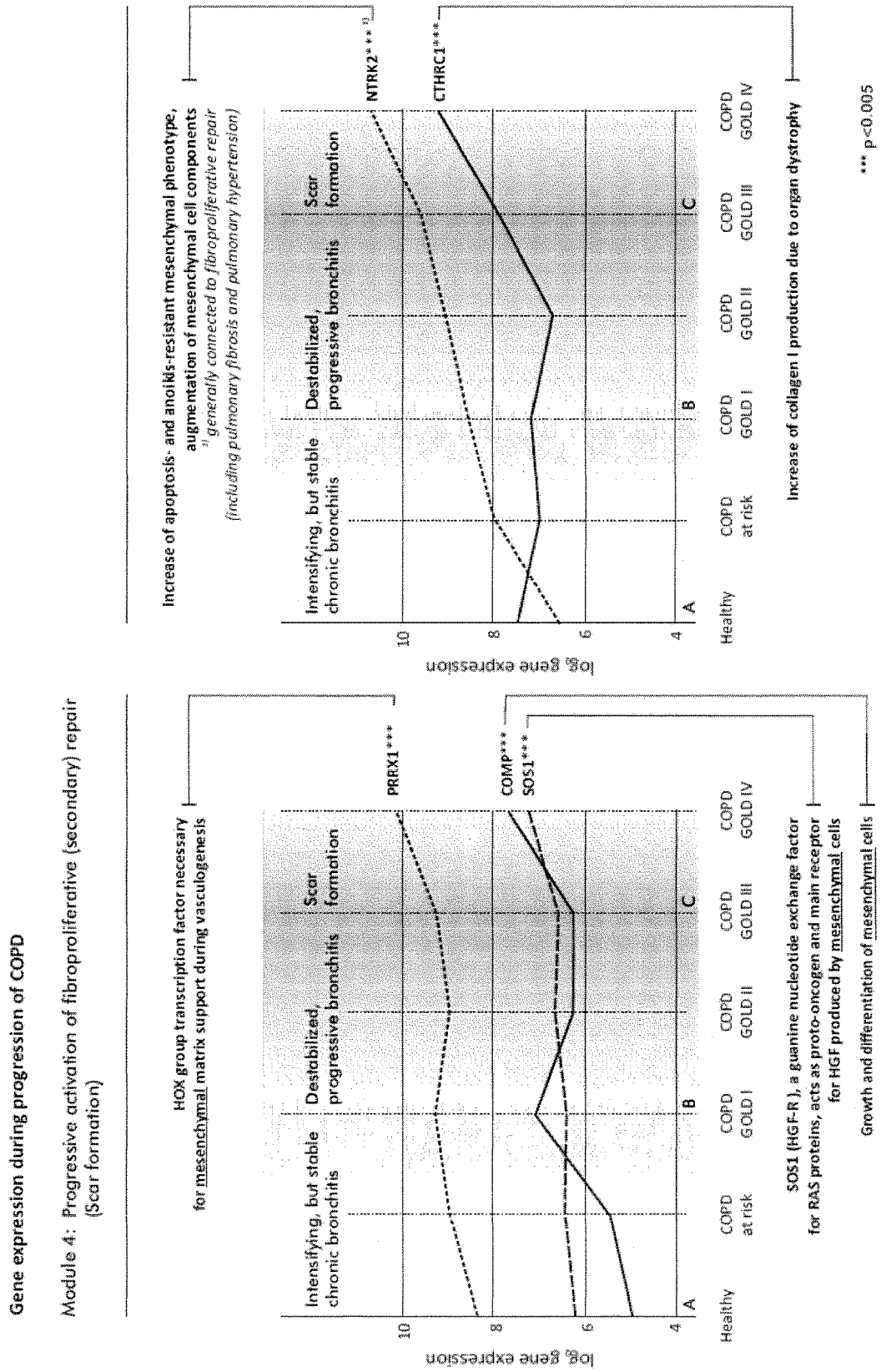
Figure 8:
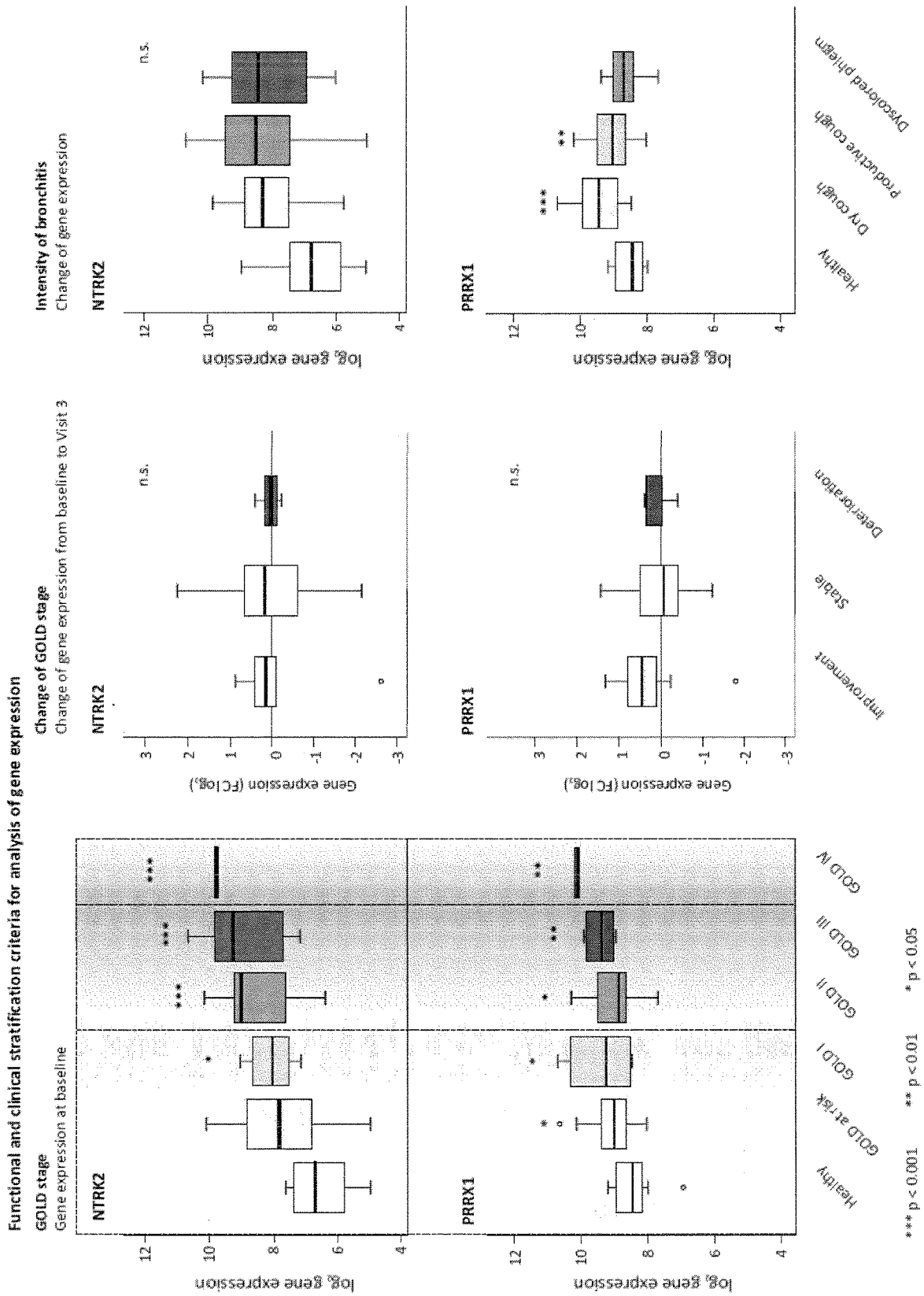
Figure 8:
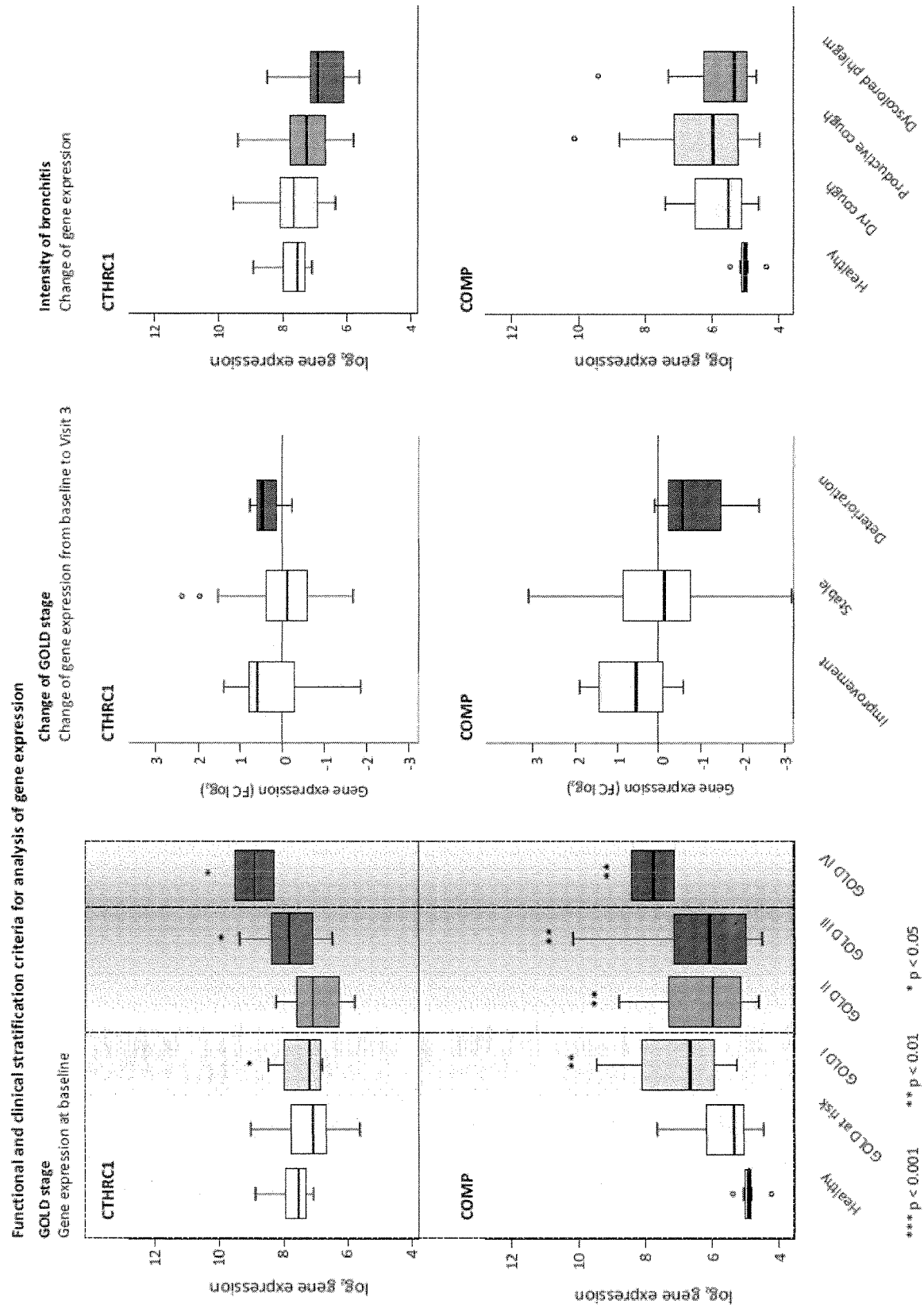
Figure 8:
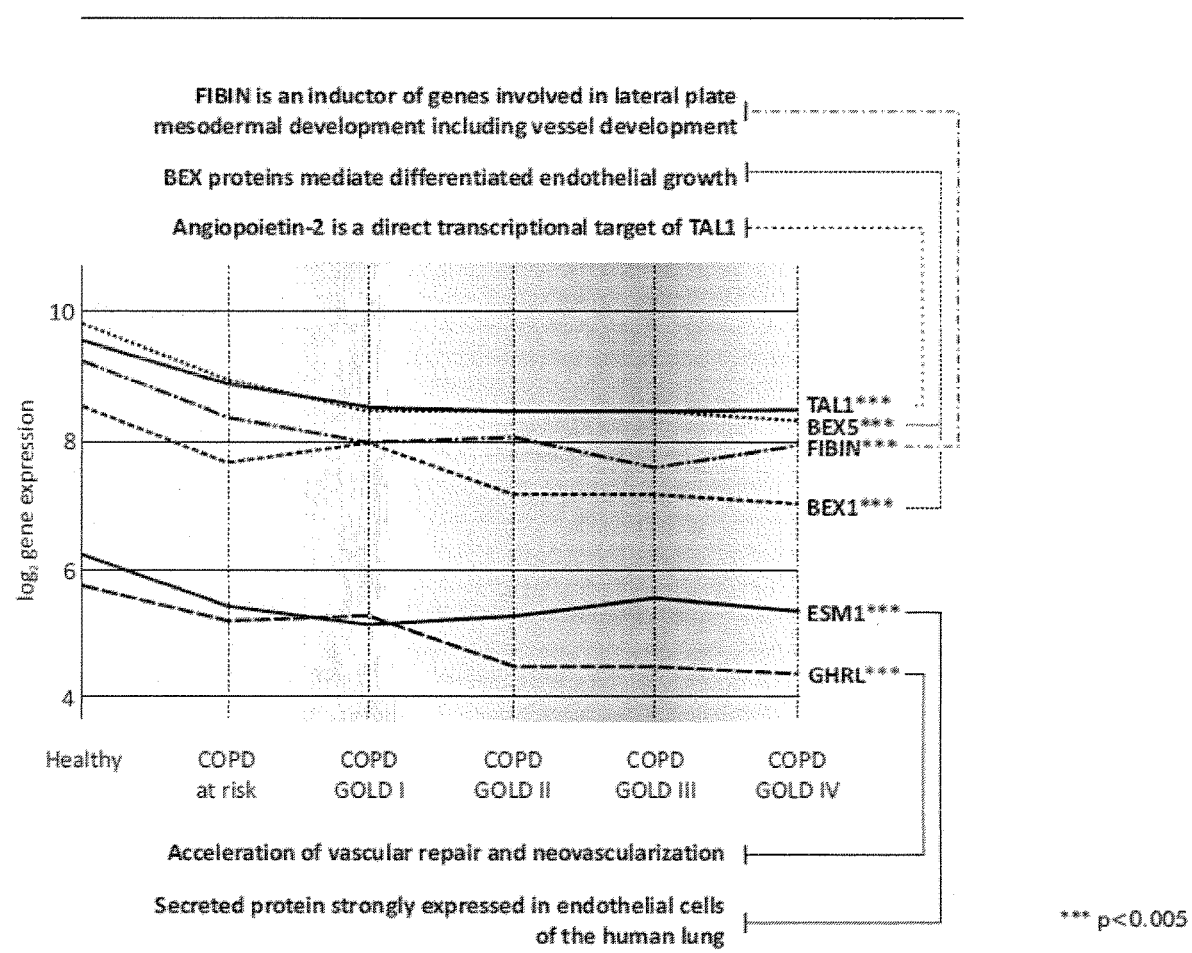

As demonstrated in Example 1 and shown in FIGS. 4A and 8A, a decrease in the level of expression of NTRK2 and/or RASGRF2 is indicative of an amelioration/improvement of COPD whereas an increase in the level of expression of these genes is indicative of a worsening of COPD. Monitoring the progression of COPD in a subject suffering from this disease can be useful, e.g., for assessing the prospects of success of a treatment, of a new medication, or of a new dosing regimen.

In the eleventh aspect, it is preferred that the level of expression of the gene NTRK2 and optionally of the gene RASGRF2 is determined. More preferably, the level of expression of the genes NTRK2 and RASGRF2 is determined.

The level of expression of the above-mentioned marker genes in the first sample and in the second sample according the eleventh aspect of the invention can be determined as described in connection with the methods of the second to fourth aspects of the invention. For example, the level of transcription or the level of translation of the marker gene(s) NTRK2 and/or RASGRF2 can be determined. It is preferred that the level of expression of the one or more genes selected from NTRK2 and RASGRF2 in the first sample and in the second sample is determined by determining the level of transcription of the corresponding gene(s). The level of transcription is preferably determined using qRT-PCT or a microarray.

The subject to be tested in the method according to the eleventh aspect of the invention is as defined in connection with the methods of the second to fourth aspects of the invention, and preferably is a human or a non-human mammal, more preferably a human. It is furthermore preferred that the subject to be tested/monitored in accordance with the eleventh aspect is a subject (preferably a human) that has been diagnosed as suffering from COPD (e.g., at the point in time when the first sample was obtained).

While the first sample and the second sample obtained from the subject can, in principle, be any tissue sample or serum from the subject, they should both originate from the same type of tissue of the subject (or should both be serum samples). Preferably, the first sample and the second sample are lung tissue samples. More preferably, the first sample and the second sample are transbronchial lung biopsy samples or they are bronchoalveolar lavage (BAL) samples.

The second sample has been obtained from the subject at a later point in time than the first sample. For instance, the second sample may have been obtained from the subject about 2 months to about 12 months, preferably about 3 months to about 9 months (e.g., about 3 months, or about 4 months, or about 5 months, or about 6 months, or about 7 months, or about 8 months, or about 9 months), and more preferably about 3 months to about 6 months after the first sample was obtained from the subject.

As used herein, the term "about" refers to ±10% of the indicated numerical value, and in particular to +5% of the indicated numerical value. Whenever the term "about" is used, a specific reference to the exact numerical value indicated is also included. If the term "about" is used in connection with a parameter that is quantified in integers, such as the number of nucleotides in a given nucleic acid, the numbers corresponding to ±10% or ±5% of the indicated numerical value are to be rounded to the nearest integer. For example, the expression "about 25 nucleotides" refers to the range of 23 to 28 nucleotides, in particular the range of 24 to 26 nucleotides, and preferably refers to the specific value of 25 nucleotides.

It is to be understood that the present invention specifically relates to each and every combination of features and embodiments described herein, including any combination of general and/or preferred features/embodiments. In particular, the invention specifically relates to all combinations of preferred features (including all degrees of preference) of the methods and uses provided herein.

In this specification, a number of documents including patent applications, scientific literature and manufacturers' manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention is also described by the following illustrative figures. The appended figures show:

FIG. 1: Study design of the COPD-AUVA study conducted at the Vienna Medical University (see Example 1).

Figure 2:
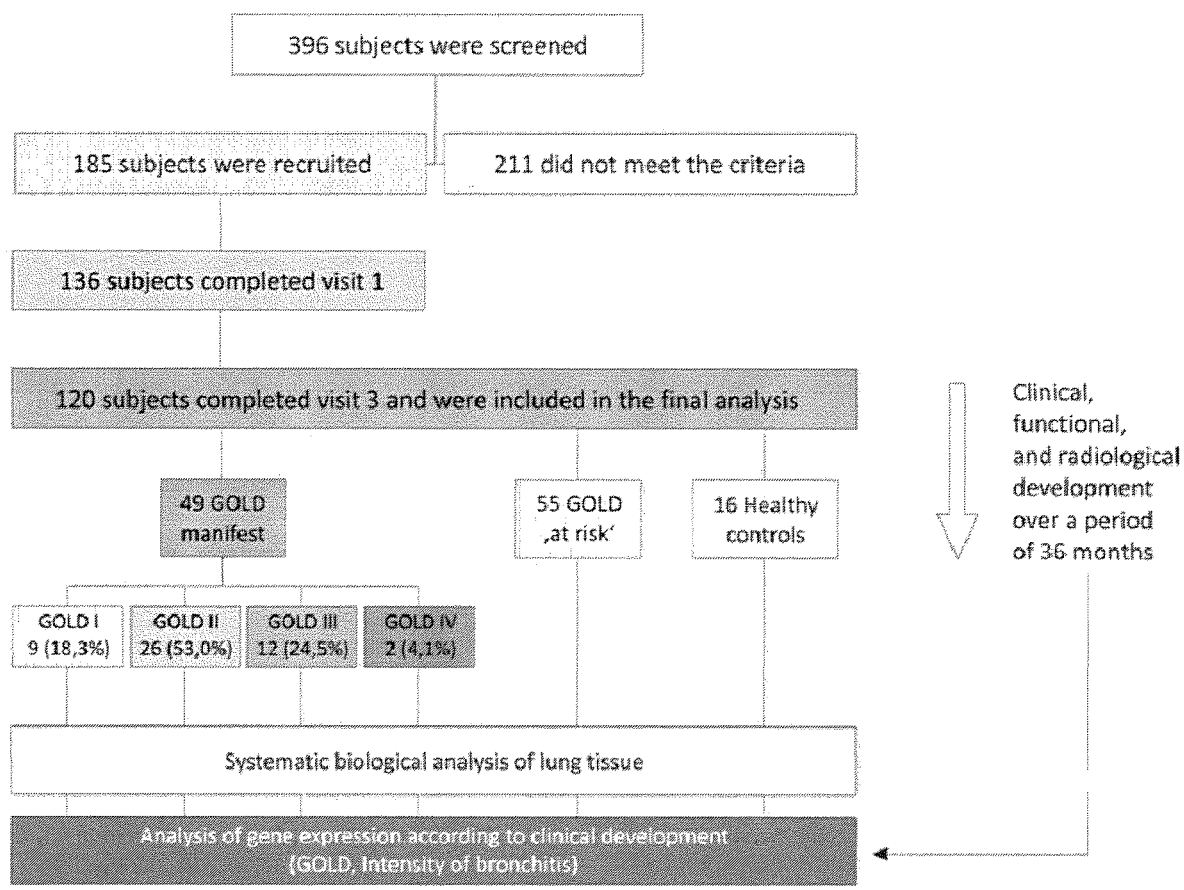

FIG. 2: Overview of the numbers of subjects of different disease states who underwent the COPD-AUVA study.

FIGS. 3A-D: Overview of healthy subjects (A) and of subjects with either chronic bronchitis but no signs of pulmonary obstruction (COPD "at risk"; "GOLD 0") at visit 1 (B) or with manifest COPD at visit 1 (C), as well as the development of COPD (severity according to GOLD criteria), bronchitis and smoking habits in these subjects over the period from visit 1 (day 0) to visit 2 (12 months) to visit 3 (36 months). The term "pack years" refers to a person's cigarette consumption calculated as the packs of cigarettes (each pack containing 20 cigarettes) smoked per day, multiplied by the length of cigarette consumption in years. (D) Clinical characteristics of participants in the COPD-AUVA study and changes between baseline and visit 3 (see Example 1).

FIGS. 4A-D: COPD Pathology module 1: Development of chronic bronchitis: Progressive inhibition of adaptive motility of mucosal cells caused by the inhibition of coordinated actin cytoskeleton movements.

Chronic bronchitis starts with the significant downregulation of genes that control assembly, polymerization, motility, stabilization and energy supply of F actin-mediated cytoskeleton movements (suppression of thymosin beta 15A (TMSB15A), dipeptidyl-peptidase 6 (DPP6), nudix (nucleoside diphosphate linked moiety X)-type motif 11 (NUDT11), and integrin alpha 10 (ITGA10)). At the same time, expression of the RASGRF2 gene known to inhibit Cdc42-mediated polymerization of actin during cellular movements is progressively increased during advancement of COPD (FIGS. 4A and 4D) indicating that the inhibition of cellular motility is not only a leading mechanism in early stages of COPD development, but also part of the progressive membrane destruction in later stages of COPD.

Of note, reduced expression of these genes is also connected to increasing intensity of bronchial inflammation. This characteristic expression pattern includes the SLC51B gene (FIG. 4D) which is as yet largely known for its capacity to transport steroid-precursor molecules in intestinal cells.

The compensatory activation of the GTPase RND1 (Rho family GTPase 1) best known for its ability to control the organization of the actin cytoskeleton in response to growth factor stimulation is just increased up to COPD GOLD stage II not only indicating a complete failure of actin-dependent cellular cytoskeleton organization in later stages of COPD, but also the loss of the regenerative capacity, as also demonstrated within Module 3 (see FIGS. 6A-6E). This in turn concurs rather well with the progressive downregulation of the cystatin M/E (CST6) gene being annotated with both functional differentiation of epithelial cells and maintenance of surface integrity.

As the coordinated action of these molecules is required for controlled movements of epithelial cells during pivotal processes, such as growth, intercalation and extrusion of cells within a cohesive cell layer system, the loss of these functions causes a profound disturbance of membrane integrity allowing for the development of non-specific bronchial inflammation that basically reflects all constituents of ventilated air including combustion products, such as cigarette smoke or welding fumes.

FIGS. 5A-H: COPD Pathology module 2: Bi-phasic activation of mucosal immunity.

Driven by this loss of cellular cohesion, the bronchus develops a diverse mucosal immune response that combines mechanisms of acute inflammation, such as the expression of fibrinogen (FGG) (FIGS. 5A and 5D), the upregulation of carcinoembryonic antigen-related cell adhesion molecule 5 (CEACAM 5) (FIGS. 5A and 5D), and aryl hydrocarbon receptor (AHR) signaling, the latter characterized by increased expression of cytochrome P450, family 1, subfamily A polypeptide 1 (CYP1A1) and cytochrome P450, family 1, subfamily B polypeptide 1 (CYP1B1) (FIGS. 5A and 5E, 5F). Intensity of AHR signaling is significant, in spite of the increased compensatory expression of the aryl hydrocarbon receptor repressor gene (AHRR), most likely reflecting the continuous impact of smoke. As CEACAMs have recently been shown to act as surface receptors for gram-negative bacteria such as *Neisseria meningitidis*, *Haemophilus influenzae* and *Moraxella catarrhalis* being frequently found in progressive bronchitis, this mechanism is prone to contribute to episodes of intensified bronchial inflammation.

Nonetheless, neither FGG nor CEACAM5 expression causes short-term worsening of non-reversible pulmonary obstruction (FIG. 5D, middle panel), although the activation of both genes significantly contributes to the intensity of bronchial inflammation (FIG. 5D, right panel). This differs from CYP1A2, KIAA1199 and phospholipase Al member A (PLA1A) expression (FIG. 5B and 5E) that all correlate with a significant deterioration of pulmonary function. While CYP1A2 expression as part of a smoke-induced AHR signaling response fits well to the current perception of COPD development, the strong correlation of KIAA1199 and PLA1A expression with deterioration of pulmonary function according to GOLD criteria points towards another direction, the complete failure of the bronchial compartment system. KIAA1199 has recently been demonstrated to activate matrix hyaluronidases while phospholipase Al member A (PLA1A) is known to activate T cells in response to non-specific inflammatory stimulation. It has presently been found that the significant upregulation of KIAA1199 is characteristic for the second phase of increased bronchial inflammation in GOLD stages III and IV (FIG. 5B) which follows a phase of non-progressive bronchial inflammation characterizing GOLD stage I (FIG. 5A). Notably, during this stabilization phase both the expression of KIAA1199 and of PLA1A is reduced as well (FIG. 5B). Given the strong proinflammatory impact of a degradation of high molecular mass hyaluronan, these observations indicate that the final increase of inflammatory activity in COPD GOLD stage III and IV is the combined result of permanently disturbed epithelial integrity and a secondary destruction of the hyaluronan matrix within the bronchial wall by the activation of matrix hyaluronidases. This view is supported by the expression pattern of matrix hyaluronidase 2 (HYAL2) itself which represents the leading hyaluronan-degrading enzyme in humans (FIG. 5C).

FIGS. 6A-E: COPD Pathology module 3: The impact of intensified regenerative repair: temporary suspension of progressive bronchial inflammation.

Maintaining the structural integrity of the mucosa as well as upholding essential components of the bronchial wall is part of effective wound healing and as such an indispensable measure to prevent the intrusion of antigens, allergens and infectious agents into submucosal compartments. It is thus not surprising that various genes guiding functions of epithelial repair are upregulated in response to increased inflammation, as demonstrated in FIG. 6A. However, only a small group of these genes is significantly contributing to the temporary suspension of progressive bronchial inflammation in GOLD stage I, genes known to participate in epithelial regeneration and differentiation, bacterial defense and transepithelial water transport (FIGS. 6A-6C): a) deleted in malignant brain tumors 1 (DMBT1), b) zinc-binding alpha-2-glycoprotein 1 (AZGP1), and c) aquaporin 3 (AQP3). However, this regenerative impulse does not last long as expression of these genes decreases again once progression of inflammation resumes stressing the impact of KIAA1199 expression and matrix degradation on bronchial inflammation. Although further genes closely related to epithelial repair, such as stratifin (SFN), the G protein-coupled orphan receptor 110 (GPR110), the smoke-inducible growth differentiation factor 15 (GDF15), and E74-like factor 5 (ELFS) are expressed throughout a much longer period of COPD development (FIG. 6A), the effectiveness of this wound healing approach is evidently not sufficient to maintain bronchial integrity and to balance bronchial inflammation in the presence of epithelial disintegration and progressive hyaluronan breakdown.

As a result, simultaneous measurement of DMBT1 and KIAA1199 gene expression is capable of discerning stable from progressive COPD (according to GOLD criteria), if the difference between DMBT1 and KIAA1199 expression exceeds a value of 3.63 (FIG. 6E). The importance of intensified KIAA1199 expression for progressive epithelial inflammation is further stressed by the fact that in chronic inflammatory wound healing of diabetic skin, expression of KIAA1199 is significantly upregulated, whereas in normal skin repair, KIAA1199 expression is reduced (see FIG. 8). It should also be noted that KIAA1199 expression in aged skin is in general significantly higher than in the skin from younger individuals ($p<0.01$).

Figure 7:
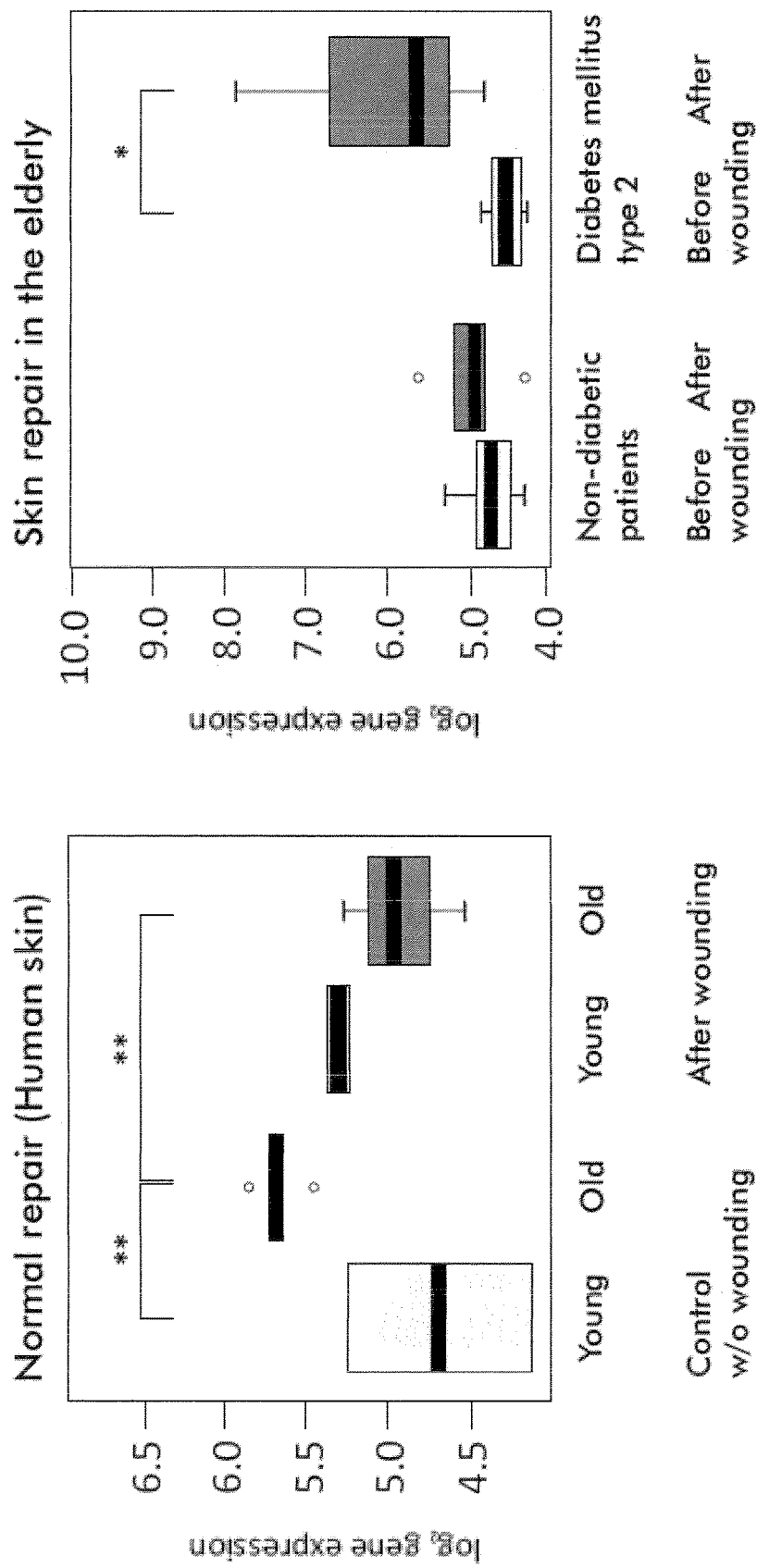

FIG. 7: Expression of KIAA1199 in skin wound healing.

FIGS. 8A-D: COPD Pathology module 4: Scar formation by predominant mesenchymal repair as the result of regenerative failure in the presence of a prevailing structural deficit.

As in any situation of prevailing unresolved repair that is not life-threatening, activation of "secondary" mesenchymal repair will serve as the exit strategy to remove the structural deficit and to terminate wound healing. During progression of COPD, coordinated gene activation in this regard can be divided into two categories: a) permanent support of mesenchymal repair (expression of NTRK2 and SOS1 genes) (FIGS. 8A and 8B), b) support of mesenchymal repair during both functional "primary" repair and non-functional "secondary" wound healing (expression of COMP, PRRX1 and CTHRC1 genes) (FIGS. 8A-8C).

As in any form of predominantly mesenchymal repair, expression of genes controlling vascular growth and differentiation is progressively diminished. FIG. 8D provides a synopsis of the expression pattern and relevant annotations for all genes related to vascular outgrowth and repair which are significantly regulated during progression of COPD.

The invention will now be described by reference to the following examples which are merely illustrative and are not to be construed as a limitation of the scope of the present invention.

EXAMPLES

Example 1

Controlled Prospective Pilot Trial Aimed at Identifying Symptom-Based Molecular Metabolic Markers for Progressive COPD (Vienna COPD-AUVA Study)

Introduction

In the context of the present invention, a controlled prospective pilot trial aimed at the identification of symptom-based molecular metabolic markers for progressive COPD was conducted at the Vienna Medical University between 2007 and 2012. The Vienna COPD-AUVA study combined the assessment of validated clinical measures for COPD following in part the overall strategy of the ECLIPSE trial (Vestbo et al., 2011), the largest and most elaborate study addressing progress and variability of COPD.

For stratification of patients, a three-year analysis (day 0, 12 months, and 36 months) of symptom scoring (St. George Respiratory questionnaire, activity and symptom score), assessment of pulmonary function, cardiopulmonary exercise testing, and radiological evaluation by computer-assisted tomography (high-resolution mode) were combined with whole genome transcription analysis plus quantitative RT-PCR assessment and mass spectrometry proteomics. As shown in FIG. 1, the patients were grouped into three strata, two of which presented at the start of the study with regular lung function, either without any sign of a cardiopulmonary disease (healthy volunteers) or with symptoms of chronic bronchitis (COPD "at risk"), and a group of volunteers having symptoms of chronic bronchitis together with deteriorated lung function (COPD at GOLD stages I-IV).

Study visits were performed at base line and after 12 and 36 months, respectively. Each visit was performed on an ambulatory basis and included medical history, physical examination, pulmonary function tests (PFT), cardiopulmonary exercise tests (CPET), radiological assessment by computer-assisted tomography (CAT) scans and a bronchoscopy. On each visit, both personal and occupational history was taken as well as smoking history which comprised onset and duration of symptoms related to COPD, production of phlegm (frequency, quantity, and color), intensity of symptoms measured by the St. George Respiratory Questionnaire (SGRQ; activity and symptom score index) and assessment of life quality using the SF-36 questionnaire. The rate of exacerbations (frequency, number of hospitalizations, use of antibiotics, corticosteroids or combined treatment) and the individual medication were also recorded.

Pulmonary function tests (PFT) were taken at each visit and included blood drawings, body plethysmography, spirometry and quantitative measurement of pulmonary gas exchange at rest and during symptom-limited cardiopulmonary exercise testing (CPET). PFT was performed with an Autobox DL 6200 (Sensor Medics, Vienna, Austria), and CPET on a treadmill using the Sensormedics 2900 Metabolic Measurement Cart. Formulas for calculation of reference values were taken from Harnoncourt et al., 1982. Predicted values were derived from the reference values of the Austrian Society of Pneumology following the recommendations of the European Respiratory Society (Rabe et al., 2007).

Serum samples were analyzed for complete cellular blood count, electrolytes, glucose, C-reactive protein, fibrinogen, and coagulation parameters.

Prior to bronchoscopy, CAT scans encompassing high resolution-computed tomography (HRCT) were performed. Following additional informed consent on each visit, bronchoscopy was performed. During bronchoscopy, both bronchoalveolar lavage (BAL) samples and transbronchial biopsy samples (five per segment in each middle lobe) were taken.

Biological analysis was performed in transbronchial lung biopsies taken during bronchoscopy from two pulmonary localizations (5 each) of the middle-lobe after radiological assessment by computer-assisted tomography (CAT) scans including high-resolution scanning. CAT scans were used for the assessment of emphysema formation as well as for the exclusion of tumor development and infection. During the controlled observational period, combined assessment of clinical and molecular development was finally possible in 120 volunteers. Biomarkers were identified in each case by means of the individual changes of pulmonary function and clinical symptoms characteristic for the progression of COPD. As a result, this approach makes use of the well-known variability of clinical phenotypes in COPD and their variable course of progression while at the same time identifying the very set of biomolecules responsible for this type of disease progression.

Clinical Analysis

The study protocol was approved by the ethical committee of the Medical University of Vienna (ClinicalTrials.gov Identifier: NCT00618137). Following informed consent during screening, individuals were stratified at visit 1 (day 0) if they fulfilled the following criteria:

TABLE 2

Stratification of subjects at visit 1 (day 0).

| | Inclusion criteria | Occupational history |
|---|---|---|
| Healthy Controls | Age 18-70 years<br>No history or clinical findings suggestive of any disease<br>Never Smoker<br>Normal pulmonary function test at study entry | No occupation with increased exposure towards combustion products, particularly no welding or professional car driving |
| COPD, at risk' | Age 18-70 years<br>Chronic bronchitis according to WHO with repeated episodes of phlegm production<br>No history or clinical findings suggestive of bronchial asthma<br>Normal PFT according to GOLD criteria at study entry<br>Smoking history of at least 10 years<br>No history or clinical findings suggestive of cardiovascular or malign disease | Professional car driver or welder with increased occupational exposure towards combustion products of at least 10 years |
| COPD manifest | Age 18-70 years<br>Chronic bronchitis according to WHO with repeated episodes of phlegm production<br>No history or clinical findings suggestive of bronchial asthma<br>Pathological PFT according to GOLD criteria at study entry<br>Smoking history of at least 10 years<br>No history or clinical findings suggestive of cardiovascular or malign disease | Professional car driver or welder with increased occupational exposure towards combustion products of at least 10 years |

396 individuals were screened, 185 of whom met the study criteria. 136 participants finished visit 2 after 12 months, and 120 completed the final visit after 36 months of controlled observation. Throughout the study, all participants were residing and occupied in the greater Vienna area in order to ensure comparable environmental conditions. The control group consisted of 16 healthy volunteers who had never smoked (7 females and 9 males; mean age 36±12.2 years), as also shown in Table 2 above. None of the healthy participants developed any symptom of pulmonary disease during the study period. At the start of the study, 104 participants presented with clinical symptoms of chronic bronchitis according to WHO definition, 55 of whom did not have signs of non-reversible bronchial obstruction (GOLD "at risk"), while the other 49 participants showed bronchial obstruction ranging from GOLD stage I to IV as determined by PFT (see FIG. 3D). All participants in the COPD and COPD "at risk" groups were active cigarette smokers with a smoking history of more than 10 pack years, except for one welder who in addition to a daily expectoration of phlegm reported about frequent episodes of bronchial infection (>2 per year) without radiological signs of bronchiectasis. 64 participants were working as taxi or bus drivers (53%) and 40 active welders (33%) with a previous exposure to welding fumes of more than 10 years.

At visit 1, the majority of participants with manifest COPD had bronchial obstruction GOLD stage II and III (n=38), while the remaining subjects were in COPD GOLD stage I (n=9) and IV (n=2) (see FIG. 3D). Mean age in GOLD stages I and II was 50±9.5 and 56±10.4 yrs. respectively, compared to 52±9.0 yrs. in GOLD stage III and 63±11 yrs. in GOLD stage IV. 29% of the participants in the GOLD "at risk" group were already presenting with a continuous daily expectoration of sputum, and sputum was frequently discolored (yellow, green, brown) in 27%.

During controlled observation (36 months), 14 participants (12%) had a progression of disease according to GOLD, 7 (13%) in the GOLD "at risk" group, 1 (11%) in GOLD I, 3 (12%) in GOLD II, and 3 (25%) in GOLD Ill. Improvement of bronchial obstruction according to GOLD was observed in 13 individuals (5 participants in both GOLD stage I and II, and 3 cases in GOLD stage Ill and IV), mostly connected to a cessation of cigarette smoking.

As part of the observational design of the study, participants were not specifically encouraged to stop smoking. Accordingly, smoking habits changed only slightly: only 5 participants of the "COPD at risk" group (9%) and 2 participants in the "manifest COPD" group (4%) stopped smoking during the observational period, while 31% reduced cigarette smoking (data not shown). These changes did not significantly alter both occurrence and intensity of chronic bronchitis symptoms, as 27 participants (23%) demonstrated improvement and deterioration of cough and sputum production.

Biological/Molecular Analysis (Gene Transcription in Pulmonary Tissue)

RNAlater (Ambion, lifetechnologies) was used for tissue asservation. The lung biopsy material was disrupted using Lysing Matrix D ceramic balls in a Fastprep 24 system (MP Biomedical, Eschwege). A chaotropic lysis buffer (RLT, RNeasy Kit, Qiagen, Hilden) was used, followed by a phenol/chloroform extraction and subsequent clean up using the spin column approach of the RNeasy Mini Kit (Qiagen, Hilden) according to the manufacturer's manual, including a DNase I digestion on the chromatography matrix. RNA quantification was done spectrophotometrically using a NanoDrop 1000 device (Thermo Scientific) and quality control was performed on the Agilent 2100 Bioanalyzer. A cut off for the amount of 1 microgram and a RNA integrity number of 7.0 was chosen.

Total RNA samples were hybridized to Human Genome U133plus 2.0 array (Affymetrix, St. Clara, CA), interrogating 47,000 transcripts with more than 54,000 probe sets.

Array hybridization was performed according to the supplier's instructions using the "GeneChip® Expression 3' Amplification One-Cycle Target Labeling and Control reagents" (Affymetrix, St. Clara, Calif.). Hybridization was carried out overnight (16h) at 45° C. in the GeneChip® Hybridization Oven 640 (Affymetrix, St. Clara, Calif.). Subsequent washing and staining protocols were performed with the Affymetrix Fluidics Station 450. For signal enhancement, antibody amplification was carried out using a biotinylated anti-streptavidin antibody (Vector Laboratories, U.K.), which was cross-linked by a goat IgG (Sigma, Germany) followed by a second staining with streptavidin-phycoerythrin conjugate (Molecular Probes, Invitrogen). The scanning of the microarray was done with the GeneChip® Scanner 3000 (Affymetrix, St. Clara, Calif.) at 1.56 micron resolution.

The data analysis was performed with the MAS 5.0 (Microarray Suite statistical algorithm, Affymetrix) probe level analysis using GeneChip Operating Software (GCOS 1.4) and the final data extraction was done with the DataMining Tool 3.1 (Affymetrix, St. Clara, Calif.).

CEL files were imported and processed in R/Bioconductor (Gentleman et al., 2004). Briefly, data was preprocessed using quantile normalization (Gentleman et al., 2004) and combat (Johnson et al., 2007), linear models were calculated using limma (Smyth GK, 2005) and genes with a p-value of the f-statistics <5e-3 were called significant. Those genes were grouped into 20 clusters of co-regulated genes. The procedure of modeling and clustering was repeated for GOLD and phlegm as covariates.

For subsequent Gene Ontology (GO)-analysis it was necessary to separate the effects of GOLD and phlegm on gene expression. To this end, the GOLD classifications were grouped into "no COPD" (healthy and GOLD 0) and "COPD" (GOLD grades I-IV). Similarly, phlegm was reclassified into a "phlegm" group (productive or severe) and a "no phlegm" group (health or no/dry). Based on these reclassifications, gene expression was modeled using a 2×2 factorial design, resulting in five different lists of genes: (1) genes which are regulated with phlegm in the presence of COPD, (2) genes which are regulated with phlegm in the absence of COPD, (3) genes which are regulated with COPD in the presence of COPD, (4) genes which are regulated with COPD in the absence of COPD and finally (5) genes which are regulated differently with COPD, depending on whether there is phlegm or not.

These lists were annotated with respect to their biological functions as catalogued in the Gene Ontology (GO) database using the ClueGO plugin for the Cytoscape framework.

Results of Combined Clinical and Molecular Analysis

Activation of Epithelial Repair Mechanisms

Systematic analysis of the significant changes of gene expression during COPD development reveals a differentiated picture: As shown in FIGS. 6A to 6D, mechanisms of regeneration and repair commence as soon as the chronic inflammatory process in the peripheral bronchial tree is established. This is already the case in persistent or repeatedly manifesting bronchitis (COPD "at risk"). The functions associated with this kind of aberration from the normal equilibrium, in ontological terms still only potential COPD, include mediators involved in the regulation of embryonic epidermal and pulmonary growth, such as ELFS (E74-like factor 5; ETS domain transcription factor) which confers spatially controlled outgrowth of epithelial structures (Metzger et al., 2008; Yaniw et al., 2005) as well as mucosal immunity of the lung (Lei et al., 2007). Not surprisingly, the expression of ELFS is accompanied by a significant upregulation of stratifin (SFN) conferring increased epidermal regeneration and differentiation (Medina et al., 2007), yet also reduced deposition of matrix proteins including collagen I (Chavez-Munoz et al., 2012) and reduced functions of non-specific surface immunity (Butt et al., 2012). This regenerative phase of repair involves not only the G protein-coupled orphan receptor GPR110 and the smoke-inducible growth differentiation factor 15 (GDF15) (Wu et al., 2012), a member of the bone morphogenic protein-transforming growth factor-beta superfamily, but also mediators directing differentiated epithelial repair, such as the zinc-binding alpha-2-glycoprotein 1 (AZGP1), and the DMBT1 gene (deleted in malignant brain tumors 1) which is strongly upregulated during acute but resolving bacterial inflammation in enteral epithelia during appendicitis (Kaemmerer et al., 2012), suggesting a functional relevance for mucosal defense (Diegelmann et al., 2012). The almost identical expression profile of DMBT1 and AZGP1, a mediator capable of inducing a strong epithelial transdifferentiation in tumor cells (Kong et al., 2010), suggests an as yet undefined combinatory effect of both mediators on cellular differentiation during epithelial regeneration. Notably, the expression of these genes is strongly increased in individuals with COPD GOLD I and decreases significantly with progression of COPD, as also shown in FIG. 6A. In line with this observation, all mediators conveying epithelial regeneration and differentiation were found to be significantly downregulated during the transition from COPD stage III to COPD stage IV.

Activation of mediators of regenerative repair was also found in individuals demonstrating significant symptoms of bronchial inflammation, as demonstrated by a uniform increase of gene expression of SFN, GPR110 (see also FIG. 6D), and aquaporin 3 (AQP3) (see FIG. 6A) being an additional mediator known to guide proliferation and differentiation of epithelial cells (Nakahigashi et al., 2011; Kim et al., 2010). However, expression of these factors did not further increase with an increase of severity of bronchial inflammation, much in contrast to mediators capable of intensifying inflammation on epithelial surfaces, such as the carcinoembryonic antigen-related cell adhesion molecule 5 (CEACAMS) (see FIGS. 5A and 5D), or factors being part of the preferentially mesenchymal wound healing response during inflammatory repair (Agarwal et al., 2012; Agarwal et al., 2013), such as the cartilage oligomeric matrix protein (COMP) (see FIGS. 8A and 8C). The study design allowed as well for the measurement of changes of gene expression occurring throughout the study period of 3 years, possibly indicating significant changes of repair during short-term progression of COPD. Here, a significant downregulation of GPR110 and DMBT1 genes correlating with deteriorated lung function according to GOLD was found, as also shown in FIGS. 6B and 6D. This decrease of regenerative gene activity started already in GOLD stage II, where it was accompanied by a striking increase of repair functions related to mesenchymal wound healing (see also FIG. 8).

Progressive Activation of Mesenchymal Repair

During later stages of COPD, expression of mediators favoring mesenchymal repair became increasingly prominent. This did not only relate to the increased expression of the COMP gene (see FIGS. 8A and 8C), but also to the expression of potent activators of mesenchymal stem cells, such as the son of sevenless homolog 1 (SOS1) gene, a guanine nucleotide exchange factor for RAS proteins acting as the cognate receptor for hepatocyte growth factor, and to the paired related homeobox 1 gene (PRRX1), a transcriptional co-activator of RAS transcription factors belonging to the HOX family of early differentiation factors able to induce mesenchymal outgrowth in liver cirrhosis (Jiang et al., 2008) as well as epithelial-to-mesenchymal transition (EMT) during cancer development (Ocaña et al., 2012). While their pattern of expression indicates that both COMP and PRRX1 genes take also part in the regenerative phase of wound healing characterizing GOLD stage I and II, their later increase during transition from GOLD stage III to IV suggests an additional involvement in the progressive scarring of the airways. Increased expression of pro-fibrotic factors is further demonstrated by the striking increase of expression of neurotrophic tyrosine kinase receptor type 2 (or tropomyosin receptor kinase B receptor; TrkB) (NTRK2). NTRK2/TrkB, thus far known to act as high affinity receptor for various neurotrophic growth factors during nerve development, is also capable of promoting resistance of mesenchymal cells towards apoptosis and anoikis (Frisch et al., 2013). The combined increase of profibrotic mediators includes as well the expression of the collagen triple helix repeat containing 1 gene (CTHRC1) capable of conferring fibrotic organ dystrophy (Spector et al., 2013). Notably, while the increased expression of CTHRC1 starts only at GOLD stage II, cumulative activation of NTRK2/TrkB is a hallmark throughout progression of COPD in general, suggesting a permanent contribution of NTRK2/TrkB signaling to the aberrant repair response in the peripheral airways during COPD development. This view is further supported by the observation that a disturbed TrkB axis may contribute to experimental pulmonary fibrosis (Avcuogiu et al., 2011).

With the exception of COMP expression, where clinical deterioration correlates with worsening of bronchial obstruction according to GOLD (see also FIG. 8C), neither increased long-term expression of NTRK2 (see also FIG. 8B), nor of PRRX1 (see also FIG. 8B) or CTHRC1 genes (see also FIG. 8C) demonstrate a comparable short-term impact on bronchial obstruction during the controlled 3-year observational study period. Corresponding results were obtained when assessing the correlation of gene expression with progressive bronchial inflammation: while the expression of all genes favoring mesenchymal repair is increased as a result of intensified bronchitis, significant changes were only found for the PRRX1 and CTHRC1 genes (see also FIGS. 8B and 8C).

Loss of Structural Integrity of Epithelial Surfaces

Unexpectedly, the present analysis revealed a very significant downregulation of expression of a group of genes which guide movement, distribution and activation of the cellular cytoskeleton and which, as a result, are likely to profoundly influence structural integrity and barrier function of the mucosal surface. The downregulation of these genes takes place already during establishment of chronic bronchitis, well before the establishment of bronchial obstruction according to GOLD, as also shown in FIG. 4A. The genes closely connected to this development are thymosin beta 15 A (TMSB15A), dipeptidyl-peptidase 6 (DPP6), nudix (nucleoside diphosphate linked moiety X)-type motif 11 (NUDT11), integrin alpha 10 (ITGA10), cystatin E/M (CST6), and PRICKLE2 (data not shown). Notably, the two genes most significantly decreased during progression of COPD, TMSB15A and DPP6, are also significantly downregulated in correlation with symptoms of increased bronchial inflammation (see also FIG. 4B). Beta thymosins are controllers of both composition and sequestration of the actin cytoskeleton (Hannappel, 2007; Huff et al., 2001; Malinda et al., 1999), by that influencing membrane structure, surface stability and cellular phenotype (Husson et al., 2010).

One of the outcomes of elevated levels of beta thymosins during wound healing seems to be a protection from fibrotic aberrations of repair (De Santis et al., 2011), in part by preventing the expression of a-smooth muscle stress fibers preventing them from a transdifferentiation into myofibroblasts most characteristic for fibrotic tissue development. Currently, little is known about the function of DPP6 in regenerative wound healing. However, DPP6, a member of the S9B family of membrane-bound serine proteases which is lacking any detectable protease activity, has recently been demonstrated to confer membrane stability and controlled outgrowth of cells during nerve development including close control of cell attachment and motility (Lin et al., 2013). Moreover, given its proven association with and control of membrane-bound ion channel expression and activation (Jerng et al., 2012), in particular of voltage-gated potassium channels, expression of DPP6 is also capable of controlling the resting membrane potential (Nadin et al., 2013), thereby controlling both activity and intracellular distribution of the actin cytoskeleton (Mazzochi et al., 2006; Chifflet et al., 2003).

Combined with the striking reduction of TMSB15A gene expression, the significant decrease of DPP6 expression suggests a severe disturbance of regular movement and distribution of the cellular actin skeleton, reducing physicochemical integrity of the epithelial lipid bilayers. As this occurs already very early in COPD development, this finding could indicate an initiating and possibly predisposing mechanism leading to non-specific surface inflammation.

Cystatin M/E (CST6), on the other side, is an epithelium-specific protease inhibitor belonging to the cystatin family of secreted cysteine protease inhibitors indispensable for the physiological regulation of protease activity during growth and differentiation of epithelial structures. CST6 is expressed both in dermal and bronchial epithelia where it characterizes the status of functional differentiation (Zeeuwen et al., 2009). Significant downregulation of CST6 has already been shown to cause a marked disturbance of both surface integrity and differentiation status in the dermis of mice (Zeeuwen et al., 2010). Progressive downregulation of CST6 as observed during advancement of COPD is thus likely to destabilize the intricate balance between proteases and protease inhibitors, by that contributing to a loss of surface stability as well as cellular adhesion and differentiation in the regenerating bronchial epithelium. Within this context, significant downregulation of two other genes intricately involved in the regulation of cell adhesion and motility has also been observed, namely of integrin a10 (ITGA10) being part of differentiated mesenchymal structures, and the nudix (nucleoside diphosphate linked moiety X)-type motif hydrolase 11 (NUDT11), capable of hydrolyzing diphosphoinositol polyphosphates derived from cellular lipid bilayer structures, and diadenosine polyphosphates, mostly based on adenosine triphosphate (ATP).

The consequence of these changes in gene expression is expected to be a disintegration of the epithelial barrier function, probably starting on the cellular level (continuous shear stress within the cellular lipid bilayer due to uncoordinated accumulation and movements of the actin cytoskeleton attached to it), and aggravated by disintegration of the extracellular matrix composition itself. This is supported by the significant increase of gene expression of the KIAA1199 gene during progression of CORD from GOLD stage I to GOLD stage IV (see FIG. 5B). Increased expression of KIAA1199, in addition to mediating cellular attachment and contact inhibition (Tian et al., 2013), has just recently been demonstrated to cause the leakage of endoplasmatic reticulum (ER) contents into the cytosol of cancer cells (Evensen et al., 2013). Moreover, increased expression of KIAA1199 is capable of activating hyaluronidases (HAase), enzymes capable of degrading high-molecular mass hyaluronic acid (HMM-HA), one of the major constituents of the extracellular matrix (Toole, 2004). Biological responses triggered by hyaluronic acid (HA) depend on the HA polymer length. HMM-HA has strong anti-inflammatory properties (Kothapalli et al., 2007), whereas low-molecular-mass HA promotes inflammation and concomitant cellular proliferation (Pure et al., 2009). In support of this view, degradation of HA has been shown to trigger skin inflammation by generation of low molecular weight fragments of HA (Yoshida et al., 2013).

In line with this, expression of HA synthases (HAS1-3) is not changed during progression of COPD (see FIG. 5G), while the hyaluronidase 2 (HYAL2) gene is upregulated between GOLD stages I and III (see also FIG. 5C). Indeed, the pattern of expression of both HYAL1 and HYAL2 follows the expression pattern of KIAA1199, showing a downregulation during the most intense regenerative phase of repair in COPD progression (chronic bronchitis and CORD GOLD 1). Upregulation of KIAA1199 in turn is synchronous to that of the PLAZA gene (see FIG. 5B) which is a phosphatidylserine-specific phospholipase expressed in macrophages stimulated by typical mechanisms of surface immunity, such as toll-like receptor 4 (TLR4) signaling (Wakahara et al., 2007). Both intensified KIAA1199 and PLA1A expression were found to be connected to short-term worsening of pulmonary function according to GOLD criteria (see also FIG. 5B).

Decrease of Pro-Angiogenic Mediators During Progression of COPD

Effective organ repair involves mechanisms concomitantly directing spatially controlled epithelial, mesenchymal and endothelial outgrowth. However, in contrast to gene functions contributing to epithelial and mesenchymal repair, gene expression promoting angiogenesis and vascular differentiation was found to decrease as soon as chronic bronchitis was present. During development of COPD (GOLD stage I and II), this pattern of gene expression proceeded significantly, as also shown in FIG. 8D. Even the increase of Bex1 and Ghrelin (GHRL) gene expression occurring at GOLD stage I is rather small and insignificant compared to gene functions aimed at the regeneration of epithelial outgrowth, such as DMBT1 and AZGP1. Some of the functions, such as FIBIN (fin bud initiation factor homolog), ESM1 (endothelial cell-specific molecule 1) and ghrelin (GHRL) are known to act, in part, as mediators in the early phases of organ development. For instance, FIBIN takes part in mesodermal lateral plate development (Wakahara et al., 2007) which is crucial for early vasculogenesis (Paffett-Lugassy et al., 2013), ESM1 mediates VEGF-A-dependent signaling (Zhang et al., 2012) and is typically expressed in growing vascular tissue which includes tumor angiogenesis (Zhang et al., 2012; Roudnicky et al., 2013; Chen et al., 2010) and regenerative wound healing (Béchard et al., 2001).

Ghrelin, on the other hand, is a typical marker of microvascular development (Li et al., 2007; Wang et al., 2012; Rezaeian et al., 2012) being vital for continuous epithelial oxygen and energy supply preventing excessive apoptosis characteristic for emphysema development (Mimae et al., 2013). BEX1 and BEX5 (Brain Expressed, X-Linked 1 and 5) are genes encoding adapter molecules interfering with p75NTR signaling events. p75NTR is one of the two receptors central to nerve growth factor (NGF) signaling. While BEX1 is known to induce sustained cell proliferation under conditions of growth arrest in response to NGF, much less is known about its possible involvement in angiogenesis and vessel formation, although NGF signaling itself is well-known to promote angiogenesis (Cantarella et al., 2002). One possible interaction could be that reduced BEX1 gene expression would increase p75NTR signaling efficacy causing increased endothelial apoptosis, as the blockade of p75NTR signaling significantly decreases endothelial apoptosis (Han et al., 2008; Caporali et al., 2008). The BEX5 promoter, in turn, contains regulatory binding sites for TAL1 (T-cell acute lymphocytic leukemia 1), a direct transcriptional activator of angiopoietin 2, which is significantly upregulated during angiogenesis (Deleuze et al., 2012). TAL1, however, is downregulated as well during progression of COPD, as also shown in FIG. 8D.

Stage-Dependent Activation of the Immune Response

Based on the significant changes of gene expression measured during progression of COPD, four sequential phases of gene expression were distinguished: Phase 1 is characterized by a rapid increase of genes involved in the acute immune response, such as fibrinogen (FGG) (Duvoix et al., 2013; Cockayne et al., 2012), and products of aryl hydrocarbon receptor (AHR) signaling, such as CYP1A1 (cytochrome P450, family 1, subfamily A, polypeptide 1) and CYP1B1 (cytochrome P450, family 1, subfamily B, polypeptide 1) expression, as also shown in FIGS. 5A to 5E. This includes as well an increased expression of carcinoembryonic antigen (CEA)-related cell adhesion molecules (CEACAMs), particularly of the CEACAMS gene (see FIGS. 5A and 5D). At this early stage, still representing chronic bronchitis without significant changes of pulmonary function (COPD "at risk"), expression of genes mediating functions of primarily adaptive immunity, such as RAS-GRF2 (Ras protein-specific guanine nucleotide-releasing factor 2), KIAA1199 or CXCL3 was not significantly changed (see also FIGS. 5H and 5F). At phase 2 (representing GOLD stage I), expression of these genes remained stable or even decreased to some extent (see FIGS. 4A and 5A), probably reflecting the stabilizing outcome of regenerative repair efforts which was most intense at GOLD stage I (see also FIG. 6A). However, phase 3 which includes GOLD stages II and III was characterized by a significant increase of expression of all genes related to immunity including genes indicating increased AHR signaling, such as CYP1A1, CYP1A2 and CYP1B1 (see also FIGS. 5A, 5E and 5F). The latter ones most likely reflect the impact of cigarette smoking, ail the more as three quarters of the participants were still actives smokers at this stage (see FIG. 3C). Increased gene expression reflecting intensified AHR signaling could be demonstrated in spite of elevated levels of the aryl hydrocarbon receptor repressor (AHRR) gene known to inhibit AHR signaling events, particularly during GOLD stages II and III.

Nonetheless, short-term analysis of gene expression addressing a development of COPD over a period of 3 years (see also FIGS. 5A and 5D, middle) indicates that the overall impact of AHR signaling on the deterioration of pulmonary function is more important than the additional expression of CEACAMS which, comparable to FGG expression (see also FIG. 5D), seems to reflect the intensity of bronchitis much better. Phase 4 representing GOLD stage IV shows a striking downregulation of the majority of immune-related functions upregulated during earlier phases of COPD development, comparable to the regulation of genes controlling cellular regeneration and differentiation. interestingly, however, this does not apply to the expression of KIAA1199 and RAS-GRF2 genes which are both upregulated even at GOLD stage IV, the latter one being again capable of influencing cellular movements by inhibition of the actin cytoskeleton (Calvo et al., 2011): RASGRF2 belongs to a group of activators of the GTPase RAS involved as well in the activation of T cells and required for the induction of NF-AT, IL-2 and TNF-α (Ruiz et al., 2007).

Within this context, the slow yet constant and highly significant upregulation of the guanine-nucleotide exchange factor (GEF) son of sevenless homolog 1 (SOS1) (see FIG. 8A), capable of continually activating RAS, could significantly contribute to the chronic inflammatory process facilitating the bronchial wall scarring characteristic for late stage COPD.

Members of the carcinoembryonic antigen-related cell adhesion molecule (CEACAM) family serve as cellular receptors for typical gram-negative bacteria frequently colonizing the surface of the human airways, such as *Neisseria meningitidis*, *Haemophilus influenzae* and *Moraxella catarrhalis* expressing opacity (Opa) proteins (Muenzner et al., 2010; Bookwalter et al., 2008; Muenzner et al., 2005). It was recently suggested that non-typable *Haemophilus influenzae* and *Moraxella catarrhalis* are able to increase the expression of their respective receptors on host cells (Klaile et al., 2013). However, no correlation between the expression of members of the CEACAM family and COPD was found under the conditions employed in that study. In the present study, only the expression of the CEACAM5 gene was significantly increased up to GOLD stage III, in that following the inflammatory reaction in general, while significantly decreasing afterwards in GOLD stage IV. This does not, however, exclude the aggravation of mucosa! inflammation as a result of a persistent upregulation of CEACAM5, all the more as the expression of CEACAM5 was found to be increased in combination with a growing intensity of bronchial inflammation (see FIG. 5D).

Conclusions

Between 2007 and 2012, a controlled prospective pilot trial was conducted in finally 120 volunteers in order to identify metabolic markers indicative of the progression of COPD. By adopting parts of the design of the ECLIPSE trial (Vestbo et al., 2011), the largest and most elaborate study performed thus far to identify clinical markers describing both progress and variability of COPD, the Vienna COPD study combined controlled assessment of validated clinical measures with unsupervised assessment of genome-wide gene transcription in pulmonary tissue representing the focus of COPD pathology (Hogg JC, 2004 (b)). The correlation of gene expression with clinical development was based a) on the extent of non-reversible pulmonary obstruction at visit 1 (according to the Global Initiative for Obstructive Lung Disease; GOLD), b) on the worsening of non-reversible obstruction according to GOLD between visit 1 and 3 (covering a period of three years), and c) on symptoms indicative of an increasing intensity of bronchitis being recorded during structured clinical history at visits 1 and 3.

This analysis revealed changes of gene expression indicative of six major deviations from regular maintenance of pulmonary structure and defense: (1) Progressive loss of functions guiding epithelial and (2) vascular regeneration combined with (3) persistent and increasing activation of mechanism of fibroproliferative repair, together indicating a transition from regenerative to fibrotic repair during progression of COPD; (4) intensifying bronchial inflammation being antagonized at GOLD stage I when regenerative repair activity is highest, and culminating afterwards at GOLD stages II and III; (5) a complete loss of structural maintenance at GOLD stage IV connected to a finally failing immunity, both suggestive of the formation of scar tissue; and lastly, a rapid and persistent downregulation of functions controlling the intracellular distribution, aggregation and sequestration of actin polymers which form the cytoskeleton (6). The latter finding is of particular interest as the changes in the transcription of the corresponding genes, in particular the downregulation of TMSB15A, DPP6, NUDT11 and PRICKLE2, were already observed at GOLD stage 0 (COPD "at risk"), well before any change of pulmonary function was measurable. This striking loss occurs together with a significant increase of functions determining bronchial inflammation suggesting that these changes might be the first to predispose the bronchi to persistent inflammation. The outcome of such an early and simultaneous downregulation of the TMSB15A, DPP6, NUDT11 and PRICKLE2 genes will be discussed in the following.

Thymosin beta 15A (TMSB15A) belongs to the group of WH2 (WASP-homologue 2) domain binding proteins which are necessary for the depolymerization of actin filaments during cellular movements (Husson et al., 2010; Hertzog et al., 2004). Formation and rapid movement of actin filaments in turn are indispensable for processes such as cell division, intercalation and cellular extrusion. This applies as well to the regulation of apicobasal cell polarity (Nishimura et al., 2012), and even more important, to the formation and maintenance of tight and adherens junctions (Shen et al., 2005; Calautti et al., 2002). These complex membrane dynamics are not only an answer to external and internal stress, but also part of regular tissue growth and as such energy-dependent. The assembly of the actin skeleton is highly dynamic and creates a layer of epidermal cells acting as an impenetrable fluid-like shield composed of the constantly moving lipid border of the cells (Guillot et al., 2013). Thus, a persistent downregulation of TMSB15A is likely to prevent any fast adaptive arrangement of the surface lipid layers during cellular movements causing repeated perturbations of the epithelial barrier function.

DPP6, on the other hand, is known to stabilize the membrane potential by acting on membrane-bound potassium channels, and has also a profound impact on the organization of the actin cytoskeleton (Chifflet et al., 2003), supporting the perception of a failing barrier function. The same applies to the downregulation of NUDT11 gene expression. The nucleoside diphosphate linked moiety X (nudix)-type motif 11 (NUDT11) gene encodes a type 3 diphosphoinositol polyphosphate phosphohydrolase which generates energy-rich phosphates essential for vesicle trafficking, maintenance of cell-wall integrity in Saccharomyces and for the mediation of cellular responses to environmental salt stress (Dubois et al., 2002). As the adaptive assembly of F and G actin fibers within the cytoskeleton occurs in seconds, it is easily conceivable that energy-rich diphosphoinositol polyphosphates being integral constituents of any cell membrane will be utilized as rapidly accessible source of energy.

These findings point towards a synchronized dysregulation of genes necessary for upholding the epithelial barrier. Moreover, the downregulation of the PRICKLE2 gene was also shown to be vital for the formation of polarized epithelial layers during mouse embryogenesis (Tao et al., 2012). Decreased expression of all four genes (i.e., TMSB15A, DPP6, NUDT11 and PRICKLE2), however, was associated with significantly increased bronchial inflammation, suggesting a functional correlation between the downregulation of genes that guide functionally interrelated features of cytoskeleton assembly with the activation of bronchitis. This sheds a new light on the progression of bronchial inflammation as it indicates a direct connection between the loss of a protective epithelial shield and the aggravation of chronic bronchitis. Based on the physico-chemical nature of such an effect, penetration of the epithelial membranes by any potential antigen or allergen is likely to be enhanced, particularly during intensified repair due to repeated smoke-induced damage or following viral infections. This could not only explain the remarkable heterogeneity of inflammatory conditions characteristic for COPD, but also the observation that the capacity to achieve intense cellular regeneration in spite of ongoing inflammation might be helpful in suppressing pro-inflammatory gene expression.

This view is further supported by the significant downregulation of the protease inhibitor cystatin M/E (CST6) during progression of COPD (see also FIG. 4A). CST6 is known to control the homeostasis of the stratum corneum, its deficiency in mice causing severe ichthyosis and neonatal lethality (Zeeuwen et al., 2009). The progressive loss of a protease inhibitor in later phases of COPD known to preserve the integrity of epithelial structures wiii most likely contribute to a failure of the protective barrier function, not only by a disintegration of the epithelial layer but also by facilitating the breakdown of the matrix itself.

In this context, the strong upregulation of the KIAA1199 gene which has been demonstrated to significantly increase the activity of matrix hyaluronidases, is probably equally important, as this upregulation is directly associated with a significant worsening of lung function, even within the relatively short observational period of the present study (see also FIG. 5B). It has recently been shown that matrix structures containing large amounts of high molecular mass hyaluronan as well as the inhibition of hyaluronidase activity protect against both inflammation and cancer progression (Tian et al., 2013). In summary, these findings provide the first conclusive evidence for a progressive breakdown of bronchial surface integrity during the course of COPD development causing growing non-specific bronchial inflammation that varies with frequency and intensity of the physicochemical assaults attacking the bronchial surfaces.

According to results described herein, the response to these assaults is a slow progressive scarring process in the peripheral bronchi, whereby the combined upregulation of CTHRC1, SOS1 and NTRK2 genes (see also FIG. 8A) is likely to indicate mechanisms of preferentially mesenchymal wound healing while the stage dependent expression of the PRRX1 and COMP genes suggests their participation in regular organ repair as well demonstrating the ambiguity between regular matrix support during regenerative repair and scar formation as a result of a progressive failure of the organ's regenerative repair capacity.

This fits well to the progressive downregulation of genes mainly controlling functions of regenerative growth of the vascular tree as demonstrated by the concomitant decrease of the expression of FIBIN, TAL1, BEX1/5, and Ghreiin (GHRL) genes (see also FIG. 8D). Here again, the increasing capacity of the peripheral lung to employ mechanisms of preferentially regenerative repair during GOLD stage I becomes evident as BEX1 and GHRL increase at this stage while progressively decreasing during further progression of COPD.

Thus, in the COPD AUVA study, the clinical progression of COPD has been successfully correlated with the biological analysis of gene expression in pulmonary tissue. In particular, it has been demonstrated that the expression of the genes KIAA1199, DMBT1, ELFS, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is increased in pulmonary tissue samples from subjects prone to develop progressive COPD, while the expression of the genes TMSB15A, DPP6, SLC51B, NUDT11, PLA1A, HYAL2, CST6, ITGA10, CTHRC1, TAL1, FIBIN, BEXS, BEX1, ESM1 and GHRL is decreased in pulmonary tissue samples from subjects prone to develop progressive COPD, as compared to the expression of the corresponding genes in pulmonary tissue samples from healthy subjects. These molecular biomarkers can thus be used for assessing the susceptibility/proneness of a subject to develop progressive COPD in accordance with the present invention, particularly in the method of the second aspect of the invention. Moreover, it has also been demonstrated that the expression of the genes DMBT1, ELFS, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and COMP is increased in pulmonary tissue samples from subjects suffering from or prone to suffer from stable COPD, while the expression of the genes KIAA1199, TMSB15A, DPP6, SLC51B, NUDT11, PLA1A, HYAL2, CST6, ITGA10, CTHRC1, TAL1, FIBIN, BEXS, BEX1, ESM1 and GHRL is decreased in pulmonary tissue samples from subjects suffering from or prone to suffer from stable COPD, as compared to the expression of the corresponding genes in pulmonary tissue samples from healthy subjects, indicating that these biomarkers are suitable for diagnosing stable COPD or assessing the susceptibility of a subject to develop stable COPD in accordance with the invention, particularly in the method of the third aspect of the invention.

REFERENCES

Agarwal P, et al. *J Biol Chem.* 2012; 287(27):22549-59. doi:10.1074/jbc.M111.335935.

Agarwal P, et al. *Matrix Biol.* 2013; 32(6):325-31. doi:10.1016/j.matbio.2013.02.010.

Avcuoglu S, et al. *Am J Respir Cell Mo! Biol.* 2011; 45(4):768-80. doi:10.1165!rcmb.2010-01950C.

Béchard D, et al. *J Biol Chem.* 2001; 276(51):48341-9.

Bookwalter J E, et al. *Infect Immun.* 2008; 76(1):48-55.

Butt A Q, et al. *J Biol Chem.* 2012; 287(46):38665-79. doi:10.1074/jbc.M112.367490.

Calautti E, et al. *J Cell Biol.* 2002; 156:137-48.

Calvo F, et al. *Nat Cell Biol.* 2011; 13(7):819-26. doi:10.1038/ncb2271.

Cantarella G, et at. *FASEB J.* 2002; 16(10):1307-9.

Caporali A, et al. *Circ Res.* 2008; 103(2):e15-26. doi:10.1161/CIRCRESAHA.108.177386.

Chavez-Muñoz C, et al. *J Cell Biochem.* 2012; 113(8):2622-32. doi:10.1002/jcb.24137.

Chen L Y, et al. *J Int Med Res.* 2010; 38(2):498-510.

Chifflet S, et al. *Exp Cell Res.* 2003; 282(1):1-13.

Cockayne D A, et al. *PLoS One.* 2012; 7(6):e38629. doi:10.1371/journal.pone.0038629.

Cole S P C, et al. *Monoclonal Antibodies and Cancer Therapy.* 1985; 27:77-96.

De Santis M, et al. *Respir Res.* 2011; 12:22. doi:10.1186/1465-9921-12-22.

Deleuze V, et al. *PLoS One.* 2012; 7(7):e40484. doi:10.1371/journal.pone.0040484.

Diegelmann J, et al. *J Biol Chem.* 2012; 287(1):286-98. doi:10.1074/jbc.M111.294355.

Ding C, et al. *J Biochem Mol Biol.* 2004; 37(1):1-10.

Dubois E, et al. *J Biol Chem.* 2002; 277:23755-63.

Duvoix A, et al. *Thorax.* 2013; 68(7):670-6. doi:10.1136/thoraxjnl-2012-201871.

Evensen N A, et al. *J Natl Cancer Inst.* 2013; 105(18):1402-16. doi:10.1093/jnci/djt224.

Frisch S M, et al. *J Cell Sci.* 2013; 126(Pt1):21-9. doi:10.1242/jcs.120907.

Gentleman R, et al. *Genome Biology.* 2004; 5:R80.

Green, M R et al. *Molecular Cloning: A Laboratory Manual.* Cold Spring Harbor Laboratory Press. Fourth Edition. 2012. ISBN: 978-1936113422.

Guillot C, et al. *Science.* 2013; 340:1185-9.

Halbert R J, et al. *Eur Respir J.* 2006; 28:523-32.

Han Y, et al. *Biochem Biophys Res Commun.* 2008; 366(3):685-91.

Han M K, et al. *Am J Respir Crit Care Med.* 2010; 182:598-604.

Hannappel E. *Ann NY Acad Sci.* 2007; 1112:21-37. doi:10.1196/annals.1415.018.

Harlow E, et al. *Using Antibodies: A Laboratory Manual.* Cold Spring Harbor Laboratory Press. 1998. ISBN: 978-0879695446.

Harnoncourt K, et al. *Osterreich Arzteztg.* 1982; 37:1640-2.

Hertzog M, et al. *Cell.* 2004; 117:611-623.

Hogg J C, et al. *N Engl J Med.* 2004; 350:2645-2653. (a)

Hogg J C. *Lancet.* 2004; 364:709-721. (b)

Huff T, et al. *Int J Biochem Cell Biol.* 2001; 33:205-220. doi:10.1016/S1357-2725(00)00087-X.

Hurst J R, et al. *N Engl J Med.* 2010; 363:1128-1138.

Husson C, et at. *Ann NYAcad Sci.* 2010; 1194:44-52. doi:10.1111/j.1749-6632.2010.05473.x.

Jerng H H, et al. *PLoS One.* 2012; 7(6):e38205. doi:10.1371/journal.pone.0038205.

Jiang F, et al. *Exp Biol Med (Maywood).* 2008; 233(3):286=96. doi:10.3181/0707-RM-177.

Johnson W E, et al. *Biostatistics.* 2007; 8(1):118-127.

Kaemmerer E, et al. *Histopathology.* 2012; 60(4):561-9.doi:10.1111/j.1365-2559.2011.04159.x.

Kim N H, et al. *J Invest Dermatol.* 2010; 130(9):2231-9. doi:10.1038/jid.2010.99.

Klaile E, et al. *Respir Res.* 2013; 14:85. doi:10.1186/1465-9921-14-85.

Köhler G, et al. *Nature.* 1975; 256(5517):495-7.

Kong B, et al. *Oncogene.* 2010; 29(37):5146-58. doi:10.1038/onc.2010.258.

Kothapalli D, et al. *J Cell Biol.* 2007; 176:535-44.

Kozbor D, et al. *Immunol Today.* 1983; 4(3):72-9.

Lei W, et al. *Am J Physiol Lung Cell Mol Physiol.* 2007; 293(5):L1359-68.

Li A, et at. *Biochem Biophys Res Commun.* 2007; 353 (2):238-43.

Lin L, et al. *Nat Commun.* 2013; 4:2270. doi:10.1038/ncomms3270.

Malinda K M, et al. *J Invest Dermatol.* 1999; 113(3):364-8. doi:10.1046/j.1523-1747.1999.00708.x.

Mazzochi C, et al. *Am J Physiol Renal Physiol.* 2006; 291(6):F1113-22.

Medina A, et al. *Mol Cell Biochem.* 2007; 305:255-64.

Metzger D E, et al. *Dev Biol.* 2008; 320(1):149-60. doi:10.1016/j.ydbio.2008.04.038.

Mimae T, et al. *Thorax.* 2013. doi:10.1136/thoraxjnl-2013-203867.

Muenzner P, et al. *J Cell Biol.* 2005; 170(5):825-36. doi:10.1083/jcb.200412151

Muenzner P, et al. *Science.* 2010; 329(5996):1197-201. doi:10.1126/science.1190892.

Murray C J L, et al. *Lancet.* 1997; 349:1498-504.

Nadin B M, et al. PLoS One. 2013; 8(4):e60831. doi:10.1371/journal.pone.0060831.

Nakahigashi K, et al. *J Invest Dermatol.* 2011; 131(4):865-73. doi:10.1038/jid.2010.395.

Nishimura T, et al. *Cell.* 2012; 149(5):1084-97. doi:10.1016/j.cell.2012.04.021.

Ocaña O H, et al. *Cancer Cell.* 2012; 22(6):709-24. doi:10.1016/j.ccr.2012.10.012.
Paffett-Lugassy N, et al. *Nat Cell Biol.* 2013; 15(11):1362-9. doi:10.1038/ncb2862.
Pauwels, R A et al. *Am J Respir Crit Care Med.* 2001; 163(5):1256-76.
Price D, et al. *Prim Care Respir J.* 2011; 20(1):15-22. doi:10.4104/perj.2010.00060.
Pure E, et al. *Cell Signal.* 2009; 21(5):651-5. doi:10.1016/j.cellsig.2009.01.024.
Rabe K F, et al. *Am J Respir Crit Care Med.* 2007; 176(6):532-55.
Rezaeian F, et al. *Am J Physiol Heart Circ Physiol.* 2012; 302(3):H603-10. doi:10.1152/ajpheart.00390.2010.
Roudnicky F, et al. *Cancer Res.* 2013; 73(3):1097-106. doi:10.1158/0008-5472.CAN-12-1855.
Ruiz S, et al. *Mol Cell Biol.* 2007; 27(23):8127-42.
Shen L, et al. *Mol Bio Cell.* 2005; 16:3919-36.
Smyth G K. Iimma: linear models for microarray data. In: Gentleman R, et al. Bioinformatics and Computational Biology Solutions using R and Bioconductor. 2005. Springer, N.Y., pages 397-420.
Spector I, et al. *Am J Pathol.* 2013; 182(3):905-16. doi:10.1016/j.ajpath.2012.11.004.
Tao H, et al. *Dev Biol.* 2012; 364(2):138-48. doi:10.1016/j.ydbio.2012.01.025.
Tian X, et al. *Nature.* 2013; 499(7458):346-9. doi:10.1038/nature12234.
Toole B P. *Nat Rev Cancer.* 2004; 4(7):528-39.
US Burden of Disease Collaborators. *JAMA.* 2013; 310 (6):591-608.
Vestbo J, et al. *N Engl J Med.* 2011; 365(13):1184-92.
Vestbo J, et al. *Am J Respir Crit Care Med.* 2013; 187(4):347-65. doi:10.1164/rccm.201204-0596PP.
Wang L, et al. *Peptides.* 2012; 33(1):92-100. doi:10.1016/j.peptides.2011.11.001.
Wakahara T, et al. *Dev Biol.* 2007; 303(2):527-35.
Wedzicha J A. *Thorax.* 2000; 55:631-632.
Wu Q, et al. *Innate Immun.* 2012; 18(4):617-26. doi:10.1177/1753425911429837.
Yaniw D, et al. *Cell Res.* 2005; 15(6):423-9.
Yoshida H, et al. *Proc Natl Acad Sci USA.* 2013; 110(14):5612-7. doi:10.1073/pnas.1215432110.
Zeeuwen P L J M, et al. *J Invest Dermatol.* 2009; 129:1327-38. doi:10.1038/jid.2009.40.
Zeeuwen P L J M, et al. *FASEB J.* 2010; 24:3744-55. doi:10.1096/fj.10-155879.
Zhang S M, et al. *Biotech Histochem.* 2012; 87(3):172-8. doi:10.3109/10520295.2011.577754.

The invention claimed is:

1. A method of treating chronic obstructive pulmonary disease (COPD), in
   a human subject that is prone to develop progressive COPD involving the appearance of irreversible lung damage, the method comprising:
   a) testing the level of RNA expression of the gene KIAA1199 in a lung tissue sample obtained from the human subject;
   b) comparing the level of RNA expression of KIAA1199 in the lung tissue sample from the human subject to a control RNA expression level of KIAA1199 in a healthy human subject;
   c) identifying the subject as being prone to develop progressive COPD involving the appearance of irreversible lung damage based on detecting an increase in the level of RNA expression of KIAA1199 in the lung tissue sample from the human subject as compared to the control RNA expression level of KIAA1199; and
   d) treating the subject identified in step c) with a drug against COPD.

2. The method of claim 1, wherein the drug against COPD is bitolterol, carbuterol, fenoterol, pirbuterol, procaterol, reproterol, rimiterol, salbutamol, levosalbutamol, terbutaline, tulobuterol, arformoterol, bambuterol, clenbuterol, formoterol, olodaterol, salmeterol, indacaterol, beclometasone, betamethasone, budesonide, ciclesonide, flunisolide, fluticasone, mometasone, triamcinolone, aclidinium bromide, glycopyrronium bromide, ipratropium bromide, oxitropium bromide, tiotropium bromide, cromoglicate, nedocromil, acefylline, ambuphylline, bamifylline, doxofylline, enprofylline, etamiphylline, proxyphylline, theobromine, theophylline, aminophylline, choline theophyllinate, montelukast, pranlukast, zafirlukast, zileuton, ramatroban, seratrodast, ibudilast, roflumilast, amlexanox, eprozinol, fenspiride, omalizumab, epinephrine, hexoprenaline, isoprenaline, isoproterenol, orciprenaline, metaproterenol, atropine, or a pharmaceutically acceptable salt of any of the aforementioned agents, or any combination thereof.

3. The method of claim 1, wherein the drug against COPD is roflumilast.

4. A method of treating or preventing chronic obstructive pulmonary disease (COPD), the method comprising administering a drug against COPD to a human subject that has been identified-as suffering from stable COPD or as being prone to suffer from stable COPD, the human subject having been identified by a method comprising:
   a) testing the level of RNA expression of the gene KIAA1199 in a lung tissue sample obtained from the human subject;
   b) comparing the level of RNA expression of KIAA1199 in the lung tissue sample from the human subject to a control RNA expression level of KIAA1199 in a healthy human subject; and
   c) identifying the subject as suffering from stable COPD or as being prone to suffer from stable COPD if the level of RNA expression of KIAA1199 in the lung tissue sample from the human subject is decreased as compared to the control RNA expression level of KIAA1199.

5. The method of claim 4, wherein the drug against COPD is bitolterol, carbuterol, fenoterol, pirbuterol, procaterol, reproterol, rimiterol, salbutamol, levosalbutamol, terbutaline, tulobuterol, arformoterol, bambuterol, clenbuterol, formoterol, olodaterol, salmeterol, indacaterol, beclometasone, betamethasone, budesonide, ciclesonide, flunisolide, fluticasone, mometasone, triamcinolone, aclidinium bromide, glycopyrronium bromide, ipratropium bromide, oxitropium bromide, tiotropium bromide, cromoglicate, nedocromil, acefylline, ambuphylline, bamifylline, doxofylline, enprofylline, etamiphylline, proxyphylline, theobromine, theophylline, aminophylline, choline theophyllinate, montelukast, pranlukast, zafirlukast, zileuton, ramatroban, seratrodast, ibudilast, roflumilast, amlexanox, eprozinol, fenspiride, omalizumab, epinephrine, hexoprenaline, isoprenaline, isoproterenol, orciprenaline, metaproterenol, atropine, or a pharmaceutically acceptable salt of any of the aforementioned agents, or any combination thereof.

6. A method of treating chronic obstructive pulmonary disease (COPD), the method comprising administering a drug against COPD to a human subject suffering from stable COPD and identified as being prone to develop progressive COPD involving the appearance of irreversible lung damage by a method comprising:
  a) testing the level of RNA expression of the gene KIAA1199 in a lung tissue sample obtained from the human subject;
  b) comparing the level of RNA expression of KIAA1199 in the lung tissue sample from the human subject to a control expression level of KIAA1199 in a human subject suffering from stable COPD; and
  c) identifying the human subject as being prone to develop progressive COPD involving the appearance of irreversible lung damage if the level of RNA expression of KIAA1199 in the lung tissue sample from the human subject is increased as compared to the control RNA expression level of KIAA1199.

7. The method of claim 6, wherein the drug against COPD is bitolterol, carbuterol, fenoterol, pirbuterol, procaterol, reproterol, rimiterol, salbutamol, levosalbutamol, terbutaline, tulobuterol, arformoterol, bambuterol, clenbuterol, formoterol, olodaterol, salmeterol, indacaterol, beclometasone, betamethasone, budesonide, ciclesonide, flunisolide, fluticasone, mometasone, triamcinolone, aclidinium bromide, glycopyrronium bromide, ipratropium bromide, oxitropium bromide, tiotropium bromide, cromoglicate, nedocromil, acefylline, ambuphylline, bamifylline, doxofylline, enprofylline, etamiphylline, proxyphylline, theobromine, theophylline, aminophylline, choline theophyllinate, montelukast, pranlukast, zafirlukast, zileuton, ramatroban, seratrodast, ibudilast, roflumilast, amlexanox, eprozinol, fenspiride, omalizumab, epinephrine, hexoprenaline, isoprenaline, isoproterenol, orciprenaline, metaproterenol, atropine, or a pharmaceutically acceptable salt of any of the aforementioned agents, or any combination thereof.

8. The method of claim 1, further comprising:
  testing the level of RNA expression of one or more further genes, the one or more further gene(s) being DMBT1, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 or GHRL in the lung tissue sample obtained from the human subject;
  comparing the level of RNA expression of the one or more further genes to a control expression level of the one or more further gene(s) in a healthy human subject
  an increase in the level of RNA expression of KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the lung tissue sample from the human subject as compared to the control RNA expression level of the one or more further gene(s) being indicative of a proneness to develop progressive COPD, and
  a decrease in the level of RNA expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the lung tissue sample from the human subject as compared to the control RNA expression level of the one or more further gene(s) being indicative of a proneness to develop progressive COPD.

9. The method of claim 8, wherein the level of RNA expression of DMBT1 and TMSB15A is tested.

10. The method of claim 8, comprising testing the lung tissue sample to determine the level of RNA expression of DMBT1, TMSB15A and at least one further gene that is FGG, CYP1A1, CEACAM5, CTHRC1, NTRK2, RASGRF2, ELF5, AZGP1, PRRX1, AQP3, SFN, GPR110, GDF15, RASGRF2, RND1, DPP6, SLC51B or NUDT11.

11. The method of claim 8, comprising testing the lung tissue sample to determine that the subject is prone to develop progressive COPD involving the appearance of irreversible lung damage if the level of RNA expression of a majority of the number of genes tested is altered in the sense that (i) the level of RNA expression of KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control RNA expression level of the gene(s) and (ii) the level of RNA expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control expression level of the gene(s).

12. The method of claim 8, comprising testing the lung tissue sample to determine that the subject is prone to develop progressive COPD involving the appearance of irreversible lung damage if the level of RNA expression of a majority of the number of genes tested is altered in the sense that (i) the level of RNA expression of KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold increased as compared to the control RNA expression level of the gene(s) and (ii) the level of RNA expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold decreased as compared to the control RNA expression level of the gene(s).

13. The method of claim 8, comprising testing the lung tissue sample to determine that the subject is prone to develop progressive COPD involving the appearance of irreversible lung damage if the level of RNA expression of at least 70% of the number of genes tested is altered in the sense that (i) the level of RNA expression of KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is increased as compared to the control RNA expression level of the gene(s) and (ii) the level of RNA expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is decreased as compared to the control RNA expression level of the gene(s).

14. The method of claim 8, comprising testing the lung tissue sample to determine that the subject is prone to develop progressive COPD involving the appearance of irreversible lung damage if the level of RNA expression of at least 70% of the number of genes tested is altered in the sense that (i) the level of RNA expression of KIAA1199, DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the sample from the subject is at least 3-fold increased as compared to the control RNA expression level of the gene(s) and (ii) the level of RNA expression of TMSB15A, DPP6, SLC51B, NUDT11, PLA1A, HYAL2, CST6, ITGA10, CTHRC1, TAL1, FIBIN, BEX5, BEX1, ESM1 and/or GHRL in the sample from the subject is at least 3-fold decreased as compared to the control RNA expression level of the gene(s).

15. The method of claim 1, the sample obtained from the subject being a transbronchial lung biopsy sample or a bronchoalveolar lavage sample.

16. The method of claim 1, the level of RNA expression being determined using a quantitative reverse transcriptase polymerase chain reaction or a microarray.

17. The method of claim 4, further comprising:
testing the level of RNA expression of one or more further genes, the one or more further genes being DMBT1, TMSB15A, DPP6, SLC51B, NUDT11, ELF5, AZGP1, PRRX1, AQP3, SFN, GPR110, GDF15, RASGRF2, RND1, PLA1A, FGG, CEACAM5, HYAL2, AHRR, CXCL3, CYP1A1, CYP1B1, CYP1A2, CST6, NTRK2, COMP, ITGA10, CTHRC1, TAL1, FIBIN, BEX5, BEX1, ESM1 or GHRL in the lung tissue sample obtained from the human subject;
comparing the level of RNA expression of the one or more further genes to a control RNA expression level of the one or more gene(s) in a healthy human subject; and
an increase in the level of RNA expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the lung tissue sample from the human subject as compared to the control RNA expression level of the one or more gene(s) being indicative of stable COPD or a proneness to stable COPD, and
a decrease in the level of RNA expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the lung tissue sample from the human subject as compared to the control RNA expression level of the one or more further gene(s) being indicative of stable COPD or a proneness to stable COPD.

18. The method of claim 17, comprising testing the lung tissue sample to determine if the human subject suffers from stable COPD or is prone to suffer from stable COPD if the level of RNA expression of a majority of the number of genes tested is altered in the sense that (i) the level of RNA expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the lung tissue sample from the human subject is increased as compared to the control RNA expression level of the one or more gene(s) and (ii) the level of RNA expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the lung tissue sample from the human subject is decreased as compared to the control RNA expression level of the one or more gene(s).

19. The method of claim 17, comprising testing the lung tissue sample to determine if the human subject suffers from stable COPD or is prone to suffer from stable COPD if the level of RNA expression of at least 70% of the number of genes tested is altered in the sense that (i) the level of RNA expression of DMBT1, ELF5, AZGP1, PRRX1, AQP3, SFN, GPR110, GDF15, RASGRF2, RND1, FGG, CEACAM5, AHRR, CXCL3, CYP1A1, CYP1B1, CYP1A2, NTRK2 and/or COMP in the lung tissue sample from the human subject is at least 3-fold increased as compared to the control expression level of the gene(s) and (ii) the level of RNA expression of KIAA1199, TMSB15A, DPP6, SLC51B, NUDT11, PLA1A, HYAL2, CST6, ITGA10, CTHRC1, TAL1, FIBIN, BEX5, BEX1, ESM1 and/or GHRL in the lung tissue sample from the human subject is at least 3-fold decreased as compared to the control RNA expression level of the gene(s).

20. The method of claim 4, the level of RNA expression being determined using a quantitative reverse transcriptase polymerase chain reaction or a microarray.

* * * * *